United States Patent
Modlin et al.

(10) Patent No.: US 12,043,847 B2
(45) Date of Patent: Jul. 23, 2024

(54) COMPOSITIONS AND METHODS FOR TREATING ACNE

(71) Applicants: The Regents of the University of California, Oakland, CA (US); University of Pittsburgh—Of The Commonwealth System of Higher Education, Pittsburgh, PA (US)

(72) Inventors: Robert L. Modlin, Sherman Oaks, CA (US); Jeffery F. Miller, Santa Monica, CA (US); Laura J. Marinelli, Los Angeles, CA (US); Graham F. Hatfull, Pittsburgh, PA (US)

(73) Assignees: The Regents of the University of California, Oakland, CA (US); University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 1101 days.

(21) Appl. No.: 16/301,984

(22) PCT Filed: May 12, 2017

(86) PCT No.: PCT/US2017/032422
§ 371 (c)(1),
(2) Date: Nov. 15, 2018

(87) PCT Pub. No.: WO2017/200873
PCT Pub. Date: Nov. 23, 2017

(65) Prior Publication Data
US 2019/0249149 A1     Aug. 15, 2019

Related U.S. Application Data

(60) Provisional application No. 62/336,680, filed on May 15, 2016.

(51) Int. Cl.
| | | |
|---|---|---|
| *C12N 7/00* | (2006.01) | |
| *A61K 9/00* | (2006.01) | |
| *A61K 35/76* | (2015.01) | |
| *A61K 45/06* | (2006.01) | |
| *A61P 17/10* | (2006.01) | |
| *C12N 15/11* | (2006.01) | |

(52) U.S. Cl.
CPC ............. *C12N 7/00* (2013.01); *A61K 9/0014* (2013.01); *A61K 35/76* (2013.01); *A61K 45/06* (2013.01); *A61P 17/10* (2018.01); *C12N 15/11* (2013.01); *C12N 2310/20* (2017.05); *C12N 2795/10321* (2013.01); *C12N 2795/10332* (2013.01)

(58) Field of Classification Search
None
See application file for complete search history.

(56) References Cited

FOREIGN PATENT DOCUMENTS

| | | | |
|---|---|---|---|
| EP | 2489275 A1 | * | 8/2012 |
| WO | WO-2007/007055 A1 | | 1/2007 |
| WO | WO-2013/142378 A1 | | 9/2013 |
| WO | WO-2017/200873 A8 | | 1/2019 |
| WO | WO-2019/113066 A1 | | 6/2019 |

OTHER PUBLICATIONS

Dreno, B., "Topical Antibacterial Therapy for Acne Vulgaris", Drugs, 2004, 64 (21): 2389-2397.*
Marinelli et al. 2012. Propionibacterium acnes bacteriophages display limited genetic diversity and broad killing activity against bacterial skin isolates. mBio 3(5): e00279-12. doi:10.1128/mBio.00279-12.*
Brown, Teagan L., et al. "The formulation of bacteriophage in a semi solid preparation for control of Propionibacterium acnes growth," Mar. 10, 2016, PloS one 11.3 (2016): e0151184. doi.org/10.1371/journal.pone.0151184 Retrieved from the internet: http://journals.plos.org/plosone/article?id=10.1371/journal.pone.0151184.
International Search Report and Written Opinion for International Application No. PCT/US2017/032422 dated Aug. 7, 2017.
Marinelli et al., "Propionibacterium acnes bacteriophages display limited genetic diversity and broad killing activity against bacterial skin isolates," Dec. 25, 2012, MBio 3.5 (2012): e00279-12. doi: 10.1128/mBio.00279-12 Retrieved from the internet: <http://mbio.asm.org/content/3/5/e00279-12.full> Dec. 25, 2012 (Dec. 25, 2012) pp. 7-8, p. 10 left column last paragraph, table 1, figures 8, 9.
Database EMBL, "Propionibacterium phage ATCC29399B_C complete genome.," XP002797068, Retrieved from EBI Accession No. EM_STD: JX262225, Database Accession No. JX262225 (2012).
Database EMBL, "Propionibacterium phage PHL132NOO complete genome.," XP002797066, Retrieved from EBI Accession No. EM_STD: KJ578780, Database Accession No. KJ578780 (2015).
Database EMBL, "Propionibacterium phage PHL152MOO complete genome.," XP002797067, Retrieved from EBI Accession No. EM_STD: KJ578785, Database Accession No. KJ578785 (2015).
Database EMBL, "Propionibacterium phage PHL171M01 complete genome.," XP002797064, Retrieved from EBI Accession No. EM_STD: KJ578787, Database Accession No. KJ578787 (2015).
Database Geneseq, "Siphoviridae (bacteriophage) DNA sequence, SEQ ID 1.," XP002797065, Retrieved from EBI Accession No. GSN: BCN40213, Database Accession No. BCN40213 (2016).
Extended European Search Report for EP application No. EP17799914 mailed Jan. 21, 2020.
Database EMBL "Propionibacterium phage Lauchelly, complete genome.", retrieved from EBI accession No. EM STD:KR337650 Database accession No. KR337650.

(Continued)

*Primary Examiner* — Suzanne M Noakes
(74) *Attorney, Agent, or Firm* — Foley Hoag LLP; David P. Halstead; Allison L. Gilder

(57) ABSTRACT

In certain aspects, the disclosure relates to compositions and methods relating to mutant bacteriophage that target *Propionibacterium acnes*. In certain aspects, compositions and methods described herein are useful for the treatment of acne.

10 Claims, 14 Drawing Sheets

Specification includes a Sequence Listing.

(56) References Cited

OTHER PUBLICATIONS

Database EMBL "Propionibacterium phage PAC9, complete genome.", retrieved from EBI accession No. EM STD:KR902986 Database accession No. KR902986.
Database EMBL "Propionibacterium phage PAS50, complete - genome.", retrieved from EBI accession No. EM STD:FJ706172 Database accession No. FJ706172.

* cited by examiner

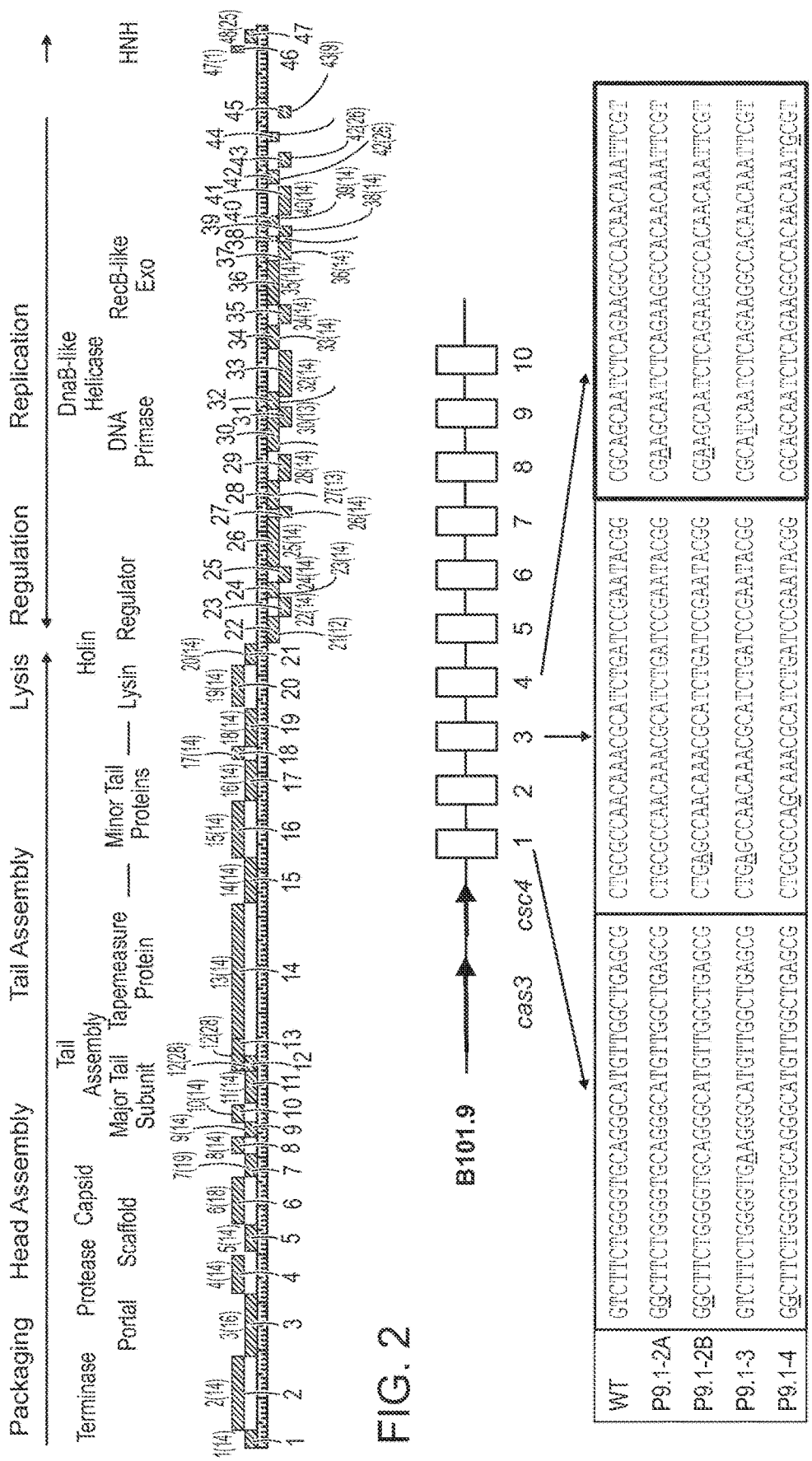

| Phage | B101.9 | B66.8 | Putative Mutants | Confirmed Mutants |
|---|---|---|---|---|
| P1.1 | ✓ | ✓ | 8 | 4 |
| P9.1 | ✓ | ✓ | 4 | N/A |
| P100A | No | No | N/A | N/A |
| P100D | No | No | N/A | N/A |
| P100.1 | ✓ | ✓ | | |
| P101A | ✓ | No | | 3 |
| P104A | ✓ | ✓ | | |
| ATCC_C | ✓ | No | | |

FIG. 12

| | Spacer | ---GTCTTCTGGGGTGCAGTCGATGTTGGCTGAGCG | Sensitivity |
|---|---|---|---|
| Protospacers | Parent φ3 | GAAGTCTTCTGGGGTGCAGTCTATGTTGGCTGAGCG | R |
| | P1.1-6* | GCAGTCTTCTGGGGTGCAGTCTATGTTGGCTGAGCG | S |
| | P1.1-7* | GCAGTCTTCTGGGGTGCAGTCTATGTTGGCTGAGCG | S |
| | P1.1-8* | GACGTCTTCTGGGGTGCAGTCTATGTTGGCTGAGCG | S |

FIG. 14

| Isolates | Phage-P9.1 Derivatives | | | | | | | | |
|---|---|---|---|---|---|---|---|---|---|
| | WT | 2A | 2B | 3 | 4 | 5 | 6 | 7/8 | 10 |
| 6919 | | | | | | | | | |
| B101.9 | <10⁻⁶ | | | | | | | | |
| 6921 | | | | | | | | | |
| 11827 | | 0.1 | 0.1 | 0.1 | 0.1 | | | | |
| 29399 | | | | | | | | | |
| B69.7 | | | | | | | | | |
| B102.1 | | | | | | | | | |
| B102.8 | | | | | | | | | |
| B102.10 | | | | | | | | | |

| Isolates | Phage-P1.1 Derivatives | | | | | | | | |
|---|---|---|---|---|---|---|---|---|---|
| | WT | 1 | 2 | 3 | 4 | 5 | 6 | 7 | 8 |
| 6919 | | | | | | | | | |
| B101.9 | <10⁻⁶ | | | | | 10⁻⁶ | 10⁻⁶ | 10⁻⁶ | 10⁻⁶ |
| B66.8 | <10⁻⁶ | | | | | | | | |
| 6921 | | | | | | | | | |
| 11827 | | | | | | | | | |
| 29399 | | | | | | | | | |
| B69.7 | | | | | | | | | |
| B102.1 | | | | | | | | | |
| B102.8 | | | | | | | | | |
| B102.10 | | | | | | | | | |

FIG. 15

COMPOSITIONS AND METHODS FOR TREATING ACNE

RELATED APPLICATIONS

This application is a § 371 national-stage application based on PCT/US2017/032422, filed May 12, 2017, which claims the benefit of priority to U.S. Provisional Patent Application Ser. No. 62/336,680, filed May 15, 2016, each of which is hereby incorporated by reference herein in its entirety.

STATEMENT REGARDING FEDERALLY SPONSORED RESEARCH

This invention was made with government support under Grant Numbers AR060382 and AR060655, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 6, 2018, is named UCH-00425_SL.txt and is 119,344 bytes in size.

FIELD OF THE INVENTION

This invention relates to the use of *Propionibacterium acnes* bacteriophages with expanded host ranges for use in treating acne.

BACKGROUND OF THE INVENTION

Acne is a significant cause of emotional and physical morbidity in the U.S. population. Acne vulgaris affects more than 45 million people, and more than 80% of people in the U.S. report suffering from acne in their lives. U.S. consumers spend more than $1.2 billion per year for acne treatment. The disease can significantly affect patients' self-esteem and lead to long-term effects such as scarring.

*Propionibacterium acnes* (*P. acnes*), the major species implicated in the pathogenesis of acne, is increasingly becoming resistant to antibiotic therapy. The Gram-positive skin commensal *P. acnes* is the dominant inhabitant of the human pilosebaceous follicle (2) and is thought to play a major role in the pathogenesis of acne vulgaris, in part by eliciting a host inflammatory response (3). There is a significant increase in *P. acnes* colonization at puberty, the time during which acne commonly develops, and teenagers with acne can have as many as 100-fold more *P. acnes* bacteria present on their skin than healthy age-matched counterparts (4). The efficacy of antibiotics in acne is related to the reduction of the number of *P. acnes* bacteria on the skin, as well as to direct anti-inflammatory properties (5), which reflects the multifactorial etiology of acne. The emergence of antibiotic-resistant strains of *P. acnes*, as measured in up to 60% of clinical isolates (6-8), highlights the need for improved therapeutics (5).

Thus, there is a long-felt need in the art for providing methods and compositions useful for the treatment of severe acne. The present invention described herein, provides such compositions and methods.

SUMMARY

Provided herein are methods and compositions related to treating and/or preventing skin conditions such as acne. In some aspects, provided herein are *Propionibacterium acnes* (*P. Acnes*) bacteriophage mutants (e.g., Clustered Regularly Interspaced Short Palindromic Repeats (CRISPR) escape mutants) and compositions (e.g., pharmaceutical compositions) comprising bacteriophage mutants capable of infecting bacteriophage resistant *P. Acnes*. Provided herein are methods of treating or preventing acne in a subject by administering the bacteriophages mutants and compositions disclosed herein. In some embodiments, the mutant comprises one or more mutations in a protospacer selected from 1, 3, and 4. In some embodiments, the mutations are selected from: T6502G, C6514A, G2762T, T2757C, G5919T, C5917A, A5892C, P9.1-2A, P9.1-2B, P9.1-3 and P9.1-4. The bacteriophage may comprise a nucleotide sequence having at least about 95% sequence homology to SEQ ID NO:1 or the reverse complement thereof; and the nucleotide sequence comprises a mutation to one or more nucleotides selected from A2, A3, T5, C6, T7, T8, C9, G11, G12, G13, G14, C17, G20, G21, and G22 of SEQ ID NO:1. The bacteriophage mutant may comprise one or more mutations to SEQ ID NO:1 selected from A2T, A2C, A3C, T5G, G11T, G14T, C17A, G20T, G21C, C22G, and C22T. In some embodiments, gene 9 of the bacteriophage comprises the nucleotide sequence. In some embodiments, the bacteriophage comprises a nucleotide sequence having at least about 95% sequence homology to SEQ ID NO: 2 or the reverse complement thereof; and the nucleotide sequence comprises a mutation to one or more nucleotides selected from A2, A3, T5, C6, T7, T8, C9, G11, G12, G13, G14, C17, T20, C21, and T22 of SEQ ID NO:2. The nucleotide sequence may comprise one or more mutations to SEQ ID NO:2 selected from A2T, A2C, A3C, T5G, G11T, G14T, C17A, T20G, C21G, T22G, and T22C. In some embodiments, gene 9 of the bacteriophage comprises the nucleotide sequence.

In some embodiments, the bacteriophage comprises a nucleotide sequence having at least about 95% sequence homology to SEQ ID NO:3 or the reverse complement thereof; and the nucleotide sequence comprises a mutation to one or more nucleotides selected from A2, A3, A5, T6, T7, G8, A9, T11, T12, G13, G14, T20, G23, T25, T30, and G31 of SEQ ID NO:3. The nucleotide sequence may comprise one or more mutations to SEQ ID NO:3 selected from T7C, T20G, G23A, T25G, T30G, and G31T. In some embodiments, gene 16 of the bacteriophage comprises the nucleotide sequence.

In some embodiments, the bacteriophage mutant comprises a nucleotide sequence having at least about 95% sequence homology to SEQ ID NO:4 or the reverse complement thereof; and the nucleotide sequence comprises a mutation to one or more nucleotides selected from A2, A3, T5, G6, C7, G8, C9, A11, A12, C13, A14, A15, A16, and G18 of SEQ ID NO:4. In some such embodiments, the nucleotide sequence comprises one or more mutations to SEQ ID NO:4 selected from A3T, A3C, A3G, C7A, C9A, A12G, C13A, A15G, A16C, A16T, and G18T. In some embodiments, gene 3 of the bacteriophage comprises the nucleotide sequence.

In some embodiments, the bacteriophage comprises a nucleotide sequence having at least about 95% sequence homology to SEQ ID NO:5 or the reverse complement thereof; and the nucleotide sequence comprises a mutation to one or more nucleotides selected from A2, A3, T5, G6, C7, G8, C9, A11, A12, C13, A14, G15, T16, and T18 of SEQ ID NO:5. In some such embodiments, the nucleotide sequence comprises one or more mutations to SEQ ID NO:5 selected from A3T, A3C, A3G, C7A, C9A, A12G, C13A, G15A, T16C, T16A, and T18G. In some embodiments, gene 3 of the bacteriophage comprises the nucleotide sequence.

In some embodiments, the bacteriophage comprises a nucleotide sequence having at least about 95% sequence homology to SEQ ID NO:6 or the reverse complement thereof; and the nucleotide sequence comprises a mutation to one or more nucleotides selected from A2, A3, G5, C6, A7, G8, C9, A11, T12, C13, T14, A31, T33, and G35 of SEQ ID NO:6. In some such embodiments, the nucleotide sequence comprises one or more mutations to SEQ ID NO:6 selected from C6A, A7G, G8T, A31G, T33G, and G35A. In some embodiments, gene 7 of the bacteriophage comprises the nucleotide sequence.

In some embodiments, the genome of the bacteriophage has at least about 95%, 96%, 97%, 98%, or 99% sequence homology with SEQ ID NO:7, and the bacteriophage comprises one or more mutations selected from G2761T, T2762C, G2767T, T2771C, T2771G, C6477A, A6507C, A6508C, T13160G, T13170G, G13171T, C13734A, T20501G, C23365A, G27713T, T28115G, and G28199T.

In some embodiments, the bacteriophage of any one of the preceding claims, wherein the genome of the bacteriophage has at least about 95%, 96%, 97%, 98%, or 99% sequence homology with SEQ ID NO:12, and the bacteriophage comprises one or more mutations selected from T2757C, G2760T, G2762T, T2766C, G3704T, C5890A, C5890T, A5892C, C5917A, G5919T, A6499C, T6502G, G6508T, G6511T, C6514A, A12404C, C16536A, G17863T, and G26907A.

In some aspects, provided herein are pharmaceutical compositions comprising a bacteriophage disclosed herein. The pharmaceutical compositions may comprise one or more antimicrobial agents, such as an anti-acne agent (e.g., retinoid, benzoyl peroxide and an antibiotic). Pharmaceutical compositions may be formulated for topical use.

Provided herein are methods of treating acne in a subject (e.g., a subject in need thereof) in need thereof by administering a therapeutically effective amount of a composition disclosed herein (e.g., pharmaceutical compositions comprising one or more *Propionibacterium acnes* (*P. Acnes*) bacteriophage mutants capable of infecting bacteriophage resistant *P. Acnes*. The acne may be associated with phage-resistant *P. Acnes*. In some embodiments, the bacteriophage mutant is a Clustered Regularly Interspaced Short Palindromic Repeats (CRISPR) escape mutant. In some embodiments, the bacteriophage mutants are bacteriophage mutants disclosed herein.

BRIEF DESCRIPTION OF THE DRAWINGS

For the purpose of illustrating the invention, there are depicted in the drawings certain embodiments of the disclosure. However, the disclosure is not limited to the precise arrangements and instrumentalities of the embodiments depicted in the drawings.

FIG. 1 depicts the genome map of *P. acnes* phage P100D.

FIG. 2 depicts mutations in phage escape mutants. In each of four mutants, mutations (underlined) are located in three of the protospacers; 1 (yellow), 3 (green), and 4 (brown). FIG. 2 discloses SEQ ID NOS 17-31, top to bottom, respectively, in order of columns.

FIG. 6 discloses SEQ ID NOS 32-34, respectively, in order of appearance.

FIG. 8 discloses SEQ ID NOS 35, 2, 1, 36-45, 5, 4, 46-56, 6, and 57-65, top to bottom, respectively, in order of columns.

FIG. 9 discloses SEQ ID NOS 66, 3, 67-76, 45, 5, 4, 46-56, 6, and 57-65, top to bottom, respectively, in order of columns.

Figure 12:
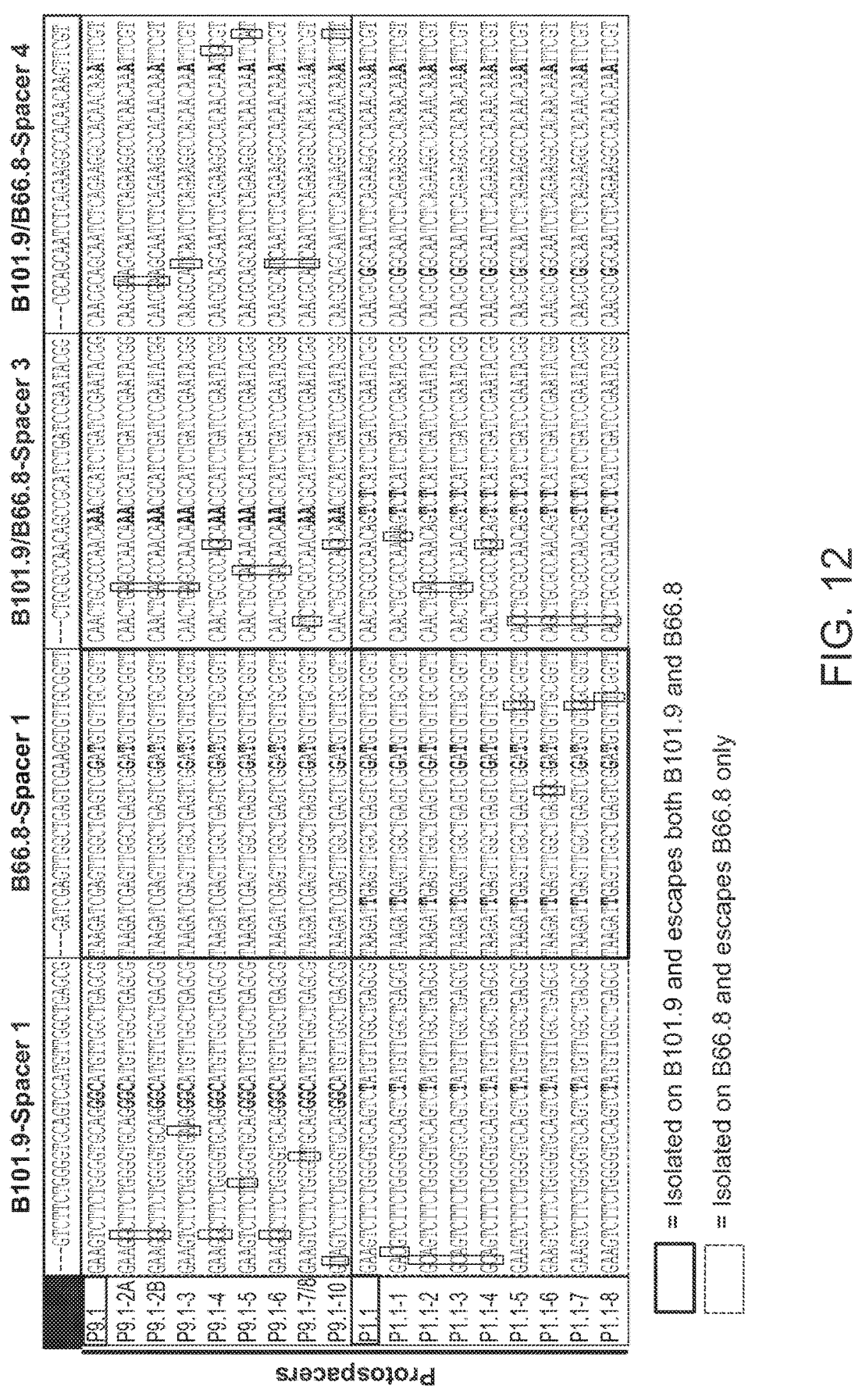

FIG. 12 shows PSs and PAMs in CRISPR escape mutants contain point mutations. FIG. 12 discloses SEQ ID NOS 35, 1, 77-84, 2, 85-92, 66-67, 93-100, 3, 101-108, 45, 4, 109-116, 5, 117-124, 55, 6, 125-132, 56, and 133-140, top to bottom, respectively, in order of columns.

FIG. 13 discloses SEQ ID NOS 35 and 141-144, respectively, in order of appearance.

FIG. 14 shows that the host range of escape mutants on non-resistant isolates is unaffected.

Figure 15:
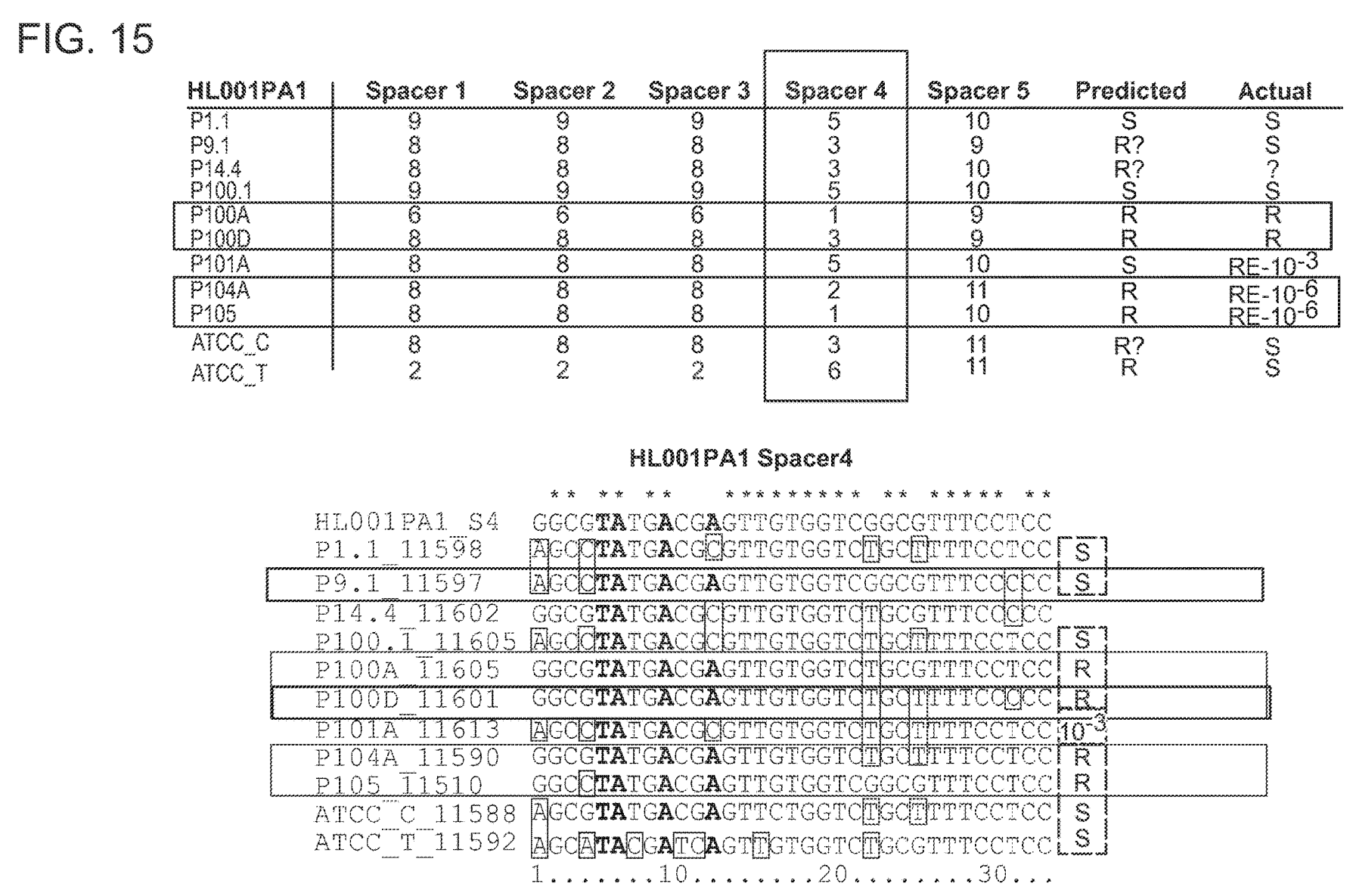

FIG. 15 depicts mutations in phage escape mutants. FIG. 15 discloses SEQ ID NOS 145-156, respectively, in order of appearance.

DETAILED DESCRIPTION OF THE INVENTION

I. Overview

Figure 3:
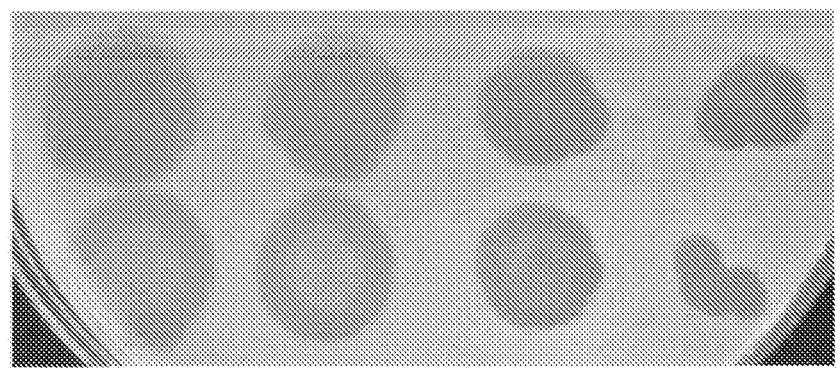
FIG. 3 shows serial dilutions of ATCC_C (top) and ATCC_T (bottom) showing plaque morphotypes.

Current therapy is inadequate, and phage-based therapy provides a new antimicrobial approach for acne treatment. Oral antibiotic therapy for acne is often unsuccessful due to resistance among clinical strains (6-8), and can lead to undesirable systemic effects: GI upset, photosensitivity, vaginal yeast infections and discoloration of teeth. Topical retinoids result in irritation and photosensitivity, and systemic retinoids are effective but have multi-system side effects, including hepatotoxicity and teratogenicity. Thus there is significant need for development of safer and more effective therapies that specifically target *P. acnes*.

Phage therapy. Although phage therapy has been utilized for over 90 years (10), use in the US was limited by the discovery of antibiotics and long-standing questions regarding efficacy (11,12). However, the emergence of antibiotic resistance in pathogenic bacteria has stimulated renewed interest in phage therapy. Importantly, bacteriophages have been administered to humans without toxicity (13), and the efficacy of phage therapy has been demonstrated in animal models of infection by *Shigella dysenteriae* (14), *Escherichia coli* (15) and cutaneous *Staphylococcus aureus* (16-18). Topical phage therapy has been used to effectively treat *Pseudomonas* infections that are a complication of skin grafts in a guinea pig model (19), and their therapeutic utility, both in human burn victims and in dogs with chronic ear infections has been shown (20,21). The FDA has approved a phage cocktail consisting of six individually purified phages for use against *Listeria monocytogenes* in meat and poultry products (10) and a similar product for controlling *E. coli* contamination has been approved. Currently many companies are actively developing therapeutic phages (10), and there are several active phage therapy trials (ClinicalTrials.gov). All this notwithstanding, many human bacterial infections present serious challenges to phage therapy, with dosage, specificity, route of application, resistance, clearance, and immunity remaining ill-defined. In contrast, acne is a serious but non-life threatening affliction, responds to a topical application, and presents an attractive model for advancing phage therapy approaches.

Strategies have been developed to overcome the potential of phage resistance (22) including: i) a high density of phage particles to achieve the "inundation threshold" (23), ii) phage "cocktails" containing mixtures of phage which target different bacterial receptors; and/or iii) a combination of phage and antibiotics which act synergistically (24). The use of a high phage dose and phage-derived pyocins provides passive therapy, leading to bacterial lysis. These approaches lack the host-dependent amplification of intact phage particle that facilitates phage therapy. Phage-derived products based on endolysins are highly effective antimicrobials against some bacteria and resistance is non-detectable (25-27).

The use of topical phage therapy in acne represents an innovative approach that avoids the complexities associated with systemic therapy. In addition, this will provide a means by which to directly and specifically target *P. acnes*.

II. DEFINITIONS

As used herein, the term "about" refers to a range of values of plus or minus 10% of a specified value. For example, the phrase "about 200" includes plus or minus 10% of 200, or from 180 to 220, unless clearly contradicted by context.

As used herein, the term "administering" means the actual physical introduction of a composition into or onto (as appropriate) a patient that results in contact with acne associated *P. acnes*. Any and all methods of introducing the composition into the host or cell are contemplated according to the invention; the method is not dependent on any particular means of introduction and is not to be so construed. Means of introduction are well-known to those skilled in the art, and also are exemplified herein.

As used herein, administering "in combination" refers to both simultaneous and sequential administration of two or more agents or compositions. Concurrent or combined administration, as used herein, means that two or more agents or compositions are administered to a subject either (a) simultaneously, or (b) at different times during the course of a common treatment schedule. In the latter case, the two or more agents or compositions are administered sufficiently close in time to achieve the intended effect.

As used herein, the term "bacteriophage" refers to a virus that infects and replicates within bacteria. Bacteriophages are composed of proteins that encapsulate a genome comprising either DNA or RNA. Bacteriophages replicate within bacteria following the injection of their genome into the bacterial cytoplasm. Bacteriophages include "lytic bacteriophages," which disrupt bacterial metabolism and cause the bacterium to lyse, i.e., break open. In preferred embodiments, bacteriophages of the disclosure are capable of infecting *P. acnes*. In preferred embodiments, bacteriophages of the disclosure are capable of infecting multiple strains of *P. acnes*. In preferred embodiments, bacteriophages of the disclosure comprise mutations that overcome phage resistance.

As used herein, the terms "effective amount", "effective dose", "sufficient amount", "amount effective to", "therapeutically effective amount" or grammatical equivalents thereof mean a dosage sufficient to produce a desired result, to ameliorate, or in some manner, reduce a symptom or stop or reverse progression of a condition and provide either a subjective relief of a symptom(s) or an objectively identifiable improvement as noted by a clinician or other qualified observer. Amelioration of a symptom of a particular condition by administration of a pharmaceutical composition described herein refers to any lessening, whether permanent or temporary, lasting, or transitory, that can be associated with the administration of the pharmaceutical composition.

By the term "filler" is meant a pharmaceutically acceptable bulking agent which may facilitate material handling during production and lyophilization. Suitable fillers include inorganic salts such as sodium chloride, and water soluble sugars or sugar alcohols such as sucrose, maltose, mannitol or trehalose.

The terms "isolated," "purified" or "biologically pure" refer to material that is substantially or essentially free of components that normally accompany it as found in its native state.

The terms "modulate," "modulation," or "modulating" are art-recognized and refer to up-regulation (i.e., activation, stimulation, increase), or down-regulation (i.e., inhibition, suppression, reduction, or decrease) of a response, or the two in combination or apart.

As used herein, "optional" or "optionally" means that the subsequently described event or circumstance may or may not occur, and that the description includes instances where said event or circumstance occurs and instances where it does not.

As used herein, the term "mutation" means a change in a nucleic acid sequence (in comparison to a wild type or normal nucleic acid sequence) that alters or eliminates the function of an encoded polypeptide, that alters or eliminates the amount of an encoded polypeptide produced, or that alters or eliminates a regulatory function of the nucleic acid having acquired a mutation. Mutations include, but are not limited to, point mutations, deletions, insertions, inversions, duplications, etc. as known in the art.

As used herein, the term "parenteral" route means a route other than the oral and topical routes. A parenteral route that is suitable for use in the invention may be, for example, the nasal route.

As used herein, the term "bacteriophage resistance" refers to an increased capacity for bacteria to resist infection by bacteriophages. In preferred embodiments, bacteriophage resistance is associated with bacterially encoded Clustered Regularly Interspaced Short Palindromic Repeats (CRISPRs).

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the *U.S. Pharmacopeia* or other generally recognized pharmacopeia for use in animals, and more particularly in humans.

As used herein, the terms "treat", "treating", and "treatment" include inhibiting the pathological condition, disorder, or disease, e.g., arresting or reducing the development of the pathological condition, disorder, or disease or its clinical symptoms; or relieving the pathological condition, disorder, or disease, e.g., causing regression of the pathological condition, disorder, or disease or its clinical symptoms. These terms encompass also therapy and cure. Treatment means any manner in which the symptoms of a pathological condition, disorder, or disease are ameliorated or otherwise beneficially altered. Preferably, the subject in need of such treatment is a mammal, more preferably a human. "w/v" refers to weight/volume.

III. COMPOSITIONS

The inventors have observed, surprisingly and unexpectedly, that the administration of mutant *P. acnes* bacteriophage is useful for treating acne. In addition, compositions described herein are useful for treating phage-resistant *P. acnes*.

*P. acnes* strains and methods of isolating and determining strain type are known to one of skill in in the art (see WO2013/142378, incorporated herein by reference).

In certain embodiments, the disclosure provides mutant *P. acnes* bacteriophages capable of infecting bacteriophage-resistant *P. acnes*. In certain embodiments, the bacteriophage mutant is a Clustered Regularly Interspaced Short Palindromic Repeats (CRISPR) escape mutant. In certain embodiments, the bacteriophage mutant comprises one or more mutations in a protospacer selected from 1, 3 and 4. In certain embodiments, the bacteriophage mutant comprises one or more mutations selected from: T6502G, C6514A, G2762T, T2757C, G5919T, C5917A and A5892C. In certain embodiments, the bacteriophage mutant is selected from P9.1 and the derivatives P9.1-2A, P9.1-2B, P9.1-3 and P9.1-4.

The bacteriophage may comprise a nucleotide sequence that has at least about 95%, 96%, 97%, 98%, or 99% sequence homology with SEQ ID NO:1 (GAAGTCT TCTGGGGTGCAGGGCATGTTGGCTGAGCG) or the reverse complement thereof. SEQ ID NO:1 is a subsequence of phage P9.1 gene 9 (residues 6445-6735 of SEQ ID NO:12). This subsequence may be recognized by protospacer 1 of *P. acnes* strain B101.9. The nucleotide sequence may comprise mutations to one or more nucleotides selected from G1, A2, A3, G4, T5, C6, T7, T8, C9, T10, G11, G12, G13, G14, C17, G20, G21, and G22 of SEQ ID NO:1. In preferred embodiments, the nucleotide sequence comprises mutations to one or more nucleotides selected from A2, A3, T5, G11, G14, and C17 of SEQ ID NO:1. The nucleotide sequence may comprise one or more mutations selected from G1A, A2T, A2C, A3C, G4A, T5G, T7G, T8C, T10G, G11T, G13T, G14T, C17A, G20T, G21C, C22G, and C22T. In preferred embodiments, the nucleotide sequence comprises one or more mutations selected from A2T, T5G, G11T, G14T, and C17A. In some embodiments, the bacteriophage comprises at least one mutation that does not occur in naturally-occurring bacteriophage, e.g., the one or more mutation may include at least one mutation that does not naturally occur in bacteriophage P1.1, P9.1, P14.4, P100.1, P100A, P100D, P101A, P104A, P015, ATCC_C, or ATCC_T.

The bacteriophage may comprise a nucleotide sequence that has at least about 95%, 96%, 97%, 98%, or 99% sequence homology with SEQ ID NO:2 (GAAGTCTT CTGGGGTGCAGTCTATGTTGGCTGAGCG) or the reverse complement thereof. SEQ ID NO:2 is a subsequence of phage P1.1 gene 9 (residues 6453-6743 of SEQ ID NO:7). This subsequence may be recognized by protospacer 1 of *P. acnes* strain B101.9. The nucleotide sequence may comprise mutations to one or more nucleotides selected from G1, A2, A3, G4, T5, C6, T7, T8, C9, T10, G11, G12, G13, G14, C17, T20, C21, and T22 of SEQ ID NO:2. In preferred embodiments, the nucleotide sequence comprises mutations to one or more nucleotides selected from A2, A3, T5, G11, G14, and C17 of SEQ ID NO:2. The nucleotide sequence may comprise one or more mutations selected from G1A, A2T, A2C, A3C, G4A, T5G, T7G, T8C, T10G, G11T, G13T, G14T, C17A, T20G, C21G, T22G, and T22C. In preferred embodiments, the nucleotide sequence comprises one or more mutations selected from A2C and A3C. In some embodiments, the bacteriophage comprises at least one mutation that does not occur in naturally-occurring bacteriophage, e.g., the one or more mutation may include at least one mutation that does not naturally occur in bacteriophage P1.1, P9.1, P14.4, P100.1, P100A, P100D, P101A, P104A, P015, ATCC_C, or ATCC_T.

The bacteriophage may comprise a nucleotide sequence that has at least about 95%, 96%, 97%, 98%, or 99% sequence homology with SEQ ID NO:3 (TAAGATT GAGTTGGCTGAGTCGGATGTGTTGCGGTT) or the reverse complement thereof. SEQ ID NO:3 is a subsequence of phage P1.1 gene 16 (residues 12239-13399 of SEQ ID NO:7). This subsequence may be recognized by protospacer 1 of *P. acnes* strain B66.8. The nucleotide sequence may comprise mutations to one or more nucleotides selected from A2, A3, A5, T6, T7, G8, A9, T11, T12, G13, G14, T16, G19, T20, G23, T25, T30, and G31 of SEQ ID NO:3. In preferred embodiments, the nucleotide sequence comprises mutations to one or more nucleotides selected from T20, T30, and G31 of SEQ ID NO:3. The nucleotide sequence may comprise one or more mutations selected from T7C, T16A, T16G, G19A, T20G, G23A, T25G, T30G, and G31T. In preferred embodiments, the nucleotide sequence comprises one or more mutations selected from T20G, T30G, and G31T. In some embodiments, the bacteriophage comprises at least one mutation that does not occur in naturally-occurring bacteriophage, e.g., the one or more mutation may include at least one mutation that does not naturally occur in bacteriophage P1.1, P9.1, P14.4, P100.1, P100A, P100D, P101A, P104A, P015, ATCC_C, or ATCC_T.

The bacteriophage may comprise a nucleotide sequence that has at least about 95%, 96%, 97%, 98%, or 99% sequence homology with SEQ ID NO:4 (CAACTGCGC CAACAAACGCATCTGATCCGAATACGG) or the reverse complement thereof. SEQ ID NO:4 is a subsequence of phage P9.1 gene 3 (residues 1881-3206 of SEQ ID NO:12) (residues 6445-6735 of SEQ ID NO:15). This subsequence may be recognized by protospacer 3 of *P. acnes* strains B101.9 and B66.8. The nucleotide sequence may comprise mutations to one or more nucleotides selected from A2, A3, C4, T5, G6, C7, G8, C9, C10, A11, A12, C13, A14, A15, A16, and G18 of SEQ ID NO:4. In preferred embodiments, the nucleotide sequence comprises mutations to one or more nucleotides selected from A3, C7, C9, and A12 of SEQ ID NO:4. The nucleotide sequence may comprise one or more mutations selected from A3T, A3C, A3G, C4T, C7A, C7G, C9A, C10T, A12G, C13A, C13T, A15G, A16C, A16G, A16T, and G18T. In preferred embodiments, the nucleotide sequence comprises one or more mutations selected from A3T, C7A, C9A, and A12G. In some embodiments, the bacteriophage comprises at least one mutation that does not occur in naturally-occurring bacteriophage, e.g., the one or more mutation may include at least one mutation that does not naturally occur in bacteriophage P1.1, P9.1, P14.4, P100.1, P100A, P100D, P101A, P104A, P015, ATCC_C, or ATCC_T.

The bacteriophage may comprise a nucleotide sequence that has at least about 95%, 96%, 97%, 98%, or 99% sequence homology with SEQ ID NO:5 (CAACTGCGC-CAACAGTCTCATCTGATCCGAATACGG) or the reverse complement thereof. SEQ ID NO:5 is a subsequence of phage P1.1 gene 3 (residues 1886-3211 of SEQ ID NO:7). This subsequence may be recognized by protospacer 3 of *P. acnes* strains B101.9 and B66.8. The nucleotide sequence may comprise mutations to one or more nucleotides selected from A2, A3, C4, T5, G6, C7, G8, C9, C10, A11, A12, C13, A14, G15, T16, and T18 of SEQ ID NO:5. In preferred embodiments, the nucleotide sequence comprises mutations to one or more nucleotides selected from A3, C7, A12, and C13 of SEQ ID NO:5. The nucleotide sequence may comprise one or more mutations selected from A3T, A3C, A3G, C4T, C7A, C7G, C9A, C10T, A12G, C13A, C13T, G15A, T16A, T16C, T16G, and T18G. In preferred embodiments, the nucleotide sequence comprises one or more mutations selected from A3C, A3G, C7A, A12G, and C13A. In some embodiments, the bacteriophage comprises at least one mutation that does not occur in naturally-occurring bacteriophage, e.g., the one or more mutation may include at least one mutation that does not naturally occur in bacteriophage P1.1, P9.1, P14.4, P100.1, P100A, P100D, P101A, P104A, P015, ATCC_C, or ATCC_T.

The bacteriophage may comprise a nucleotide sequence that has at least about 95%, 96%, 97%, 98%, or 99% sequence homology with SEQ ID NO:6 (CAACGC AGCAATCTCAGAAGGCCACAACAAATTCGT) or the reverse complement thereof. SEQ ID NO:6 is a subsequence of phage P9.1 gene 7 (residues 5610-6089 of SEQ ID NO:12). This subsequence may be recognized by protospacer 4 of *P. acnes* strains B101.9 and B66.8. The nucleotide sequence may comprise mutations to one or more nucleotides selected from A2, A3, G5, C6, A7, G8, C9, A11, T12, C13, T14, A16, A30, A31, T33, C34, G35, and T36 of SEQ ID NO:6. In preferred embodiments, the nucleotide sequence comprises mutations to one or more nucleotides selected from A3, C7, A12, and C13 of SEQ ID NO:6. The nucleotide sequence may comprise one or more mutations selected from C6A, C6T, A7G, G8T, T12C, A16G, A30G, A31G, T33G, C34A, G35A, and T36A. In preferred embodiments, the nucleotide sequence comprises one or more mutations selected from C6A, G8T, T33G, and G35A. In some embodiments, the bacteriophage comprises at least one mutation that does not occur in naturally-occurring bacteriophage, e.g., the one or more mutation may include at least one mutation that does not naturally occur in bacteriophage P1.1, P9.1, P14.4, P100.1, P100A, P100D, P101A, P104A, P015, ATCC_C, or ATCC_T.

In some embodiments, the invention relates to a nucleotide sequence encoding gene 9 of a *P. acnes* bacteriophage (e.g., residues 6453-6743 of SEQ ID NO:7 or residues 6445-6735 of SEQ ID NO:12), wherein the nucleotide sequence has at least about 95%, 96%, 97%, 98%, or 99% sequence homology with SEQ ID NO:1 (GAAGTCTT CTGGGGTGCAGGGCATGTTGGCTGAGCG) or the reverse complement thereof. SEQ ID NO:1 is a subsequence of phage P9.1 gene 9 (residues 6445-6735 of SEQ ID NO:12). This subsequence may be recognized by protospacer 1 of *P. acnes* strain B101.9. In some embodiments, the invention relates to a nucleotide sequence having at least about 95%, 96%, 97%, 98%, or 99% sequence homology with residues 6453-6743 of SEQ ID NO:7 or residues 6445-6735 of SEQ ID NO:12, e.g., wherein a subsequence of the nucleotide sequence has at least about 95%, 96%, 97%, 98%, or 99% sequence homology with SEQ ID NO:1. The nucleotide sequence may comprise mutations to one or more nucleotides selected from G1, A2, A3, G4, T5, C6, T7, T8, C9, T10, G11, G12, G13, G14, C17, G20, G21, and G22 of SEQ ID NO:1. In preferred embodiments, the nucleotide sequence comprises mutations to one or more nucleotides selected from A2, A3, T5, G11, G14, and C17 of SEQ ID NO:1. The nucleotide sequence may comprise one or more mutations selected from G1A, A2T, A2C, A3C, G4A, T5G, T7G, T8C, T10G, G11T, G13T, G14T, C17A, G20T, G21C, C22G, and C22T relative to SEQ ID NO:1. In preferred embodiments, the nucleotide sequence comprises one or more mutations selected from A2T, T5G, G11T, G14T, and C17A relative to SEQ ID NO:1. In some embodiments, the nucleotide sequence does not occur in a naturally-occurring organism, e.g., the nucleotide sequence does not occur in bacteriophage P1.1, P9.1, P14.4, P100.1, P100A, P100D, P101A, P104A, P015, ATCC_C, or ATCC_T. In some embodiments, the invention relates to a protein encoded by gene 9, comprising an amino acid sequence that has at least about 95%, 96%, 97%, 98%, or 99% sequence homology with the amino acid sequence encoded by the open reading frame of SEQ ID NO:1, wherein the protein comprises one or more amino acid substitutions corresponding to one or more of the foregoing nucleotide mutations, e.g., wherein each nucleotide mutation is a nonsynonymous mutation. In some embodiments, the invention relates to a protein comprising an amino acid sequence that has at least about 95%, 96%, 97%, 98%, or 99% sequence homology with the amino acid set forth in SEQ ID NO:10 or SEQ ID NO:15, wherein the protein comprises one or more amino acid substitutions corresponding to one or more of the foregoing nucleotide mutations, e.g., wherein each nucleotide mutation is a nonsynonymous mutation. In some embodiments, the protein does not occur in a naturally-occurring organism, e.g., the protein does not occur in bacteriophage P1.1, P9.1, P14.4, P100.1, P100A, P100D, P101A, P104A, P015, ATCC_C, or ATCC_T. In some aspects, the invention relates to a cell or bacteriophage comprising the aforementioned nucleotide sequence or protein.

In some embodiments, the invention relates to a nucleotide sequence encoding gene 9 of a *P. acnes* bacteriophage (e.g., residues 6453-6743 of SEQ ID NO:7 or residues 6445-6735 of SEQ ID NO:12), wherein the nucleotide sequence has at least about 95%, 96%, 97%, 98%, or 99% sequence homology with SEQ ID NO:2 (GAAGTCTT CTGGGGTGCAGTCTATGTTGGCTGAGCG) or the reverse complement thereof. SEQ ID NO:2 is a subsequence of phage P1.1 gene 9 (residues 6453-6743 of SEQ ID NO:7). This subsequence may be recognized by protospacer 1 of *P. acnes* strain B101.9. In some embodiments, the invention relates to a nucleotide sequence having at least about 95%, 96%, 97%, 98%, or 99% sequence homology with residues 6453-6743 of SEQ ID NO:7 or residues 6445-6735 of SEQ ID NO:12, e.g., wherein a subsequence of the nucleotide sequence has at least about 95%, 96%, 97%, 98%, or 99% sequence homology with SEQ ID NO:2. The nucleotide sequence may comprise mutations to one or more nucleotides selected from G1, A2, A3, G4, T5, C6, T7, T8, C9, T10, G11, G12, G13, G14, C17, T20, C21, and T22 of SEQ ID NO:2. In preferred embodiments, the nucleotide sequence comprises mutations to one or more nucleotides selected from A2, A3, T5, G11, G14, and C17 of SEQ ID NO:2. The nucleotide sequence may comprise one or more mutations selected from G1A, A2T, A2C, A3C, G4A, T5G, T7G, T8C, T10G, G11T, G13T, G14T, C17A, T20G, C21G, T22G, and T22C relative to SEQ ID NO:2. In preferred embodiments, the nucleotide sequence comprises one or more mutations selected from A2C and A3C relative to SEQ ID NO:2. In some embodiments, the nucleotide sequence does not occur in a naturally-occurring organism, e.g., the nucleotide sequence does not occur in bacteriophage P1.1, P9.1, P14.4, P100.1, P100A, P100D, P101A, P104A, P015, ATCC_C, or ATCC_T. In some embodiments, the invention relates to a protein encoded by gene 9, comprising an amino acid sequence that has at least about 95%, 96%, 97%, 98%, or 99% sequence homology with the amino acid sequence encoded by the open reading frame of SEQ ID NO:2, wherein the protein comprises one or more amino acid substitutions corresponding to one or more of the foregoing nucleotide mutations, e.g., wherein each nucleotide mutation is a nonsynonymous mutation. In some embodiments, the invention relates to a protein comprising an amino acid sequence that has at least about 95%, 96%, 97%, 98%, or 99% sequence homology with the amino acid set forth in SEQ ID NO:10 or SEQ ID NO:15, wherein the protein comprises one or more amino acid substitutions corresponding to one or more of the foregoing nucleotide mutations, e.g., wherein each nucleotide mutation is a nonsynonymous mutation. In some embodiments, the protein does not occur in a naturally-occurring organism, e.g., the protein does not occur in bacteriophage P1.1, P9.1, P14.4, P100.1, P100A, P100D, P101A, P104A, P015, ATCC_C, or ATCC_T. In some aspects, the invention relates to a cell or bacteriophage comprising the aforementioned nucleotide sequence or protein.

In some embodiments, the invention relates to a nucleotide sequence encoding gene 16 of a *P. acnes* bacteriophage (e.g., residues 12239-13399 of SEQ ID NO:7 or residues 12238-13398 of SEQ ID NO:12), wherein the nucleotide sequence has at least about 95%, 96%, 97%, 98%, or 99% sequence homology with SEQ ID NO:3 (TAAGATTGAGTTGGCTGAGTCGGATGTGTTGCGGTT) or the reverse complement thereof. SEQ ID NO:3 is a subsequence of phage P1.1 gene 16 (residues 12239-13399 of SEQ ID NO:7). This subsequence may be recognized by protospacer 1 of *P. acnes* strain B66.8. In some embodiments, the invention relates to a nucleotide sequence having at least about 95%, 96%, 97%, 98%, or 99% sequence homology with residues 12239-13399 of SEQ ID NO:7 or residues 12238-13398 of SEQ ID NO:12, e.g., wherein a subsequence of the nucleotide sequence has at least about 95%, 96%, 97%, 98%, or 99% sequence homology with SEQ ID NO:3. The nucleotide sequence may comprise mutations to one or more nucleotides selected from A2, A3, A5, T6, T7, G8, A9, T11, T12, G13, G14, T16, G19, T20, G23, T25, T30, and G31 of SEQ ID NO:3. In preferred embodiments, the nucleotide sequence comprises mutations to one or more nucleotides selected from T20, T30, and G31 of SEQ ID NO:3. The nucleotide sequence may comprise one or more mutations selected from T7C, T16A, T16G, G19A, T20G, G23A, T25G, T30G, and G31T relative to SEQ ID NO:3. In preferred embodiments, the nucleotide sequence comprises one or more mutations selected from T20G, T30G, and G31T relative to SEQ ID NO:3. In some embodiments, the nucleotide sequence does not occur in a naturally-occurring organism, e.g., the nucleotide sequence does not occur in bacteriophage P1.1, P9.1, P14.4, P100.1, P100A, P100D, P101A, P104A, P015, ATCC_C, or ATCC_T. In some embodiments, the invention relates to a protein encoded by gene 16, comprising an amino acid sequence that has at least about 95%, 96%, 97%, 98%, or 99% sequence homology with the amino acid sequence encoded by the open reading frame of SEQ ID NO:3, wherein the protein comprises one or more amino acid substitutions corresponding to one or more of the foregoing nucleotide mutations, e.g., wherein each nucleotide mutation is a nonsynonymous mutation. In some embodiments, the invention relates to a protein comprising an amino acid sequence that has at least about 95%, 96%, 97%, 98%, or 99% sequence homology with the amino acid set forth in SEQ ID NO:11 or SEQ ID NO:16, wherein the protein comprises one or more amino acid substitutions corresponding to one or more of the foregoing nucleotide mutations, e.g., wherein each nucleotide mutation is a nonsynonymous mutation. In some embodiments, the protein does not occur in a naturally-occurring organism, e.g., the protein does not occur in bacteriophage P1.1, P9.1, P14.4, P100.1, P100A, P100D, P101A, P104A, P015, ATCC_C, or ATCC_T. In some aspects, the invention relates to a cell or bacteriophage comprising the aforementioned nucleotide sequence or protein.

In some embodiments, the invention relates to a nucleotide sequence encoding gene 3 of a *P. acnes* bacteriophage (e.g., residues 1886-3211 of SEQ ID NO:7 or residues 1881-3206 of SEQ ID NO:12), wherein the nucleotide sequence has at least about 95%, 96%, 97%, 98%, or 99% sequence homology with SEQ ID NO:4 (CAACTGCGCCAACAAACGCATCTGATCCGAATACGG) or the reverse complement thereof. SEQ ID NO:4 is a subsequence of phage P9.1 gene 3 (residues 1881-3206 of SEQ ID NO:12). This subsequence may be recognized by protospacer 3 of *P. acnes* strains B101.9 and B66.8. In some embodiments, the invention relates to a nucleotide sequence having at least about 95%, 96%, 97%, 98%, or 99% sequence homology with residues 1886-3211 of SEQ ID NO:7 or residues 1881-3206 of SEQ ID NO:12, e.g., wherein a subsequence of the nucleotide sequence has at least about 95%, 96%, 97%, 98%, or 99% sequence homology with the reverse complement of SEQ ID NO:4. The nucleotide sequence may comprise mutations to one or more nucleotides selected from A2, A3, C4, T5, G6, C7, G8, C9, C10, A11, A12, C13, A14, A15, A16, and G18 of SEQ ID NO:4. In preferred embodiments, the nucleotide sequence comprises mutations to one or more nucleotides selected from A3, C7, C9, and A12 of SEQ ID NO:4. The nucleotide sequence may comprise one or more mutations selected from A3T, A3C, A3G, C4T, C7A, C7G, C9A, C10T, A12G, C13A, C13T, A15G, A16C, A16G, A16T, and G18T relative to SEQ ID NO:4. In preferred embodiments, the nucleotide sequence comprises one or more mutations selected from A3T, C7A, C9A, and A12G relative to SEQ ID NO:4. In some embodiments, the nucleotide sequence does not occur in a naturally-occurring organism, e.g., the nucleotide sequence does not occur in bacteriophage P1.1, P9.1, P14.4, P100.1, P100A, P100D, P101A, P104A, P015, ATCC_C, or ATCC_T. In some embodiments, the invention relates to a protein encoded by gene 3, comprising an amino acid sequence that has at least about 95%, 96%, 97%, 98%, or 99% sequence homology with the amino acid sequence encoded by the open reading frame of SEQ ID NO:4, wherein the protein comprises one or more amino acid substitutions corresponding to one or more of the foregoing nucleotide mutations, e.g., wherein each nucleotide mutation is a nonsynonymous mutation. In some embodiments, the invention relates to a protein comprising an amino acid sequence that has at least about 95%, 96%, 97%, 98%, or 99% sequence homology with the amino acid set forth in SEQ ID NO:8 or SEQ ID NO:13, wherein the protein comprises one or more amino acid substitutions corresponding to one or more of the foregoing nucleotide mutations, e.g., wherein each nucleotide mutation is a nonsynonymous mutation. In some embodiments, the protein does not occur in a naturally-occurring organism, e.g., the protein does not occur in bacteriophage P1.1, P9.1, P14.4, P100.1, P100A, P100D, P101A, P104A, P015, ATCC_C, or ATCC_T. In some aspects, the invention relates to a cell or bacteriophage comprising the aforementioned nucleotide sequence or protein.

In some embodiments, the invention relates to a nucleotide sequence encoding gene 3 of a *P. acnes* bacteriophage (e.g., residues 1886-3211 of SEQ ID NO:7 or residues 1881-3206 of SEQ ID NO:12), wherein the nucleotide sequence has at least about 95%, 96%, 97%, 98%, or 99% sequence homology with SEQ ID NO:5 (CAACTGCGCCAACAGTCTCATCTGATCCGAATACGG) or the reverse complement thereof. SEQ ID NO:5 is a subsequence of phage P1.1 gene 3 (residues 1886-3211 of SEQ ID NO:7). This subsequence may be recognized by protospacer 3 of *P. acnes* strains B101.9 and B66.8. In some embodiments, the invention relates to a nucleotide sequence having at least about 95%, 96%, 97%, 98%, or 99% sequence homology with residues 1886-3211 of SEQ ID NO:7 or residues 1881-3206 of SEQ ID NO:12, e.g., wherein a subsequence of the nucleotide sequence has at least about 95%, 96%, 97%, 98%, or 99% sequence homology with the reverse complement of SEQ ID NO:5. The nucleotide sequence may comprise mutations to one or more nucleotides selected from A2, A3, C4, T5, G6, C7, G8, C9, C10, A11, A12, C13, A14, G15, T16, and T18 of SEQ ID NO:5. In preferred embodiments, the nucleotide sequence comprises mutations to one or more nucleotides selected from A3, C7, A12, and C13 of SEQ ID NO:5. The nucleotide sequence may comprise one or more mutations selected from A3T, A3C, A3G, C4T, C7A, C7G, C9A, C10T, A12G, C13A, C13T, G15A, T16A, T16C, T16G, and T18G relative to SEQ ID NO:5. In preferred embodiments, the nucleotide sequence comprises one or more mutations selected from A3C, A3G, C7A, A12G, and C13A relative to SEQ ID NO:5. In some embodiments, the nucleotide sequence does not occur in a naturally-occurring organism, e.g., the nucleotide sequence does not occur in bacteriophage P1.1, P9.1, P14.4, P100.1, P100A, P100D, P101A, P104A, P015, ATCC_C, or ATCC_T. In some embodiments, the invention relates to a protein encoded by gene 3, comprising an amino acid sequence that has at least about 95%, 96%, 97%, 98%, or 99% sequence homology with the amino acid sequence encoded by the open reading frame of SEQ ID NO:5, wherein the protein comprises one or more amino acid substitutions corresponding to one or more of the foregoing nucleotide mutations, e.g., wherein each nucleotide mutation is a nonsynonymous mutation. In some embodiments, the invention relates to a protein comprising an amino acid sequence that has at least about 95%, 96%, 97%, 98%, or 99% sequence homology with the amino acid set forth in SEQ ID NO:8 or SEQ ID NO:13, wherein the protein comprises one or more amino acid substitutions corresponding to one or more of the foregoing nucleotide mutations, e.g., wherein each nucleotide mutation is a nonsynonymous mutation. In some embodiments, the protein does not occur in a naturally-occurring organism, e.g., the protein does not occur in bacteriophage P1.1, P9.1, P14.4, P100.1, P100A, P100D, P101A, P104A, P015, ATCC_C, or ATCC_T. In some aspects, the invention relates to a cell or bacteriophage comprising the aforementioned nucleotide sequence or protein.

In some embodiments, the invention relates to a nucleotide sequence encoding gene 7 of a *P. acnes* bacteriophage (e.g., residues 5618-6097 of SEQ ID NO:7 or 5610-6089 of SEQ ID NO:12), wherein the nucleotide sequence has at least about 95%, 96%, 97%, 98%, or 99% sequence homology with SEQ ID NO:6 (CAACGCAGCAATCTCAGAAGGCCACAACAAATTCGT) or the reverse complement thereof. SEQ ID NO:6 is a subsequence of phage P9.1 gene 7 (5610-6089 of SEQ ID NO:12). This subsequence may be recognized by protospacer 4 of *P. acnes* strains B101.9 and B66.8. In some embodiments, the invention relates to a nucleotide sequence having at least about 95%, 96%, 97%, 98%, or 99% sequence homology with residues 5618-6097 of SEQ ID NO:7 or 5610-6089 of SEQ ID NO:12, e.g., wherein a subsequence of the nucleotide sequence has at least about 95%, 96%, 97%, 98%, or 99% sequence homology with the reverse complement of SEQ ID NO:6. The nucleotide sequence may comprise mutations to one or more nucleotides selected from A2, A3, G5, C6, A7, G8, C9, A11, T12, C13, T14, A16, A30, A31, T33, C34, G35, and T36 of SEQ ID NO:6. In preferred embodiments, the nucleotide sequence comprises mutations to one or more nucleotides selected from A3, C7, A12, and C13 of SEQ ID NO:6. The nucleotide sequence may comprise one or more mutations selected from C6A, C6T, A7G, G8T, T12C, A16G, A30G, A31G, T33G, C34A, G35A, and T36A relative to SEQ ID NO:6. In preferred embodiments, the nucleotide sequence comprises one or more mutations selected from C6A, G8T, T33G, and G35A relative to SEQ ID NO:6. In some embodiments, the nucleotide sequence does not occur in a naturally-occurring organism, e.g., the nucleotide sequence does not occur in bacteriophage P1.1, P9.1, P14.4, P100.1, P100A, P100D, P101A, P104A, P015, ATCC_C, or ATCC_T. In some embodiments, the invention relates to a protein encoded by gene 7 comprising an amino acid sequence that has at least about 95%, 96%, 97%, 98%, or 99% sequence homology with the amino acid sequence encoded by the open reading frame of SEQ ID NO:6, wherein the protein comprises one or more amino acid substitutions corresponding to one or more of the foregoing nucleotide mutations, e.g., wherein each nucleotide mutation is a nonsynonymous mutation. In some embodiments, the invention relates to a protein comprising an amino acid sequence that has at least about 95%, 96%, 97%, 98%, or 99% sequence homology with the amino acid set forth in SEQ ID NO:9 or SEQ ID NO:14, wherein the protein comprises one or more mutations corresponding to one or more of the foregoing nucleotide mutations, e.g., wherein each nucleotide mutation is a nonsynonymous mutation. In some embodiments, the protein does not occur in a naturally-occurring organism, e.g., the protein does not occur in bacteriophage P1.1, P9.1, P14.4, P100.1, P100A, P100D, P101A, P104A, P015, ATCC_C, or ATCC_T. In some aspects, the invention relates to a cell or bacteriophage comprising the aforementioned nucleotide sequence or protein.

In some embodiments, the bacteriophages of the disclosure are used in combination with one or more other bacteriophages (bacteriophage cocktail). The combinations of bacteriophages can target the same strain or different strains of *P. acnes*. Bacteriophage cocktails may be applied contemporaneously—that is, they may be applied at the same time (e.g., in the same application or even the same composition), or may be applied in separate applications spaced in time such that they are effective at the same time. The bacteriophage may be applied as a single application, periodic applications, or as a continuous application.

The bacteriophage or combination of bacteriophages may be used in combination with one or more other antimicrobials. Antimicrobials may include known anti-acne agents, such as retinoids, benzoyl peroxide or antibiotics, or novel antimicrobials, such as granulysin or P. acnes phage endolysin protein. In some embodiments, an antibiotic or a combination of antibodies is selected from penicillins, cephalosporins, carbapenems, aminoglycosides, sulfonamides, quinolones, macrolides, tetracyclines, lipopeptides and oxazolidinones.

Antibiotics refer to a group of agents, but are not limited to, aminoglycoside antibiotics, glycopeptide antibiotics, macrolide antibiotics, and combinations thereof. Exemplary antibiotics may be active against gram-negative bacteria, as well as, active against both gram-positive and gram negative bacteria. Non-limiting examples of antibiotics include erythromycin, garamycin, gentamicin, kanamycin, neomycin, netilmicin, paromomycin, tobramycin, vancomycin, and their analogs, and a combination thereof. There are a variety of antibiotics that can be used in a method of the present invention. In some embodiments, an antibiotic or a combination of antibodies is selected from penicillins, cephalosporins, carbapenems, aminoglycosides, sulfonamides, quinolones, macrolides, tetracyclines, lipopeptides and oxazolidinones. Suitable antibiotics can be substituted in cases wherein a subject has a known or suspected hypersensitivity to a class of antibiotics, such as cephalosporins and combinations thereof.

In some embodiments, the antibiotic or combination of antibiotics may be specifically selected based on the resistance profile of a subject's bacterial microbiota.

In some embodiments, an antibiotic or an antibiotic cocktail (comprising at least two antibiotics) is selected from amoxicillin, ampicillin, bacampicillin, carbenicillin, cloxacillin, dicloxacillin, flucloxacillin, mezlocillin, nafcillin, oxacillin, penicillin G, penicillin V, Piperacillin, Pivampicillin, Pivmecillinam, Ticarcillin, cefacetrile, cefadroxil, cephalexin, cefaloglycin, cefalonium, cefaloridine, cefalotin, cefamandole, cefapirin, cefatoxin, cefatrizine, cefazaflur, cephalexin, cefazedone, cefazolin, cefepime, cefradine, cefroxadine, ceftezole, cefaclor, cefonicid, cefprozil, cefuroxime, cefuzonam, cefinetazole, cefotetan, cefoxitin, loracarbef, cefbuperazone, cefinetazole, cefminox, cefotetan, cefoxitin, cefcapene, cefdaloxime, cefdinir, cefditoren, cefetamet, cefixime, cefinenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, imipenem, meropenem, ertapenem, doripenem, panipenem, betamipron, biapenem, razupenem, amikacin, arbekacin, gentamicin, kanamycin, neomycin, netilmicin, paromomycin, rhodostreptomycin, streptomycin, tobramycin, apramycin, framycetin, ribostamycin, bekanamycin, dibekacin, tobramycin, spectinomycin, hygromycin B, paromomycin sulfate, sisomicin, isepamicin, verdamicin, astromicin, sulfasalazine, sulfamethoxazole, sulfamethizole, sulfisoxazole, fluoroquinolone, ketolide, ceftobiprole, flumequine, nalidixic acid, oxolinic acid, piromidic acid, pipemidic acid, rosoxacin, ciprofloxacin, enoxacin, lomefloxacin, nadifloxacin, norfloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, azithromycin, erythromycin, clarithromycin, dirithromycin, roxithromycin, telithromycin, demeclocycline, doxycycline, minocycline, oxytetracycline, tetracycline, linezolid, clindamycin, metronidazole, vancomycin, rifabutin, rifampin, nitrofurantoin, chloramphenicol, and combinations thereof.

In some embodiments, a composition comprises an antibiotic having an elimination half-life of less than 20 hours. In some embodiments, a composition comprises an antibiotic having an elimination half-life of about 1 to 12 hours. The following are examples of some antibiotics with half-lives of about 1 to 12 hours from which an antibiotic or a combination of antibiotics can be selected: Cefadroxil, cefazolin, cephalexin, cephalothin, cephapirin, cephacelor, cephprozil, cephadrine, cefamandole, cefonicid, ceforanide, cefuroxime, cefixime, cefoperazone, cefotaxime, cefpodoxime, ceftaxidime, ceftibuten, ceftizoxime, ceftriaxone, cefepime, cefmetazole, cefotetan, cefoxitin, loracarbef, imipenem, erythromycin (and erythromycin salts such as estolate, ethylsuccinate, gluceptate, lactobionate, stearate), azithromycin, clarithromycoin, dirithromycin, troleanomycin, penicillin V, penicillin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) mezlocillin, piperacillin, piperacillin and taxobactam, ticarcillin, ticarcillin and clavulanate potassium, clindamycin, vancomycin, novobiocin, aminosalicylic acid, capreomycin, cycloserine, ethambutol HCl and other salts, ethionamide, and isoniazid, ciprofloxacin, levofloxacin, lomefloxacin, nalidixic acid, norfloxacin, ofloxacin, sparfloxacin, sulfacytine, sulfamerazine, sulfamethazine, sulfamethixole, sulfasalazine, sulfisoxazole, sulfapyrizine, sulfadiazine, sulfinethoxazole, sulfapyridine, metronidazole, methenamine, fosfomycin, nitrofurantoin, trimethoprim, clofazimine, co-triamoxazole, pentamidine, and trimetrexate.

In some embodiments, the antibiotic is selected from an aminoglycoside antibiotic, a glycopeptide antibiotic, a macrolide antibiotic, and a combination thereof. In some embodiments, the antibiotic is selected from erythromycin, gentamicin, tobramycin, vancomycin, and a combination thereof. In some embodiments, the antibiotic is gentamicin.

The antibiotic or a combination of at least two antibiotics (sometimes referred to as antibiotic cocktail) can be administered to a subject per se, or in a pharmaceutical composition where they are mixed with suitable carriers or excipients.

IV. FORMULATION, DOSAGE AND ADMINISTRATION

A P. acnes bacteriophage of the invention may be formulated in a composition in a proportion of at least 0.0001% expressed as dry weight, in particular in a proportion from 0.0001% to 30%, in particular in a proportion from 0.001% to 20% and more particularly in a proportion from 0.01% to 15% by weight, in particular from 0.1% to 10% by weight and from 1% to 5% by weight relative to the total weight of the composition containing it.

The compositions and methods of the present invention may be utilized to treat an individual in need thereof. In certain embodiments, the individual is a mammal such as a human, or a non-human mammal. When administered to an animal, such as a human, the composition or the bacteriophage is preferably administered as a pharmaceutical composition comprising, for example, a bacteriophage of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, the aqueous solution is pyrogen free, or substantially pyrogen free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, powder, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize or to increase the absorption of a bacteriophage of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition (preparation) also can be a liposome or other polymer matrix, which can have incorporated therein, for example, a bacteriophage of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The bacteriophage may also be formulated for inhalation. In certain embodiments, a bacteriophage may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the bacteriophage which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a bacteriophage of the invention, with the carrier and, optionally, one or more accessory ingredients. In general, the formulations are prepared by uniformly and intimately bringing into association a bacteriophage of the present invention with liquid carriers, or finely divided solid carriers, or both, and then, if necessary, shaping the product.

In some embodiments of the present invention, a bacteriophage that is suitable for use in the invention may be administered orally, topically or parenterally, and in particular topically.

Dosage forms for the topical or transdermal administration include powders, sprays, ointments, pastes, creams, lotions, gels, solutions, patches and inhalants. The bacteriophage may be mixed under sterile conditions with a pharmaceutically acceptable carrier, and with any preservatives, buffers, or propellants that may be required.

The ointments, pastes, creams and gels may contain, in addition to a bacteriophage, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Exemplary identities of various constituents of the topical formulations of some embodiments of the present invention are described below.

Vehicles

Suitable topical vehicles and vehicle components for use with the formulations/compositions of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol, dimethicone, and dimethicone copolyol; hydrocarbon-based materials such as petrolatum and squalane; and other vehicles and vehicle components that are suitable for administration to the skin, as well as mixtures of topical vehicle components as identified above or otherwise known to the art.

In one embodiment, the compositions of the present invention are oil-in-water emulsions. Liquids suitable for use in formulating compositions of the present invention include water, and water-miscible solvents such as glycols (e.g., ethylene glycol, butylene glycol, isoprene glycol, propylene glycol), glycerol, liquid polyols, dimethyl sulfoxide, and isopropyl alcohol. One or more aqueous vehicles may be present.

In some embodiments, formulations do not have methanol, ethanol, propanols, or butanol.

Surfactants and Emulsifiers

Many topical formulations contain chemical emulsions which use surface active ingredients (emulsifiers and surfactants) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures (droplets) that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, but are not limited to: cetyl alcohol, polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate (ceteth-10 is the polyethylene glycol ether of cetyl alcohol where n has an average value of 10; ceteth-10 phosphate is a mixture of phosphoric acid esters of ceteth-10), ceteth-20, Brij S10 (polyethylene glycol octadecyl ether, average Mn 711), and Poloxamers (including, but not limited to, Poloxamer 188 $(HO(C_2H_4O)_a(CH(CH_3)CH_2O)_b(C_2H_4O)_aH$, average molecular weight 8400) and Poloxamer 407 $(HO(C_2H_4O)_a(CH(CH_3)CH_2O)b(C_2H_4O)_aH$, wherein a is about 101 and b is about 56)). Appropriate combinations or mixtures of such surfactants may also be used according to the present invention. Many of these surfactants may also serve as emulsifiers in formulations of the present invention.

Other suitable emulsifiers for use in the formulations of the present invention include, but are not limited to, behentrimonium methosulfate-cetearyl alcohol, non-ionic emulsifiers like emulsifying wax, polyoxyethylene oleyl ether, PEG-40 stearate, cetostearyl alcohol (cetearyl alcohol), ceteareth-12, ceteareth-20, ceteareth-30, cetearyl alcohol, Ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, and PEG-100 stearate, ceramide 2, ceramide 3, stearic acid, cholesterol, steareth-2, and steareth-20, or combinations/mixtures thereof, as well as cationic emulsifiers like stearamidopropyl dimethylamine and behentrimonium methosulfate, or combinations/mixtures thereof.

Moisturizers, Emollients, and Humectants

One of the most important aspects of topical products in general, and cosmetic products in particular, is the consumer's perception of the aesthetic qualities of a product. For example, while white petrolatum is an excellent moisturizer and skin protectant, it is rarely used alone, especially on the face, because it is greasy, sticky, does not rub easily into the skin and may soil clothing. Consumers highly value products which are aesthetically elegant and have an acceptable tactile feel and performance on their skin. Suitable moisturizers for use in the formulations of the present invention include, but are not limited to, lactic acid and other hydroxy acids and their salts, glycerol, propylene glycol, butylene glycol, sodium PCA, sodium hyaluronate, Carbowax 200, Carbowax 400, and Carbowax 800. Suitable emollients or humectants for use in the formulations of the present invention include, but are not limited to, panthenol, cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, Theobroma grandiflorum seed butter, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, safflower oil, oleyl alcohol, oleic acid, stearic acid, dicaprylate/dicaprate, diethyl sebacate, isostearyl alcohol, pentylene glycol, isononyl isononanoate, and 1,3-bis(N-2-(hydroxyethyl) palmitoylamino)-2-hydroxypropane. In addition, appropriate combinations and mixtures of any of these moisturizing agents and emollients may be used in accordance with the present invention.

Preservatives and Antioxidants

The composition may further include components adapted to improve the stability or effectiveness of the applied formulation.

Suitable preservatives for use in the present invention include, but are not limited to: ureas, such as imidazolidinyl urea and diazolidinyl urea; phenoxyethanol; sodium methyl paraben, methylparaben, ethylparaben, and propylparaben; potassium sorbate; sodium benzoate; sorbic acid; benzoic acid; formaldehyde; citric acid; sodium citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; Vitis vinifera seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfate, butylated hydroxytoluene, butylated hydroxyanisole, tocopherols, tocopheryl acetate, sodium ascorbate/ascorbic acid, ascorbyl palmitate, propyl gallate, and chelating agents like EDTA (e.g., disodium EDTA), citric acid, and sodium citrate.

In some embodiments, the antioxidant or preservative comprises (3-(4-chlorophenoxy)-2-hydroxypropyl)carbamate.

In some embodiments, antioxidants or preservatives of the present invention may also function as a moisturizer or emollient, for example.

In addition, combinations or mixtures of these preservatives or anti-oxidants may also be used in the formulations of the present invention.

Additional constituents suitable for incorporation into the compositions of the present invention include, but are not limited to: skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, immunomodulators, and pH adjusters (e.g., citric acid, sodium hydroxide, and sodium phosphate). For example, lipids normally found in healthy skin (or their functional equivalents) may be incorporated into the emulsions of the present invention. In certain embodiments, the lipid is selected from the group consisting of ceramides, cholesterol, and free fatty acids. Examples of lipids include, but are not limited to, ceramide 1, ceramide 2, ceramide 3, ceramide 4, ceramide 5, ceramide 6, hydroxypropyl bispalmitamide MEA, and hydroxypropyl bislauramide MEA, and combinations thereof.

Examples of peptides that interact with protein structures of the dermal-epidermal junction include palmitoyl dipeptide-5 diaminobutyloyl hydroxythreonine and palmitoyl dipeptide-6 diaminohydroxybutyrate.

Examples of skin soothing agents include, but are not limited to algae extract, mugwort extract, stearyl glycyrrhetinate, bisabolol, allantoin, aloe, avocado oil, green tea extract, hops extract, chamomile extract, colloidal oatmeal, calamine, cucumber extract, and combinations thereof.

In certain embodiments, the compositions comprise bergamot or bergamot oil. Bergamot oil is a natural skin toner and detoxifier.

In some embodiments, the composition comprises a vitamin. Examples of vitamins include, but are not limited to, vitamins A, D, E, K, and combinations thereof. Vitamin analogues are also contemplated; for example, the vitamin D analogues calcipotriene or calcipotriol. In some embodiments, the vitamin may be present as tetrahexyldecyl ascorbate. This compound exhibits anti-oxidant activity, inhibiting lipid peroxidation. In certain embodiments, use can mitigate the damaging effects of UV exposure. Studies have shown it to stimulate collagen production as well as clarifying and brightening the skin by inhibiting melanogenesis (the production of pigment) thereby promoting a more even skin tone.

In some embodiments, the composition comprises a sunscreen. Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof.

Suitable fragrances and colors may be used in the formulations of the present invention. Examples of fragrances and colors suitable for use in topical products are known in the art.

Powders and sprays can contain, in addition to a bacteriophage, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a bacteriophage of the present invention to the body. Such dosage forms can be made by dissolving or dispersing the bacteriophage in the proper medium. Absorption enhancers can also be used to increase the flux of the bacteriophage into the host. The rate of such flux can be controlled by either providing a rate controlling membrane or dispersing the bacteriophage in a polymer matrix or gel.

A *P. acnes* bacteriophage of the invention may be formulated with an excipient and component that is common for such oral compositions or food supplements, e.g., especially fatty and/or aqueous components, humectants, thickeners, preserving agents, texturizers, flavor enhancers and/or coating agents, antioxidants and preserving agents. Formulating agents and excipients for oral compositions, and especially for food supplements, are known in this field and will not be the subject of a detailed description herein.

In the case of a composition in accordance with the invention for oral administration, the use of an ingestible support is preferred. The ingestible support may be of diverse nature according to the type of composition under consideration. Tablets, gel capsules or lozenges, suspensions, oral supplements in dry form and oral supplements in liquid form are especially suitable for use as food supports.

Formulation of the oral compositions according to the invention may be performed via any usual process known to those skilled in the art for producing drinkable solutions, sugar-coated tablets, gel capsules, gels, emulsions, tablets to be swallowed or chewed, wafer capsules, especially soft or hard wafer capsules, granules to be dissolved, syrups, solid or liquid foods, and hydrogels allowing controlled release.

In particular, a *P. acnes* bacteriophage according to the invention may be incorporated into any form of food supplement or enriched food, for example food bars, or compacted or loose powders. The powders may be diluted with water, with soda, with dairy products or soybean derivatives, or may be incorporated into food bars.

In some embodiments, a composition according to the invention administered orally may be formulated in the form of sugar-coated tablets, gel capsules, gels, emulsions, tablets, wafer capsules, hydrogels, food bars, compacted or loose powders, liquid suspensions or solutions, confectioneries, fermented milks, fermented cheeses, chewing gum, toothpaste or spray solutions.

An effective amount of bacteriophage may be administered in a single dose per day or in fractional doses over the day, for example two to three times a day. By way of example, the administration of a bacteriophage according to the invention may be performed at a rate, for example, of 3 times a day or more, generally over a prolonged period of at least a week, 2 weeks, 3 weeks, 4 weeks, or even 4 to 15 weeks, optionally comprising one or more periods of stoppage or being repeated after a period of stoppage.

As one of skill in the art will appreciate, compositions of the present invention, not having adverse effects upon administration to a subject, may be administered daily to the subject.

Preferred embodiments of this invention are described herein. Of course, variations, changes, modifications and substitution of equivalents of those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

V. EXAMPLES

The below examples are meant to illustrate specific embodiments of the methods and compositions described herein and should not be construed as limiting the scope of the invention in any way.

Example 1

Background and Preliminary Data

Isolation of *P. acnes* and *P. acnes* bacteriophages. Initially, phages were used to type *P. acnes* strains, and some were found to exhibit a broad host range against *P. acnes* clinical subtypes (30-32). However, despite the relative ease with which *P. acnes* bacteriophages can be isolated from human skin, the complete genome sequences of only three *P. acnes* phages had been reported (33,34), and little was known about either their genetic diversity or the molecular basis of their relationships with their bacterial hosts (33,34). 11 novel *P. acnes* phages were sequenced from both healthy individuals and those with acne, and performed a detailed comparative genomic analysis as well as a phenotypic characterization of these phages (1). The striking finding was a lack of diversity, in morphology, gene content, nucleotide sequence and host range.

All phages have identical siphoviral morphologies, with an isometric head~50 nm in diameter and a long flexible tail. These closely resemble the *P. acnes* phages reported previously (32-36), and lack the diversity of forms observed in other phage-populations. For example, mycobacteriophages—which are genetically related to *P. acnes* phages—have both siphoviral (long non-contractile tails) and myoviral morphologies (contractile tails)—including those with prolate heads (37,38)—and phages of other hosts (e.g. *E. coli, Staphylococcus* and *Pseudomonas* phages) include podoviral morphologies (i.e. with short stubby tails) (39,40).

Genomic characterization of *P. acnes* bacteriophages. The genomes of all 11 phages are similar in size (29.5 kbp) and structure to the three previously reported *P. acnes* phages (33,34) and there is little variation in GC % from genome to genome, (although it varies from the *P. acnes* hosts). This contrasts to the considerable GC % variation of other phages. There is a high level of nucleotide sequence similarity extending across all 14 genomes, and this lack of diversity is a departure from the general diversity of the phage population. Alignment of *P. acnes* phage genome maps reveals the striking similarity of the phage genomes. Finally, the limited *P. acnes* phage diversity is illustrated by gene content network maps (1).

Organization of the *P. acnes* phage genomes. The *P. acnes* phage genomes are relatively small (30 kbp) and are organized with the DNA packaging and virion structure and assembly genes (1-19) occupying the left halves of the genome (coordinates 1-~15 kbp) in a rightwards-transcribed operon with few intergenic gaps (FIG. 1). These genes are highly conserved at the nucleotide level, with the notable exception of the last of the putative minor tail protein genes (P100D gene 19 and its relatives) (34). The variation is greatest within the 3' halves of these genes, and the protein products vary substantially in the corresponding C-terminal parts. Their high glycine content (~20%) and the presence of variable numbers of collagen-like GXXG repeats (from 17 to 42) supports their likely role as tail fibers, and the variation likely contributes to host recognition and host-range determination. A lysis cassette encoding an endolysin (gp20) and a putative holin (gp21) to the right of the tail genes promotes peptidoglycan hydrolysis and cell lysis (41).

With the exception of 1-2 genes at the extreme right ends, other genes are transcribed leftwards, closely spaced, and presumably co-transcribed (FIG. 1). Only a small number have predicted functions, and these are implicated in DNA metabolism and regulation, including P100D genes 30/31, 33, and 36 (and their relatives) that encode DNA Primases, DnaB-like helicases, and RecB-like exonucleases, respectively. P100D gene 23 and its relatives encode potential repressors with strongly predicted helix-turn-helix DNA-binding motifs. Approximately one-third of the genes have mycobacteriophage homologues (1).

*P. acnes* phage host preference and CRISPR-mediated resistance. The *P. acnes* phages have broad but not universal host ranges against a panel of 27 *P. acnes* strains. Most phages infect all host strains—albeit with variable plating efficiencies. However, two strains—B66.8 and B101.9—are distinct in that they are highly resistant to nine and ten of the phages, respectively; plating efficiencies are reduced at least 100,000-fold compared to strain 6919. Resistance could arise from a variety of mechanisms, including receptor variation, restriction-modification, abortive infection, lysogenic immunity, or innate immunity conferred by CRISPRs (42). However, CRISPRs of the type I-E subfamily have been described in *P. acnes* genomes (43), and six of the *P. acnes* isolates have CRISPR-associated (Cas) genes indicating they have similar CRISPR loci. Two of these (B66.8 and B101.9) have 9-10 spacers—some of which have close matches to phage protospacers—and are phage-resistant (1). The other four have few spacers with no phage matches, and are phage-sensitive. Comparative genomic analysis supports the hypothesis that the CRISPR spacers are responsible for resistance in the phages containing the matching protospacers (1). *P. acnes* acquisition of new spacers is anticipated but has yet to be demonstrated.

CRISPR escape mutants. Plating of high titer phage lysates on non-permissive hosts can reveal expanded host range mutants. For example, phage P9.1 plaques capable of infecting strain B101.9 are detected a frequency of $\sim 10^{-6}$. Four individual plaques were propagated, shown to re-infect both hosts at equivalent efficiencies, and the mutations mapped to protospacers (FIG. 2). Mutants have been observed with eight other host-phage combinations, but are not yet genomically characterized.

*P. acnes* phage lysis efficiency. A stock of phage ATCC 29399B was obtained from the ATCC. Upon plating, two plaque morphologies were observed on the bacterial host, ATCC 6919, one clear and one turbid (FIG. 3). These phages are referred to as ATCC_C (clear) and ATCC_T (turbid). ATCC_C is not a simple lytic (repressor-defective) variant of ATCC_T, as genomic analysis shows that all of the 1,420 nucleotide differences map between coordinates 22 and 13,920, within the virion structure and assembly genes (in all of genes 1-17, FIG. 1). The phenotype could results from disruption of structural gene expression, but not from repressor loss. As efficient killing is desirable for therapy, these observations are important for the general approach. Although there is a striking limited diversity of the phage genomes, here we take advantage of the limited differences to identify mechanisms that regulate lysis efficacy as proposed in Aim 3. We note that survivors of ATCC_C remain susceptible to infection, and may result from recombination-dependent localized amplification of a chromosomal locus.

Experimental Plan

To optimize *P. acnes* bacteriophage for use as a therapeutic modality in acne, straightforward experimentation can be conducted.

1. Genetic selection for "super-phage", able to circumvent CRISPRs and other resistance mechanisms. Successful phage therapy for acne will benefit from viruses that infect and kill all, or mostly all, of the clinical spectrum of *P. acnes* strains associated with disease. In practice, a broad spectrum of phages is desirable to circumvent the anticipated development of resistance. Beyond existing findings that *P. acnes* phages are of limited genetic diversity and have broad host ranges, a super-phage that will circumvent host resistance mechanisms may be identified and selected. For example, the CRISPR elements that target specific sequences in the phage, conferring a system of prokaryotic innate immunity, as well as tail fiber-receptor interactions may be important areas of optimization. Based on the hypothesis that a "super-phage" must be immune from CRISPR resistance, forward genetic strategies can be used to isolate phages that escape CRISPR defense or other host defense mechanisms.

1.1. Isolate escapee mutants that overcome resistance by serial selection through *P. acnes* clinical isolates. Two *P. acnes* isolates, B66.8 and B101.9, display high levels of phage resistance, likely due to CRISPR-mediated interference (1). Challenging these isolates with high titers ($>10^9$ plaque forming units [pfus]) of each phage to which they are resistant (phages P1, P8, P14, P100A, P100D, P100.1, P101A, P104A and P105) can result in the identification of additional mutants. B101.9 was resistant and B66.8 partially resistant to ATTC_C. High titer lysates can be serially plated on lawns of each bacterial isolate and individual plaques purified and high titer stocks prepared. For example, twelve independent lysates (grown from single plaques) may be used, 1-2 mutants recovered from each lysate, and analyzed together with current mutants. By iteratively isolating and testing mutants, one can identify a broad range of mutations that give rise to host preference determination.

1.2. Establish the host ranges of these mutants using *P. acnes* clinical isolates of known ribotypes. The host preferences for each of the mutants can be determined by measuring efficiencies of plating on distinct *P. acnes* strains isolated from pilosebaceous units and classified according to 16S rDNA ribotype. Ten major ribotypes were described, of which two, RT4 and RT5, were associated with acne and RT6 with normal skin (29). It is noteworthy that CRISPR elements are found in RT2, which is present in both acne and healthy skin and RT6, which is predominantly found in healthy skin, and not in the ribotypes derived from acne patients. The identification of disease-specific ribotypes and the presence of CRISPRs in specific ribotypes is preliminary. Nevertheless, the collection of 90 *P. acnes* strains contains at least 3 strains for each of the top six ribotypes and a total of 12 strains containing CRISPRs. Host range analysis can be performed using all 12 CRISPR strains from RT2 and RT6 and 3 each of the other four ribotypes, for a total of 24. During this host range analysis, additional escape mutants appearing on other resistant strains may be observed, and if so they can be recovered and characterized as in 1.

1.3. Explore the mechanisms of resistance by comparative genomics of wild-type vs. mutant phage.

By sequencing the entire genomes of two isolates from each host-phage pair one can determine whether the mutations lie within the protospacer regions. If so, PCR amplification and sequencing of the protospacer regions of all isolates can identify a broad spectrum of mutational events.

If there are mutations outside of the protospacers, one can expand the sequencing to more whole phage genomes.

Recovering phages with altered proto-spacers that circumvent CRISPR-mediated interference will identify key CRISPR-protospacer matches contributing to resistance. Engineering phage genomes to interrogate specific roles of protospacer mutations can help isolate the effects of individual mutations. Furthermore, P. acnes strain ribotypes associated with disease that lack CRISPRS or specific spacers may become phage-resistant either due to CRISPR (or spacer) acquisition or other mechanisms. Forward genetic approaches will enable broad understanding of the possible genetic bases for phage resistance.

Combining beneficial mutations into a single (or small number) of 'superphage' will permit these improved strains to be developed as therapeutic agents, or combined with existing drugs for targeted delivery.

2. Construct a "super-phage" by engineering of the phages' genomes. The use of a forward genetic strategy to identify CRISPR escape mutants will allow the identification of phages with greater resistance to CRISPR-mediated immunity. However, it is unlikely to yield a single isolate with all of the desired host range properties, and the roles of individual mutations will be unclear. For effective phage therapy it will be necessary to kill all P. acnes strains, to reduce the P. acnes load, and to anticipate the acquisition of CRISPRs by pathogenic strains. A "super-phage" that incorporates a number of advantageous mutations may be extremely useful in achieving these goals.

2.1. Develop a P. acnes system for recombineering using mycobacteriophage-encoded recombinases. Adapting the Bacteriophage Recombineering of Electroporated DNA (BRED) method developed for mycobacteriophage genomes in the Hatfull lab (44) for use on P. acnes and its phages (a P. acnes recombineering system is not available) will assist in the generation of desired bacteriophage genomes. Mycobacterial recombineering plasmids (45-48) can be evaluated in P. acnes, or novel plasmids containing the recombineering functions and inducible expression systems coupled with P. acnes plasmid replication properties can be generated (49). These plasmids can be introduced into P. acnes (49), and recombination can be assayed using ssDNA substrates that introduce drug-resistant mutations (45). This is efficient and enables rapid optimization. These techniques can be adapted to phage DNA engineering using the BRED strategy (44).

2.2. Use the recombineering system to test the role of individual phage mutations in host resistance. Recombineering will be used to construct defined phage mutants with single mutations identified in 1. Engineering can be performed using phage genomic DNA as described previously (44), and single mutations can be introduced to generate isogenic phage strains. Mutants can be identified by PCR, purified, and stocks prepared. The host preferences of these mutants will then be evaluated.

2.3. Use the recombineering system to construct super-phage with the desired features, and other potential refinements. In a second round of mutagenesis, one can combine multiple mutations into a single phage scaffold genome to achieve the broadest possible host range. An iterative process of mutant construction and host range testing can be employed. Specific mutations may generate predictable host range phenotypes, but in other circumstances they may not, especially where resistance is conferred by mechanisms other than CRISPRs. However, these may also lead to phage mutant/host combinations generating escape mutants that can be isolated and characterized. This integration of forward and reverse genetic approaches provides a powerful and attractive aspect of the overall strategy.

The ability to engineer the phage genomes opens up a broad array of refinements that would enhance the use of the phage. For example, anti-CRISPR phage genes have been described (50) and these (or related versions) could be engineered into P. acnes phage genomes with a view to adding broad CRISPR avoidance, a strategy that could overcome relatively short-lived mutational CRISPR avoidance. One could also engineer mutations that restrict the numbers of replication rounds, and are thus self-limiting.

Given the phylogenetic relatedness between propionibacteria and mycobacteria, mycobacterial recombineering systems can be adapted to function in P. acnes, e.g., with optimization of protein expression and electroporation. Alternatively, one can use M. smegmatis as a surrogate host, electroporating P. acnes phage DNA into recombineering-proficient M. smegmatis and plating in an infectious center assay on lawns of P. acnes. The use of M. smegmatis as a surrogate for P. acnes phage genetics is attractive because of its simplicity, the potential to make full use of the mycobacterial genetic toolbox, and similar surrogate host use has been shown previously (28). Other strategies for mutant construction relying on host-mediated exchange and extensive screening to identify mutants are also available, but are less efficient than recombineering.

Employing a recombineering system on P. acnes enables construction of defined phage mutants and phages with multiple desirable mutations.

3. Isolation of "super-phage" with optimal potency for killing P. acnes isolates. The phages isolated from the pilosebaceous unit of acne and healthy skin are variable in their efficiency by which they lyse P. acnes. An improved "super-phage" for treatment of acne will benefit from both broad host range and have high potency. Mapping the determinants that endow phages with the ability to efficiently kill clinical isolates of P. acnes will help clarify the interplay of the various effects.

3.1. Map the genetic determinants of the enhanced killer phenotype in ATCC_C. Phage ATCC_C is an efficient killer of P. acnes, whereas ATCC_T is not. By mapping the genetic determinants one can learn what mutations to add to super-phage to optimize potency. There are >1,420 base differences between the two, but are all within the left arm structural genes. Mapping the differences responsible for the phenotype can be readily achieved. One can use adapted BRED recombineering (as discussed above) to introduce unique restriction sites into the two phages, spaced approximately 5 kbp apart. Genomes can then be digested and re-ligated in vitro, and the potency phenotypes of the recombinant determined. Once the mutations are mapped to a 5 kbp interval, one can then do simple phage crosses, recover recombinants, sequence the intervals, and correlate mutations with the phenotype. Recombineering the identified mutations into a clean genetic background and confirming the mutations and genes that contribute to killing potency completes the process.

3.2. Construct a therapeutic phage that is CRISPR-resistant and has great potency. Recombineering can be used to construct a super-phage carrying all of the mutations required for maximal host range and potency. There may be genetic conflicts between some mutations, and it may be necessary to construct several different specific combinations. If there are additional potency mutations emerging from other phenotypic comparisons, these can be added to the super phages. Potency can be tested for all phages with a spectrum of *P. acnes* clinical isolates spanning the different ribotypes.

The mapping of the ATCC mutations can be achieved using the BRED strategy. However, alternative strategies relying solely on phage crosses, or mapping from recombinant plasmids can be alternatively or additionally be applied. For example, constructing recombinant plasmids carrying phage genome segments, propagating phages on these strains, and identifying recombinants can also achieve the desired goal.

Mapping mutations contributing to efficient killing enhances the therapeutic potential of the phages, and when combined with broad host range will benefit super-phage effectiveness.

Example 2—*P. acnes* Bacteriophage CRISPR Escape Mutants

Clustered Regularly Interspaced Short Palindromic Repeats (known as CRISPRs) are bacterially-encoded chromosomal elements that mediate phage resistance. CRISPRs function in a sequence-specific manner; that is, phage resistance depends on sequence homology between segments in the CRISPR locus called 'spacers' and corresponding regions, known as 'proto-spacers' in the phage genome.

Figure 9:
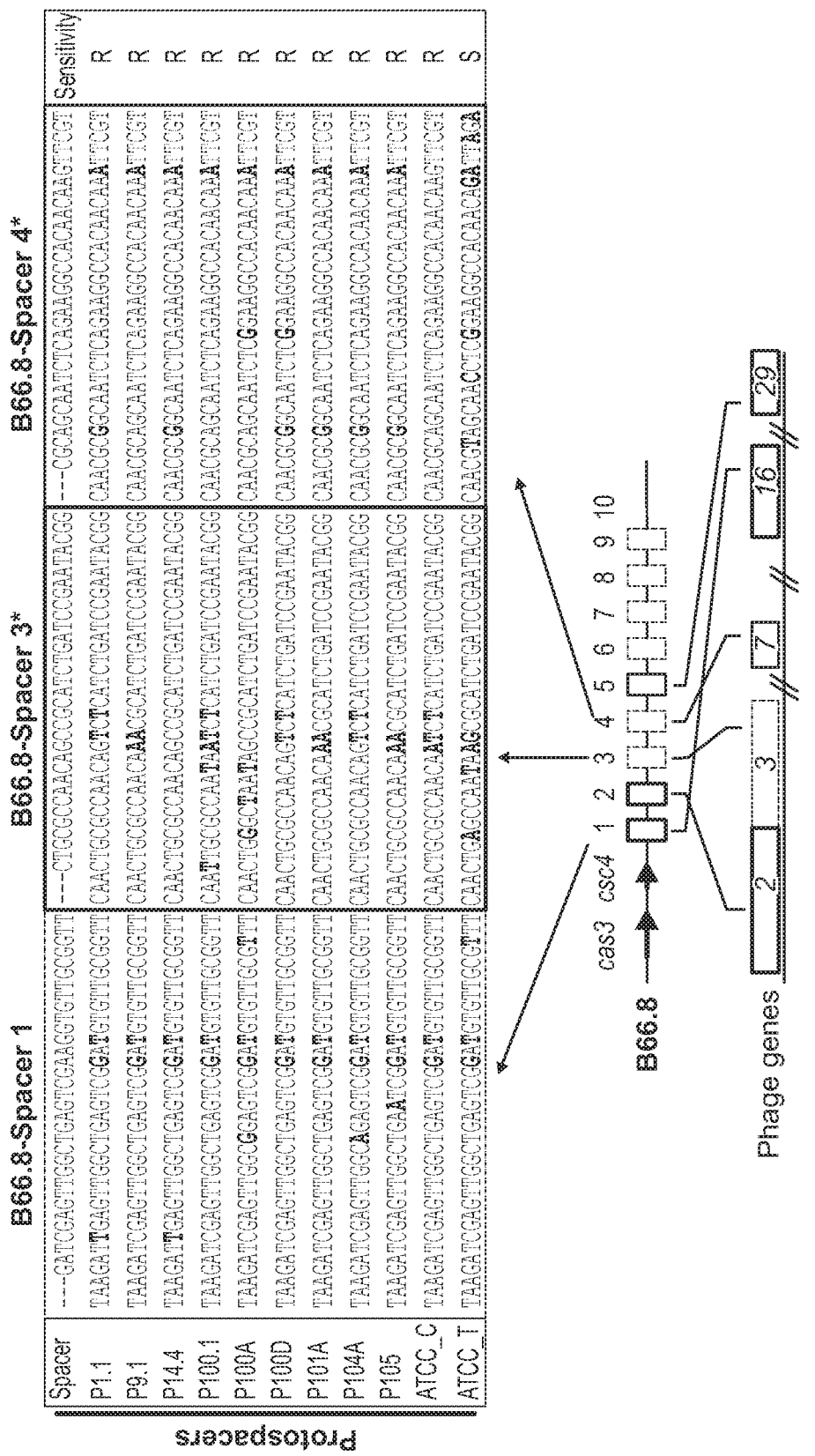
FIG. 9 depicts *P. acnes* phage PS matching B166.8 spacers.
Figure 10:
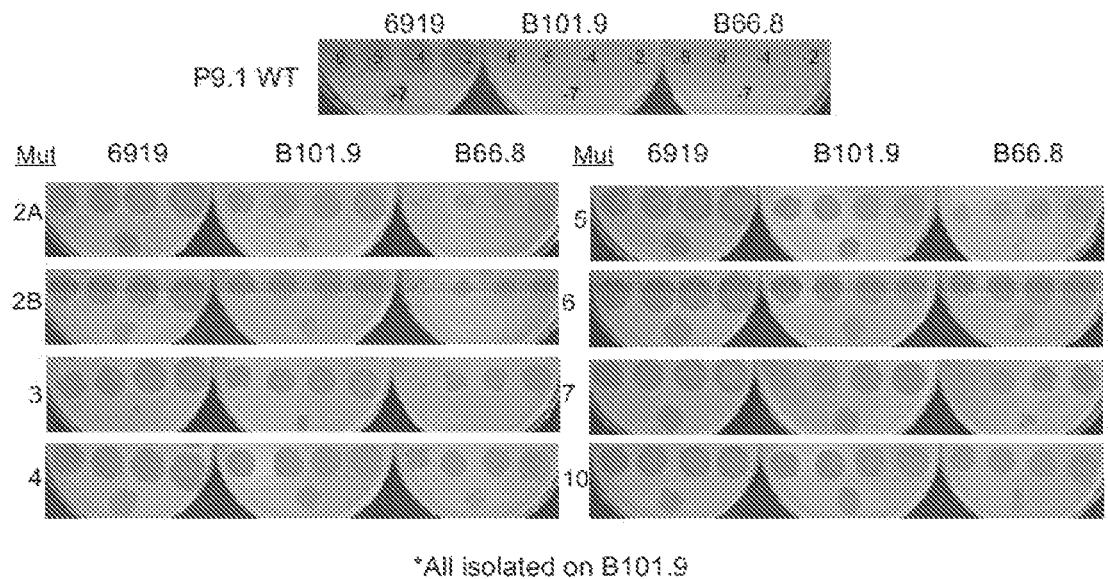
FIG. 10 shows P91 escape mutants efficiently infect isolates that are resistant to WT phage.
Figure 11:
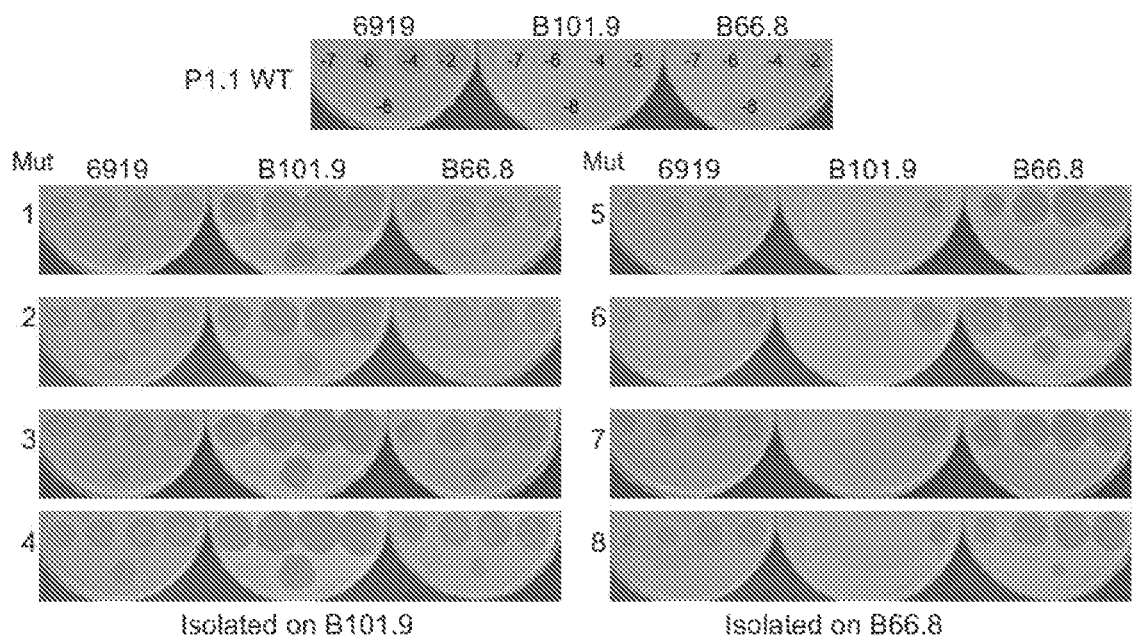
FIG. 11 shows P91 escape mutants efficiently infect isolates that are resistant to WT phage. Mutants isolated on B101.9 infect both this isolate and B66.8, wherein mutants isolated on B66.8 only infect this isolate.
Figure 13:
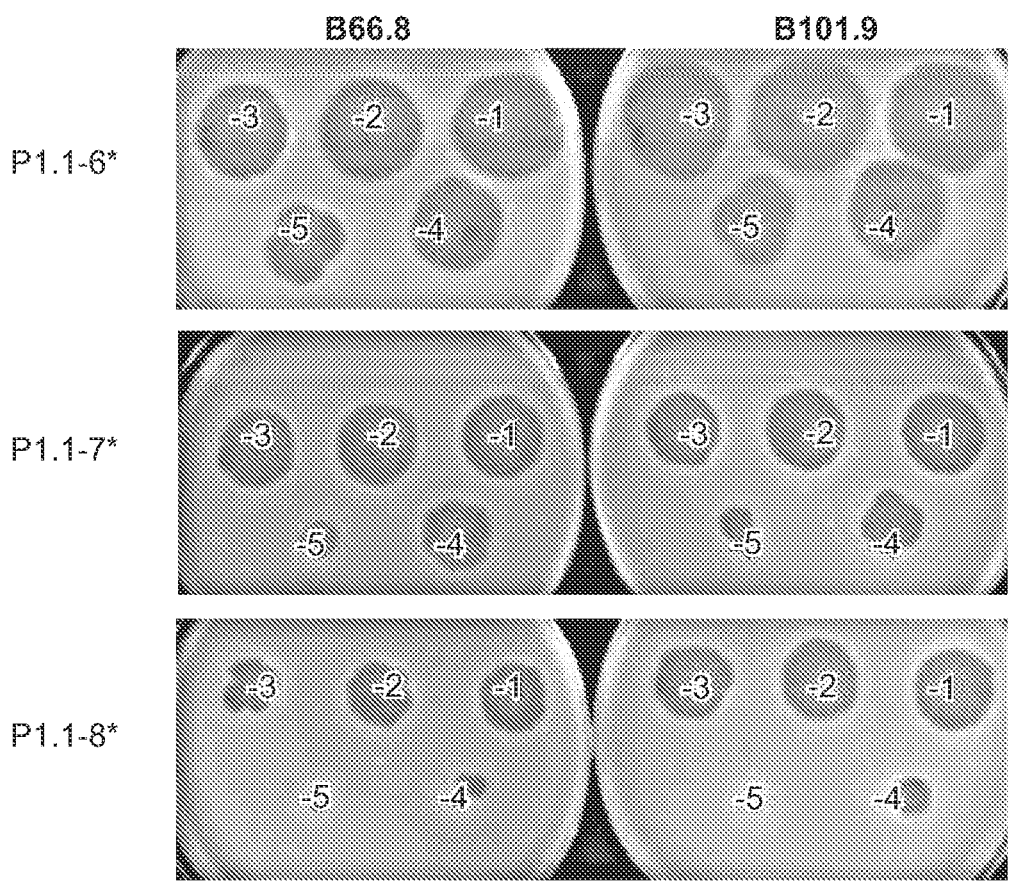
FIG. 13 shows secondary escape mutants obtained from mutants first isolated on B66.8 and then passaged through B101.9 efficiently infect B101.9 and contain point mutations in the B101.9 PS-1 PAMs.

Six of the *P. acnes* clinical isolates contain CRISPR loci, and of these, two (B66.8 and B101.9) have multiple spacers that match segments in bacteriophage genomes and thus would be predicted to confer resistance. Accordingly, these isolates do show broad phage resistance, which is correlated with spacer matches strongly implying this is due to CRISPR-mediated interference (1). (Marinelli et al. 2012, see FIG. 9).

Figure 4:
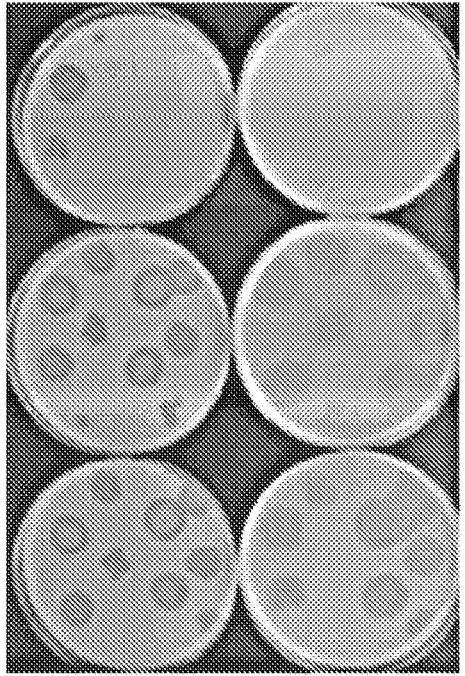
FIG. 4 depicts the number of isolated phage escape mutants and shows plaque morphotypes.

Based on these observations, it was sought to isolate CRISPR escape mutants that overcome this resistance. Isolates were challenged with high titers (>$10^9$ plaque forming units [pfus]) of each phage to which they are resistant (phages P1, P8, P14, P100A, P100D, P100.1, P101A, P104A and P105). Although most phages do not efficiently infect these resistant isolates, in some cases, plaques were recovered at low frequencies under these conditions. Plaques were recovered and purified that were obtained and confirmed their phenotype (e.g. ability to efficiently infect resistant CRISPR-containing isolates). See FIG. 4.

Figure 5:
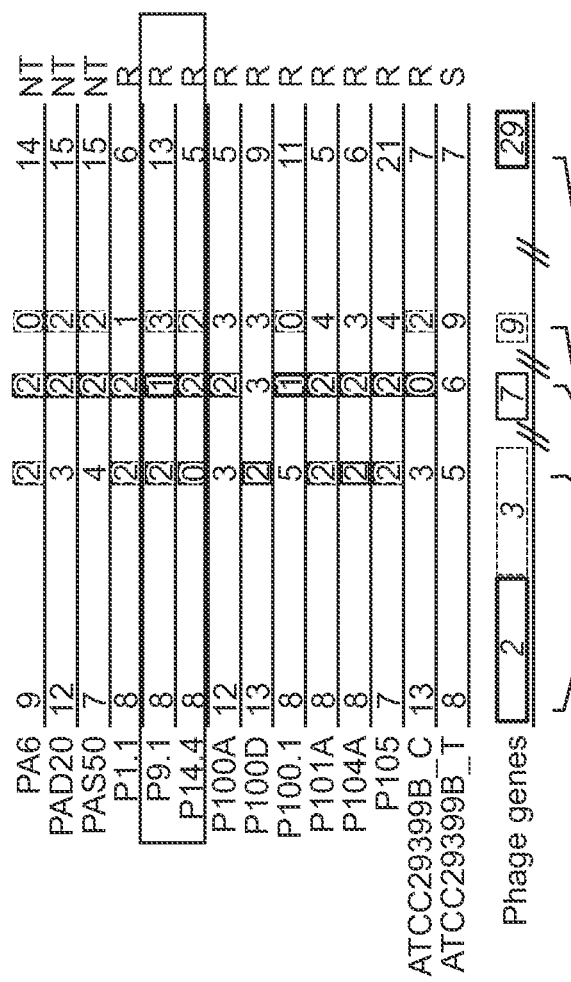
FIG. 5 depicts mutations in phage escape mutants.
Figure 6:
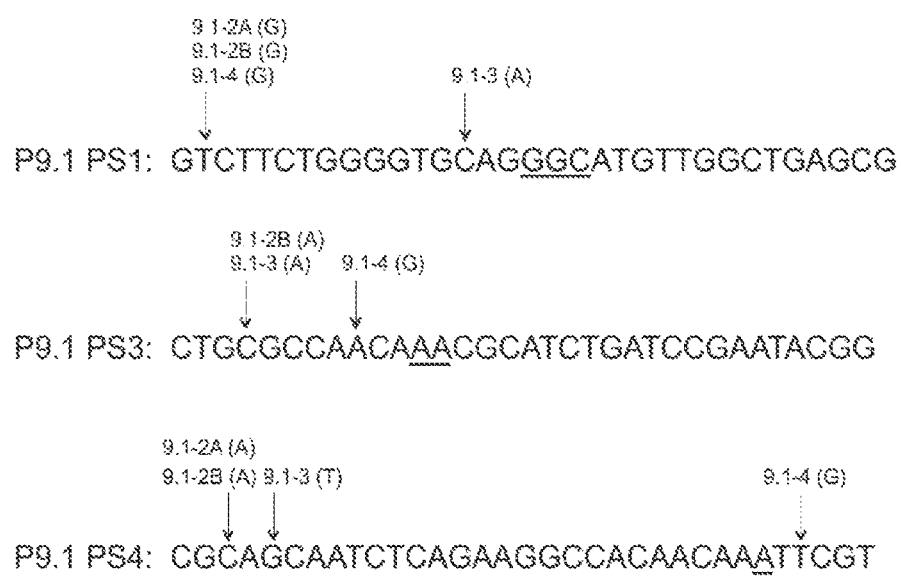
FIG. 6 depicts the sequences of proto-spacer mutations in P9.1 mutants.
Figure 7:
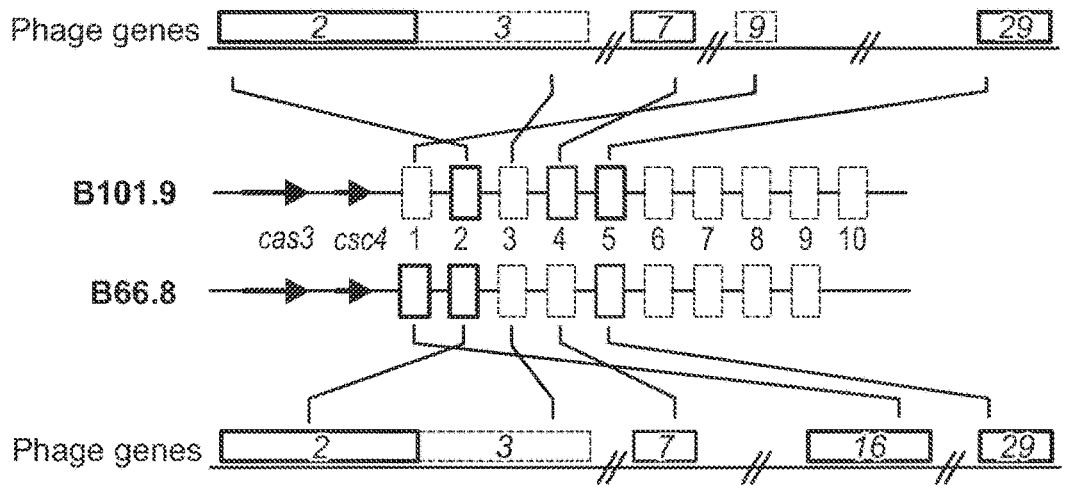
FIG. 7 is a sequence illustration of two CRISPR containing isolates that are phage resistant.
Figure 8:
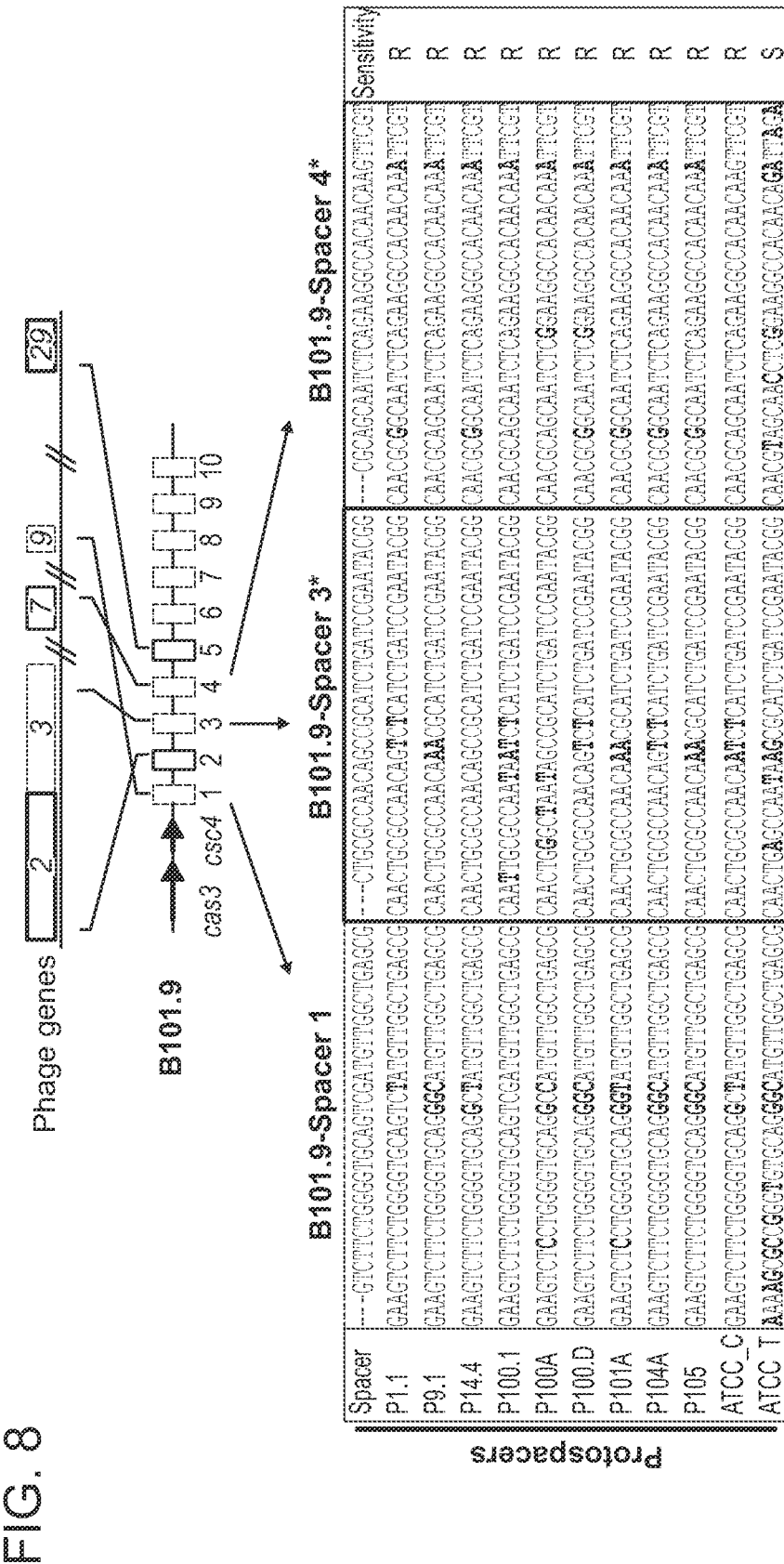
FIG. 8 depicts *P. acnes* phage PS matching B101.9 spacers.

The proto-spacer regions of putative mutants were sequenced to determine whether these were mutated in CRISPR-escape phages. As predicted, it was found that CRISPR escape mutants contain point mutations in their proto-spacer regions (whereas it was confirmed that WT phage did not contain any point mutations within the proto-spacer regions). Additionally, mutants isolated on one CRISPR-containing *P. acnes* strain, have the ability to efficiently infect other CRISPR resistant isolate; currently, it is being tested whether this is true for other CRISPR-containing isolates (from BEI) and whether these phages may further evolve for enhanced virulence against *P. acnes*. See FIGS. 5 and 6. The location and identity of all point mutations in genomes of CRISPR escape mutants may be found in the Table below.

TABLE 1

| | Location of Mutations | | | | |
|---|---|---|---|---|---|
| Mutants | B101.9/B66.8 PS3 gene 3 | B101.9/B66.8 PS4 gene 7 | B101.9 PS1 gene 9 | B66.8 PS1 gene 16 | Other mutations |
| P1.1-1 | G2761T (S)[1] | None | A6508C (NS) (PAM)[2] | None | |
| P1.1-2 | G2767T (S) | None | A6507C (NS) (PAM) | None | C6477A gene g (NS) |
| P1.1-3 | G2761T (S) G2767T (S) | None | A6507C (NS) (PAM) | None | |
| P1.1-4 | T2762C (S) | None | A6507C (NS) (PAM) | None | |
| P1.1-5 | T2771G (NS) (PAM) | None | None | T13170G (NS) | |
| P1.1-6 | T2771C (S) (PAM) | None | None | T13160G (NS) | |
| P1.1-7 | T2771G (NS) (PAM) | None | None | T13170G (NS) | T20501G gene 29 (NS) |
| P1.1-8 | T2771G (NS) (PAM) | None | None | G13171T (NS) | |
| P9.1-2A | G2762T (S) | G5919T (NS) | T6502G (NS) | None | A12404C gene 16 (NS) C16536A gene 21 (NS) |
| P9.1-2B | G2762T (S) | G5919T (NS) | T6502G (NS) | None | |
| P9.1-3 | G2762T (S) | C5917A (NS) | C6514A (NS) | None | |
| P9.1-4 | T2757C (S) | A5892C (NS) | T6502G (NS) | None | |
| P9.1-5 | G2760T (NS) | C5890T (NS) | G6508T (NS) | None | |
| P9.1-6 | G2760T (NS) | C5917A (NS) | T6502G (NS) | None | G26907A gene 43 (NS) |
| P9.1-7/8 | T2766C (S) (PAM) | C5917A (NS) | G6511T (NS) | None | |
| P9.1-10 | T2757C (S) | C5890A (NS) | A6499C (NS) (PAM) | None | G3704T gene 4 (S) G17863T gene 24 (S) G26907A gene 43 (NS) |
| P1.1-6* | T2771C (S) (PAM) | None | A6507C (NS) (PAM) | T13160G (NS) | C13734A gene 17 (NS) G27713T Intergenic G28199T Intergenic |
| P1.1-7* | T2771G (NS) (PAM) | None | A6507C (NS) (PAM) | T13170G (NS) | T20501G gene 29 (NS) T28115G Intergenic |
| P1.1-8* | T2771G (NS) (PAM) | None | A6508C (NS) (PM4) | G13171T (NS) | C23365A gene 35 (NS) |

[1] S = Synonymous mutation, NS = Nonsynonymous mutation
[2] (PAM) indicates mutation occurs in the PAM associated with the indicated PS.

Table 2 blow shows Efficency in plating when sequencing escape mutant genomes to identify mutations.

| | Efficiency of Plating | | |
|---|---|---|---|
| Phage | 6919 | B101.9 | B66.8 |
| P9.1 WT | 1 | <$10^{-6}$ | <$10^{-6}$ |
| P9.1-2A | 1 | $1/10^{-1}$ | $10^{-1}$ |
| P9.1-2B | 1 | 1 | $10^{-1}$ |
| P9.1-3 | 1 | 1 | $10^{-1}$ |
| P9.1-4 | 1 | 1 | 1 |
| P9.1-5 | 1 | 1 | $10^{-1}$ |
| P9.1-6 | 1 | 1 | 1 |
| P9.1-7/8 | 1 | 1 | $10^{-1}$ |
| P9.1-10 | 1 | 1 | $10^{-1}$ |
| P1.1 WT | 1 | <$10^{-6}$ | $10^{-4}$ |
| P1.1-1 | 1 | 1 | $10^{-1}$ |
| P1.1-2 | 1 | 1 | $10^{-1}$ |
| P1.1-3 | 1 | 1 | 1 |
| P1.1-4 | 1 | 1 | $10^{-1}$ |
| P1.1-5 | 1 | $10^{-6}$ | 1 |
| P1.1.-6 | 1 | $10^{-6}$ | 1 |
| P1.1-7 | 1 | $10^{-6}$ | 1 |
| P1.1-8 | 1 | $10^{-6}$ | 1 |

Figure 16:
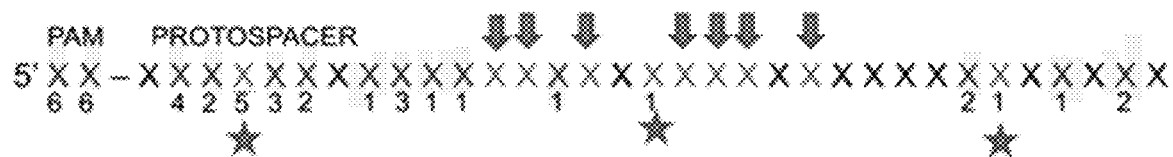
FIG. 16 shows that escape mutations are enriched in the 5' end of the PS.

In addition, escape mutations are enriched in the 5' end of the PS. See FIG. 16.

Numbers indicate the number of times that mutant was recovered

Residues in highlight indicate those that are mutated in CRISPR escape mutant phages Residues with an arrow indicate those that appear in WT phage that do not inactivate the PS (e.g. when this residue is mutated, at least one additional mutation is required for escape)

Residues with a star indicate those that do not inactivate the PS in some contexts, but can mediate escape in combination with other mutations Underlined residue is also one that appears to inactivate B101.9/B66.8 PS-4 in WT P1.1; however, it is the same residue is a mismatch in B66.8 PS-1 and escape mutants seem to require at least one additional mutation for escape

REFERENCES

All publications, including but not limited to patents and patent applications, cited in this specification, to the extent that they provide exemplary procedural or other details supplementary to those set forth herein, are specifically incorporated herein by reference as if each individual publication were specifically and individually indicated to be incorporated by reference herein as though fully set forth.

1. Marinelli L J, Fitz-Gibbon S, Hayes C, Bowman C, Inkeles M, Loncaric A, Russell D A, Jacobs-Sera D, Cokus S, Pellegrini M, Kim J, Miller J F, Hatfull G F, Modlin R L. *Propionibacterium acnes* bacteriophages display limited genetic diversity and broad killing activity against bacterial skin isolates. *M Bio.* 3: 2012.
2. Bek-Thomsen M, Lomholt H B, Kilian M. Acne is not associated with yet-uncultured bacteria. *J. Clin. Microbiol.* 46:3355-3360, 2008.
3. Kim J, Ochoa M T, Krutzik S R, Takeuchi O, Uematsu S, Legaspi A J, Brightbill H D, Holland D, Cunliffe W J, Akira S, Sieling P A, Godowski P J, Modlin R L. Activation of toll-like receptor 2 in acne triggers inflammatory cytokine responses. *J Immunol* 169: 1535-1541, 2002.
4. Leyden J J, McGinley K J, Mills O H, Kligman A M. Propionibacterium levels in patients with and without acne vulgaris. *J. Invest Dermatol.* 65:382-384, 1975.
5. Eady E A, Cove J H, Holland K T, Cunliffe W J. Erythromycin resistant propionibacteria in antibiotic treated acne patients: association with therapeutic failure. *Br. J. Dermatol.* 121:51-57, 1989.
6. Cooper A J. Systematic review of *Propionibacterium acnes* resistance to systemic antibiotics. *Med. J. Aust.* 169:259-261, 1998.
7. Coates P, Vyakrnam S, Eady E A, Jones C E, Cove J H, Cunliffe W J. Prevalence of antibiotic-resistant propionibacteria on the skin of acne patients: 10-year surveillance data and snapshot distribution study. *Br. J. Dermatol.* 146:840-848, 2002.
8. Ross J I, Snelling A M, Carnegie E, Coates P, Cunliffe W J, Bettoli V, Tosti G, Katsambas A, Galvan Perez Del Pulgar J I, Rollman O, Torok L, Eady E A, Cove J H. Antibiotic-resistant acne: lessons from Europe. *Br. J. Dermatol.* 148:467-478, 2003.
9. Leeming J P, Holland K T, Cuncliffe W J. The microbial colonization of inflamed acne vulgaris lesions. *Br. J. Dermatol.* 118:203-208, 1988.
10. Housby J N and Mann N H. Phage therapy. *Drug Discov Today* 14:536-540, 2009.
11. Straub M E and Applebaum M. Studies on commercial bacteriophage products. *JAMA* 100:110-113, 1933.
12. Eaton M D and Bayne-Jones S. Bacteriophage therapy. *JAMA* 103:1769-1776, 1934.
13. Ochs H D, Davis S D, Wedgwood R J. Immunologic responses to bacteriophage phi-X 174 in immunodeficiency diseases. *J. Clin. Invest* 50:2559-2568, 1971.
14. Dubos R J, Straus J H, Pierce C. The multiplication of bacteriophage in vivo and its protective effect against an experimental infection with *Shigella dysenteriae*. *J. Exp. Med.* 78:161-168, 1943.
15. Smith H W and Huggins M B. Successful treatment of experimental *Escherichia coli* infections in mice using phage: its general superiority over antibiotics. *J. Gen. Microbiol.* 128:307-318, 1982.
16. Capparelli R, Ventimiglia I, Roperto S, Fenizia D, Iannelli D. Selection of an *Escherichia coli* O157:H7 bacteriophage for persistence in the circulatory system of mice infected experimentally. *Clin. Microbiol. Infect.* 12:248-253, 2006.
17. Wills Q F, Kerrigan C, Soothill J S. Experimental bacteriophage protection against *Staphylococcus aureus* abscesses in a rabbit model. *Antimicrob. Agents Chemother.* 49:1220-1221, 2005.
18. Matsuzaki S, Yasuda M, Nishikawa H, Kuroda M, Ujihara T, Shuin T, Shen Y, Jin Z, Fujimoto S, Nasimuzzaman M D, Wakiguchi H, Sugihara S, Sugiura T, Koda S, Muraoka A, Imai S. Experimental protection of mice against lethal *Staphylococcus aureus* infection by novel bacteriophage phi MR11. *J. Infect. Dis.* 187:613-624, 2003.
19. Soothill J S. Bacteriophage prevents destruction of skin grafts by *Pseudomonas aeruginosa*. *Burns* 20:209-211, 1994.
20. Soothill J, Hawkins C, Anggard E, Harper D. Therapeutic use of bacteriophages. *Lancet Infect Dis* 4:544-545, 2004.
21. Marza J A, Soothill J S, Boydell P, Collyns T A. Multiplication of therapeutically administered bacteriophages in *Pseudomonas aeruginosa* infected patients. *Burns* 32:644-646, 2006.

22. Levin B R and Bull J J. Population and evolutionary dynamics of phage therapy. *Nat. Rev. Microbiol.* 2:166-173, 2004.
23. Cairns B J and Payne R J. Bacteriophage therapy and the mutant selection window. *Antimicrob. Agents Chemother.* 52:4344-4350, 2008.
24. Comeau A M, Tetart F, Trojet S N, Prere M F, Krisch H M. [The discovery of a natural phenomenon, "Phage-Antibiotic Synergy". Implications for phage therapy]. *Med. Sci. (Paris)* 24:449-451, 2008.
25. Loeffler J M, Nelson D, Fischetti V A. Rapid killing of *Streptococcus pneumoniae* with a bacteriophage cell wall hydrolase. *Science* 294:2170-2172, 2001.
26. Loeffler J M, Djurkovic S, Fischetti V A. Phage lytic enzyme Cpl-1 as a novel antimicrobial for pneumococcal bacteremia. *Infect Immun* 71:6199-6204, 2003.
27. Fischetti V A. Bacteriophage lysins as effective antibacterials. *Curr Opin Microbiol* 11:393-400, 2008.
28. Jacobs-Sera D, Marinelli L J, Bowman C, Broussard G W, Guerrero B C, Boyle M M, Petrova Z O, Dedrick R M, Pope W H, Modlin R L, Hendrix R W, Hatfull G F. On the nature of mycobacteriophage diversity and host preference. *Virology* 434:187-201, 2012.
29. Fitz-Gibbon S, Tomida S, Chiu B H, Nguyen L, Du C, Liu M, Elashoff D, Erfe M C, Loncaric A, Kim J, Modlin R L, Miller J F, Sodergren E, Craft N, Weinstock G M, Li H. *Propionibacterium acnes* Strain Populations in the Human Skin Microbiome Associated with Acne. *J. Invest Dermatol.* 133:2152-2160, 2013.
30. Zierdt C H, Webster C, W.S. R. Study of the anaerobic corynebacteria. *Int. J. Syst. Bacteriol.* 18:33-47, 1968.
31. Jong E C, Ko H L, Pulverer G. Studies on bacteriophages of *Propionibacterium acnes*. *Med Microbiol Immunol* 161:263-271, 1975.
32. Webster G F and Cummins C S. Use of bacteriophage typing to distinguish *Propionibacterium acne* types I and II. *J Clin Microbiol* 7:84-90, 1978.
33. Farrar M D, Howson K M, Bojar R A, West D, Towler J C, Parry J, Pelton K, Holland K T. Genome sequence and analysis of a *Propionibacterium acnes* bacteriophage. *J Bacteriol* 189:4161-4167, 2007.
34. Lood R and Collin M. Characterization and genome sequencing of two *Propionibacterium acnes* phages displaying pseudolysogeny. *BMC. Genomics* 12:198, 2011.
35. Zierdt C H. Properties of *Corynebacterium acnes* bacteriophage and description of an interference phenomenon. *J Virol.* 14:1268-7, 1974.
36. Lood R, Morgelin M, Holmberg A, Rasmussen M, Collin M. Inducible Siphoviruses in superficial and deep tissue isolates of *Propionibacterium acnes*. *BMC Microbiol* 8:139, 2008.
37. Hatfull G F, Jacobs-Sera D, Lawrence J G, Pope W H, Russell D A, Ko C C, Weber R J, Patel M C, Germane K L, Edgar R H, Hoyte N N, Bowman C A, Tantoco A T, Paladin E C, Myers M S, Smith A L, Grace M S, Pham T T, O'Brien M B, Vogelsberger A M, Hryckowian A J, Wynalek J L, Donis-Keller H, W. B M, Peebles C L, Cresawn S G, Hendrix R W. Comparative genomic analysis of sixty mycobacteriophage genomes: Genome clustering, gene acquisition and gene size. *Journal of Molecular Biology* 397:119-143, 2010.
38. Pope W H, Jacobs-Sera D, Russell D A, Peebles C L, Al-Atrache Z, Alcoser T A, Alexander L M, Alfano M B, Alford S T, Amy N E, Anderson M D, Anderson A G, Ang A A, Ares M, Jr., Barber A J, Barker L P, Barrett J M, Barshop W D, Bauerle C M, Bayles I M, Belfield K L, Best A A, Borjon A, Jr., Bowman C A, Boyer C A, Bradley K W, Bradley V A, Broadway L N, Budwal K, Busby K N, Campbell I W, Campbell A M, Carey A, Caruso S M, Chew R D, Cockburn C L, Cohen L B, Corajod J M, Cresawn S G, Davis K R, Deng L, Denver D R, Dixon B R, Ekram S, Elgin S C, Engelsen A E, English B E, Erb M L, Estrada C, Filliger L Z, Findley A M, Forbes L, Forsyth M H, Fox T M, Fritz M J, Garcia R, George Z D, Georges A E, Gissendanner C R, Goff S, Goldstein R, Gordon K C, Green R D, Guerra S L, Guiney-Olsen K R, Guiza B G, Haghighat L, Hagopian G V, Harmon C J, Harmson J S, Hartzog G A, Harvey S E, He S, He K J, Healy K E, Higinbotham E R, Hildebrandt E N, Ho J H, Hogan G M, Hohenstein V G, Holz N A, Huang V J, Hufford E L, Hynes P M, Jackson A S, Jansen E C, Jarvik J, Jasinto P G, Jordan T C, Kasza T, Katelyn M A, Kelsey J S, Kerrigan L A, Khaw D, Kim J, Knutter J Z, Ko C C, Larkin G V, Laroche J R, Latif A, Leuba K D, Leuba S I, Lewis L O, Loesser-Casey K E, Long C A, Lopez A J, Lowery N, Lu T Q, Mac V, Masters I R, McCloud J J, McDonough M J, Medenbach A J, Menon A, Miller R, Morgan B K, Ng P C, Nguyen E, Nguyen K T, Nguyen E T, Nicholson K M, Parnell L A, Peirce C E, Perz A M, Peterson L J, Pferdehirt R E, Philip S V, Pogliano K, Pogliano J, Polley T, Puopolo E J, Rabinowitz H S, Resiss M J, Rhyan C N, Robinson Y M, Rodriguez L L, Rose A C, Rubin J D, Ruby J A, Saha M S, Sandoz J W, Savitskaya J, Schipper D J, Schnitzler C E, Schott A R, Segal J B, Shaffer C D, Sheldon K E, Shepard E M, Shepardson J W, Shroff M K, Simmons J M, Simms E F, Simpson B M, Sinclair K M, Sjoholm R L, Slette I J, Spaulding B C, Straub C L, Stukey J, Sughrue T, Tang T Y, Tatyana L M, Taylor S B, Taylor B J, Temple L M, Thompson J V, Tokarz M P, Trapani S E, Troum A P, Tsay J, Tubbs A T, Walton J M, Wang D H, Wang H, Warner J R, Weisser E G, Wendler S C, Weston-Hafer K A, Whelan H M, Williamson K E, Willis A N, Wirtshafter HS, Wong T W, Wu P, Yang Y, Yee B C, Zaidins D A, Zhang B, Zuniga M Y, Hendrix R W, Hatfull G F. Expanding the diversity of mycobacteriophages: insights into genome architecture and evolution. *PLoS. ONE.* 6:e16329, 2011.
39. Kwan T, Liu J, Dubow M, Gros P, Pelletier J. The complete genomes and proteomes of 27 *Staphylococcus aureus* bacteriophages. *Proc Natl Acad Sci USA* 102:5174-5179, 2005.
40. Ceyssens P J and Lavigne R. Bacteriophages of *Pseudomonas*. *Future. Microbiol.* 5:1041-1055, 2010.
41. Loessner M J. Bacteriophage endolysins—current state of research and applications. *Curr. Opin. Microbiol.* 8:480-487, 2005.
42. Labrie S J, Samson J E, Moineau S. Bacteriophage resistance mechanisms. *Nat. Rev. Microbiol.* 8:317-327, 2010.
43. Bruggemann H, Lomholt H B, Tettelin H, Kilian M. CRISPR/cas Loci of Type II *Propionibacterium acnes* Confer Immunity against Acquisition of Mobile Elements Present in Type I *P. acnes*. *PLoS. ONE.* 7:e34171, 2012.
44. Marinelli L J, Piuri M, Swigonova Z, Balachandran A, Oldfield L M, van Kessel J C, Hatfull G F. BRED: a simple and powerful tool for constructing mutant and recombinant bacteriophage genomes. *PLoS ONE* 3:e3957, 2008.

45. van Kessel J C and Hatfull G F. Efficient point mutagenesis in mycobacteria using single-stranded DNA recombineering: characterization of antimycobacterial drug targets. *Mol Microbiol* 67:1094-1107, 2008.
46. van Kessel J C and Hatfull G F. Mycobacterial recombineering. *Methods Mol Biol* 435:203-215, 2008.
47. van Kessel J C and Hatfull G F. Recombineering in *Mycobacterium tuberculosis. Nature Methods* 4:147-152, 2007.
48. van Kessel J C, Marinelli L J, Hatfull G F. Recombineering mycobacteria and their phages. *Nat Rev Microbiol* 6:851-857, 2008.
49. Cheong D E, Lee H I, So J S. Optimization of electrotransformation conditions for *Propionibacterium acnes. J Microbiol Methods* 72:38-41, 2008.
50. Bondy-Denomy J, Pawluk A, Maxwell K L, Davidson A R. Bacteriophage genes that inactivate the CRISPR/Cas bacterial immune system. *Nature* 493:429-432, 2013.

```
Propionibacterium phage P1.1 genome
GenBank accession No. JX262223.1
                                                          SEQ ID NO: 7
AGTGAAATACCTCCCCTTTGTGGATTTGTCTGTTTGTCGACTTTTTGTGTTGGTGGTGAGTGTTGTGCAG

CCTGAGCTTCCTGATAGTCGTGATTGGTGTGGGGAGACGCGTCGTTGGTGGAGTGTGTGGGGTGATGATA

GCCGCGCGCAGTATGTGTCTGATGAGGAGTGGCTGTTTCTCATGGATGCTGCGGTGATTCATGATTGTGT

GTGGCGTGAGGGTCGCGCGGATTTGGTGGCTTCGCTTCGTGCTCATGTGAAGGCTTTTATGGGCATGTTG

GATCGGTATTCGGTTGATGTGGCGTCTGGTGGCCGTGGTGGGGGTTCTGCGGTGGCGATGATTGACCGGT

ATAGGAAGCGTAGGGGGGCCTGATTAGGTGTCTGGTGTTGTTGGGTCTCAGGTGCCTCGTCACCGTGTGG

CTGCGGCGTATTCGGTGTCTGCTGGCGGTGATGCTGGGGAGTTGGGTCGTGCGTATGGGTTGACGCCTGA

TCCGTGGCAGCAGCAGGTGTTGGATGATTGGCTTGCTGTTGGTAGTAATGGCAGGCTTGCTTCGGGTGTG

TGTGGGGTGTTTGTGCCTCGCCAGAATGGCAAGAACGCGATCCTTGAGGTTGTGGAGTTGTTTAAGGCGA

CTATTCAGGGTCGCCGTATTTTGCATACGGCTCACGAGTTGAAGTCGGCTCGTAAGGCGTTTATGCGGTT

GCGTTCGTTTTTTGAGAATGAGCGGCAGTTTCCTGACTTGTATCGTATGGTGAAGTCGATTCGTGCGACG

AATGGTCAGGAGGCTATTGTGTTGCATCATCCGGATTGTGCCACGTTTGAGCGTAAGTGTGGTTGTCCGG

GTTGGGGTTCGGTTGAGTTTGTGGCCCGTAGCCGGGGTTCGGCTCGCGGGTTTACGGTTGATGATTTGGT

GTGTGATGAGGCTCAGGAGTTGTCGGATGAGCAGTTGGAGGCTTTGCTTCCTACGGTGAGTGCTGCCCCG

TCTGGTGATCCGCAGCAGATTTTCCTTGGCACGCCGCCTGGGCCGTTGGCGGATGGTTCTGTGGTGTTGC

GTTTGCGTGGGCAGGCTTTGTCGGGTGGTAAAAGGTTTGCGTGGACGGAGTTTTCGATTCCTGACGAGTC

TGATCCGGATGATGTGTCGCGGCAGTGGCGGAAGTTGGCGGGGGATACGAATCCGGCGTTGGGTCGTCGT

TTGAATTTTGGGACCGTGAGCGATGAGCATGAGTCGATGTCTGCTGCCGGGTTTGCTCGGGAGCGGCTTG

GCTGGTGGGATCGTGGCCAGTCTGCTGCGTCGGTGATTCCTGCGGATAAGTGGGCTCAGTCTGCGGTGGA

TGAGGCGGCTCTGGTTGGCTGGAAAGTGTTTGGTGTCTCGTTTTCTCGTTCTGGGGATCGGGTTGCTTTG

GCGGGTGCTGGCCGGACTGATGCTGGGGTTCATGTTGAGGTTATTGATGGGCTGTCGGGAACGATTGTTG

ATGGTGTGGGCCGGTTGGCTGACTGGTTGGCGGTTCGTTGGGGTGATACTGACCGGATCATGGTTGCCGG

GTCTGGTGCGGTGTTGTTGCAGAAGGCGTTGACGGATCGTGGTATTCCGGGCCGTGGCGTGGTGGTTGCT

GATACTGGTGTGTATGTGGAGGCTTGTCAGGCGTTTCTTGAGGGGGTTCGTTCGGGTGTTGTGTCTCATC

CTCGTGCTGATTCTCGCCGTGACATGTTGGATATTGCTGTGAGGTCGGCTGTGCAGAAGCGTAAGGGGTC

TGCCGTGGGGTTGGGGTTCCTCGTTTAAGGATGGTTCTGAGGTTCCTTTGGAGGCTGTGTCGTTGGCGTAT

CTTGGTGCGAAGATGGCGAAAGCGAAGCGGCGTGAACGGTCTGGTAGGAAGCGGGTGTCTGTGGTATGAA

CTCGGATGAGTTGGCTCTGATTGAGGGCATGTACGATCGTATTAAGAGGTTGTCTTCGTGGCATTGTCGC

ATTGAGGGCTACTATGAGGGCTCTAATCGGGTGCGTGATTTGGGGGTGGCTATTCCGCCGGAGTTGCAGC

GTGTGCAAACGGTGGTGTCGTGGCCTGGTATAGCTGTGGATGCTTTGGAGGAGCGTCTGGATTGGCTGGG

CTGGACTAATGGTGACGGCTACGGTTTGGATGGTGTGTATGCTGCGAATCGGCTTGCTACGGCTTCGTGT

GATGTGCATTTGGATGCACTAATTTTTGGGTTGTCGTTTGTGGCTGTTATCCCCCAGGGGGATGGGTCGG

TGTTGGTTCGTCCGCAGTCACCAAAGAATTGTACTGGCCGGTTTTCGGCTGATGGGTCTCGTTTGGATGC
```

-continued

```
TGGCCTTGTGGTGCAGCAGACGTGTGATCCTGAGGTTGTTGAGGCGGAGTTGTTGCTGCCTGATGTGATT
GTTCAGGTTGAGCGGCGTGGGTCTCGTGAGTGGGTTGAGACGGGCCGTATCGTGAATGTGTTGGGTGCGG
TTCCGTTGGTGCCTATTGTGAATCGTCGCCGTACTTCTAGGATTGATGGCCGTTCGGAGATTACGAGGTC
TATTAGGGCTTACACGGATGAGGCTGTGCGCACACTGTTGGGGCAGTCTGTGAATCGTGATTTTTATGCG
TATCCTCAGCGTTGGGTGACTGGCGTGAGCGCGGATGAGTTTTCGCAGCCTGGCTGGGTCCTGTCGATGG
CTTCTGTGTGGGCTGTGGATAAGGATGATGATGGTGACACTCCGAATGTGGGGTCGTTTCCTGTCAATTC
GCCTACACCGTATTCGGATCAGATGAGACTGTTGGCGCAGTTGACTGCGGGTGAGGCGGCTGTTCCGGAA
CGCTATTTCGGGTTTATCACGTCTAACCCACCTAGTGGGGAGGCTTTGGCTGCCGAGGAATCTCGGCTTG
TGAAGCGTGCTGAGCGGCGTCAAACGTCGTTTGGTCAGGGCTGGCTGTCGGTTGGTTTCCTGGCTGCCAG
GGCGCTTGATTCGAGTGTTGATGAGGCCGATTTTTTTGGTGATGTTGGTTTGCGTTGGCGTGATGCTTCG
ACGCCTACCCGGGCGGCTACGGCTGATGCTGTGACGAAGCTTGTTGGTGCCGGTATTTTGCCTGCTGATT
CTCGTACGGTGTTGGAGATGTTGGGGCTTGATGATGTGCAGGTTGAGGCTGTGATGCGTCATCGTGCTGA
GTCGTCTGACCCGTTGGCGGCACTGGCTGGGGCTATATCGCGTCAAACTAACGAGGTTTGATAGGCGATG
GCTTCGGGGGTTGAGGCGAGGCTTGCTGCGACTGAGTATCAGCGTGAGGCGGTCAGGTTTGCTGGGAAGT
ATGCGGGCTATTATTCTGAGCTTGGTCGTTTGTGGCGTGCCGGCAGGATGAGTGACACGCAGTATGTGCG
TTTGTGTGTGGAGTTGGAGCGTGCCGGCCATGATGGTTCGGCATCGTTGGCTGCCGGGTTTGTGTCGGAT
TTTCGCCGGTTGAATGGTGTGGATCCTGGTTTGATTGTGTATGACGAGTTTGATGCTGCGGCGGCTTTGG
CTAGGTCGTTTTCGACTATGAAGATTCTTGAGAGTGACCCGGATAGGGCGAATGACACGATTGATGCGAT
GGCGGCGGGTTTTGATCGGGCTGTCATGAATGCTGGCCGTGACACGGTTGAGTGGTCGGCGGGTGCGCAG
GGTAGGTCGTGGCGTCGGGTTACTGATGGTGATCCGTGTGCTTTTTGTGCCATGTTGGCTACGAGGTCGG
ATTATACGACTAAGGAACGGGCACTTACTACTGGTCATACTCGGCGTCATAAGCGTGGTGGTAAGCGTCC
GTTTGGTTCGAAGTATCATGATCATTGTGGTTGTACGGTGGTTGAGGTTGTTGGCTCTTGGGAACCAAAT
AGGGCTGATGCCGGGTATCAGAGGACGTATGAGAAGGCCCGTGAGTGGGTTGATGATCATGGGTTGCAGC
AGTCGCCTAGCAATATTTTGAAGGCGATGCGTACTGTTGGCGGCATGAGATAATTTGATGTGGTTTCCGG
TTGTGCGCCGCCGGTTATCGGTGCACAGGGTTGTCTCCCGCACGGGGGTCAACAATGTTGTGTTGTTTTC
CGCAAGGAGTGTAGGGTTAGGCTATGGCCGATCAGAGTGTTGAGGAACAGAATGTTGACAATGATGTTGT
GGAGTCCGGAAAGGATAACGGCATTGTTGATACAGTAAAAGACGATGGCGGGCAGGAGGTAGCCGACAAT
CAGTTGAAGAATGAAGGCGAGGGTAAATCGCCGGGGACTGATTGGAAGGCGGAGGCCCGTAAGTGGGAGT
CTCGTGCTAAAAGTAATTTCGCCGAGTTGGAGAAGCTTCGTACATCGAGTGACGATTCTGGATCTACTAT
TGATGAGCTTCGCCGCAAGAATGAGGAACTCGAAGACAGGATCAACGGGTTTGTTCTTGAGGGTGTGAAG
CGCGAGGTGGCTTCAGAGTATGGTTTGTCCAGTGATGCGATCGCTTTCTTGTCGGGTGGCGATAAGGAGT
CGCTTGCCGAGTCTGCGAAAGCTTTGAAGGGTTTGATCGACCATAGTAGTGGTGGCGCGGGTGTGCGCCG
TCTTGCGGGGAGTGCCCCCGTTGATGATGTTAAACGACGTGAGGGTGTCGCGTTTGTGGATGCTCTTGTC
AATAATTCTAGGAGATGATTTGTGATGGCTGACGATTTTCTTTCTGCAGGGAAGCTTGAGCTTCCTGGTT
CTATGATTGGTGCGGTTCGTGACCGTGCTATCGATTCTGGTGTTTTGGCGAAGCTTTCGCCGGAGCAGCC
GACTATTTTCGGTCCTGTTAAGGGTGCCGTGTTTAGTGGTGTTCCTCGCGCTAAGATTGTTGGTGAGGGC
GAGGTTAAGCCTTCCGCGTCTGTTGATGTTTCGGCGTTTACTGCGCAGCCTATCAAGGTTGTGACTCAGC
AGCGTGTCTCGGACGAGTTTATGTGGGCTGATGCTGATTACCGTCTGGGTGTTTTGCAGGATCTGATTTC
GCCTGCTCTTGGTGCTTCGATTGGTCGCGCTGTTGATCTGATTGCTTTCCACGGTATTGATCCGGCTACG
GGTAAGCCTGCTGCGGCTGTGAAGACTTCGCTGGATAAGACGAAGCATATTGTTGATGCCACGGATTCTG
```

-continued

```
CTACGACCGATCTGGTCAAGGCTGTCGGTCTTATCGCTGGTGCCGGTTTGCAGGTTCCTAACGGGGTTGC

TTTGGATCCCGCTTTCTCGTTTGCCCTGTCTACTGAGGTGTATCCGAAGGGGTCTCCGCTTGCCGGCCAG

CCTATGTATCCTGCCGCCGGGTTTGCCGGTTTGGATAATTGGCGCGGCCTGAATGTTGGTGCTTCTTCGA

CTGTTTCTGGCGCCCCGGAGATGTCGCCTGCCTCTGGTGTTAAGGCTATTGTTGGCGATTTCTCTCGTGT

TCATTGGGGTTTCCAGCGTAACTTCCCGATCGAACTGATCGAGTATGGTGACCCGGATCAGACTGGGCGT

GACCTGAAGGGCCATAATGAGGTTATGGTTCGTGCCGAGGCTGTGCTGTATGTGGCTATCGAGTCGCTTG

ATTCGTTTGCTGTTGTGAATGAGAAGGCTGCCCCGAAGCCTAATCCGCCGGCCGAGAACTGATTTATTGT

TGCGGTGATGTGTCAATGTGCAGGGGGTGGTGTTGATGGGTATCATTTTGAAGCCTGAGGATATTGAGCC

TTTCGCCGATATTCCTAGAGAAGCTTGAGGCGATGATTGCCGATGTGGAGGCTGTGGCTATCAGTGTC

GCCCCTGTATCGCTAAACCGGATTTCAAATACAAGGATGCCGCTAAGGCTATTCTGCGCAGGGCTTTGT

TGCGCTGGAATGATACTGGCGTGTCGGGTCAGGTGCAGTATGAGTCTGCTGGTCCGTTCGCCCAGACTAC

ACGGTCTAGTACTCCCACGAATTTGTTGTGGCCTTCTGAGATTGCCGCGTTGAAGAAGCTGTGTGAGGGT

GATGGTGGGGCTGGTAAAGCGTTCACTATCACTCCCACTATTAATGGTCGATATGCACATTCTGAGGTGT

GTTCCACGGTGTGGGGTGAGGGTTGCTCGTGCGGGTCGAATATTAACGGCTACGCTGGCCCTTTGTGGGA

GATATGATATGACCAGTTTTCCTTATGGTGAAACGGTTGCGATGCTTCAACCGACTGTTCGTGTCGATGA

TCTTGGTGACAAGGTTGAGGATTGGTCTAAGCCTGTCGAGACTGTGTACCATAACGTGGCCATATATGCT

TCCGTTTCGCAGGAGGATGAGGCGGCAGGCCGTGACTCTGACTATGAGCATTGGTCGATGCTTTTCAAGC

AGCCTGTTGTGGGTGCCGGTTATCGTTGCCGGTGGCGTATCCGGGGTGTTGTGTGGGAGGCTGACGGGTC

TCCTATGGTGTGGCATCACCCCATGTCCGGTTGGGATGCCGGTACGCAGATCAATGTGAAGCGTAAGAAG

GGCTGATGGGTAGTGGCTCAGGATGTGAATGTGAAGCTGAACTTGCCGGGTATTCGTGAGGTGTTGAAGT

CTTCTGGGGTGCAGTCTATGTTGGCTGAGCGTGGCGAGCGTGTCAAGCGTGCGGCATCGGCGAATGTGGG

CGGTAACGCTTTCGATAAGGCCCAATACCGTGCAGGGTTATCGTCGGAGGTGCAGGTTCACCGTGTTGAG

GCTGTCGCTCGTATAGGCACCACATATAAGGGTGGGAAGCGTATTGAGGCGAAGCATGGCACGTTGGCTC

GTTCGATTGGGGCTGCGTCGTGATCGTCTACGATGACCCCAGGAAGTGGGCTAAACGCGTGCTCAAGGAT

GATGGCTGGCTGTCGGATATACCCTGTGTGGGGACGGTGCCCGATGATTTTACGGGTGACCTGATTTGGT

TGGCGTTGGATGGTGGCCCGCAGTTGCATGTGCGTGAGCGAGTGTTTTTGCGGGTGAACGTGTTTTCTGA

TATGCCTGATCGTGCTATGTCGCTAGCCAGGCGGGTGGAGGCTGTCCTGGCTGACGGGGTGGACGGTGAC

CCGGTGGTGTTTTGTAGGCGTTCTACGGGTCCTGATTTGCTGGTTGATGGTGCACGTTTTGATGTGTATT

CGCTGTTCGAGCTGATATGCAGGCCTGTCGAATCTGAGTAAACGTATTTGTTTTTGTTTTAATGTAATTG

TTTGATATTTAATGGGGGTTGTGATGGCTGCAACACGTAAAGCGTCTAATGTTCGCTCTGCTGTTACGGG

TGACGTCTATATTGGTAAAGCTCATGCCGGTGACACTATTGATGGTGTGAAGACGGTTCCTGATGGGCTT

ACCGCTTTAGGGTACCTGTCTGATGACGGGTTTAAGATTAAGCCTGAGCGTAAAACGGATGATTTGAAGG

CTTGGCAGAATGCGGATGTTGTTCGCACTGTGGCCACGGAGTCGTCTATCGAGATTTCTTTCCAGCTGAT

CGAATCCAAGAAAGAGGTTATCGAACTGTTTTGGCAGTCGAAGGTTACTGCCGGAGCCGATTCGGGTTCG

TTCGATATTTCTCCTGGTGCCACAACAGGTGTTCACGCCTTGTTGATGGATATTGTTGATGGTGATCAGG

TTATTCGCTACTATTTCCCTGAGGTTGAGTTGATTGATCGTGACGAGATTAAGGGTAAGAATGGCGAAGT

GTACGGGTATGGTGTGACGTTGAAGGCGTATCCTGCCCAGATTAATAAGGAGGGTGATGCGGTGTCTGGT

CGGGGGTGGATGACGGCTTTAAAAGCTGATACTCCTCCGGTTCCGCCTTCTCCGAAGCCTCAGCCGGATC

CGAATCCGCCGTCTAATAACTGATACACATAGTTTGAGGGATTGTTGATAGATGAGTGACACAGGTTACA

CGTTGAAGATTGGTGACCGTAGCTGGGTGTTGGCGGATGCGGAGGAGACGGCTCAGGCTGTTCCTGCCCG

CGTTTTCCGTCGTGCAGCTAAGATTGCCCAGTCGGGGGAGTCTGCGGATTTCGCCCAGGTTGAGGTGATG
```

-continued

```
TTTTCTATGTTGGAGGCTGCCGCCCCGGCTGACGCGGTGGAGGCCCTGGAGGGGCTTCCTATGGTTCGTG
TGGCCGAGATTTTCCGCCAGTGGATGGAATACAAGCCTGACGGTAAGGGTGCCTCGCTGGGGGAATAGTT
TGGCTCCACGGCCTGATTGATGATTATCGTGGGGCCATCGAATACGATTTCCGCACCAAGTTTGGTGTTT
CTGTTTATAGTGTTGGTGGCCCGCAGATGTGTTGGGGTGAGGCTGTCCGGCTGGCTGGCGTGTTGTGTAC
TGACACGTCTAGCCAGTTGGCGGCCCACCTTAATGGTTGGCAGCGCCCGTTTGAGTGGTGCGAGTGGGCT
GTGTTGGACATGCTGGATCATTACAGGTCTGCTAATAGTGAGGGGCAGCCGGAGCCTGTGGCGAGGCCTA
CGGATGAGCGTAGGGCCCGGTTTACGTCTGGGCAGGTGGACGATATTTTGGCGCGTGTTCGTGCCGGTGG
CGGGGTGTCTCGCGAGATTAATATTATGGGGTGAATAGTGTATGTCTGGTGAGATTGCTTCCGCATATGT
GTCGTTGTATACGAAGATGCCGGGTTTGAAGGCGGATGTTGGTAAACAGCTTTCTGGGGTGATGCCTGCT
GAGGGTCAGCGTTCGGGTAGTCTTTTTGCTAAGGGCATGAAGTTGGCGCTTGGTGGTGCCGCAATGGTGG
GCGCTATCAATGTTGCTAAGAAGGGCCTCAAGTCTATCTATGATGTGACTATTGGTGGCGGTATTGCTCG
CGCTATGGCTATTGATGAGGCTCAGGCTAAACTTACTGGTTTGGGTCATACGTCTTCTGACACGTCTTCG
ATTATGAATTCGGCTATTGAGGCTGTGACTGGTACGTCGTATGCGTTGGGTGATGCGGCTTCTACTGCGG
CGGCGTTGTCTGCTTCGGGTGTGAAGTCTGGCGGGCAGATGACGGATGTGTTGAAGACTGTCGCCGATGT
GTCTTATATTTCGGGTAAGTCGTTTCAGGATACGGGCGCTATTTTTACGTCTGTGATGGCCCGCGGTAAG
TTGCAGGGCGATGACATGTTGCAGCTTACGATGGCGGGTGTTCCTGTACTGTCTTTGCTTGCCAGGCAGA
CTGGTAAAACCTCGGCTGAGGTGTCGCAGATGGTGTCGAAGGGGCAGATTGATTTTGCCACGTTTGCGGC
TGCGATGAAGCTTGGCATGGGTGGTGCTGCGCAGGCGTCTGGTAAGACGTTTGAGGGCGCTATGAAGAAT
GTTAAGGGCGCCCTGGGTTATCTTGGTGCCACGGCTATGGCGCCGTTTCTTAACGGCCTGCGGCAGATTT
TTGTTGCGTTGAATCCGGTTATCAAATCTATCACGGATTCTGTGAAGCCGATGTTTGCTGCCGTCGATGC
TGGTATTCAGCGTATGATGCCGTCTATTTTGGCGTGGATTAACCGTATGCCGGCTATGATCACTCGAATG
AATGCACAGATGCGCGCCAAGGTGGAGCAGTTGAAGAGCATTTTTGCGAGAATGCATTTACCTGTCCCTA
AAGTGAATTTGGGTGCCATGTTTGCTGGCGGCACCGCAGTGTTTGGTATTGTTGCTGCGGGTGTGGGGAA
GCTTGTCGCGGGGTTTGCCCCGTTGGCGGTGTCGGTGAAGAATCTGTTGCCGTCGTTTGGTGCTTTAAAG
GGTGCCGCTGGCGGGCTTGGCGGCGTGTTTCGCGCCCTGGGTGGCCCTGTCGGGATTGTGATCGGCTTGT
TTGCTGCCATGTTTGCCACTAACGCCCAGTTCCGTGCCGCGGTGATGCAGCTTGTCGGGGTTGTTGGCCA
GGCTTTGGGGCAGATCATGGCAGCTATTCAGCCGCTGTTTGGTTTGGTTGCCGGGCTGGCGGCACAGTTG
GCGCCAGTGTTCGGCCAGATTATCGGTATGGTTGCCGGTTTGGCTGCCCAGCTTATGCCTGTGATTAGTA
TGCTTGTCGCCCGGCTGGTTCCTGTTATCACCCAGATTATTGGTGCGGTGACACAGGTGGCGGCCATGTT
GTTGCCTGCGCTTATGCCGGTGCTTCAGGCTGTTGTGGCTGTGATACGGCAGGTTGTTGGCGTGATCATG
CAGTTGGTGCCTGTTTTGATGCCTGTGATTCAACAGATTTTGGGTGCGGTCATGTCTGTGCTGCCACCTA
TCATCGGCCTGATCCGGTCGTTGATACCAGTCATCATATCGATTATGCGTGTGGTGATGCAGGTTGTTGG
TGCCGTGCTACAGGTGGTGGCCCGCATTATTCCGGTTGTGATGCCGATTGTGACAGCTGTGATCGGGTTT
GTTGCACGTATTCTTGGCGCTATTGTGTCTGCTGCAGCCCGCATTATTGGGACTGTCACCCGTGTCATCT
CATGGGTTGTGAATCATTTAGTGTCTGGCGTGAGGTCTATGGGCACGGCCATCTTGAATGGCTGGAATCA
TATTAGAGCGTTTACGTCTGCGTTTATTAACGGTTTCAAGTCGGTGATTTCTGGCGGCGTGAACGCTGTT
GTGGGGTTTTTTGCCCGGCTGGGTTCTTCGGTTGCCTCCCATGTGAGGTCTGGTTTTAACGCGGCCCGTG
GCGCTGTTTCTTCTGCGATGAATGCTATCCGGAGTGTTGTGTCTTCGGTGGCGTCTGCTGTTGGCGGGTT
TTTCAGTTCGATGGCGTCTAGGGTTCGTAGTGGTGCTGTGCGCGGGTTTAATGGTGCCCGGAGTGCGGCT
TCTTCTGCTATGCATGCTATGGGGTCCGCTGTATCTAGCGGCGTGCATGGTGTGCTAGGGTTTTTCCGGA
```

-continued

```
ATTTGCCTGGCAATATTCGGCGTGCGCTTGGTAATATGGGGTCCTTGTTGGTGTCTGCCGGCCGTGATGT
GGTGTCTGGTTTGGGTAATGGTATCCGGAATGCTATGAGTGGCCTGTTGGATACGGTGCGTAATATGGGT
TCTCAGGTTGCTAATGCGGCGAAGTCGGTGTTGGGTATTCATTCCCCGTCTCGGGTGTTTCGTGACCAGG
TTGGCCGGCAGGTTGTTGCCGGTTTGGCTGAGGGGATCACCGGGAATGCGGGTTTGGCGTTGGATGCGAT
GTCGGGTGTGGCTGGCCGGCTGCCTGATGCGGTTGATGCCCGGTTTGGTGTGCGATCGTCTGTGGGCTCG
TTTACCCCGTATGGCAGGTATCAGCGTATGAATGATAAGAGTGTTGTGGTGAATGTTAACGGACCCACGT
ATGGTGATCCTAACGAGTTTGCGAAGCGGATTGAGCGGCAGCAGCGTGACGCTTTGAATGCGTTGGCTTA
CGTGTGATTGGGGGTGTTGTGCATGTTTATTCCTGACTCGTCGGATCGTTCTGGTTTGACTGTGACCTGG
TTTATGGATCCGCTGTTTGGCGACGAGCGTGTGCTTCATTTGACGGATTATACGGGTGCGTCTCCTGTCA
TGTTGTTGAATGATTCGTTGCGCGGTTTGGGTGTTCCCGAGGTTGAGCATTTTTCTCAAACTCATGTTGG
GGTGCACGGCTCGGAGTGGCGCGGGTTTAATGTGAAGCCTCGCGAGGTGACGCTGCCGGTGTTGGTGTCG
GGTGTTGACCCGGATCCGGTGGGCGGGTTTCGTGACGGTTTTTTGAAAGCCTATGACGCGTTGTGGTCTG
CTTTTCCTCCCGGGGAGGAGGGGGAGTTGTCTGTGAAGACTCCTGCCGGTGTTGAGCGTGTGTTGAAGTG
TCGGTTTGATTCGGCTGATGACACGTTTACGGTGGATCCGGTGAATCGTGGCTATGCGCGCTATCTGTTG
CATTTGACAGCTTATGACCCGTTTTGGTATGGGGATGAGCAGAAGTTTCGTTTTAGTAATGCGAAGTTGC
AGGATTGGTTGGGTGGCGGCCCTGTCGGCAAGGATGGCACGGCGTTTCCTGTGGTGTTGACGCCTGGTGT
TGGTTCGGGTTGGGATAATCTGTCTAATAAGGGTGATGTGCCTGCGTGGCCTGTGATTCGTGTTGAGGGG
CCTTTGGAGTCGTGGTCTGTGCAGATTGATGGTTTGCGTGTGTCTTCGGATTATCCTGTCGAGGAGTATG
ATTGGATACACTATTGATACGGATCCTCGTAAACAGTCTGCGTTGTTGAATGGGTTTGAGGATGTGATGGA
TCGTTTGACAGAGTGGGAGTTTGCGCCTATCCCGCCTGGCGGTTCGAAGAGTGTGAATATTGAGATGGTT
GGTTTGGGTGCCATTGTTGTGTCGGTGCAGTACAGGTTTTTGAGGGCTTGGTGAATAGTTGATGGCTGGT
CTTGTTCCGCATGTAACGTTGTTTACGCCGGATTATCGTCGTGTGGCGCCTATCAATTTTTTGAGTCGT
TGAAGTTGTCGTTGAAGTGGAATGGTTTGTCGACGCTGGAGTTGGTGGTGTCGGGTGATCATTCTAGGCT
TGACGGGTTGACTAAGCCGGGTGCACGGCTGGTTGTTGATTATGGTGGTGGCCAGATTTTTTCTGGGCCT
GTGCGTCGGGTTCATGGTGTGGGTCCGTGGCGTTCTTCGCGGGTGACTATCACGTGTGAGGATGATATCC
GCCTGTTGTGGCGTATGCTGATGTGGCCTGTGAATTATCGTCCTGGTATGGTTGGTATGGAGTGGCGTGC
CGACAGGGATTATGCCCACTATTCGGGTGCGGCTGAGTCGGTGGCTAAGCAGGTGTTGGGGGATAATGCT
TGGCGTTTTCCGCCTGGTTTGTTTATGACCGATGATGAGCGTCGTGGACGCTATATTAAGGATTTTCAGG
TGCGGTTCCACTTGTTTGCAGACAAGTTGTTGCCGGTGTTGTCGTGGGCTCGGATGACTGTCACGGTGAA
CCAGTTTGAGGATGCGAAGTTTGATCAGCGTGGTTTGGTGTTTGATTGTGTGCCGGCTGTGACGCGTAAG
CATGTGTTGACTGCCGAGTCTGGTTCGATTGTGTCGTGGGAGTATGTGAGGGATGCCCCTAAGGCGACAT
CTGTGGTGGTTGGTGGCCGCGGCGAGGGTAAGGATCGGCTGTTTTGTGAGGATGTTGATTCGATGGCCGA
GGGGGACTGGTTTGATCGTGTCGAGGTGTTTAAGGATGCCCGTAACACGGATTCTGAGCGCGTGTCTCTT
GTTGAGGAGGCTGAGCAGGTGTTGTCAGAGTCGGGGGCCACGTCGGGGTTTAAGATTGAGTTGGCTGAGT
CGGATGTGTTGCGGTTTGGGCCGGCAATCTGATGCCGGGTGATCTTATCTATGTGGATGTGGGTTCTGG
CCCTATTGCGGAGATTGTTCGGCAGATTGATGTGGAGTGTGATTCGCCTGGTGATGGTTGGACGAAGGTG
ACACCGGTTGCTGGGGATTATGAGGATAATCCGTCGGCCCTGTTGGCTCGCCGTGTGGCTGGTTTGGCTG
CGGGTGTTCGGGATTTGCAAAAGTTTTAGTAAGTGATTGGGGTTTGTTGTGGGTATTGTGTGTAAAGGGT
TTGATGGTGTGTTGACCGAGTATGATTGGGCTCAAATGTCTGGTCTGATGGGTAATATGCCGTCTGTGAA
GGGCCCGGACGATTTTCGTGTGGGCACTACGGTTCAGGGTGCCACAGTGTTGTGTGAGGTTTTGCCGGGG
CAGGCTTGGGCTCACGGGGTGATGTGCACGTCGAATAGTGTTGAGACGGTAACGGGCCAGCTTCCGGGCC
```

-continued

```
CTGGTGAGACCCGATACGACTATGTGGTGTTGTCTCGGGATTGGGAGCAGAACACAGCCAAGTTGGAGAT
TGTTCCTGGGGGGCGTGCGGAGCGTGCCTGTGACGTGTTGCGTGCCGAGCCTGGCGTGTACCATCAGCAG
CTGTTGGCTACTTTGGTGGTGTCGTCTAACGGGTTGCAGCAGCAGCTGGATAGGCGTGCTATAGCGGCCA
GGGTGGCGTTTGGCGAGTCTGCGGCTTGTGATCCTACCCCTGTGGAGGGTGACCGCGTGATGGTTCCTTC
GGGGGCTGTGTGGGCTAATCATGCTAACGAGTGGATGTTGTTGTCTCCGCGGATCGAGACGGGTTCGAAG
TCGATCATGTTTGGCGGGTCTGCTGTGTATGCTTACACGATCCCGTTTGAGCGGCCGTTTGGTAGTGCGC
CTGTTGTGGTGGCGTCTATGGCTACGGCGGCTGGGGGCACGCAGCAGATTGATGTGAAAGCCTACAATGT
GACTGCCAAGGATTTTGGTTTGGCGTTTATCACGAATGACGGGTCTAAACCGAATGGTGTGCCTGCGGTG
GCTGATTGGATTGCTGTCGGCGTGTAATGCGCGGCTTGTGTATATGTGACGTGTTGTGGTGGTTGTAGTG
GTAGGGGGCTGTAGTGTCATGGCTTACACCTACACTCGTGGCCTCTCTTTGTACCGCTATCGCTACTGTT
CTTGGTTCGATTCAGGCGGTTACGTACAGGTCGAAGAAGAGGCTTAGGCAGTTGTCTGCGCAGGTTGATG
CGATGGAAGAATACACATGGAATATTCGCCATATTGTTCATCGCTATAACGCGAATTTGCCTGAGAATGT
TGAGCCGGTGAAGATGCCTGATTTGCCTGAGTTTTTGAAGGATACTGTTGATGGTGGTGGGGGTGAATT
GTGAGGGAGTTGGAGGAAGAGAAGCGGCAGCGCCGCTCGTTTGAGAAGGCTTCCCTGATATTGTTGTTCC
TGTCGCTTGTGCTGTTGGTGGCGATGGCTGGGGGTGCTTTGCGGTATGGTTCTGTGGCTTCGCAAAGGGA
TTCGGAGCAGGCTAAAGCCCAGTCGAATGGTACAGCCGCTAAAGGGTTGGCTGCCCGTGTGCGGCAGGCG
TGCGCTTCGGGTGGGCAGGAGTCGGTGCGTCTTCACCGGTCTGGCTTGTGTGTGGATGCTCAGCGTGTTG
AGCTTAGCGTGCAGGGTGTGCCGGGTCCTGCCGGTGTGCGTGGCCCGCAAGGGCCGCAGGGCCCGGCTGG
TGTTGATGGTTCGTCGGGTGTTGTGGGGCCTGTTGGTCCTCAGGGTTCCCCGGGTTTGAATGGTGTGGCT
GGTCCTGACGGGCTGCCCGGTGCTAACGGCAAGGATGGTGTCGATGGTGTTCCAGGTCGTGCAGGTGCTG
ACGGTGTGAACGGGGTTGACGGCGCTGATGGTCGGGATGGTTCGGCCGGTGAGCGCGGTGATGTGGGCCC
TTCAGGTCCTGCCGGCCCGCAAGGTGCACAGGGTGAACGGGGTCCTGCTGGCCCTGTTGGTCCGCAGGGT
TCTCCCGGTGCCGATGGCACGAATGGTAAAGACGGTAAGGATGGGCGCTCGGTGGTGTCTGTGTACTGTT
CCGGGGGCCGCCTGGCTGTGAAATATAGTGACGGTACGGCTTCTACAATATCGGGTTCGGTGGCCTGCGA
GAGTGTGAAACCGTCGCCTATAGTGACTATATCATCCCACAAATAGAAAGGAGTGGCTGTGATGGTAGTG
TTTGGTGGTGACATGCGGTGAGGTTTATTCCTGCAGCGCATCACTCAGCCGGTTCGAATAGTCCGGTGAA
CCGTGTTGTGATTCATGCAACATGCCCGGATGTGGGGTTTCCGTCTGCATCGCGTAAGGGGCGGGCGGTG
TCTACAGCAAACTATTTTGCTTCCCCATCGTCTGGTGGTTCGGCGCATTATGTGTGTGATATTTCGGAGA
CTGTGCAGTGCTTGTCGGAGTCTACGATTGGGTGGCATGCCCCGCCGAATCCGCATTCTTTGGGTATAGA
GATTTGCGCGGATGGGGGTTCGCACGCCTCGTTCCGTGTGCCAGGGCATGCTTACACGAGGGAGCAGTGG
CTGGATCCTAGGGTGTGGCCTGCGGTGGAGAAGGCTGCCATCCTGTGTAGACGTTTGTGTGACAAATATA
ATGTTCCGAAAAGGAAACTGTCGGCTGCCGATTTGAAGGCTGGCAGGCGGGGTGTGTGTGGCCATGTGGA
TGTGACTGATGCGTGGCATCAGTCGGATCATGATGATCCTGGGCCGTGGTTTCCGTGGGACAGGTTTATG
GCCGTCGTCAACGGCGGTAGTGGTAGTGAGGAGTTAACTGTGGCTGATGTGAAAGCCTTGCATGATCAGA
TTAAACAATTGTCTGCTCAGCTTACTGGTTCGGTGAATAAGCTGCACCATGATGTTGGTGTGGTTCAGGT
TCAGAATGGTGATTTGGGTAAACGTGTTGATGCCCTGTCGTGGGTGAAGAATCCGGTGACGGGGAAACTG
TGGCGCACTAAGGATGCTTTGTGGAGTGTCTGGTATTACGTGCTGGAGTGTCGTAGCCGTATTGACAGGC
TTGAGTCGACTGTTAACGGTTTGAAAAAGTGATGGTGGTTTGTTGTGGGTAAACAGTTTTGGTTGGGCCT
GCTGGAGCGTGCCCTGAAAACTTTTATTCAAACGTTTGTTGCCGTGTTGGGGGTTACTGCGGGTGTCACG
TATACTGCGGAGTCGTTTCGCGGTTTGCCGTGGGAGTCTGCCCTGATCACAGCCACGGTTGCTGCGGTGC
```

-continued

```
TGTCGGTGGCTACCTCGTTTGGTAACCCGTCGTTTGTGGCCGGCAAGCCTAAAACCACGGTTGTGGATGC

GGGTTTGGTTCCACCGGATGATGGGGGCTTGGTTGAGCCGCATATGGTGGATGTGTCGGATCCTGGCATG

ATAGAGCCTGCAGATGATGCTGATCTTGGTGGCTATGTGCCGAAACACGCTGCCGAGTCGGAGGTTGGGA

CGGTAGAGTCTACTGTTGCATAATTGAACATAGATGTGTGCCCCAGCGGCAACCACCACACGATCGTGGC

AGCACCGCTTGGGCACTATTTCTGTTTATACGGTGTGGCTATGATTCGTTGCGGTCGATGGTGTCTTCGA

GCATCTGATACAGGTGGAGGCAGGTAGAGATCGTATCGCTGGCCTGGTCTAGAACGTTCCGGCCGATAAC

GTTTTTGTGGTTGTCGCAGTGGCGGATGATAGCCCACCTGATCTCGTCGGCTGCCGCCTGCAATAGTTTT

GCCTGGTATGCGATTCCGGCAAGCCAGTCTAGTGCTTCCTGGCTTGCATAGGGGCTCTGGTCCTCGCTGT

TGTCACGGGTGTTGCTGTTGTTTGTGGGGTGTCCTGTACTGTCGCATAACCACAGGATTTCGCTGCACTC

GTCTAGCGTGTCCTGGTCGATAGCGAGATCGTCGAGGCTGACTTCGTTGACGGTAAGGTTCACGTTGTCG

AGGGAGATGGGTACACCGTACTGGTTTTCGACACTGTCAACAATGTTTTCCAGCTGTTGCATGTTGGTGG

GCTGTTGTTGGACGATACGGTGTATCGCTGTGTTGAGGGTGGTGTAGGTGATATTGTGTGTGTTGTTCAT

GGTTTTATCCCATCCCTGTGCTTTCGTCGTTTTCGTCTGGATAGTATCTACTGTTTGCGTAGCCTGTTAG

GGTGATCAGTGTTTGGTCTGCCCACTGTTTCACAGTCTGCCGGGTGACTCCGAGTCGTTGGGCGGCCGAC

GCATATGTTTGGTCATATCCATAGACTTCCCGGAATGCGGCTAGTCGGGCGAAGTGTTTTCGCTGTTTGG

ATGGCTGGCAGGTGAGGGTGTAGTCGTCGATGGCGAGCTGTAGATCGATCATGGAGACGATGTTGTTGCC

GTGGTGTTGTGGCGCGGTTGGTGGTGGTGGCATTCCTGGTTCGACGCTGGGTTTCCATGGGCCTCCGTTC

CAGATCCATTGGGCGGCTTGGATGATGTCGGCGGTGGTGTAGGTTCGGTTCACTGGTAATCCTTAAACAA

GTCGTTCATGTTGCTGGTGTCGAATCGTCCGACGCAGTGGCAGTAGTCGTACATGAGTTTAATAATGTGT

TGGTGGTCGCCGAGGTAGGTGTTTCCGCTGATGCTGTAGGTGGCTGTGCCGTCTTTACTGATGGTGTATT

TGGCGGTGATGGTTTCGGGGTTTTCGGTGTCGGTGATGATGGCTGTGGTGGTGGTGCCTACGGTTTGTAG

CACGGTGGTTTGGGTTCCGTCGTCGATGGTGGTTTTAACCATGAGGGGTTCTCCTTTTAAATGCTGGTTT

GGTTGTCGGCTAGATGAATAATATCGGATAAAGGTTTCGGTTGGTCGAGGTGTTGTATGGTTTTGTTGGC

TAGCCGTTTGGCTACCCTGTAACACATTTTGGTGTAGTGTTTGTTGTCTAGGTTGTGGTATTGTTCCCGC

ACCGCAATATATAGCAAAGAGTCTTGGTACAGGTCGTCTGCACTGATTGCGGGGTAGTGTCCGGCTGTTT

TGGTGCATGCCCGGTTGAGTGTGCGAAGATGATGGTTTGTGGCCCACACCCACGATGCGGTGGTGGCCAG

GTCTGCTTTTGTTTGTCGTCTGCTCATGGCATCTCTTTCATCTGGCTATCTGGTAGTTGTTTGGTGTTTT

GTTGTGGATAGTGTAGCACACTAGTCCGGGGTGGCCGGTGGTGCCTGTGCGGTGCCGGTACCAGACGGAT

TCGCCTTCCATGGATGGGCATTGGATGAAGGTGCGTTGTCCTTGCTCGGAGATTTCTAGGTGGTGCCGGT

GCCCGGCCATGAGAATATTAGATACGGTGCCGTTGTGGAATTCTTGGCCGCGCCACCACTCGTAGTGTTG

GTTGTTGCGCCATTGGTGGCCGTGGGCGTGCAGTATCCGTGTGCCGGCCACATCGACGGTGGTGGTCATT

TCGTCTCGGCTGGGGAAGTGGAAGTGAAGGTTGGGATATTGGTTGTTGAGCTGGTAGGCTTCTGCGATGG

CGCGGCAGCAGTCCACATCGAAGGAGTCGTCGTAGGTGGTGACTCCTTTGCCGAAGCGCACGGCTTCTCC

GTGGTTGCCGGGGATGGATGTGATGGTGACGTTGGCGCAGTGGTCGAACATGTGGACGAGTTGCATCATG

GCCATGCGGGTGAGCCTGATTTGTTCGGTGAGGGGTGTTTGTGTGCGCCAGGCGTTGTTGCCGCCTTGTG

ACACGTATCCTTCGATCATGTCGCCGAGGAATGCGATGTGGACTCGTTCGGGTTTGCCTGCCTGTTGCCA

GTAGTGTTTTGCGACTATGAGGGAGTGTAGGTAGTCGTCTGCGAATCGGCTGGTTTCTCCGCCGGGGATG

CCTTTGCCGATTTGGAAGTCTCCCGCCCCGATGACGAAGGCCGCATTGCTGTAGTCGGTGTGTGTGTCCT

GTTCGGGTTTTGGGGGTGTCCATTCGGCTAGTTTATCGACGAGTTCGTCCACGGGATACGGGTCGGTTGC

GGGTTGGTGGTCGATGATTTTTTGTATGGATCGGCCTGTTTCTCCGTTGGGGAGTGTCCATTCGGAGATG

CGTGTGCGGCGTACGGTGCCGTTGGCGAGATCATCATTAATGGTGTCGATGGCGTTGTCGTGGTTGGCTA
```

-continued

```
GCTGTGTGAGTAGCCGGTCTATATTGTCTATCACTGGTTTTCCTCTTCTTTTTTCTGTGTGGTGTTGGCT

TGTTTGCGGCGATAGTCTTTGATGACGGTGGCGGAGATGGGGTATCCGGCTTGGGTGAGCATTCGGCTA

GCTGTGTGGCGGGTATAGACTTGTCGGCGAGGACGTCTGCGGCTTTGTTGCCGTAGCGTTGGATGATGGT

TTCAGTTTTGGTTGCCATGATGTCCTAGGGGTTGTGTGGTGGGTTGCCATCCTGTGCGGCAGTCGCCGTC

GTGTCCTGGTTTGCGTGTGCACCACGATACGGTTCCGTCTGTGTGGTTGAGTGTTTTACCGCACATGACG

TTTTGTAGATGCTCCGGCGGCTCGCTATCGCTATCGTCTTGCTCGTCTAGCAAAGTTTTTTGTTGGGTGA

AAAACTCGGACACGGTGCCGTTGTGGACTGGGAGTATCCATGTTTTCCATTGTTGTTGCATCCGGGTGTT

CCAGTGGAATTGTTTGGCCGCGTTTTCGGCCTGTTTTAAGGTTTTGAAATAGCCGACGAGGATGCGCTGG

TGTTCACGGTCGGGAGGGTTTTGGCCTCGCCAGTATTGTGCCGCTACAGCGTAGCGGTTGCTGGCTGTGA

AGGCGTCCCAGCAGTATTCAATAATGTGTTGCAACATACTGTCTGGCAGGCTGTCAGGGTTGATGGTGGT

GTTTTGGGTGATCATGCCACGGATGGCTTGCCGGTTTCGGGTGGTGGGTTTGAACGAGATGCTCACGATA

GTACCGGCTGGTCGTCTTGCATGAACTGGTTGAAGGTGTTGTTCCCGGCGTGTTGGGCTTGTGTGATTTG

TTGGTCGGTCCAGTCTGGGTGTTGCTGTTTCAGATAGTGCCAGCGGCACGCATTGTAGGTTTCGTTTTGT

AGCCGGGTGAGATTGTTTTCGGTGATGATTTGTTTCCACATTGTCCACGAGACGTCGAGTCGTTTGAGCA

TGTCGATGGCTGGCACGTTGAAGGAGTTGAGGAACAGGATTTCGTGGGTGTAGTAGTTTTTCTCGTAGGC

GTCCCATCCGCTTCGGTGCCTGTTGGGCTGGTTTTTGGGGTAGGCTTCCCGGCATGCTTTGTGTAACCGT

TTGGCCATGTCTTTGGGTAGTTTAATGTCGGGGTTGGCGCGGATCATGGATCGCATCCCATCGTAGGTGG

TGCCCCAGGTGTGCATGATGCGGAGTGGGTCTTCACCATCAGCCCATTTTTCGGCGATGATGGCGAGGCG

GATACGCCTCCTGGCCGCTTGGCTGGTGTTGCGCCGGTGGGGGATTGGGCATGTGTCGAGGGGGTCCATG

ATGCTTTTTATACCTTTTCTTGAGGTGATGTTTGTTTGCTTTGTGTGGTTTTATTGTAGCACTGTGTTGA

GGGCTTGTGTCAACCCTGTTTTGCCGGCCTGCAGGTAGGTGTCTGTGACATCCCCCAGGGTGAGGGGCAC

GTGTATGGCTTGGGGGAGTGCTGTCTGGAGGGTTTGGGCCATCTGGTGGCCTGCCTGGTCTGGGTCGGAC

CAGATGTAGATGTGGTCGTAGCCTTCGAAGAATTTGGTCCAAAAGTTTTGCCACGAGGTGGCGCCGGGTA

GGGCGACGGCCGACCATCCGCATTGTTCGAGGATCATGGAGTCGAATTCGCCTTCGCAAATGTGCATTTC

GGCTGCCGGGTTGGCCATGGCGACCATGTTGTAGATGGAGCCTGTGTCTCCGGCCGGTGTCAAATATTTG

GGGTGGTTGTGGGTTTTGCAGTCGTGCGGGAGTGAGCAGCGGAAACGCATTTTTCTTATTTCGGCTGGCC

GCCCCCAAACGGGGTACATGTAGGGGATGGTGATGCACTGGTTGTAGTTTTCGTGGCCTGGGATGGGGTC

ATTGTCGATGTATCCAAGGTGGTGGTAGCGGGCTGTTTCTTCGCTGATGCCTCTTGCTGAGAGGAGGTCG

AGTATGTTTTCGAGGTGGGTTTCGTAGCGGGCTGAGGCTTTCTGGATTCGGCGGCGTTCCGCAATGTTGT

ATGGGCGTATGCTGTCGTACATTCGGGTTTTCTTTCTCAGTCGTTGTTGTAGCTTGGTGAGTCCGCCTC

CGACACCGCATGTGTGGCAGTACCAGACGCCCTTGTCGAGGTTGATGCTCATGGAGGGCTGGTGGTCGTC

GTGGAACGGGCAGAGGATGTGTTGCTCGTTTTTGGACGGGTTGTACCGTATCTGGTAGGTGTCGAGGAGG

CGGCGGGTGTCAGAGGTGTGGGAGGAGCTCGTTGAGGGTTGATACCACATAGGCTTCGCTCCAGGGTTTG

TTGCGTTGTTTCATGACGACGAGTCCGATGGTGGATTGGTTTTCGCGGTTTCGGTGGGTTTCGTAGTTGC

GTGCCTCTCGGCTGGCTTGTTTCACGAATTGGGCTAGGTGTGGTTGCCCGGCTTTGGCTTCTATCACATA

GGTTTTGTTGCCGGTTGTGAGGATGAGGTCGCCTTCGTCTTCGCGGCCGTTGAGGTGGAGGCGTTCTATA

TCATGGCCGGTGTCGCGTAGCTGGTGGAGGAGTCGTGTTTCCCATTCTGCTCCGGCTCGGCGGTTGCGTG

CCTGTTGTGTTGACATGATAGTCCTTTGTGTGTTGGGGTCATGTTCCATGGCTGTTTTTCGGCGAGGGGC

CCGAAGAATGTGTATTCGGGGTAGGCTCGTAGTCGTTCGTATCGGGTGCCGTCGGGGCTGGATTTGCCTG

TGCGTTGTTTGAGGACGGCGATGCGTGCCTCTGCCGGTATCGTGAGCCCGTTGCCGTTGTCTTCGCCGCC
```

-continued
ATAGAGTGAGACTCCGAGGATGAGTTGTGGTTTTCGGAGAGGCCGTTTTTGATTTCTCGCCGGGCTGGC

GGGTGTTCGATGTCGGAGCCGGTTTTGTCTGTTGCGTGGTGTGTGACGATGATGGTGGAGCCAGTATCCC

TACCCAATGCTGTGATCCATTGCATGGCTTCTTGCTGTGCCTGGTAGTCGGATTCGCAGTCTTGAATGTC

CATCAGGTTGTCGATGACGATGATGGGTGGGAAGGTGTTCCACATTTCCATGTAGGCTTGTAGCTCCATG

GTGATGTCGGTCCATGTGATGGGTGACTGGAATGAGAATGTGATGTGTTGGCCGTGGTGGATGCTGTCTC

GATAGTATTCTGGCCCGTAGTCGTCGATGTTTTGTTGTATCTGTGTGGTGGTGTGTTGGGTGTTGAGTGA

GATGATTCGTGTGGAGGCCTCCCAGGGTGTCATGTCCCCTGATATGTAGAGGGCTGGCTGGTTGAGCATC

GCTGTGATGAACATGGCTAGCCCTGATTTTTGGCTGCCGGAGCGCCCCGCGATCATGACTAGGTCCCCTT

TGTGGATGTGCATGTCCAGGTTGTGGTAGAGGGGTTCTAGTTGTGGTATGCGGGGCAGCTCGGCGGCTGT

TTGGGAGGCTCTCTCGAAGGATCTTTGGAGAGAGAGCATCGGAGCCTTAATCTATCTGTCTATCGGTTGG

ATGATGTTTTGGTGGTCAGATGGAGTCGATATCGATGTCAGCATCAGTTGAGGCTGTTGTGTCGTCTAGC

TGGCCGTTATCGCGCTTGTCTACGTATTCGGCAACCTTATCGTAGATGGCGTCGTCTAGGGGTTTGAGCA

CGACCGCGTTGAAGCCGTTTTTGGTGCGTACGGTGGCGAGTTTGAAGGCCTGCTCCTCGCCAAGGTAGGT

TTCTAGGTCGCGGATCATGGAGTGTGGGCGATCATTGTTGCCTCGCGCTTTCTCAATAATGGCGTTGGGG

ATGGTTTCTGGGGTGCCGTTGTTGAGGTCGTCTAGGGTGTGGAAGATTGTGACATCAGCGTAGATGCGGT

CTGCGACCTGTCCGCCGTAGCCTTCGGTGTTGTGTTCTACGTCGTGGACTTTGAAGGCGATGGCGGTGGC

GTCCTGGTTTCGGGAGGGGTTGAAGAAGGTGCTGTTGCTGTTGTTGTGCGGTAGTTGGCGAGTGCCATG

ATTGTTGTTTCCTTTACTGTTTTGTTGGTTTGTGTCGGTTTTTATCGGGTGAGGCTGTTTCGCTTATTCC

GGAAAGCTTCGGAAACATCACTGTTACTGGTGATGATCTTTTTGTACTGTTTGAGTAGGTCGGCTAGCTG

TGCTTTACTGGTGGCTTTGTTGATCTGGTCGATGATAATCTCATTTTCCTGTGATGCGATGTTGTTTACG

TAGTCTTTGGCTGCTTTATCGTATTTGTCTTGGAGGATGATGGCTGCGCTTGCTACCAAAGTGGCTAAAT

CCCAATCCTCAGAGACGGTGTTGTCTTTGAGTCCGCCTAGCAGGTCGATGATGGCCTGTTTTGTCTGCTC

TGCTGTGTCTCCTCGGATGACCGCCCATGGTGCAGCATAGTCTCCACCATATTTGAGTGTGATCGTGAGT

CGATCATTGTCGATCTTGTCTTTATCGGTCATTTGGTGTCCTTTTCTTTATTGTCTGTTTGGGGTGGCTG

TACGGTGGATTCTACCGGGTATCTGTAGGCGTCTTTCCCGTCTACAGCCCAGCAGGCGTCCTTGACGGGG

CATCCTTTGCAGAGTGCTGTGACGTGGGGTACGAAGATGCCTTGACTGATTCCTTTCATTGCTTGACTGT

ACATGGATGATACATGCCGGTAGGTGTTGTTGTCAAGATCGTACAGTTCGGTGGATGTGCCTTGTGTCGG

GGACTTGTCGTCGTTGCGGCTGGTGGCTGGCGTCCAAAACATGCCTTTCGTGACGTTTATGTCGTGTTGG

TTGAGCATGTACCGGTATGTGTGCAGCTGCATGCTGTCGGCGGGTAGACGGCCGGTTTTGAGGTCGAGGA

TGAAGGTTTCGCCGGTGTCGGTGTCGGTGAAAACGCGGTCGATGTAGCCGACTATTTTTGTGTCATCGTC

GAGGATGGTTTCTACCGGGTATTCGATGCCTGGCTGGCCGTCCAGGATTGCGGTGATGTATTCTGGGTGG

TTGCGCCTCCAGGTTTTCCAGCGGTCGACGAAGGTGGGGCCGTAAACCATCCACCAGCCGTAGTCTTTCT

TGTGTGGCCCGCCCGACTCGCACATGTTTTTGCATATTCTGCCGGAGGGTTTGATTTCTGTGCCTTCGGA

TTCGGCGAGGGCGACTTGGGTGTCGAAAATGTTTTCGAAGGATGAGAGTTTGTCTGGCAGTGCAGGGTAT

TCGGCGGGATTGTACAGGTGTAGGTCGTATTGTTCGGTGATGTGGTGTATGCGCTTCCGGCGATGGTGG

CGTACCAGGTGTGGTGTTGGGCATGGTAGCCGTGTGAGAGGCGCCATTTTTCGCCGCATTCGGCCCACTG

TGACAGTGATGAGTAGGAGATGTGGCCTGGATGGTGGATGGTTTTCGGATATTGTGCTAGAGGCATTACT

TGTCGCTTTTGTTCCATGGGTTGCGGGTGTCTTGGCCGGCATCGTGTTGCTGGTATGCGAGGAGTGCGAG

GCAGTGCCAGGCTGCATGGGCTAGATGCGGCAGCCCGGATTCACGGTCGAGGTTGTTGCCTTGCTGCCAT

GATAGCAGGTGCCGGTAGAGGGCGTCGACACTGTGGCTCCACGGGTATCCTCCGGTCCAGTTGTTGTCGC

CGTATTTGGTGGCACCGTATCCGGCTACTTCGCCGAGAGCGTGCAAGGCTGTAGGGTCGATGAGGGAGAG

-continued

```
CCTGCATTGTTTGAGTTCTTTTCGGGCTCCGGTGTTGGGGTCGGTGTACATGCGGGTGGGCTCATCCATG

GGTATGTGCGCCTTTCTAGGGGGTGGGTTACTGGTTGGGGTTGTGGGCGAGTGCTACTGCGAGAATAATG

ATGGCGAGGGTTTCCGCGATGAGGATGGGTGTTGTGATCATTTGTGGTCTTTGGGCTGGTAGGTGAGTGT

GGAGGCGCCTAGGAGGGTGGCGAGGGCGCATGCGGCAATAATGGCGAGGGCTGCCTTGTGTGGGGTGCCG

GTTGCGTACATCCATGTGATGATGGCGCCTTGGATCCAGGCGAGGCTGGTGAAGAACGTTTCATAGCTGT

GTAGCTCAATGTTGTTGTTGGGTGTGTTCATGCTTGCTCCTGAAGAATGGTGTTGATGGTTTTATAAATG

TTGTACAGGTCGGCTTCGATGGTTTGTAGCTGTTTGATTTGGTGGTCGAGATCAATGTCTGGATTGAGGG

TGTTGATGCGGGAGGCAATATCGGTTGCTGTGCGTAGTGTGCCGCCGGTGTGGTGAATAATGTGTGCCGT

GTCGGCTAGTCCGGTGGTGACAGCGTAGTGGGAGAGGAGAGGCATAGCTGGGGGGGTGCTCCTTGGCGGG

TTACTGTTGCGGGTTGATGTTGAGGTCGGTGACGTGGGGGTGGTCTTCTGTTCCGGTGACGAGGCAGTGG

ACGGTGACGGGTAGTTTGGATGCGCCGGGCTGTTTCGCGGTGGCGCCGTAGACGATGGAGAAGGTGTCTT

TACCAATAATTTTGTGGAGTTGGAGGTCGATGTCGGGGTTGCCGTTCCAGTTGAGGCTGTGTGCGGCGGC

CTGTTGTTCGGCTTTGCGGTTGCAGGTGTGTGCGGCCGTGATCATGGTGAGTCCGGTGGCGGTTTCTTCA

CCCCTTGCTTGGGCTTGCTTGTGGGCTTTCTGCTGTTCGGCTTGTAGGGAGCGGACTGCTGCGGCCTGGC

GGGCTTTCTTCTCGGCTTTGCGCTGTTGGACGGTTTTGGGTGTCCAATTAGTGTTGGCTGTGGTGGCCTG

TGGGGCTGGCTGTGAGGCGAGTGGCGGGTTGTCGTCGGGTGCTGGTATGAATGAGGCGGCGGCGATGATG

GCGGCTGTGATTCCGGCGATGGTGTAGCCGTTTTTCTTGTTCATGGCTGTTGTCCCCTTTCCGGGGTGTT

GTTCGTTGCTGACATGGTTAATATTTCCAGACTGGACTACCACTGTCAAGGTGTCGCTCAGTTTGTGTGA

GCGTTTCCTGTGTGGCTAGGTGTTTTATCGGGCGAACAGGGTGAGTAGATGGCCAACATTGATGCGGCTC

ACGTTCCAGTAGAGTTGTGTGGCTTCACCGCCGGTGAGCGGCTTCCACTCGTTGTGGCTGAACACGGTGC

CATCGGATGCGATGAATGTGTCGGGCGTAGCTTGTGAAGCTCGGCTTCTACGCTCTGCCGGTAGGCTTC

GGCGAGGCCCTCAAAATCCATGTGGTCGCAGGAGAGGTTTTCGAGGCGTGTCAGGTCGAAGGGTGTAGGG

ATGTCGTAGCTGGCGGGGCTGTAGAGCTGGGTGAAGTGGTTGGCGATCTTCTGCATGACGGGTTCCTTTC

TGGTGTGTGGATGTTTTTTATCGTGTGGCTTCTTTGAGGATTGTGGTGGTGTCGATGGTGTCGATCTGCC

AGGCGAGTTCCTCGGCCTCATCCGCCGTGAGCTGTTGCCAGTCTTGTGGGCCGGTGACTGATCCGTCGAG

GGCGAGGGTCCAGTCGGGGCGGAAGAGGTTTAAGGCTTCTTGCACAGCATCCCGGTAGACATGTTTGGCG

GCGTCAAGGTTGATGTGTTTGGCGTGTCGGCCGGCTAGCTGAGTGAGGTCGAGTGGGTCGATTTCTGTCT

GCCCATAGAGGGATGTGAAGGATGGGGTGATGAGTGTGGTGGCCATTTTTGGTGTGTCCTTTCGGTGGTG

TAGGGGTTGTTGTGGTTTCTAGACTGTGCGGGCTGCGACCCCACAGTCAAGGTTGCGCTCAAACCCAGTG

AGCGTTTCATATGGGTGTGGCATGGGATGTGGCGTATCTCACTTAAGCCTTTATGGCCTCTCTCAGCGCC

TCAAATCCTCTGGGGGTAGGATTATATAGGGTTGACCCTGCTGATCGATTCTAGAGCACTTCTAGGGCGT

CTCAGGGGTATGTCTGGGTTATGGCAGATGACCCGGCAGATCCACCTTGGCTTTCATCGCGGGGTCGAG

GTGCCAGATCTGGGCATGGAATCTACACCCTCATACTATGTGAAATGTATCACACTCGCCTAGTATGGTG

TGCACTCTCGAGGCCACTCTGTCGATCTGGCGTGGAGGGTGTAGCCCAGAAATGCCGTTTAAAGCCTTCA

CACGGCGCCTAGGAGCGCCTTGCGGGGTGGGGGCTAGGTATTTATACCCCCAGCACATTCTGATCGATTC

TAGACGCCTCCCAGAGCCTGATACACGATCCGCTATACAGACACAGATCACCAGCCCCTATCCTGGTTAG

CTAAGCCTCAACTATGTGGACAGTGTGGGATGCTCAAGGGGAAGAAGGACACGGTAAAAGAAAGAAGGGG

GAGCATCAGCTTTCACGCCTTAAGTACTTAAGTTCACCTGAGGGTCTTAGCACCGAGCCCCTCAAGGGCT

CGGCATCAGTCCGAGCAGGCTCAGCCCATCCGGCACGGCCCTGAAAGGGGTACACGCCATCAGGGAAGGC

TTGAGAGTACGAGGAGCTCTAGCGACGAGTACTCGAAAGCCTGAGGGAACACCCTCAGCACTGATGGGCC
```

```
TAGCGTGTTCGGAAAGGACACAAGGGTACAGTGTGAGAGCTGTTCGGGAGTGAAACCCGTTCTGACTAGG

AGTTTCAGCCTTAACAACCCTCAAAGGTTACAAGACTCTAAGAAAATTTAAGGAAAAGTTTAGGTTTAAT

TTTTGGACCTTTACTACCAAAAACGGGTGTCTACACCCCTCAAACCCGCCTATAGAGCCAAATCCACCAG

TTTGACTCATCCCAGGTGGGGTATGATAGGCTGGACAGGTAGCCAGCTGGACGCAAGGCCAGAAAGTGCT

GACGCACTTCCCGACCTCGCTTACCATCAGTCTACCAAACACTTTAAAGCTTCAAGGCTTAGCGTTAAGG

TCTTAAGGGCTTACACACTTAGCACCGAGCCCCCTCAAGGGCTCGGCATCAGTATAAAGACCTTAACACT

TAAGTTAATATTTAAACCTTAAAGGCTTAGCACTTAAGGATACAAACTTAACATCAGTGTTTAAGATTTT

AAAACTTAAAGTTAACCATCAGTCTTAAACTTTAATATTATAACCTATAAGTCTTAAAGCTTATAAGTTA

TAAAAGTTTTAGAAGAGCTAAGGGGTTAACTTCTTTACTTCTCTACTCTCTTTGGTACTTTCTCTCTTCT

CTTCTTTTCTTCATCAGGGGAGAAGAGAAACCTTTTGCCGTCAACGCCGATGGACTTTTCACCGTGTGAC

TCGTGTGCTTCTGGTCGCAAGCTCCCATCGCACACTCACCGCACCTCACCTTGCCCGTGTACTTTAAGCT

TAGCGTGTTTCACTTCAGGCGTACGGCGTGTCACGCTAACACCCTTAACACCGGGTGAGACTTAAAGTGT

ATATTATATGTAGAAGACTTTAAAACCTATAAGGTGTTCCCGCTTAGCCTGTGTCCTACACCGCTAGGCG

CCAAGCGCTAAGCTGTGAAACGCGAACACACACCCACCCCCCTTTTTCTTTCGTGTCCTTCTCTTTTGAC

ACAGCTGGGGGGCGATGTGATATTTTTCACATGCCAGGGGGTAGTGGAGAAAACAAACACCCCAGCACAA

ACAGAACACCCCCTCAAACGAACAAAACGCCCCCATAATCGATGAGCAGGGCAAGGGCAAGGTATTCAT

ACCCCCAACACCTTTCAGGCCGTTAGAGAGGCAATGAGAGACTCACAGGCTACCATAGGTGATCGGAGAC

GTGATGGCACATACCAACCGCACCGCATCCGCCTCACACCGGCGCTGGCGGCAACGACTCATCACCCAAG

CCAGACAGCAAGGCCAAACTGAATGCCCACTCTGCGGAGCCACCATCACCTGGAACACACACGACCTGCC

AACCAGCCCCGAAGCCGACCACATCACACCCGTCAGCAGGGGAGGACTCAACACCCTCGACAACGGGCAA

ATCATCTGCAGAACATGCAACAGAAGCAAAGGCAATCGCAGCGAACCAAACATCAAGTTCCAACAACAAA

CCACAAAAACCTTGATCCCATGGTGAAAAACCCGCCAACCCCCACCGGGGACACCCCCTGCACACCCGTG

CAAGACCTCGTACGGCTT
```

*Propionibacterium* phage P1.1 Gene 3 protein product-portal protein
encoded by residues 1886-3211 of SEQ ID NO: 7
GenBank accession No. AFT97827.1

SEQ ID NO: 8

```
MNSDELALIEGMYDRIKRLSSWHCRIEGYYEGSNRVRDLGVAIPPELQRVQTVVSWPGIAVDALEERLDW

LGWTNGDGYGLDGVYAANRLATASCDVHLDALIFGLSFVAVIPQGDGSVLVRPQSPKNCTGRFSADGSRL

DAGLVVQQTCDPEVVEAELLLPDVIVQVERRGSREWVETGRIVNVLGAVPLVPIVNRRRTSRIDGRSEIT

RSIRAYTDEAVRTLLGQSVNRDFYAYPQRWVTGVSADEFSQPGWVLSMASVWAVDKDDDGDTPNVGSFPV

NSPTPYSDQMRLLAQLTAGEAAVPERYFGFITSNPPSGEALAAEESRLVKRAERRQTSFGQGWLSVGFLA

ARALDSSVDEADFFGDVGLRWRDASTPTRAATADAVTKLVGAGILPADSRTVLEMLGLDDVQVEAVMRHR

AESSDPLAALAGAISRQTNEV
```

*Propionibacterium* phage P1.1 Gene 7 protein product-hypothetical protein
encoded by residues 5618-6097 of SEQ ID NO: 7
GenBank accession No. AFT97831.1

SEQ ID NO: 9

```
MQGVVLMGIILKPEDIEPFADIPREKLEAMIADVEAVAISVAPCIAKPDFKYKDAAKAILRRALLRWNDT

GVSGQVQYESAGPFAQTTRSSTPTNLLWPSEIAALKKLCEGDGGAGKAFTITPTINGRYAHSEVCSTVWG

EGCSCGSNINGYAGPLWEI
```

*Propionibacterium* phage P1.1 Gene 9 protein product-hypothetical protein
encoded by residues 6453-6743 of SEQ ID NO: 7
GenBank accession No. AFT97833.1

SEQ ID NO: 10

```
MAQDVNVKLNLPGIREVLKSSGVQSMLAERGERVKRAASANVGGNAFDKAQYRAGLSSEVQVHRVEAVAR

IGTTYKGGKRIEAKHGTLARSIGAAS
```

-continued

*Propionibacterium* phage P1.1 Gene 16 protein product-hypothetical protein
encoded by residues 12239-13399 of SEQ ID NO: 7
GenBank accession No. AFT97840.1

SEQ ID NO: 11

MMAGLVPHVTLFTPDYRRVAPINFFESLKLSLKWNGLSTLELVVSGDHSRLDGLTKPGARLVVDYGGGQI

FSGPVRRVHGVGPWRSSRVTITCEDDIRLLWRMLMWPVNYRPGMVGMEWRADRDYAHYSGAAESVAKQVL

GDNAWREPPGLFMTDDERRGRYIKDFQVREHLFADKLLPVLSWARMTVTVNQFEDAKEDQRGLVEDCVPA

VTRKHVLTAESGSIVSWEYVRDAPKATSVVVGGRGEGKDRLFCEDVDSMAEGDWFDRVEVEKDARNTDSE

RVSLVEEAEQVLSESGATSGFKIELAESDVLREGPGNLMPGDLIYVDVGSGPIAEIVRQIDVECDSPGDG

WTKVTPVAGDYEDNPSALLARRVAGLAAGVRDLQKF

*Propionibacterium* phage P9.1 genome
GenBank accession No. JX262215.1

SEQ ID NO: 12

AGTGAAATACCTCCCTTTTGTGGATTTGTCTGTTTGTCGACTTTTTGTGTTGGTGGTGAGTGTTGTGCAG

CCTGAGCTTCCTGATAGTCGTGATTGGTGTGGGGAGACGCGTCGTTGGTGGCGCGTGTGGGGTGAGGATC

CGCGTGCCGGGTTTGTGTCTGATGAGGAGTGGTTGTTTCTCATGGATGCTGCGGTGATTCATGATTGTGT

GTGGCGTGAGGGTCGTGCGGATCTGGTGGCTTCGCTTCGTGCTCATGTGAAGGCTTTTATGGGTATGTTG

GATCGGTATTCGGTTGATGTGGTGTCTGGTGGCCGTGGTGGGGGTTCTGCGGTGGCGATGATTGACCGGT

ATAGGAAGCGTAAAGGGGCCTAATGTCGAGCTTTGTTGGTTCTCAGGTGCCTCGTCACCGGGTGGCTGCG

GCGTATTCGGTGTCTGCTGGCGGTGATGCTGGGGAGTTGGGTCGTGCGTATGGGTTGACGCCTGATCCGT

GGCAGCAGCAGGTGTTGGATGATTGGCTGGCTGTCGGTAGCAATGGCAGGCTTGCTTCGGGTGTGTGTGG

GGTGTTTGTGCCTCGACAGAATGGCAAGAACGCGATCCTTGAGGTTGTGGAGTTGTTTAAGGCGACTATT

CAGGGTCGCCGTATTTTGCATACGGCTCACGAGTTGAAGTCGGCTCGTAAGGCGTTTATGCGGTTGAGGT

CGTTTTTTGAGAATGAGCGGCAGTTTCCTGACTTGTATCGTATGGTGAAGTCGATTCGTGCGACGAATGG

TCAGGAGGCTATTGTGTTGCATCATCCGGATTGTGCCACGTTTGAGAAGAAGTGTGGTTGTCCGGGTTGG

GGTTCGGTGGAGTTTGTGGCTCGTTCTCGGGGTTCGGCTCGCGGGTTTACGGTTGATGATTTGGTGTGTG

ATGAGGCTCAGGAGTTGTCGGATGAGCAGTTGGAGGCTTTGCTTCCTACGGTGAGCGCGGCTCCTTCGGG

TGATCCGCAGCAGATTTTCCTTGGCACGCCGCCTGGGCCGTTGGCGGACGGTAGCGTGGTGTTGCGTCTT

CGTGGGCAGGCGCTTGGTGGCGGTAAAAGGTTTGCGTGGACGGAGTTTTCGATTCCTGACGAGTCTGATC

CGGATGATGTGTCGCGGCAGTGGCGGAAGTTGGCTGGTGATACTAATCCTGCGCTGGGTCGTCGCCTGAA

TTTTGGGACCGTAAGCGATGAGCATGAGTCGATGTCTGCTGCCGGGTTTGCTCGGGAGCGGCTTGGCTGG

TGGGATCGTGGCCAGTCTGCTTCGTCGGTGATACCAGCCGATAAGTGGGTTCAGTCGGCTGTGGGTGAGG

CGGCTCTGGTTGGCGGGAAGGTTTTTGGTGTCTCGTTTTCTCGTTCTGGGGATCGGGTTGCTTTGGCGGG

TGCTGGCCGGACTGATGCTGGGGTTCATGTTGAGGTGATTGATGGGCTGTCGGGGACGATTGTTGATGGT

GTGGGCCGGTTGGCTGACTGGTTGGCGGTTCGTTGGGGTGATACTGACCGGATCATGGTTGCCGGGTCTG

GTGCGGTGTTGTTGCAGAAGGCGTTGACGGATCGTGGTGTTCCGGGTCGTGGCGTGATTGTGGCTGATAC

TGGGGTGTATGTGGAGGCGTGTCAGGCGTTCCTGGAGGGTGTAAGGTCTGGTGTGGTTTCTCACCCTAGG

GCTGATTCGAGGCGTGACATGTTGGATATTGCTGTGAGGTCGGCTGTGCAGAAGAAGAAGGGTTCTGCGT

GGGGTTGGGGTTCCTCGTTTAAGAATGGTTCTGAGGTTCCTTTGGAGGCTGTGTCTTTGGCTTATCTTGG

TGCGAAGATGGCGAAGGCTAGGCGGCGTGAACGGTCTGGTAGGAAGCGGGTGTCTGTGGTATGAACTCGG

ATGAGTTGGCTCTGATTGAGGGCATGTTTGATCGTATCCAAAGGTTGTCTTCGTGGCATTGCCGTATTGA

GGGCTACTATGAGGGCTCTAATCGGGTGCGTGATTTGGGGGTGGCTATTCCGCCGGAGTTGCAGCGTGTG

CAGACGTGGTGTCGTGGCCTGGTATTGCTGTGGATGCTTTGGAGGAGCGTCTGGATTGGCTTGGCTGGA

CTAATGGTGACGGCTACGGTCTGGATGGTGTGTATGCTGCGAATCGGCTTGCTACGGCGTCGTGTGACGT

-continued

```
TCACCTTGATGCACTGATTTTTGGGTTGTCGTTTGTGGCGATCATTCCCCAGGGGGATGGGTCGGTGTTG

GTTCGTCCGCAGTCGCCGAAGAATTGTACTGGCCGGTTTTCTGCTGATGGGTCTCGTTTGGATGCTGGTC

TTGTGGTGCAGCAGACGTGTGATCCTGAGGTTGTTGAGGCTGAGTTGTTGTTGCCTGATGTGATTGTTCA

GGTGGAGCGGCGTGGGTCTCGTGAGTGGGTTGAGACGGGCCGTATACCGAATGTGTTGGGTGCTGTTCCG

TTGGTGCCTGTTGTGAATCGTCGCCGTACGTCGAGGATTGATGGCCGTTCGGAGATCACTCGGTCGATTA

GGGCTTACACGGATGAGGCTGTGCGCACACTGTTGGGGCAGTCTGTGAATCGTGATTTTTATGCGTATCC

TCAGCGTTGGGTGACTGGTGTGAGCGCGGATGAGTTTTCGCAGCCTGGCTGGGTGTTGTCGATGGCTTCT

GTGTGGGCTGTGGATAAGGATGATGATGGTGACACTCCGAATGTGGGGTCGTTTCCTGTGAATTCTCCTA

CACCGTATTCGGATCAGATGCGTTTGTTGGCGCAGTTGACTGCGGGTGAGGCGGCTGTTCCGGAACGCTA

TTTCGGGTTTATCACGTCTAACCCGCCTTCTGGGGAGGCTTTGGCTGCGGAGGAGTCTCGGCTTGTGAAG

CGTGCTGAACGCAGGCAGACGTCGTTTGGTCAGGGTTGGTTGTCGGTTGGTTTCCTGGCTGCCCGGGCGT

TGGATTCGAGTGTTGATGAGGCCGCGTTTTTTGGTGATGTTGGTTTGCGTTGGCGTGATGCTTCGACGCC

GACTCGGGCGGCTACGGCTGATGCTGTGACGAAGCTTGTGGGTGCCGGTATTTTGCCTGCTGATTCTCGT

ACGGTGTTGGAGATGTTGGGTTTGGATGATGTGCAGGTTGAGGCTGTGATGCGGCATCGTGCCGAGTCTT

CGGATCCGTTGGCGGCGCTGGCTGGGGCTATTTCTCGTCAGACTAACGAGGTTTGATAGGCGATGGCTTC

GGGTGCTATGTCGAGGCTTGCTGCGACTGAGTATCAGCGTGAGGCGGTCAGGTTTGCCGGGAAGTATGCG

GGCTATTATGCTGAGCTTGGTCGTTTGTGGCATTCCGGGAAGATGACAGATGCGCAGTATGTGCGTTTGT

GTGTGGAGTTGGAGCGTGCCGGCCATGATGGTTCGGCGTCGTTGGCTGCCAGGTTTGTGTCGGATTTTCG

CCGGTTGAATGGTGTGGATCCGGGTTTGATCGTGTATGACGAGTTTGATGCTGCAGCCGCGTTGGCTAGG

TCGTTTTCGACTATGAAGATTCTTAAGAGTGACCCGGATAGGGCGAATGACACGATTGGTTCGATGGCTG

CGGGTGTTAATCGGCTGTCATGAATGCTGGCCGTGACACGGTTGAGTGGTCTGCGGGTGCGCAGGGTAG

GTCGTGGCGCAGGGTGACTGATGGTGATCCGTGCGCGTTTTGTGCCATGTTGGCTACGAGGTCGGATTAT

ACGACCAAAGAGCGGGCGCTTACTACTGGTCATACGCGGCGTCATAAGCGTGCCGGTAGGCGTCCGTTTG

GTTCGAAGTATCATGATCATTGCGGGTGTACGGTGGTTGAGGTTGTTGGCCCTTGGGAACCAAATAGGGC

TGATGCCGAGTATCAGAGGACGTATGAGAAGGCTCGTGAATGGGTTGATGATCACGGGTTGCAGCAGTCG

CCTGGCAATATTTTGAAGGCTATGCGTACTGTTGGCGACATGAGATGATGGTTTCCGGTTGTGTGCCGCC

GGTTATCGGTGCACAGGGTTGTCTCCCGCACGGGGGTCAACAATGTTGTGTTGTTTTCCGCAAGGAGTAT

AGGGTTAGGCTATGGCCGATCAAAAAGTTGAAGAACAGAATGTTGACAATGATGCTGTTGAGCCCGGAAA

GGGTGGAGACGTTGTTGATGTTGTGAAGGATGGGCAGGCTGCCGGCGATGATCATGCCGGTGATGTTTCC

GTGAAGGAGGAGTCTTCTTCTGGCACGGATTGGAAGGCTGAGGCCCGTAAGTGGGAGTCTCGTGCTAAAA

GTAATTTCGCCGAGTTGGAGAAGCTTCGCGCCTCGGATGGTGATGCGGGGTCTGTGATTGATGATCTTCG

CCGCAAGAATGAGGAACTCGAAGACCGGATTAATGGGTTTGTTCTTGGGGGTGTGAAGCGTGAGGTGGCT

GCCGAGTGTGGCCTGTCGGTGATGCGGTCGCTTTCTTGCACGGTGGCGACCGTGAAGCGTTGGTGGAGT

CTGCTAAGGCTTTGAAGGGTTTGATTGACCATAGTGGTGGTGGCGCGGGTGTGCGCCGTCTTGCGGGGAG

TGCCCCCGTTGATGATGTTAAACGACGTGAGGGTGTCGCGTTTGTGGATGCTCTTGTCAATAATTCTAGG

AGATGATTTGTGATGGCTGACGATTTTCTTTCTGCAGGGAAGCTTGAGCTTCCTGGTTCTATGATTGGTG

CGGTTCGTGACCGTGCTATCGATTCTGGTGTTTTGGCGAAGCTTCGCCGGAGCAGCCGACTATTTTGG

CCCTGTTAAGGGTGCCGTGTTTAGTGGTGTTCCTCGCGCCAAGATTGTTGATGAGGGCGAGGTTAAGCCT

TCCGCATCTGTTGATGTTTCGGCGTTTACTGCGCAGCCTATCAAGGTTGTGACTCAGCAGCGTGTCTCGG

ACGAGTTTATGTGGGCTGATGCGGATTACCGTCTGGGTGTTTTGCAGGATCTGATTTCGCCTGCTCTTGG
```

-continued

```
TGCTTCGATTGGTCGCGCCGTGGATCTGATTGCTTTCCATGGTGTTGATCCTGCTACGGGTAAGCCTGCT

GCGGCTGTGAAGACTTCGCTGGATAAGACGAAGCATATTGTTGATGCCACGGATTCTGCTACGACCGATC

TTGTCAAGGCTGTCGGTCTTATCGCTGGTGCTGGTTTGCAGGTTCCTAACGGTGTTGCTTTGGATCCGGC

GTTCTCGTTTGCCCTGTCTACTGAGGTGTATCCTAAGGGTTCGCCTCTTGCTGGCCAGCCTATGTATCCT

GCCGCCGGTTTCGCTGGTTTGGATAACTGGCGTGGCTTGAATGTTGGTGCTTCTTCGACTGTTTCGGGTG

CCCCGGAGATGTCGCCTGCCTCTGGTGTTAAGGCTATTGTTGGTGATTTCTCGCGTGTTCATTGGGGTTT

CCAGCGTAACTTCCCGATCGAGCTTATCGAGTATGGTGACCCGGATCAGACTGGGCGTGACCTGAAGGGT

CATAATGAGGTTATGGTTCGTGCCGAGGCTGTGCTGTATGTGGCTATCGAGTCGCTTGATTCGTTTGCTG

TTGTGAAGGAGAAGGCTGCCCCGAAGCCTAATCCGCCGGCCGAGAACTGATCTATTTGTTGCGATAATGT

TCATGCTGTGTGCAGGGGGTGGTGTTGATGGGTATCATTTTGAAGCCTGAGGATATTGAGCCTTTCGCCG

ATATTCCTAGAGAGAAGCTTGAGGCGATGATTGCCGATGTGGAGGCTGTGGCTGTCAGTGTCGCCCCCTG

TATCGCTAAACCGGATTTCAAATACAAGGATGCCGCTAAGGCTATTCTGCGCAGGGCTTTGTTGCGCTGG

AATGATACTGGCGTTTCTGGTCAGGTGCAGTATGAGTCTGCGGGTCCTTTCGCTCAGACTACACGGTCTA

GTACTCCCACGAATTTGTTGTGGCCTTCTGAGATTGCTGCGTTGAAGAAGTTGTGTGAGGGTGATGGTGG

GGCTGGTAAAGCGTTCACTATTACACCGACCATGAGGAGTAGTGTGAATCATTCTGAGGTGTGTTCCACG

GTGTGGGGCGAGGGTTGCTCGTGCGGGTCGAATATTAACGGCTACGCTGGCCCTTTGTGGGAGATATGAT

ATGACCAGTTTTCCTTACGGTGAAACGGTTGTGATGCTTCAACCGACTGTTCGTGTCGATGATCTTGGCG

ACAAGGTGGAAGACTGGTCTAAGCCTGTCGAGACTGTGTTTCATAACGTGGCCATCTATGCTTCCGTTTC

GCAGGAGGATGAGGCCGCGGGGCGCGACTCTGACTATGAGCATTGGTCGATGCTTTTCAAGCAGTCTGTT

GTGGGTGCCGGTTATCGTTGCCGGTGGCGTATCCGGGGTGTTGTGTGGGAGGCTGACGGGTCTCCTATGG

TGTGGCATCATCCCATGTCCGGTTGGGATGCGGGCACGCAGATCAATGTGAAGCGTAAGAAGGGCTGATA

GGTAGTGGCTCAGGATGTGAATGTGAAGCTGAACTTGCCGGGTATTCGTGAGGTGTTGAAGTCTTCTGGG

GTGCAGGGCATGTTGGCTGAGCGTGGTGAGCGTGTCAAGCGTGCGGCCTCGGCGAATGTGGGCGGTAACG

CTTTCGATAAGGCTCAATACCGTAATGGTTTGTCGTCGGAGGTGCAGGTTCACCGTGTTGAGGCTGTCGC

CAGGATTGGCACCACATATAAGGGTGGGAAGCGTATTGAGGCGAAGCATGGCACGCTGGCTAGGTCGATT

GGGGCTGCGTCGTGATCATTTACGGTGACCCAAGAGTCTGGGCTAAACGCGTGCTCAAGGATGATGGCTG

GCTGTCTGATATACCATGCACCGGGACAGTGCCTGACCGGTTTGAGGGTGACCTTATTTGGTTGGCTCTT

GATGGTGGCCCGCAGTTGCATGTTCGTGAGCAGGTTTTTTTGCGCGTGAATGTGTTTTCTGATACGCCGG

ATCGTGCTATGTCGTTGGCGCGTCGTGTTGAGGCTGTCCTGGCTGACGGGGTGGACGGTGACCCGGTGGT

GTACTGTAAGCGGTCTACTGGTCCTGATTTGCTGGTTGATGGTGCACGTTTTGATGTGTATTCGCTGTTC

GAGCTGATATGTAGGCCTGTCGAATCTGAGTAAACGTATTTGTTTTTGTTTTAATGTAATTGTTTGATAT

TTAATGGGGGTTGTGATGGCTGCAACACGTAAAGCGTCTAATGTTCGTTCAGCGGTTACTGGCGACGTTT

ATATTGGTGACGCGCACGCGGGTGATACTATTAAGGGTGTGGAGGCGGTTCCTTCCGGGCTTACCGCTTT

AGGGTATCTGTCGGATGACGGGTTTAAGATTAAGCCTGAGCGTAAAACGGATGATTTGAAGGCTTGGCAG

AATGCGGATGTTGTTCGCACTGTGGCTACCGAGTCTTCTATCGAGATTTCTTTCCAGCTGATCGAATCCA

AGAAAGAGGTCATCGAGCTGTTTTGGCAGTCGAAGGTTACTGCCGGAGCCGATTCGGGTTCGTTCGATAT

TTCTCCGGGTGCCACCACTGGCGTGCACGCTTTACTGATGGATATTGTTGATGGGGATCAGGTTATTCGC

TACTATTTCCCCGAGGTTGAGCTTATCGATCGTGACGAGATTAAGGGTAAGAATGGCGAAGTGTACGGGT

ATGGTGTGACGTTGAAGGCTTACCCTGCCCAGATTAATAAGACTGGTAATGCGGTGTCGGGTCGGGGGTG

GATGACGGCTTTAAAAGCTGATACTCCTCCGGTGCCTCCTAAGCCGCCTAAGCCTGAGCCGGATCCGAAT

CCGCCGTCTGAGAACTGATACACGATTTTAGGGATTGTTGATAGATGAGTGACACTGGTTTCACGTTGAA
```

-continued

```
GATTGGTGACCGTAGCTGGGTGTTGGCGGATGCGGAGGAGACGACTCAGGCTGTTCCTGCCCGCGTTTTC
CGTCGTGCCGCCAGGATTGCCCAGTCTGGGGAGTCTGCGGATTTCGCCCAGGTTGAGGTGATGTTTTCTA
TGTTGGAGGCTGCCGCCCCGGCTGACGCGGTGGAGGCCCTGGAGGGGCTTCCTATGGTTCGTGTGGCCGA
GATTTTCCGCCAGTGGATGGAATACAAGCCTGACGGTAAGGGTGCCTCCCTGGGGGAATAGTTTGGCTCC
ACGGCCTGATTGATGATTATCGTGGGGCCATCGAATACGATTTTCGCACTAAATTTGGTGTTTCTGTTTA
TAGTGTTGGTGGCCCGCAGATGTGTTGGGGTGAGGCTGTCCGGCTGGCTGGCGTGTTGTGTACCGATACG
TCTAGCCAGTTGGCGGCCCACCTGAATGGTTGGCAGCGCCCGTTTGAGTGGTGCGAGTGGGCTGTACTGG
ACATGCTGGATCATTACAGGTCTGCTAATAGTGAGGGGCAGCCGGAGCCTGTGGCGAGGCCTACGGATGA
GCGTAGGGCCCGGTTTACGTCCGGGCAGGTGGACGATATTTTGGCGCGTGTTCGTGCCGGTGGCGGGGTG
TCTCGCGAGATTAATATTATGGGGTGAATAGTGTATGTCTGGTGAGATTGCTTCCGCATATGTGTCTTTG
TATACGAAGATGCCTGGTTTGAAGGCGGATGTTGGTAAACAGCTTTCTGGGGTGATGCCTGCGGAGGGTC
AGCGTTCGGGTAGCTTGTTTGCTAAGGGTATGAAGTTGGCGCTTGGTGGTGCCGCAATGGTGGGTGCCAT
CAATGTTGCCAAGAAGGGCCTCAAGTCTATCTATGATGTGACTATTGGTGGCGGTATTGCTAGGGCGATG
GCTATCGATGAGGCTCAGGCTAAACTGACTGGTTTGGGTCACACGTCTTCTGACACGTCTTCGATTATGA
ATTCGGCTATTGAGGCTGTGACTGGTACGTCGTATGCGTTGGGTGATGCGGCTTCTACTGCGGCGGCGTT
GTCTGCTTCGGGTGTGAAGTCTGGCGGGCAGATGACTGACGTGTTGAAGACTGTCGCCGATGTGTCTTAT
ATTTCGGGTAAGTCGTTTCAGGATACGGGCGCTATTTTTACGTCTGTGATGGCGCGCGGTAAGTTGCAGG
GCGATGACATGTTGCAGCTTACGATGGCGGGTGTTCCTGTACTGTCTTTGCTTGCCAGGCAGACAGGTAA
AACCTCGGCTGAGGTGTCGCAGATGGTGTCGAAGGGGCAGATTGATTTTGCCACGTTTGCGGCTGCGATG
AAGCTTGGCATGGGTGGTGCTGCGCAGGCGTCTGGTAAGACGTTTGAGGGCGCTATGAAGAATGTTAAGG
GCGCCCTGGGTTATCTTGGTGCTACGGCTATGGCGCCGTTTCTTAACGGGTTGCGGCAGATTTTTGTTGC
CTTGAATCCGGTTATCAAGTCGGTGACGGATTCCGTGAAGCCCCTGTTTGCGTCGGTGGATCAGGGGATT
CAGCGGGTAATGCCGTCTATTTTGGCGTGGATTAACCGTATGCCGGGCATGATCACGAGAATGAATGCAC
AGATGCGCGCCAAGGTGGAGCAGTTGAAGGGCATTTTTGCGAGAATGCATTTGCCTGTCCCTAAAGTGAA
TTTGGGTGCCATGTTTGCGGGTGGCACCGCAGTGTTTGGTATTGTTGCTGCCGGTGTGGGGAAGCTTGTT
GCAGGGTTTGCCCCGTTGGCGGTGTCGTTGAAGAATCTGTTGCCGTCGTTTGGTGCTTTGAAGGGTGCCG
CCGGGGGCTTGGCGGCGTGTTTCGCGCCCTGGGTGGCCCTGTCGGGATTGTGATTGGCTTGTTTGCGGC
AATGTTTGCTACGAACGCCCAGTTCCGTGCCGCTGTTATGCAGCTTGTGGGGTTTGTTGGTCAGGCTTTG
GGGCAGATTATGGCCGCTGTGCAGCCGCTGTTTGGTTTGGTTGCTGGGCTGGTGGCACAGTTGGCGCCAG
TGTTCGGCCAGATTATCGGTATGGTGGCCGGGTTGGCTGCCCAGATTGTGCCTTTGATTAGTATGCTTGT
CGCCCGGCTGGTTCCTGTGATCACCCAGATTATTGGCATGGTGACACAGGTTGCGGCCATGTTGCTGCCT
ACGTTGATGCCGGTGTTGCAGGCTGTTGTTGCTGTGATACGGCAGGTTGTTGGCGTGATCATGCAGTTGG
TGCCGGTTTTGATGCCGGTGATTCAGCAGATTTTGGGTGCTGTCATGTCTGTTCTGCCACCTATCGTCGG
TCTGATCCGGTCGCTGATACCCGTCATCATGTCGATTATGCGTGTGGTGGTGCAGGTTGTTTCGGTTGTG
TTGCAGGTGGTGGCCCGCATTATTCCGGTTGTGATGCCAATTGTGACAGCTGTGATCGGGTTTGTTGCAC
GTATTCTTGGCGCTATTGTGTCTGCTGAAGCCCGCATTATTGGGACTGTCACTCGTGTCATCTCATGGGT
TGTGAATCATTTAGTGTCTGGCGTGAGGTCTATGGGCACGGCCATCTTGAATGGCTGGAATCATATTAGA
GCGTTTACGTCAGCGTTTATTAACGGTTTCAAGTCGATTGTTTCTGGCGGTGTGAACGCGGTTGTGGGGT
TTTTTGCCCGGCTTGGTTCTTCGGTTGCCTCCCATGTGAGGTCTGGTTTTAACGCGGCTCGTGGCGCTGT
TTCTTCTGCGATGAATGCTATCCGGAGTGTTGTGTCTTCGGTGGCGTCTGCTGTTGGCGGGTTTTTCAGT
```

-continued

```
TCGATGGCGTCTAGGGTTCGTAGTGGTGCTGGGCGCGGGTTTAATGGTGCCCGGAGTGCGGCTTCTTCTG

CTATGCATGCTATGGGGTCCGCTGTATCTAGCGGGGTGCATGGTGTGCTGGGTTTTTTCCGGAATTTGCC

TGGCAATATTCGGCATGCTCTCGGTAATATGGGGTCCTTGTTGGTGTCTGCTGGCCGTGATGTGGTGTCT

GGTTTGGGTAATGGTATCCGGAATGCTATGAGTGGCTTGTTGGATACGGTGCGTAATATGGGTTCCCAGG

TTGCTAATGCGGCGAAGTCGGTGTTGGGTATTCATTCCCCATCTAGGGTGTTTCGTGACCAGGTTGGCCG

TCAGGTTGTTGCCGGTTTGGCTGAGGGGATCACCGGGAATGCCGGTTTGGCGTTGGATGCGATGTCGGGT

GTAGCTGGACGGCTGCCTGATGCTGTAGATGCCCGGTTTGGTGTGCGATCGTCTGTGGGCTCGTTTACAC

CGTACGACCGGTATCGGCGTGCGAGCGAGAAGAGTGTTGTGGTTAATGTGAATGGACCCACGTATGGGGA

TCCGAACGAGTTTGCGAAGCGGATTGAGCGGCAGCAGCGTGACGCGTTGAACGCGTTGGCTTACGTGTGA

TTGGGGGTGTTGTGCATGTTTATTCCTGACCCGTCTGATCGTTCTGGTTTGACTGTGACCTGGTCTATGT

TGCCGTTGATTGGTAATGATCCGGAGCGTGTGCTTCATTTAACGGATTATACGGGCGCGTCTCCTGTCAT

GTTGTTGAATGATTCGTTGCGCGGTTTGGGTGTTCCCGAGGTTGAGCATTTTTCTCAAACTCATGTTGGG

GTGCACGGCTCGGAGTGGCGCGGGTTTAATGTGAAGCCTCGCGAGGTGACTTTGCCGGTGTTGGTGTCGG

GTGTTGACCCGGATCCGGATGGCGGGTTTCGTGACGGTTTTTTGAAAGCCTATGACGAGTTGTGGTCGGC

GTTTCCCCCGGGCGAGGTGGGGGAGTTGTCGGTTAAAACCCCGTCTGGTCGTGAGCGTGTGTTGAAGTGC

CGGTTTGATTCGGTGGATGACACGTTTACGGTTGATCCGGTGAACAGGGGCTATGCCCGCTATCTGTTGC

ATTTGACAGCCTATGACCCGTTTTGGTATGGGGATGAGCAGAAGTTTCGTTTCAGTAACGCGAAGTTGCA

GGATTGGTTGGGTGGCGGCCCTGTCGGCAAGAAGGGTACAGCGTTTCCTGTGGTGTTGACGCCTGGTGTT

GGTTCGGGCTGGGATAATCTGTCTAATAAGGGTGATGTGCCGGCGTGGCCTGTGATTCGTGTGGAGGGCC

CCCTGGAGTCGTGGTCTGTGCAGATTGATGGTTTGCGTGTGTCTTCGGATTATCCTGTCGAGGAGTATGA

TTGGATCACTATTGATACGGATCCTCGTAAGCAGTCTGCGTTGTTGGATGGGTTGAGGATGTGATGGAT

CGTTTGACGGAGTGGGAGTTTGCGCCTATTCCTCCGGGTGGTTCGAAGAGTGTGAATATTGAGATGGTTG

GTTTGGGTGCCATTGTTGTGTCGGTGCAGTACAGGTTTTTGAGGGCTTGGTGAATGGTTGATGGCTGGTC

TTGTTCCGCATGTAACATTGTTTACACCGGATTATCGCCGTGTGGCGCCTATCAATTTTTTGAGTCGTT

GAAACTGTCGTTGAAGTGGAATGGTTTGTCCACTTTGGAGTTGGTGGTGTCTGGTGATCATTCCAGGCTT

GACGGGTTGACTAAGCCGGGTGCACGGCTGGTTGTTGATTATGGTGGTGGCCAGATTTTTTCTGGGCCTG

TGCGTAAGGTTCATGGTGTGGGTCCGTGGCGTTCTTCGCGGGTGACTATCACGTGTGAGGATGATATCCG

CCTGTTGTGGCGTATGCTGATGTGGCCTGTGAATTATCGTCCTGGTATGGTTGGTATGGAGTGGCGTGCG

GACAGGGATTATGCCCACTATTCTGGTGCGGCGGAGTCGGTTGCTAAGCAGGTGTTGGTGGATAATGCTT

GGCGTTTTCCGCCTGGTTTGTTTATGAACGATGATGAGAGTCGTGGCCGCTATATTAAGGATTTTCAGGT

GCGGTTTCACGTGTTTGCCGATAAGTTGTTGCCGGTGTTGTCGTGGGCTCGGATGACTGTCACGGTGAAC

CAGTTTGAGAATGCGAAGTTTGATCAGCGGGGTTTGCTGTTTGATTGTGTGCCTGCTGTGACCCGGAAAC

ATGTGTTGACTGCCGAGTCTGGTTCGATTGTGTCGTGGGAGTATGTGCGTGACGCCCCTAAGGCTACGTC

TGTGGTGGTTGGTGGCCGCGGCGAGGGCAAGGATCGGCTGTTTTGCGAGGATGTTGATTCGGCGGCCGAG

GATGACTGGTTTGATCGTGTCGAGGTGTTTAAGGATGCCCGTAACACGGATTCTGAACATGTGCATCTCA

TTGATGAGGCTGAGCGGGTGTTGTCCGAGTCGGGGGCTACGTCGGGGTTTAAGATCGAGTTGGCTGAGTC

GGATGTGTTGCGGTTTGGGCCCGGCAATCTGATGCCAGGTGATCTTATCTATGTTGATGTGGGTTCTGGC

CCTATTGCGGAGATTGTTCGGCAGATTGATGTGGAGTGTGATTCGCCTGGTGATGGTTGGACGAAGGTGA

CACCTGTTGCGGGGGATTATGAGGATAATCCGTCGGCTTTGCTGGCGCGGCGTGTGGCTGGTTTGGCTGC

CGGTGTGCGGGATTTGCAAAAATTCTAGAATGATGGGGGTTTGTTGTGGGTATTGTGTGCAAGGGTTTTG

ATGGTGTGTTGACCGAGTATGATTGGGCTCAAATGTCTGGTCTGATGGGTAATATGCCGTCCGTGAAGGG
```

-continued

```
CCCGGACGATTTTCATGTCGGCACTACTGTTCAGGGTGCCACCGTGTTGTGTGAGGTTTTGCCGGGGCAG

GCTTGGGCTCACGGGGTGATGTGCACGTCGAATAGTGTTGAGACGGTGACAGGGCAGCTGCCTGGCCCTG

GCGAGACCCGATACGACTATGTGGTGTTATCTCGGGATTGGGAGCAGAACACGGCCAGGTTGGAGATTGT

TCAGGGTGGCCGTGCGGAGCGTGCCCGTGACGTGTTGCGTGCGGAGCCTGGCGTGTTCCATCAGCAGTTG

TTGGCGACTTTGGTGTTGTCGTCTAACGGGTTGCAGCAGCAGCTGGATCGGCGTGCTGTTGCGGCTAGGG

TGGCGTTTGGGGAGTCTGCTGCGTGTGATCCTACCCCTGTGGAGGGTGATCGTGTGATGGTGCCTTCGGG

GGCTGTGTGGGCTAACCATGCCAATGAGTGGATGTTGTTGTCTCCGCGTATCGAAACGGGTTCTAAGTCG

ATCATGTTTGGTGGTTCTGCTGTGTATGCTTACACGATCCCGTTTGCCCGCCCCTTTGGTAGTGCGCCTG

TTGTGGTGGCGTCTATGGCTACGGCGGCTGGGGGCACGGCACAGATTGATGTGAAAGCCTACAATATTAC

TAATAAGGATTTTAGTTTAGCGTTTATTACGAATGACGGGTCTAAGCCTTCTGGTGTGCCCGCGATAGCT

AACTGGATTGCTGTCGGCGTGTGACCGGGCTGTTGTTGTGGCGGATGGTGTGATGTTGGGGGCTGTGGT

GTCGTGGATTACTCCTGCACTGGTGGCCTCTATTTGTACCGCGTTGGCCACGGTTTTGGGTTCTGTTCAG

GCGGTCACGTCTAAATCTCGGAGGCGTTTGCGGCGGCTGTCGGCTCAGGTGGATGCTTTGGAGGAGTATA

CGTGGGGTGTGCGGTGTGAGGTTCGCCGGTTTAACGCCGGGCTTCCTGATGATGTGGAGCCGATGCATCT

CCCTGATGTGCCCGAGTTTTTGAAGGATACTGTTGATGGTGGAGGTGAGTAGGGTTGAGGGAGTTGGAGG

AAGAGAAGCGGCAGCGCCGCAATTTTGAGAAGGATTCCCTGATACTGTTGTTTTTGTCGCTTGTGCTGTT

GGTGGCGATGGCTGGGGGTGCTTTGCGGTATGGTTCTGTGGCTTCGCAAAGGGATTCGGAGCAGGCTAAA

GCCCAGTCGAATGGTACAGCCGCTAAAGGTTTGGCTGCCCGTGTGAAGCAGGCGTGTGCTTCGAGTGGGG

TGGAGTCTGCGCGGCTTCACCAGTCTGGCTTGTGTGTGGATGCTCAGCGTGTTGAGCGGAGTGTGCAGGG

TGTGCCGGGCCCGGCTGGTGTGCGTGGCCCGCAAGGCCCTGCAGGTGTGGATGGCCGGGATGGTGTTAAT

GGTTCGGCTGGGCTTGTTGGCCCTGTTGGTCCGCAGGGTTCTCCTGGTTTGAATGGTGTGAAGGGTCCTG

ACGGGTTGCCTGGTGTGAATGGATCGGATGGCCGTGATGGTGTTCCGGGTCGTACAGGTGCTGATGGTGT

GAATGGAGTTGCCGGGGCTGATGGTAAAGATGGCGCGAATGGCGCCGATGGTGAGCGTGGTGCTGTGGGC

CCTTCAGGTCCTGCCGGCCCCAAGGCGAACGGGGTGAGCGCGGTGCCGCTGGTGTGAACGGATCCGATG

GTAAAGATGGTAAGGATGGGCGCTCGGTGGTGTCCGTGTACTGTTCTGAGGGCCGCCTATTTGTGAAATA

TAGTGATGGTGTGGCTTCTACTATATCGGGTTCGGTTGCCTGCCAGAAGGTGAAACCGTCTCCTGTGGTT

ACCGTGTCATCCCACAAATAAAAGATAGAAAAGGAGTGACTTATGTCGATGGTGTTTGGGGGTGGTGTGT

GGTGAGATACATTCCTGCGGCGCATCATTCTGCCGGATCAAATAAGCCGGTGAACCGGGTTGTGATTCAT

GCAACATGCCCGGATGTGGGGTTTCCGTCTGCTTCGCGTAAGGGTCGGGCGGTGTCTACAGCAAACTATT

TTGCTTCCCCATCGTCTGGTGGTTCGGCGCATTATGTGTGTGATATTGGGGAGACGGTGCAGTGCTTGTC

GGAGTCTACGATTGGTTGGCATGCCCCGCCGAATCCGCATAGTTTGGGTATAGAGATTTGCGCGGATGGG

GGTTCGCACGCCTCATTCCGTGTTCCAGGGCATGCCTATACGCGGGAGCAGTGGCTTGACCCTCGGGTGT

GGCCCGCGGTGGAGAGGGCCGCCATCCTGTGTCGGCAGTTGTGTGATAAGCATGGTGTTCCGAAGAGGAA

ACTGTCTGTGGCTGATTTGAAGGCCGGTAAACGGGGTGTTTGCGGGCATGTGGATGTTACGGATGCGTGG

CATCAGTCGGATCATGACGATCCGGGGCCGTGGTTTCCGTGGACAAATTTATGGCTGTGGTGAATGGCC

ACGGCGGCGGTTCAAGTAGTGAGGAGTTGAGTATGGCTGATGTACAAGCGTTACATAATCAGATTAAACA

GTTGTCGGCACAGGTGGCCCAGTCGGTGAATAAGCTGCATCACGATGTTGGTGTGGTTCAGGTTCAGAAT

GGTGATTTGGGTAAACGTGTTGATGCCTTGTCGTGGGTGAAGAATCCGGTGACGGGGAAGCTGTGGCGCA

GCAAGGATGCTTTGTGGAGTGTCTGGTATTACGTGTTGGAGTGTCGTAGCCGTCTTGACAGGCTCGAGTC

TGCTGTCAACGATTTGAAAAAGTGATGGTGGTTTGTTGTGGGTAAACAGTTTTGGTTAGGTTTGCTAGAG
```

-continued
CGGGCGTTAAAGACTTTTGTTCAAACGTTTGTGGCTGTGTTGGGGGTTACCGCGGGTGTCACGTATACTG

CGGAGTCGTTTCGCGGTTTGCCGTGGGAGTCTGCCCTGATTACGGCCACGGTTGCTGCGGTCCTGTCGGT

GGCTACCTCGTTTGGTAGCCCGTCGTTTGTGGCCGGTAAGCCGAAAACCACGCCTGTGGATGCGGGTTTG

GTTCCGCCGGATGATCCCGGAATAGTGGAGCCTCACATGGTGGATGTGTCGGATCCTGGCATGATCGAGC

CTGCAGATGATGTGGATCTTGGTGTAGGCTATGTGCCGAAACATGCTGCCGAGTCGGAGGTTGGCACAGT

AGAGTCTACTGTTGCATAAGTGAATATAGATGTGTGCCCCAGCGGTGCTGCCACGATTGTGTGGTGGTTG

CCGCTGGGGCACTATTTTTGTATATTGCGGTGTGGCTATGATTCGTTGCTGTCGATGGTGTCTTCGAGCA

TCTGATACAGGTGGAGGCAGGTAGAGATCGTTTCGTTGGCCTGGTCGAGAACGTTCCGGCCGATAACGTT

TTTGTGGTTGTCGCGGTGGCGGATGATAGCCCACATGATCTCGCCGGCTGCCGCCTGTAATAGTTTGGCC

TGGTATGCGATTCCGGCGAGCCAGTCTAGTGCTTCCTGGCTTGCATAGGGGCTCTGGTTCTCGCTGTTGC

CGCGGGTGTTGCTGTTGTTTGTGGGGTGTCCTGCACTGTCGCAGAACCATAGGATTTCGCTGCACTCGTC

TAGCGTGTCTTGGTCGATAGCGAGATCGTCGAGGCTGACATTGTTGACGGTAAGGTTCACGTTGTCGAGG

GAGATGGGTACACCGTACTGGTTTTCGACACTGTCAACAATGTTTTGTAGTTGTTGCATGTTGGTGGGCT

GTTGTTGGACGATGCGGTGTATCGCTGTGTTGAGGGTGGTGTAGGTGATGTTGTGTGTGTTGTTCATCGT

GTTATGCCATTCCTTCGTTATCGTCTGGCATGTAGTATGTGCTGTTTGCGTACTCGGTTAACGTCATCAG

TGTTTGGTCTGCCCACTGTTTCACGGTTTGCCGGGTGATACCTAATCGTTGGGCGGCTGTGGCGTAGGTT

TGGTCGTATCCGTAGACTTCCCGGAATGCTGCCAGCCTAGCTAAATGTTTTCGCTGTTTGGATGGTTCAC

AGGTGAGTGTGTAGTCGTCGATGGCTAGCTGTAGATCGATCATGGTGACGATGTTGTTGCCGTGATGCTG

GGGGGCGGTTGGTGGGGTGGCATTCCTGGTTCGACGGATGGTTTCCATGGTCCGCCGTTCCAGATCCAT

TGGGCGGCTTGGATGATGTCGGCGGTGGTGTAGGTTCGGCTCACTTGGTCACCCCCTGAACATGTTGTCG

AGGTTGTTGGTGTTGCTGGTGTCGAATCGTCCGACGCAGTGGCAGTAGTCGTACATGAGTTTGATAATGT

GTTGGTGATCTCCCAAATAGGTGTTTCCGCTGATGCTGTAGGTGGCTGTGCCGTCTTTGCTGATGGTGTA

TTTGGCGGTGATGGTTTCGGGGTTTTCGGTGTCGGTGATGATGGCTGTGGTGGTGGCGCCTACTGTTTGT

AGCACGGTGGTTTGAGTTCCGTCGTCGATGGTGGTTTTAACCATGGTGTGTGTTCTCCCCTTTCAGTTGC

TGGTTTGGTTGTCGGCTAGATGAATGATATCGGATAAAGGTTTCGGCTGGTCGAGGTGTTGTATGGTTTT

GTTGGCTAAACGTTTGGCTACCCTGTAACACATTTTGGTGTAGTGTTTGTTGTCTAGGTTGTGGTATTGT

TCCCGCACCGCAATATATAGTAGAGAGTCTTGGTACAGGTCGTCTGCACTGATTGCGGGGTAGTGTGCGG

CTGTTTTGGTGCATGCCCGGTTGAGTGTGCGTAGATGATGGTCTGTGGCCCAAACCCACGATGCGGTGGT

GGCGAGGTCTGCTTTGGTTGGTCGTCGGCTCATGGCATCTCTTTCATCGGGCTATCTGGTAGTTGTTTGG

TGTTTTGTTGTTGATAGTGTAGCACACGAGTCCGGGGTTTCCGGTGGTGCCTGTCTTGTGCCGGTACCAT

GTGGATTCGCCTTCCATGGAGGGGCATTGGATGAAGGTGCGTTGTCCTTGTTCGGAGATTTCTAGGTGAT

GCCGGTGCCCGGCCATGAGAATATTAGATGTGGTGCCGTTGTGGAATTCTTGGCCGCGCCACCAATCATA

GTGTTGGTTGTTGCGCCATTGGTGCCCGTGGGCGTGCAGTATCCGTGTGCCTGCCACGTCGACGGTGGTG

GTCATTTCGTCTCGGCTGGGGAAGTGGAAGTGAAGGTTGGGGTATTGGTTGGTGAGCTGGTAGGCTTCTG

CGATGGCGCGGCAGCAGTCCACGTCGAAGGAGTCGTCGTAGGTGGTGACTCCTTTGCCGAATCGTACGGC

TTCGCCGTGGTTGCCGGGGATGGATGTGATGGTCACGTTTTTGCACTGGTCGAATTGGTGGATGAGTTGC

ATCATGGCCATGCGGGTGAGCCTGATTTGTTCGGTCAGGGGGTTTGTGTGCGCCAGGCGTTGTTGCCTC

CTTGTGACACGTATCCTTCGATCATGTCGCCGAGGAATGCGATGTGGACTCGCTCGGGTTTGCCTGCTTG

TTGCCAGTAGTGTTTTGCGACTATGAGTGAGTGTAGGTAGTCGTCGGCGAAGTGTGATGTTTCTCCTCCG

GGGATGCCTTTGCCGATTTGGAAGTCTCCTGCCCCGATGACGAAGGCTGCGGTTCTGTAGTCGGTGTGGG

TGTCTTGTTCGGGTTTTGGTGGCTGCCATTCGGCTAGCTTGTCGACGAGTTCGTCTACAGGGTAGGGGTT

-continued

```
GGTTGCGGGTTGGTGGTCGATGATTTTTTGTATGGATCGGCCGGTTTCTCCGTTGGGTAAGGTCCATTCA
GAGATGCGTGTGCGGCGTACGGTGCCGTTGGCTAGATTGTCGTCGATGGTGTCGATGGCGTTGTCGTGGT
TGGCTAGTTGTGTGAGTAGCCGGTCTATGTTGTCTATCACTGGGTATCCTCCTCGTGTGGGGTGGTGTTG
GCTTGTTTGCGGCGGTAGTCTTTGATGACGGTGGCGGAGATGGGGTATCCGGCTTGGGTGAGTTGTTGTG
CTAGCCAGGAGGCGGGTATGGACCTGTCTGCGAGCACGTCTGCAGCCTTATCACCGTAGCGTTGGATGAG
GGTTTCAGTTTTGGTTGCCATGGTGTCCTATCGGTTGTGTGGTGGGCTGCCATCCTGTGCGGCAGTCGCC
GTCGTGTCCTGGTTTGCGTGTGCACCACGATGTTGTTCCGTCTGTGTGGTTGAGTGTTTTACCGCACATG
ACGTTTTGGAGATGTTCCGGCAGCTGGTCATCCTGGTTGCTGGTTTGTGTGTCGAAGAGTGTTTTTTGGT
TGGTGAAATGCTCGGACACGGTGCCGTTGTGGACGGGTAGTATCCATGTTTTCCATTGTTGTTGTATCCG
GGTGTTCCAGTGGAATTGTTTGGCCGTTTTCGGCTTGTTTGGCGGTTTTGTAGTAGCCGACTAGTATG
CGCTGGTGTTCACTGTCGGGTGGGTTTTGGCCTCGCCAGTATTGTGCCGCCACGGCGTAACGGTTGTTTT
CTGTGAAGGTGTTCCAGCAGTATTCGATGATGTGTTGCAGTACACTATCGGGAATGTCTTGTGCCTGGTT
TTCGTTGAGCCATTCGGCTTCGATGATGCCGTGTATGGCGTGTTTGTCTGTGGTGGTGGGTTTGAACGAG
ATGCTCACAATGCGGGCCTGTCGTCTTGCATGAAATCGTTGAAGGATGATTCGCTTGCGCGGCGTGCCTG
GGTGATTTGCTGGTCGGTCCAGTCTGGGTGTTGCTGTTTCAGATAGTGCCAGCGGCACGCATTGTAGGTT
TCGTTCTGTAAGCGGGTGAGATTGTTTTCTTCGATGATTTGGTTCCACATGGCCCAGGATACGTCTAGCC
TGTCCAGGATTTCGAGGGCTGGGGTGTTGTATTGGTTGAGGAAGAGGGTTTCGTGGGTGTAGTATTCTTT
TTCATACTGTTCCCAGTTTGATTTGTTTTGCGATTTTTTGCCTTTAGGGTACACGGTTCGTGCAACTTTG
TGCATCTGTTTGCGCATGATGTCGGGGATGTGCACGTCGGGGTTTGAGCGGATCATGGATTTCATGCCAT
CATATGTGGCACCGTATTCCCGTATGATCTCGTATGGGTCGTCTCCGTCTTCCCATTTTTCGGCGATAAT
CTGGAGGCGTGCGTGTTGCCTTGATGCGGCGGTGCGGTCGCGGCGGTCGGGGATGGGGCAGGTTTCCATG
GTTGGCATCGGATCGGTTCTTTCTGGTTTCGTGTTGTTGACAGGTTTTACTGTAGCACAGTGTCTAGTGC
TTGTGTCAACCCTGTTTTTCCGGCCTGCAGGTAGGTGTCTGTGACATCCCCGACAGTGAGGGGCACATGG
GTGGCTTGGGGGAGCGCGGTTTGGATGGTTTGTGCCATCTGGTCGCCTGCCGAGTCTGGGTCTGACCAGA
TGTAGATGTGGTCGTAGCCTTCGAAGAATTTGGTCCAAAAGGTTTGCCACGAGGTTGCGCCGGGTAGGGC
TACTGCCGGCCATCCGCATTGTTCGAGGATCATGGAGTCGAATTCGCCTTCGCAAATGTGTATTTCGGCT
GCCGGGTTGGCCATGGCGGCCATGTTGTAGATGGAGCCTGTGTCCCCGGCTGGGGTTAAGTATTTGGGGT
GGTTGTGGGTTTTGCAGTCGTGTGGGAGTGAGCAGCGGAAACGCATTTTTCGTATTTCGGCTGGCCCTTC
CCAGACGGGGTACATGTAGGGGATGGTGATGCACTGGTTGTAGTTTTCGTGGCCTGGGATGGGGTCATTG
TCGATGTATCCAAGGTGGTGGTAGCGGGCTGTTTCTTCGCTGATGCCTCTTGCCGAGAGCAGGTCGAGTA
TGTTTTCGAGGTGGGTTTCGTAGCGGGCTGAGGCTTTCTGGATTCGACGACGTTCCGCAATGTTGTAGGG
GCGTATGCTGTCGTACATTCGGGTTTTCTTTCTCTAATCGTTGTTTCAGTTTGTGGAGTCCTCCTCCGAT
ACCGCATGTGTGGCAGTACCAGACGCCCTTGTCGAGGTTGATGCTCATGGAGGGCTGGTGGTCGTCGTGG
AACGGGCAGAGGATGTGTTGCTCGTTTCTGGACGGATTGTAGCGTATCTGGTGGCGTCTAGGAGGCGGC
AGGTGTCAGAGGTGTGGGAGGAGCTCGTTGAGGGTTGATACCACATAGGCTTCGCTCCAGGGTTTGTTGC
GCTGTTTCATGATGACGAGTCCGATGGTGGACTGGTTTTCGCGGTTTCGGTGGGTTTCGTAGTTGCGTGC
CTCCCGGCTGGCTTGTTTCACGAATTCGGCTAGGTGTGGCTGTCCTGCTTTGGCTTCGATCACATAGGTT
TTGTTGCCGGTTGTGAGGATGAGGTCGCCTTCGTCCTCGCGGCCGTTGAGGTGGAGGCGTTCGATATTGT
GGCCGGTGTCGCGTAGCTGGTGCAATAATCGTGTTTCCCATTCCGCGCCGGCCCGGCGGTTGCGTGCCTG
CTGTGTGGCCATCATAGTCCTTTGTGTGTTGTGGTCATGTTCCAGGGCTGTTTTTCAACCAGGGGTCCGA
```

```
AGAATGTGTATTCGGGGTAGGCTCTGAGCCGCTCATATTTTGTTCCGTCTGGGCTGGATTTGCCGGTTCT
CTGTTTCAACACTGCGATGCGTGCCTCTGCCGGGATGGTGAGCCCGTTGCCGTTGTCTTCGCCACCATAC
AGGGAGACTCCCAATATGAGTTGTGGTTTTTCGGAGAGGCCGTTTTTGATTTCCCGCCTAGCCGGGGGGT
GTTCAATATCGGAGCCGGTTTTGTCGGTGGCGTGGTGGGTGACAATAATGGTGGATCCGGTATCCCTACC
TAATGCTGTGATCCATTGCATGGCTTCTTGCTGTGCCTGATAGTCGGATTCGCAGTCTTGGATGTCCATC
AGGTTGTCGATAACAATAATGGGTGGGAAGGTGTTCCACATTTCCATGTAGGCTTGGAGTTCCATGGTGA
TGTCGGTCCAGGTGATGGGTGACTGGAATGAGAATGTGATGTGTTGGCCGTGGTGGATGCTGTCTCGATA
GTATTCTGGCCCGTAGTCGTCGATGTTGTGTTGTATCTGGGCGGTGGTGTGTGGGTGTTGAGTGAGATT
ATTCGTGTGGAGGCCTCCCAGGGTGTCATGTCCCCTGATATGTAGAGGGCTGGCTGGTTGAGCATGGCGG
TGATGAACATGGCTAGCCCTGATTTTTGGCTGCCGGACCGCCCCGCGATCATGACGAGATCCCCTTTGTG
TATGTGCATGTCCAGGTTGCGGTAGAGGGGTTCTAGTTGTGGTATGCGGGGCAGTTCGGCTGCTGTTTGG
GAGGCTCTCTCGAAGGATCTTTGGAGAGAGAGCATCGGAGCCTTTATCTATCTGTCTATCGGTTGGATGA
TGTTTTGGTGGTCAGATGGAGTCGATATCGATGTCAGTAGAGGCTGTGGTGTCGTCTAGCTGGCCGTTAT
CGCGTTTGTCTACGTATTCGGCAACCTTATCGTAGATGGCGTCGTCTAATGGTTTGAGCACGACCGCGTT
GAACCCGTTTTTGGTGCGCACGGTGGCGAGTTTAAAGGCCTGCTCCTCGCCAAGGTACGCTTCTAGGTCG
CGGATCATGGAGTGTGGGCGGTCGTTGTTGCCGCGGGCTTTCTCAATAATAGCGTTGGGGATGGTTTCTG
GGGTGCCGTTGTTGAGATCGTCTAGGGTGTGGAAGATGGTGACATCAGCGTAGATGCGGTCTGCGACCTG
TCCACCGTAGCCTTCGGTGTTGTGTTCTACGTCGCGGACTTTGAAGGCGATGGCGGTGGCGTCCTGGTTT
CGGGAGGGGTTGAAGAAGGTGCTGTTGCTGTTGTTGCGGTAGTTGGCGAGTCCCATAATGGTGTTATCCT
TTACTGTTGTGTCTGTTATTGTTGGCTTATATTGGTTTATCGGGTGAGGCTGTTTCGTTTAGTGCGGAAC
GCCTCAGACACGTCACTGTTACTAGTGATGGTCTTTTTGTACTGTTTGAGTAGGTCTGCTAGCTGTGTCT
TGCTGGTGGCTTTGTTGATCCGGTCAATGATGATGTCGTTTTCCTGATTGGCGATTTTGTTTACGTAGTC
TTTGGTGGCCTGATTGTATCGGTCTTGGAGGATGATGGATGCGCTGGCGATGAGGGTTGCGAGGTCCCAT
TCTTTGGATACGGTTTCGTCTTTCAATCCTCCCAATAAATCGATAATGGATTGTTTGATGTCTTCTGCGG
TGTCTCCGCGGATGACTGTCCATGGGGCAGCATAGTCTCCACCGTATTTGAGTGTGATAGTTAGCTTTTC
GTTGTCTGTGGTGTGCTCGTCGGTCACGTGTTTTCCTTTTCTTTACTGTCGGTTTGGGTTGGCTGTACGG
TGGTTTCTATCGGGTATCTGTACGAGTTTTTCCCGTTGACGGCCCAGCAGGCGTCCCTGACGGGGCATCC
TTTACAGAGTGTGGTGACGTGTGGGACGAAGATGCCTTGGCTGATTCCTTTCATTGCTTGACTGTACATG
GATGATACATGCCGGTAGGTGTTGTTGTCAAGGTCGTATAGTTCGGTTGCTGTGCCCTGCTCGGCCGATT
GCTCGTCTCCCTTGGTTGTGGCGGGTGTCCAAAACATGCCTTTCGTGACATGGATGCCATGTTGGTTGAG
CATGTACCGGTATGTGTGCAGCTGCATACTGTCGGCGGGTAGGCGTCCTGTTTTGAGGTCCAAAATGAAG
GTTTCACCCGTATTCGTATCTGTGAATACCCGGTCGATGTAGCCAACAATCTGGGTGCCGTCTTGGAGGG
TGGTTTCTACCGGGTATTCGATGCCTGGCTGGCCGTCAATAACAGCGGTAGCGTATTCTGGGTGGTTGCG
CCTCCATGTTTTCCACCGGTCCACAAAGATGGGGCCGTACATCATCCACCAATTGTAGTCTTTCTTGTTG
GGGCCCCGCTTTCGCACATGTTTTTGCACACTCGGCCGGAGGGTTTGATGTTTGTGCCTTCGGATTCGG
CGAGGGCGACTTGGGTGTCGAAAATGTTTGTGAAGGATGAGAGTTTGTCTGGCAGTTCAGGGTATTCGTC
GGGATTGTACAGGTGTAGGTCGTATTGTTCGGTGATGTGGTGTATGCGCTTCCGGCGATGGTGGCGTAC
CAGGTGTGGTGTTGGGTGTGGTAGCCGTGTTGGAGGCGCCATTTTTCACCACATTCGGCCCACTGTGACA
GTGATGAGTAGGAGATGTGGCCTGGATGGTGGATGGTTTTCGGGTATTGTGCTAGGGGCATTACTTGCCG
CCTTTGTGGGTGTTCCATGGGTTGCGGGTGTCTACCCCTGCATCGTGTTGCTGGTAGGCGAGGAGTGCGA
GGCAGTGCCATGCAGCATGGGCCAGATGCGGTAGCCCGGATTCATAATCGAGGTTGTTTCCTTGCTGCCA
```

-continued

```
TGATAACAGGTGCCTGTAGAGGGCGTCAACGCTGTGGCTCCACGGGTATCCGCCGGTCCAGTTGTTGTCG

CCGTATTTGGTGGCACCGTATCCGGCCACGGAGCCGAGGGCGTGGAGGGCTGTAGGGTCGATGAGGGATA

GCCTGCAAAGTTTGAGTTCTTTCTTGGCGCCAGTATCAGGGTTGGTGTACATGCTGGTGGGCTCATCCAT

GGTGTGTGTGCTCCTTACGTGTGGGGTTACTGGTTGGGGTTGTGGGCGAGTGCTACGGCGAGGATGATGA

TGGCGAGGGTTTCCGCGATCAGGATGGGTGTTGTGATCATTTGTGGTTTTTTGGCTGGTAGGTGAGGGTT

GAGGCACCCAGGAGGATAGTGAGGGCGCATGCGGCAATAATGGCGAGAGCTGCCTTGTGTGGGGTACCGG

TGGCGTACATCCATGTGATGATGGCGCCCTGGATCCAGGCCAGTGTGGTGAAGAACGTTTCGTAGCTGTG

CAGCTCGATACTGTTGGGTGTGTTCATGCTTGTTCCTGAAGAATGGTGTTGATGGTTTTGTAAATGTTGT

ACAGGTCGGCTTCGATGGTTTGTAGCTGTTTGATTTGGTGGTCGAGATTGATGTGTGGGTTGAGGGTGTT

GATGCGGGAGGCGATGTCGGTGGCTGTGCGTAGTGTGCCGCCGGTGTGGTGAATGATGTGTGCCGTGTCG

GCGAGTCCGGTGGTGACAGCGTAGTGGGAGAGGAGAGGCATAGCGGTCCTTGACGGGGTTACTGTTGCGG

GTTGATGTTGAGGTCGGTGACGTTGGGGTGTTCTTCTGTTCCGGTGACGAGGCAGTGGACGGTGACTGGG

AGTTTGGATGCTCCCGGCTGGCGGACGGTGGCGCCGTAGACGATGCTGAATGTGTCTTTGTGTGCTCCGA

TGACTTTGTGGAGTTGGAGGTCGATGTCGGGGTTGCCGTTCCATTTGACACCGTTTTCTGCGACTGCCTG

GGTGGCTTTCTGGTCGCAAGCATGGGCTGCCGTAATCATGGTCAGGCCGGTGGAGGTTTCTTCACCCCTT

GCTTGGGCTTGCTTGTGGGCTTTGGCCTGCTCTGCTTGTAGGGAGTGGACTGCTGCGGCCTGGCGGGCTT

TCTTCTCGGCTTTGCGCTGTTGGACGGTTTTGGGTGTCCATTCAGTGTTAGCTGTGGTGGCCTGTGGGGC

TGGCTGTGATGCGAGTGGCGGGTTGTCGTCTGGGGCTGGCATGAATGAGGCGGCGGCGATGATGGCGGCT

GTGATTCCGGCGATGGTGTAGCCTTTTTTCTTGTTCATGACTGTTGTCCCCTTTCCGGGGTGTTGTTCGT

TGCTGACATGATTAATCATGGTGTGGGCGGTGGCCCATGTCAAGGCTGCGCTCAACGATTGTGAGCGTTT

GGTGTGTGGCTAGGGGTTTTATCGAGCACACAGAGTGAGTAGGTGGCCAACATTGATGCGGCTCACATTC

CAGTAGAGTTGTGTGGCTTCCCCACTGGTGAGTGGCTTCCACTCGTTGTGGCTGAACACGGTGCCATCGG

ATGCGATGAACGTGTTGGGGCGTAGCTTGTGGAGTTCGGCTTCCACGCTCTGCCGGTAGGCTTCGGCGAG

GCCCTCAAAATCGAGGTGGTCGCAGGAGAGGTTTTCGAGGCGTGTCAGGTCGAAGGGTGTGGGGCAGTCG

TAGCTGGCGGGGGTGTAGAGCTGGGTGAAGTGGTTGGCGATCTTCTGCATGATGATGTCCTTTTCGTTGC

TGATAACGTTGTTGAGGGTTTATCGGGTGGATGCGACCAGGATGGCGTCTACGTCGATCATGTCGATCAT

GTCGTGGAGTTCCTCGGCTTCGTTCTCGGAGAGGTGGCGCCAGTCGTAGTCTCCGTATACGGCGCCGTCG

AGGGTGACAGTCCACAGTGGCCGGATGAGTCGTACGGCTTCTTGTACTTTAGCGTGGTACATGCGGCGCA

CCATATCGAGATCGATGTCGTCTGAATGGTTTCCGGTGAGGCTGTGGAGGCTGAGCGGGTCGATTTCTGT

CTGCCTGTAGAGGGATGTGAAGGATGGGGTGATGAGTGTGCCATCCATGAGTGTGCTCCTTTCGGTGGTG

TAGGGGTTGTTGTGGTTTCTAGAGTGTGTGGGCTGTGACCCACAGTCAAGGTGGCGCTCAAACCCAGTGA

GCGTTTCATGCTGGAGTGTTGGGTGTGGCAGATGATCTAGCGAGTCAAGGTGCCGAGCTGAGACATAAGA

TCTATCATCTAGGTGTGTGAGATGTATCACATCCTCCTGGCTTGATGTGCACCCTCGAGGCTACTCTGCC

GATCTGACGTGGAGGGTGTAGCCCAGAAAGGCCGTTTAAAGCCTTCGCACGGCGCCTAGGAGCGCCTTAC

AGGGTGGGGCTAGGTATTCATACCCCCAAGCAATTCTGATCGATTCTAGACGCCTCCCATGAGCCCGAT

ACACGATCAGCCATCTCTGCATAGATCATCAGCCCCTATCCTGGTTAGCTAAGCCTCAACTATGTGGACA

GTGTGGGATGCTAAGGGGGAAGAAGGACACGGTAAAAGAAAGAGGGGGAGTATCAGCCTTCAAGCCTTAA

GGTCTTAGCAGTTAGCACCGAGCCCCCTCAAGGGCTCGGCATCAGCCCGAACAGGCACAGCCCTGAAAAG

GGTACACACCATCAGGGAAGGCTTTCGAGTACGAGGAGCCTCAGCGACGAGTACTCGAAAGCCTGAGGGA

ACACCCTCAGCACTGATGGGCCTAGCGTATTCGGAAAGGACACAAGAGTCAAGTGTGACAGCTGTCCGGG
```

-continued

```
AGTGAAACCTGTTCTGACTAGGGGTTTCAGCCTGAACCACCCTCAAAGGTTACAAGACTCTAAGAAAATT

TAAGAAAACTCTTAGGAAGAAAGTTGTGTTCATATCCCCCTAAAAACACCCAAAATAGCCCTCAAACCCG

CCTATAGAGCCAAACAGTCAAGTTTGACTCGTCTAAACGGCGTATGATAGGCTGGACAGGTAGCCAGCTG

GACGCGAGGCCAGAAAGTGCTGACGCACTTCCCGACCTCGCTTACCATCAGTCTACCAAAGACTTAAAAG

CTTCAAGGCTTAGCCCTTAAGGATCTAAGTTACTATAAAAGCTTTAAAAGCTTTAAGAGCTTAACACTTA

AGTTAAGTATAAAACCTTAAAGGCTAAGCACTTAAGGATATAAACTTAACATCAGTGTTTAAGACTTTAA

GAGTTAAAGTAACTATTAAGACTTAAAGGCTTATAAGCTTTAATACTTTAAGTAACTATAAGACTTTAAA

AACCTTCAGTACTTAAAGTTAACCATCAGTCTTAAACTTTAATATTATAACCTATAAGTCTTAAAGCTTA

TAGGTATAATAATATAATATAAGTATTAAAGCTTATAAGTTATAAAAGTTTTAGAAGAGTTAAAGGGTTA

ACTTCTTTACTTCTCTTCTCTCTTTGGTTCTTTCTCTCTTCTCTTCTTTTCTTCATCAGGGGAGAAGAGG

AACCTTTACCGTCAACGCTGATGGACTTTTCGCCGTGTGTCTCGTGTGCTTCTGGTCGCAAGCTCCCATC

GCACACTCCCCACACTCTGACACTCGTGTCCCTTTACGGCTTAGCGTGTTCGGCTGAAGGCGTACGGCGT

GTCACGCTTAAACCCTTAACACCAGGTAAGACTTAAAGTACATATTATAAGTAGAAGACTTTAAAACCTT

TAAGGTGTTCCCGCTGAGCCTGTGTCCTTCAACGCTAGGCGCTAAGCCTTGAAACGTGAACACCCACCCC

ACCTTTTTTCTTTCGTGTCCTTCTTCTTTTGACACCGCTGGGGGGGTAGTGGAGACAACAAACACCCCGG

CACAAAAAGAACACCCCCCTAAACGAACAAAACAGGTCCTAGGATCGACTAGCAGGGCACCGGTAGGAT

ATTCCTACCACCAATGGTTCCCAGGCCGCTAGAGGAGCAATGAGAGGCTCACAGGGACCATAGGTGATTG

GGGGATGTGATGGCACACACCAACCGCACAGCATCCTCCGCCCATCGGCGCTGGCGGGCAAGGCTCATCA

CCCAAGCCCAACAACAAGGCCAAACCGAATGCCCACTCTGCGGAGCCCAGATAGCCTGGGGCACACACGA

TCTGCCAACCAGCCCCGAAGCCGACCACATCACACCCGTCAGCCGCGGAGGACTCAACACCCTCGACAAC

GGGCAAATCATCTGCAGAACATGCAACAGAAGCAAAGGCAATCGCAGCGAACCAAACATTAGTTTCCAAC

AACAAACCACAAAAACATTGATCCCATGGTGAAAAAAACCACAAACCCCACGGGAACCACCCCTGGCACA

CCCGTGCAAGACCTCGTACGGCTT
```

*Propionibacterium* phage P9.1 Gene 3 protein product-portal protein
encoded by residues 1881-3206 of SEQ ID NO: 12
GenBank accession No. AFT97459.1

SEQ ID NO: 13

MNSDELALIEGMFDRIQRLSSWHCRIEGYYEGSNRVRDLGVAIPPELQRVQTVVSWPGIAVDALEERLDW

LGWTNGDGYGLDGVYAANRLATASCDVHLDALIFGLSFVAIIPQGDGSVLVRPQSPKNCTGRFSADGSRL

DAGLVVQQTCDPEVVEAELLLPDVIVQVERRGSREWVETGRIPNVLGAVPLVPVVNRRRTSRIDGRSEIT

RSIRAYTDEAVRTLLGQSVNRDFYAYPQRWVTGVSADEFSQPGWVLSMASVWAVDKDDDGDTPNVGSFPV

NSPTPYSDQMRLLAQLTAGEAAVPERYFGFITSNPPSGEALAAEESRLVKRAERRQTSFGQGWLSVGFLA

ARALDSSVDEAAFFGDVGLRWRDASTPTRAATADAVTKLVGAGILPADSRTVLEMLGLDDVQVEAVMRHR

AESSDPLAALAGAISRQTNEV

*Propionibacterium* phage P9.1G ene 7 protein product-hypothetical protein
encoded by residues 5610-6089 of SEQ ID NO: 12
GenBank accession No. AFT97463.1

SEQ ID NO: 14

MQGVVLMGIILKPEDIEPFADIPREKLEAMIADVEAVAVSVAPCIAKPDFKYKDAAKAILRRALLRWNDT

GVSGQVQYESAGPFAQTTRSSTPTNLLWPSEIAALKKLCEGDGGAGKAFTITPTMRSSVNHSEVCSTVWG

EGCSCGSNINGYAGPLWEI

SEQ ID NO: 15

*Propionibacterium* phage P9.1 Gene 9 protein product-hypothetical protein
encoded by residues 6445-6735 of SEQ ID NO: 12
GenBank accession No. AFT97465.1

MAQDVNVKLNLPGIREVLKSSGVQGMLAERGERVKRAASANVGGNAFDKAQYRNGLSSEVQVHRVEAVAR

IGTTYKGGKRIEAKHGTLARSIGAAS

-continued

*Propionibacterium* phage P9.1 Gene 16 protein product-hypothetical protein encoded by residues 12238-13398 of SEQ ID NO: 12
GenBank accession No. AFT97472.1

SEQ ID NO: 16

MMAGLVPHVTLFTPDYRRVAPINFFESLKLSLKWNGLSTLELVVSGDHSRLDGLTKPGARLVVDYGGGQI

FSGPVRKVHGVGPWRSSRVTITCEDDIRLLWRMLMWPVNYRPGMVGMEWRADRDYAHYSGAAESVAKQVL

VDNAWREPPGLFMNDDESRGRYIKDFQVREHVFADKLLPVLSWARMTVIVNQFENAKEDQRGLLFDCVPA

VIRKHVLTAESGSIVSWEYVRDAPKATSVVVGGRGEGKDRLFCEDVDSAAEDDWFDRVEVEKDARNTDSE

HVHLIDEAERVLSESGATSGFKIELAESDVLRFGPGNLMPGDLIYVDVGSGPIAEIVRQIDVECDSPGDG

WTKVTPVAGDYEDNPSALLARRVAGLAAGVRDLQKF

---

We claim:

1. A *Propionibacterium acnes* (*P. acnes*) bacteriophage mutant comprising a Clustered Regularly Interspaced Short Palindromic Repeats (CRISPR) escape mutation, wherein the bacteriophage mutant is selected from the group consisting of P9.1-2A, P9.1-2B, P9.1-3, and P9.1-4.

2. A pharmaceutical composition comprising one or more bacteriophage mutants of claim 1 and an antimicrobial agent.

3. A pharmaceutical composition comprising one or more bacteriophage mutants of claim 1 and an anti-acne agent.

4. A pharmaceutical composition comprising one or more bacteriophage mutants of claim 1, wherein the pharmaceutical composition is formulated for topical use.

5. A *Propionibacterium acnes* (*P. acnes*) bacteriophage mutant capable of infecting *P. acnes* RT4, *P. acnes* RT5, or *P. acnes* RT4 and *P. acnes* RT5, wherein the bacteriophage mutant is selected from the group consisting of P9.1-2A, P9.1-2B, P9.1-3, and P9.1-4.

6. A pharmaceutical composition comprising the bacteriophage mutant of claim 5 and at least one of an antimicrobial agent and an anti-acne agent.

7. A pharmaceutical composition comprising the bacteriophage mutant of claim 5, wherein the pharmaceutical composition is formulated for topical use.

8. A method for treating acne in a subject in need thereof comprising administering to a subject a therapeutically effective amount of a composition comprising one or more *Propionibacterium acnes* (*P. acnes*) bacteriophage mutants capable of infecting bacteriophage resistant *P. acnes*, wherein the bacteriophage mutant: (i) is capable of infecting *P. acnes* RT4, *P. acnes* RT5, or *P. acnes* RT4 and *P. acnes*

RT5, (ii) comprises a Clustered Regularly Interspaced Short Palindromic Repeats (CRISPR) escape mutant, and (iii) i and ii, and is selected from the group consisting of P9.1-2A, P9.1-2B, P9.1-3 and P9.1-4.

9. The method of claim 8, further comprising administering to the subject an additional therapeutic agent.

10. The method of claim 9, wherein the additional therapeutic agent comprises an anti-acne agent.

\* \* \* \* \*

SEQUENCE LISTING

<160> NUMBER OF SEQ ID NOS: 156

<210> SEQ ID NO 1
<211> LENGTH: 36
<212> TYPE: DNA
<213> ORGANISM: Propionibacterium phage P9.1

<400> SEQUENCE: 1
gaagtcttct ggggtgcagg gcatgttggc tgagcg                              36

<210> SEQ ID NO 2
<211> LENGTH: 36
<212> TYPE: DNA
<213> ORGANISM: Propionibacterium phage P1.1

<400> SEQUENCE: 2
gaagtcttct ggggtgcagt ctatgttggc tgagcg                              36

<210> SEQ ID NO 3
<211> LENGTH: 36
<212> TYPE: DNA
<213> ORGANISM: Propionibacterium phage P1.1

<400> SEQUENCE: 3
taagattgag ttggctgagt cggatgtgtt gcggtt                              36

<210> SEQ ID NO 4
<211> LENGTH: 36
<212> TYPE: DNA
<213> ORGANISM: Propionibacterium phage P9.1

<400> SEQUENCE: 4
caactgcgcc aacaaacgca tctgatccga atacgg                              36

<210> SEQ ID NO 5
<211> LENGTH: 36
<212> TYPE: DNA
<213> ORGANISM: Propionibacterium phage P1.1

<400> SEQUENCE: 5
caactgcgcc aacagtctca tctgatccga atacgg                              36

<210> SEQ ID NO 6
<211> LENGTH: 36
<212> TYPE: DNA
<213> ORGANISM: Propionibacterium phage P9.1

<400> SEQUENCE: 6
caacgcagca atctcagaag gccacaacaa attcgt 36

<210> SEQ ID NO 7
<211> LENGTH: 29348
<212> TYPE: DNA
<213> ORGANISM: Propionibacterium phage P1.1

<400> SEQUENCE: 7

| | | | | | |
|---|---|---|---|---|---|
| agtgaaatac | ctcccctttg | tggatttgtc | tgtttgtcga | cttttttgtgt | tggtggtgag | 60 |
| tgttgtgcag | cctgagcttc | ctgatagtcg | tgattggtgt | ggggagacgc | gtcgttggtg | 120 |
| gagtgtgtgg | ggtgatgata | gccgcgcgca | gtatgtgtct | gatgaggagt | ggctgtttct | 180 |
| catggatgct | gcggtgattc | atgattgtgt | gtggcgtgag | ggtcgcgcgg | atttggtggc | 240 |
| ttcgcttcgt | gctcatgtga | aggcttttat | gggcatgttg | gatcggtatt | cggttgatgt | 300 |
| ggcgtctggt | ggccgtggtg | ggggttctgc | ggtggcgatg | attgaccggt | ataggaagcg | 360 |
| taggggggcc | tgattaggtg | tctggtgttg | ttgggtctca | ggtgcctcgt | caccgtgtgg | 420 |
| ctgcggcgta | ttcggtgtct | gctggcggtg | atgctgggga | gttgggtcgt | gcgtatgggt | 480 |
| tgacgcctga | tccgtggcag | cagcaggtgt | tggatgattg | gcttgctgtt | ggtagtaatg | 540 |
| gcaggcttgc | ttcgggtgtg | tgtggggtgt | ttgtgcctcg | ccagaatggc | aagaacgcga | 600 |
| tccttgaggt | tgtggagttg | tttaaggcga | ctattcaggg | tcgccgtatt | ttgcatacgg | 660 |
| ctcacgagtt | gaagtcggct | cgtaaggcgt | ttatgcggtt | gcgttcgttt | tttgagaatg | 720 |
| agcggcagtt | tcctgacttg | tatcgtatgg | tgaagtcgat | tcgtgcgacg | aatggtcagg | 780 |
| aggctattgt | gttgcatcat | ccggattgtg | ccacgtttga | gcgtaagtgt | ggttgtccgg | 840 |
| gttgggggttc | ggttgagttt | gtggcccgta | gccggggttc | ggctcgcggg | tttacgttg | 900 |
| atgatttggt | gtgtgatgag | gctcaggagt | tgtcggatga | gcagttggag | gctttgcttc | 960 |
| ctacggtgag | tgctgccccg | tctggtgatc | cgcagcagat | tttccttggc | acgccgcctg | 1020 |
| ggccgttggc | ggatggttct | gtggtgttgc | gtttgcgtgg | gcaggctttg | tcgggtggta | 1080 |
| aaaggtttgc | gtggacggag | ttttcgattc | ctgacgagtc | tgatccggat | gatgtgtcgc | 1140 |
| ggcagtggcg | gaagttggcg | ggggatacga | atccggcgtt | gggtcgtcgt | ttgaattttg | 1200 |
| ggaccgtgag | cgatgagcat | gagtcgatgt | ctgctgccgg | gtttgctcgg | gagcggcttg | 1260 |
| gctggtggga | tcgtggccag | tctgctgcgt | cggtgattcc | tgcggataag | tgggctcagt | 1320 |
| ctgcggtgga | tgaggcggct | ctggttggct | ggaaagtgtt | tggtgtctcg | ttttctcgtt | 1380 |
| ctggggatcg | ggttgctttg | gcgggtgctg | gccggactga | tgctgggggtt | catgttgagg | 1440 |
| ttattgatgg | gctgtcggga | acgattgttg | atggtgtggg | ccggttggct | gactggttgg | 1500 |
| cggttcgttg | gggtgatact | gaccggatca | tggttgccgg | gtctggtgcg | gtgttgttgc | 1560 |
| agaaggcgtt | gacggatcgt | ggtattccgg | gccgtggcgt | ggtggttgct | gatactggtg | 1620 |
| tgtatgtgga | ggcttgtcag | gcgtttcttg | agggggttcg | ttcgggtgtt | gtgtctcatc | 1680 |
| ctcgtgctga | ttctcgccgt | gacatgttgg | atattgctgt | gaggtcggct | gtgcagaagc | 1740 |
| gtaagggtgtc | tgcgtggggt | tggggttcct | cgtttaagga | tggttctgag | gttcctttgg | 1800 |
| aggctgtgtc | gttggcgtat | cttggtgcga | agatggcgaa | agcgaagcgg | cgtgaacggt | 1860 |
| ctggtaggaa | gcgggtgtct | gtggtatgaa | ctcggatgag | ttggctctga | ttgagggcat | 1920 |
| gtacgatcgt | attaagaggt | tgtcttcgtg | gcattgtcgc | attgagggct | actatgaggg | 1980 |
| ctctaatcgg | gtgcgtgatt | tgggggtggc | tattccgccg | gagttgcagc | gtgtgcaaac | 2040 |

```
ggtggtgtcg tggcctggta tagctgtgga tgctttggag gagcgtctgg attggctggg    2100
ctggactaat ggtgacggct acggtttgga tggtgtgtat gctgcgaatc ggcttgctac    2160
ggcttcgtgt gatgtgcatt tggatgcact aattttgggg ttgtcgtttg tggctgttat    2220
cccccagggg gatgggtcgg tgttggttcg tccgcagtca ccaaagaatt gtactggccg    2280
gttttcggct gatgggtctc gtttggatgc tggccttgtg gtgcagcaga cgtgtgatcc    2340
tgaggttgtt gaggcggagt tgttgctgcc tgatgtgatt gttcaggttg agcggcgtgg    2400
gtctcgtgag tgggttgaga cgggccgtat cgtgaatgtg ttgggtgcgg ttccgttggt    2460
gcctattgtg aatcgtcgcc gtacttctag gattgatggc cgttcggaga ttacgaggtc    2520
tattagggct tacacggatg aggctgtgcg cacactgttg gggcagtctg tgaatcgtga    2580
tttttatgcg tatcctcagc gttgggtgac tggcgtgagc gcggatgagt tttcgcagcc    2640
tggctgggtc ctgtcgatgg cttctgtgtg ggctgtggat aaggatgatg atggtgacac    2700
tccgaatgtg gggtcgtttc ctgtcaattc gcctacaccg tattcggatc agatgagact    2760
gttggcgcag ttgactgcgg gtgaggcggc tgttccggaa cgctatttcg ggtttatcac    2820
gtctaaccca cctagtgggg aggctttggc tgccgaggaa tctcggcttg tgaagcgtgc    2880
tgagcggcgt caaacgtcgt ttggtcaggg ctggctgtcg gttggtttcc tggctgccag    2940
ggcgcttgat tcgagtgttg atgaggccga tttttttggt gatgttggtt tgcgttggcg    3000
tgatgcttcg acgcctaccc gggcggctac ggctgatgct gtgacgaagc ttgttggtgc    3060
cggtattttg cctgctgatt ctcgtacggt gttggagatg ttggggcttg atgatgtgca    3120
ggttgaggct gtgatgcgtc atcgtgctga gtcgtctgac ccgttggcgg cactggctgg    3180
ggctatatcg cgtcaaacta acgaggtttg ataggcgatg gcttcggggg ttgaggcgag    3240
gcttgctgcg actgagtatc agcgtgaggc ggtcaggttt gctgggaagt atgcgggcta    3300
ttattctgag cttggtcgtt tgtggcgtgc cggcaggatg agtgacacgc agtatgtgcg    3360
tttgtgtgtg gagttggagc gtgccggcca tgatggttcg gcatcgttgg ctgccgggtt    3420
tgtgtcggat tttcgccggt tgaatggtgt ggatcctggt ttgattgtgt atgacgagtt    3480
tgatgctgcg gcggctttgg ctaggtcgtt ttcgactatg aagattcttg agagtgaccc    3540 ggataggcg aatgacacga ttgatgcgat ggcggcgggt tttgatcggg ctgtcatgaa    3600
tgctggccgt gacacggttg agtggtcggc gggtgcgcag ggtaggtcgt ggcgtcgggt    3660
tactgatggt gatccgtgtg cttttttgtgc catgttggct acgaggtcgg attatacgac    3720
taaggaacgg gcacttacta ctggtcatac tcggcgtcat aagcgtggtg gtaagcgtcc    3780
gtttggttcg aagtatcatg atcattgtgg ttgtacggtg gttgaggttg ttggctcttg    3840
ggaaccaaat agggctgatg ccgggtatca gaggacgtat gagaaggccc gtgagtgggt    3900
tgatgatcat gggttgcagc agtcgcctag caatattttg aaggcgatgc gtactgttgg    3960
cggcatgaga taatttgatg tggttttccgg ttgtgcgccg ccggttatcg gtgcacaggg    4020
ttgtctcccg cacgggggtc aacaatgttg tgttgttttc cgcaaggagt gtagggttag    4080
gctatggccg atcagagtgt tgaggaacag aatgttgaca atgatgttgt ggagtccgga    4140
aaggataacg gcattgttga tacagtaaaa gacgatggcg gcaggaggt agccgacaat    4200 cagttgaaga atgaaggcga gggtaaatcg ccggggactg attggaaggc ggaggcccgt    4260
aagtgggagt ctcgtgctaa aagtaatttc gccgagttgg agaagcttcg tacatcgagt    4320
gacgattctg gatctactat tgatgagctt cgccgcaaga atgaggaact cgaagacagg    4380
atcaacgggt ttgttcttga gggtgtgaag cgcgaggtgg cttcagagta tggtttgtcc    4440
```

```
agtgatgcga tcgctttctt gtcgggtggc gataaggagt cgcttgccga gtctgcgaaa    4500
gctttgaagg gtttgatcga ccatagtagt ggtggcgcgg gtgtgcgccg tcttgcgggg    4560
agtgcccccg ttgatgatgt taaacgacgt gagggtgtcg cgtttgtgga tgctcttgtc    4620
aataattcta ggagatgatt tgtgatggct gacgattttc tttctgcagg gaagcttgag    4680
cttcctggtt ctatgattgg tgcggttcgt gaccgtgcta tcgattctgg tgttttggcg    4740
aagctttcgc cggagcagcc gactattttc ggtcctgtta agggtgccgt gtttagtggt    4800
gttcctcgcg ctaagattgt tggtgagggc gaggttaagc cttccgcgtc tgttgatgtt    4860
tcggcgttta ctgcgcagcc tatcaaggtt gtgactcagc agcgtgtctc ggacgagttt    4920
atgtgggctg atgctgatta ccgtctgggt gttttgcagg atctgatttc gcctgctctt    4980
ggtgcttcga ttggtcgcgc tgttgatctg attgctttcc acggtattga tccggctacg    5040
ggtaagcctg ctgcggctgt gaagacttcg ctggataaga cgaagcatat tgttgatgcc    5100
acggattctg ctacgaccga tctggtcaag gctgtcggtc ttatcgctgg tgccggtttg    5160
caggttccta acggggttgc tttggatccc gctttctcgt ttgccctgtc tactgaggtg    5220
tatccgaagg ggtctccgct tgccggccag cctatgtatc ctgccgccgg gtttgccggt    5280
ttggataatt ggcgcggcct gaatgttggt gcttcttcga ctgtttctgg cgccccggag    5340
atgtcgcctg cctctggtgt taaggctatt gttggcgatt tctctcgtgt tcattggggt    5400
ttccagcgta acttcccgat cgaactgatc gagtatggtg acccggatca gactgggcgt    5460
gacctgaagg gccataatga ggttatggtt cgtgccgagg ctgtgctgta tgtggctatc    5520
gagtcgcttg attcgtttgc tgttgtgaat gagaaggctg ccccgaagcc taatccgccg    5580
gccgagaact gatttattgt tgcggtgatg tgtcaatgtg caggggtgg tgttgatggg    5640
tatcattttg aagcctgagg atattgagcc tttcgccgat attcctagag agaagcttga    5700
ggcgatgatt gccgatgtgg aggctgtggc tatcagtgtc gccccctgta tcgctaaacc    5760
ggatttcaaa tacaaggatg ccgctaaggc tattctgcgc agggctttgt tgcgctggaa    5820
tgatactggc gtgtcgggtc aggtgcagta tgagtctgct ggtccgttcg cccagactac    5880
acggtctagt actcccacga atttgttgtg gccttctgag attgccgcgt tgaagaagct    5940
gtgtgagggt gatggtgggg ctggtaaagc gttcactatc actcccacta ttaatggtcg    6000
atatgcacat tctgaggtgt gttccacggt gtggggtgag ggttgctcgt gcgggtcgaa    6060
tattaacggc tacgctggcc ctttgtggga gatatgatat gaccagtttt ccttatggtg    6120
aaacggttgc gatgcttcaa ccgactgttc gtgtcgatga tcttggtgac aaggttgagg    6180
attggtctaa gcctgtcgag actgtgtacc ataacgtggc catatatgct tccgtttcgc    6240
aggaggatga ggcggcaggc cgtgactctg actatgagca ttggtcgatg cttttcaagc    6300
agcctgttgt gggtgccggt tatcgttgcc ggtggcgtat ccggggtgtt gtgtgggagg    6360
ctgacgggtc tcctatggtg tggcatcacc ccatgtccgg ttgggatgcc ggtacgcaga    6420
tcaatgtgaa gcgtaagaag ggctgatggg tagtggctca ggatgtgaat gtgaagctga    6480
acttgccggg tattcgtgag gtgttgaagt cttctgggggt gcagtctatg ttggctgagc    6540
gtggcgagcg tgtcaagcgt gcggcatcgg cgaatgtggg cggtaacgct ttcgataagg    6600
cccaataccg tgcagggtta tcgtcggagg tgcaggttca ccgtgttgag gctgtcgctc    6660
gtataggcac cacatataag ggtgggaagc gtattgaggc gaagcatggc acgttggctc    6720
gttcgattgg ggctgcgtcg tgatcgtcta cgatgacccc aggaagtggg ctaaacgcgt    6780
```

```
gctcaaggat gatggctggc tgtcggatat accctgtgtg gggacggtgc ccgatgattt    6840
tacgggtgac ctgatttggt tggcgttgga tggtggcccg cagttgcatg tgcgtgagcg    6900 agtgttttg cgggtgaacg tgttttctga tatgcctgat cgtgctatgt cgctagccag    6960
gcgggtggag gctgtcctgg ctgacggggg ggacggtgac ccggtggtgt tttgtaggcg    7020
ttctacgggt cctgatttgc tggttgatgg tgcacgtttt gatgtgtatt cgctgttcga    7080
gctgatatgc aggcctgtcg aatctgagta aacgtatttg ttttgtttt aatgtaattg    7140 tttgatattt aatgggggtt gtgatggctg caacacgtaa agcgtctaat gttcgctctg    7200
ctgttacggg tgacgtctat attggtaaag ctcatgccgg tgacactatt gatggtgtga    7260
agacggttcc tgatgggctt accgctttag ggtacctgtc tgatgacggg tttaagatta    7320
agcctgagcg taaaacggat gatttgaagg cttggcagaa tgcggatgtt gttcgcactg    7380
tggccacgga gtcgtctatc gagatttctt tccagctgat cgaatccaag aaagaggtta    7440
tcgaactgtt ttggcagtcg aaggttactg ccggagccga ttcgggttcg ttcgatatt    7500 ctcctggtgc cacaacaggt gttcacgcct tgttgatgga tattgttgat ggtgatcagg    7560
ttattcgcta ctatttccct gaggttgagt tgattgatcg tgacgagatt aagggtaaga    7620
atggcgaagt gtacgggtat ggtgtgacgt tgaaggcgta tcctgcccag attaataagg    7680
agggtgatgc ggtgtctggt cggggtggga tgacggcttt aaaagctgat actcctccgg    7740
ttccgccttc tccgaagcct cagccggatc cgaatccgcc gtctaataac tgatacacat    7800
agtttgaggg attgttgata gatgagtgac acaggttaca cgttgaagat tggtgaccgt    7860
agctgggtgt tggcggatgc ggaggagacg gctcaggctg ttcctgcccg cgttttccgt    7920
cgtgcagcta agattgccca gtcggggag tctgcggatt cgcccaggt tgaggtgatg    7980 ttttctatgt tggaggctgc cgccccggct gacgcgtgg aggccctgga ggggcttcct    8040
atggttcgtg tggccgagat tttccgccag tggatggaat acaagcctga cggtaagggt    8100
gcctcgctgg gggaatagtt tggctccacg gcctgattga tgattatcgt ggggccatcg    8160
aatacgattt ccgcaccaag tttggtgttt ctgtttatag tgttggtggc ccgcagatgt    8220
gttggggtga ggctgtccgg ctggctgcg tgttgtgtac tgacacgtct agccagttgg    8280
cggcccacct taatggttgg cagcgcccgt ttgagtggtg cgagtgggct gtgttggaca    8340
tgctggatca ttacaggtct gctaatagtg aggggcagcc ggagcctgtg gcgaggccta    8400
cggatgagcg tagggcccgg tttacgtctg ggcaggtgga cgatattttg gcgcgtgttc    8460
gtgccggtgg cgggggtgtct cgcgagatta atattatggg gtgaatagtg tatgtctggt    8520
gagattgctt ccgcatatgt gtcgttgtat acgaagatgc cgggtttgaa ggcggatgtt    8580
ggtaaacagc tttctggggt gatgcctgct gagggtcagc gttcgggtag tcttttttgct    8640 aagggcatga agttggcgct tggtggtgcc gcaatggtgg gcgctatcaa tgttgctaag    8700
aagggcctca gtctatcta tgatgtgact attggtggcg gtattgctcg cgctatggct    8760
attgatgagg ctcaggctaa acttactggt ttgggtcata cgtcttctga cacgtcttcg    8820
attatgaatt cggctattga ggctgtgact ggtacgtcgt atgcgttggg tgatgcggct    8880
tctactgcgg cggcgttgtc tgcttcgggt gtgaagtctg gcgggcagat gacggatgtg    8940
ttgaagactg tcgccgatgt gtcttatatt tcgggtaagt cgtttcagga tacgggcgct    9000 attttttacgt ctgtgatggc ccgcggtaag ttgcagggcg atgacatgtt gcagcttacg    9060
atggcgggtg ttcctgtact gtctttgctt gccaggcaga ctggtaaaac ctcggctgag    9120
gtgtcgcaga tggtgtcgaa ggggcagatt gattttgcca cgtttgcggc tgcgatgaag    9180
```

| | |
|---|---:|
| cttggcatgg gtggtgctgc gcaggcgtct ggtaagacgt ttgagggcgc tatgaagaat | 9240 |
| gttaagggcg ccctgggtta tcttggtgcc acggctatgg cgccgtttct taacggcctg | 9300 |
| cggcagattt ttgttgcgtt gaatccggtt atcaaatcta tcacggattc tgtgaagccg | 9360 |
| atgtttgctg ccgtcgatgc tggtattcag cgtatgatgc cgtctatttt ggcgtggatt | 9420 |
| aaccgtatgc cggctatgat cactcgaatg aatgcacaga tgcgcgccaa ggtggagcag | 9480 |
| ttgaagagca tttttgcgag aatgcattta cctgtcccta agtgaatttt gggtgccatg | 9540 |
| tttgctggcg gcaccgcagt gtttggtatt gttgctgcgg gtgtggggaa gcttgtcgcg | 9600 |
| gggtttgccc cgttggcggt gtcggtgaag aatctgttgc cgtcgtttgg tgctttaaag | 9660 |
| ggtgccgctg gcgggcttgg cggcgtgttt cgcgccctgg gtggccctgt cgggattgtg | 9720 |
| atcggcttgt ttgctgccat gtttgccact aacgcccagt tccgtgccgc ggtgatgcag | 9780 |
| cttgtcgggg ttgttggcca ggctttgggg cagatcatgg cagctattca gccgctgttt | 9840 |
| ggtttggttg ccgggctggc ggcacagttg gcgccagtgt tcggccagat tatcggtatg | 9900 |
| gttgccggtt tggctgccca gcttatgcct gtgattagta tgcttgtcgc ccggctggtt | 9960 |
| cctgttatca cccagattat tggtgcggtg acacaggtgg cggccatgtt gttgcctgcg | 10020 |
| cttatgccgg tgcttcaggc tgttgtggct gtgatacggc aggttgttgg cgtgatcatg | 10080 |
| cagttggtgc ctgttttgat gcctgtgatt caacagattt tgggtgcggt catgtctgtg | 10140 |
| ctgccaccta tcatcggcct gatccggtcg ttgataccag tcatcatatc gattatgcgt | 10200 |
| gtggtgatgc aggttgttgg tgccgtgcta caggtggtgg cccgcattat tccggttgtg | 10260 |
| atgccgattg tgacagctgt gatcgggttt gttgcacgta ttcttggcgc tattgtgtct | 10320 |
| gctgcagccc gcattattgg gactgtcacc cgtgtcatct catgggttgt gaatcattta | 10380 |
| gtgtctggcg tgaggtctat gggcacggcc atcttgaatg gctggaatca tattagagcg | 10440 |
| tttacgtctg cgtttattaa cggtttcaag tcggtgattt ctggcggcgt gaacgctgtt | 10500 |
| gtgggggtttt ttgcccggct gggttcttcg gttgcctccc atgtgaggtc tggtttttaac | 10560 |
| gcggcccgtg gcgctgtttc ttctgcgatg aatgctatcc ggagtgttgt gtcttcggtg | 10620 |
| gcgtctgctg ttggcgggtt tttcagttcg atggcgtcta gggttcgtag tggtgctgtg | 10680 |
| cgcgggttta atggtgcccg gagtgcggct tcttctgcta tgcatgctat ggggtccgct | 10740 |
| gtatctagcg gcgtgcatgg tgtgctaggg tttttccgga atttgcctgg caatattcgg | 10800 |
| cgtgcgcttg gtaatatggg gtccttgttg gtgtctgccg gccgtgatgt ggtgtctggt | 10860 |
| ttgggtaatg gtatccggaa tgctatgagt ggcctgttgg atacggtgcg taatatgggt | 10920 |
| tctcaggttg ctaatgcggc gaagtcggtg ttgggtattc attccccgtc tcgggtgttt | 10980 |
| cgtgaccagg ttggccggca ggttgttgcc ggtttgctg aggggatcac cgggaatgcg | 11040 |
| ggtttggcgt tggatgcgat gtcgggtgtg gctggccggc tgcctgatgc ggttgatgcc | 11100 |
| cggtttggtg tgcgatcgtc tgtgggctcg tttaccccgt atggcaggta tcagcgtatg | 11160 |
| aatgataaga gtgttgtggt gaatgttaac ggacccacgt atggtgatcc taacgagttt | 11220 |
| gcgaagcgga ttgagcggca gcagcgtgac gctttgaatg cgttggctta cgtgtgattg | 11280 |
| ggggtgttgt gcatgtttat tcctgactcg tcggatcgtt ctggtttgac tgtgacctgg | 11340 |
| tttatggatc cgctgtttgg cgacgagcgt gtgcttcatt tgacggatta tacgggtgcg | 11400 |
| tctcctgtca tgttgttgaa tgattcgttg cgcggtttgg gtgttcccga ggttgagcat | 11460 |
| ttttctcaaa ctcatgttgg ggtgcacggc tcggagtggc gcgggtttaa tgtgaagcct | 11520 |

```
cgcgaggtga cgctgccggt gttggtgtcg ggtgttgacc cggatccggt gggcgggttt    11580
cgtgacggtt ttttgaaagc ctatgacgcg ttgtggtctg cttttcctcc cggggaggag    11640
ggggagttgt ctgtgaagac tcctgccggt gttgagcgtg tgttgaagtg tcggtttgat    11700
tcggctgatg acacgtttac ggtggatccg gtgaatcgtg gctatgcgcg ctatctgttg    11760
catttgacag cttatgaccc gttttggtat ggggatgagc agaagtttcg ttttagtaat    11820
gcgaagttgc aggattggtt gggtggcggc cctgtcggca aggatggcac ggcgtttcct    11880
gtggtgttga cgcctggtgt tggttcgggt tgggataatc tgtctaataa gggtgatgtg    11940
cctgcgtggc ctgtgattcg tgttgagggg cctttggagt cgtggtctgt gcagattgat    12000
ggtttgcgtg tgtcttcgga ttatcctgtc gaggagtatg attggatcac tattgatacg    12060
gatcctcgta aacagtctgc gttgttgaat gggtttgagg atgtgatgga tcgtttgaca    12120
gagtgggagt ttgcgcctat cccgcctggc ggttcgaaga gtgtgaatat tgagatggtt    12180
ggtttgggtg ccattgttgt gtcggtgcag tacaggtttt tgagggcttg gtgaatagtt    12240
gatggctggt cttgttccgc atgtaacgtt gtttacgccg gattatcgtc gtgtggcgcc    12300
tatcaatttt tttgagtcgt tgaagttgtc gttgaagtgg aatggtttgt cgacgctgga    12360
gttggtggtg tcgggtgatc attctaggct tgacgggttg actaagccgg gtgcacggct    12420
ggttgttgat tatggtggtg gccagatttt ttctgggcct gtgcgtcggg ttcatggtgt    12480
gggtccgtgg cgttcttcgc gggtgactat cacgtgtgag gatgatatcc gcctgttgtg    12540
gcgtatgctg atgtggcctg tgaattatcg tcctggtatg gttggtatgg agtggcgtgc    12600
cgacagggat tatgcccact attcgggtgc ggctgagtcg gtggctaagc aggtgttggg    12660
ggataatgct tggcgttttc cgcctggttt gtttatgacc gatgatgagc gtcgtggacg    12720
ctatattaag gattttcagg tgcggttcca cttgtttgca gacaagttgt tgccggtgtt    12780
gtcgtgggct cggatgactg tcacggtgaa ccagtttgag gatgcgaagt tgatcagcg    12840 tggtttggtg tttgattgtg tgccggctgt gacgcgtaag catgtgttga ctgccgagtc    12900
tggttcgatt gtgtcgtggg agtatgtgag ggatgcccct aaggcgacat ctgtggtggt    12960
tggtggccgc ggcgagggta aggatcggct gttttgtgag gatgttgatt cgatggccga    13020
gggggactgg tttgatcgtg tcgaggtgtt taaggatgcc cgtaacacgg attctgagcg    13080
cgtgtctctt gttgaggagg ctgagcaggt gttgtcagag tcgggggcca cgtcggggtt    13140
taagattgag ttggctgagt cggatgtgtt gcggtttggg ccgggcaatc tgatgccggg    13200
tgatcttatc tatgtggatg tgggttctgg ccctattgcg gagattgttc ggcagattga    13260
tgtggagtgt gattcgcctg gtgatggttg gacgaaggtg acaccggttg ctggggatta    13320
tgaggataat ccgtcggccc tgttggctcg ccgtgtggct ggtttggctg cgggtgttcg    13380
ggatttgcaa aagtttttagt aagtgattgg ggtttgttgt gggtattgtg tgtaaagggt    13440
ttgatggtgt gttgaccgag tatgattggg ctcaaatgtc tggtctgatg ggtaatatgc    13500
cgtctgtgaa gggcccggac gattttcgtg tgggcactac ggttcagggt gccacagtgt    13560
tgtgtgaggt tttgccgggg caggcttggg ctcacggggt gatgtgcacg tcgaatagtg    13620
ttgagacggt aacgggccag cttccggccc ctggtgagac ccgatacgac tatgtggtgt    13680
tgtctcggga ttgggagcag aacacagcca agttggagat tgttcctggg gggcgtgcgg    13740
agcgtgcctg tgacgtgttg cgtgccgagc ctggcgtgta ccatcagcag ctgttggcta    13800 cttttggtggt gtcgtctaac gggttgcagc agcagctgga taggcgtgct atagcggcca    13860
gggtggcgtt tggcgagtct gcggcttgtg atcctacccc tgtggagggt gaccgcgtga    13920
```

```
tggttccttc gggggctgtg tgggctaatc atgctaacga gtggatgttg ttgtctccgc    13980
ggatcgagac gggttcgaag tcgatcatgt ttggcgggtc tgctgtgtat gcttacacga    14040
tcccgtttga gcggccgttt ggtagtgcgc ctgttgtggt ggcgtctatg gctacggcgg    14100
ctgggggcac gcagcagatt gatgtgaaag cctacaatgt gactgccaag gattttggtt    14160
tggcgtttat cacgaatgac gggtctaaac cgaatggtgt gcctgcggtg gctgattgga    14220
ttgctgtcgg cgtgtaatgc gcggcttgtg tatatgtgac gtgttgtggt ggttgtagtg    14280
gtagggggct gtagtgtcat ggcttacacc tacactcgtg gcctctcttt gtaccgctat    14340
cgctactgtt cttggttcga ttcaggcggt tacgtacagg tcgaagaaga ggcttaggca    14400
gttgtctgcg caggttgatg cgatggaaga atacacatgg aatattcgcc atattgttca    14460
tcgctataac gcgaatttgc ctgagaatgt tgagccggtg aagatgcctg atttgcctga    14520
gttttttgaag gatactgttg atggtggtgg ggggtgaatt gtgagggagt tggaggaaga    14580
gaagcggcag cgccgctcgt ttgagaaggc ttccctgata ttgttgttcc tgtcgcttgt    14640
gctgttggtg gcgatggctg ggggtgcttt gcggtatggt tctgtggctt cgcaaaggga    14700
ttcggagcag gctaaagccc agtcgaatgg tacagccgct aaagggttgg ctgcccgtgt    14760
gcggcaggcg tgcgcttcgg gtgggcagga gtcggtgcgt cttcaccggt ctggcttgtg    14820
tgtggatgct cagcgtgttg agcttagcgt gcagggtgtg ccgggtcctg ccggtgtgcg    14880
tggcccgcaa gggccgcagg gcccggctgg tgttgatggt tcgtcgggtg ttgtggggcc    14940
tgttggtcct cagggttccc cgggtttgaa tggtgtggct ggtcctgacg ggctgcccgg    15000
tgctaacggc aaggatggtg tcgatggtgt tccaggtcgt gcaggtgctg acggtgtgaa    15060
cggggttgac ggcgctgatg gtcgggatgg ttcggccggt gagcgcggtg atgtgggccc    15120
ttcaggtcct gccggcccgc aaggtgcaca gggtgaacgg ggtcctgctg gccctgttgg    15180
tccgcagggt tctcccggtg ccgatggcac gaatggtaaa gacggtaagg atgggcgctc    15240
ggtggtgtct gtgtactgtt ccgggggccg cctggctgtg aaatatagtg acggtacggc    15300
ttctacaata tcgggttcgg tggcctgcga gagtgtgaaa ccgtcgccta tagtgactat    15360
atcatcccac aaatagaaag gagtggctgt gatggtagtg tttggtggtg acatgcggtg    15420
aggtttattc ctgcagcgca tcactcagcc ggttcgaata gtccggtgaa ccgtgttgtg    15480
attcatgcaa catgcccgga tgtggggttt ccgtctgcat cgcgtaaggg gcgggcggtg    15540
tctacagcaa actatttttgc ttccccatcg tctggtggtt cggcgcatta tgtgtgtgat    15600
atttcggaga ctgtgcagtg cttgtcggag tctacgattg ggtggcatgc cccgccgaat    15660
ccgcattctt tgggtataga gatttgcgcg gatgggggtt cgcacgcctc gttccgtgtg    15720
ccagggcatg cttacacgag ggagcagtgg ctggatccta gggtgtggcc tgcggtggag    15780
aaggctgcca tcctgtgtag acgtttgtgt gacaaatata atgttccgaa aaggaaactg    15840
tcggctgccg atttgaaggc tggcaggcgg ggtgtgtgtg gccatgtgga tgtgactgat    15900
gcgtggcatc agtcggatca tgatgatcct gggccgtggt ttccgtggga caggtttatg    15960
gccgtcgtca acggcggtag tggtagtgag gagttaactg tggctgatgt gaaagccttg    16020
catgatcaga ttaaacaatt gtctgctcag cttactggtt cggtgaataa gctgcaccat    16080
gatgttggtg tggttcaggt tcagaatggt gatttgggta aacgtgttga tgccctgtcg    16140
tgggtgaaga atccggtgac ggggaaactg tggcgcacta aggatgcttt gtggagtgtc    16200
tggtattacg tgctggagtg tcgtagccgt attgacaggc ttgagtcgac tgttaacggt    16260
```

```
ttgaaaaagt gatggtggtt tgttgtgggt aaacagtttt ggttgggcct gctggagcgt   16320
gccctgaaaa cttttattca aacgtttgtt gccgtgttgg gggttactgc gggtgtcacg   16380
tatactgcgg agtcgtttcg cggtttgccg tgggagtctg ccctgatcac agccacggtt   16440
gctgcggtgc tgtcggtggc tacctcgttt ggtaacccgt cgtttgtggc cggcaagcct   16500
aaaaccacgg ttgtggatgc gggtttggtt ccaccggatg atgggggctt ggttgagccg   16560
catatggtgg atgtgtcgga tcctggcatg atagagcctg cagatgatgc tgatcttggt   16620
ggctatgtgc cgaaacacgc tgccgagtcg gaggttggga cggtagagtc tactgttgca   16680
taattgaaca tagatgtgtg ccccagcggc aaccaccaca cgatcgtggc agcaccgctt   16740
gggcactatt tctgtttata cggtgtggct atgattcgtt gcggtcgatg gtgtcttcga   16800
gcatctgata caggtggagg caggtagaga tcgtatcgct ggcctggtct agaacgttcc   16860
ggccgataac gttttgtgg ttgtcgcagt ggcggatgat agcccacctg atctcgtcgg   16920
ctgccgcctg caatagtttt gcctggtatg cgattccggc aagccagtct agtgcttcct   16980
ggcttgcata ggggctctgg tcctcgctgt tgtcacgggt gttgctgttg tttgtggggt   17040
gtcctgtact gtcgcataac cacaggattt cgctgcactc gtctagcgtg tcctggtcga   17100
tagcgagatc gtcgaggctg acttcgttga cggtaaggtt cacgttgtcg agggagatgg   17160
gtacaccgta ctggttttcg acactgtcaa caatgttttc cagctgttgc atgttggtgg   17220
gctgttgttg gacgatacgg tgtatcgctg tgttgagggt ggtgtaggtg atattgtgtg   17280
tgttgttcat ggttttatcc catccctgtg ctttcgtcgt tttcgtctgg atagtatcta   17340
ctgtttgcgt agcctgttag ggtgatcagt gtttggtctg cccactgttt cacagtctgc   17400
cgggtgactc cgagtcgttg ggcggccgac gcatatgttt ggtcatatcc atagacttcc   17460
cggaatgcgg ctagtcgggc gaagtgtttt cgctgtttgg atggctggca ggtgagggtg   17520
tagtcgtcga tggcgagctg tagatcgatc atggagacga tgttgttgcc gtggtgttgt   17580
ggcgcggttg tggtggtgg cattcctggt tcgacgctgg gtttccatgg gcctccgttc   17640
cagatccatt gggcggcttg gatgatgtcg gcggtggtgt aggttcggtt cactggtaat   17700
ccttaaacaa gtcgttcatg ttgctggtgt cgaatcgtcc gacgcagtgg cagtagtcgt   17760
acatgagttt aataatgtgt tggtggtcgc cgaggtaggt gttccgctg atgctgtagg   17820 tggctgtgcc gtctttactg atggtgtatt tggcggtgat ggtttcgggg ttttcggtgt   17880
cggtgatgat ggctgtggtg gtggtgccta cggtttgtag cacggtggtt tgggttccgt   17940
cgtcgatggt ggttttaacc atgagggggtt ctccttttaa atgctggttt ggttgtcggc   18000
tagatgaata atatcggata aaggtttcgg ttggtcgagg tgttgtatgg ttttgttggc   18060
tagccgtttg gctaccctgt aacacatttt ggtgtagtgt tgttgtcta ggttgtggta   18120 ttgttcccgc accgcaatat atagcaaaga gtcttggtac aggtcgtctg cactgattgc   18180
ggggtagtgt ccggctgttt tggtgcatgc ccggttgagt gtgcgaagat gatggtttgt   18240
ggcccacacc cacgatgcgg tggtggccag gtctgctttt gtttgtcgtc tgctcatggc   18300 atctcttca tctggctatc tggtagttgt ttggtgtttt gttgtggata gtgtagcaca   18360
ctagtccggg gtgtgccggtg gtgtcctgtgc ggtgccggta ccagacggat tcgccttcca   18420
tggatgggca ttggatgaag gtgcgttgtc cttgctcgga gatttctagg tggtgccggt   18480
gcccggccat gagaatatta gatacggtgc cgttgtggaa ttcttggccg cgccaccact   18540
cgtagtgttg gttgttgcgc cattggtggc cgtgggcgtg cagtatccgt gtgccggcca   18600
catcgacggt ggtggtcatt tcgtctcggc tggggaagtg gaagtgaagg ttgggatatt   18660
```

```
ggttgttgag ctggtaggct tctgcgatgg cgcggcagca gtccacatcg aaggagtcgt    18720
cgtaggtggt gactcctttg ccgaagcgca cggcttctcc gtggttgccg gggatggatg    18780
tgatggtgac gttggcgcag tggtcgaaca tgtggacgag ttgcatcatg gccatgcggg    18840
tgagcctgat ttgttcggtg aggggtgttt gtgtgcgcca ggcgttgttg ccgccttgtg    18900
acacgtatcc ttcgatcatg tcgccgagga atgcgatgtg gactcgttcg ggtttgcctg    18960
cctgttgcca gtagtgtttt gcgactatga gggagtgtag gtagtcgtct gcgaatcggc    19020
tggtttctcc gccggggatg cctttgccga tttggaagtc tcccgccccg atgacgaagg    19080
ccgcattgct gtagtcggtg tgtgtgtcct gttcgggttt tgggggtgtc cattcggcta    19140
gtttatcgac gagttcgtcc acgggatacg ggtcggttgc gggttggtgg tcgatgattt    19200
tttgtatgga tcggcctgtt tctccgttgg ggagtgtcca ttcggagatg cgtgtgcggc    19260
gtacggtgcc gttggcgaga tcatcattaa tggtgtcgat ggcgttgtcg tggttggcta    19320
gctgtgtgag tagccggtct atattgtcta tcactggttt tcctcttctt ttttctgtgt    19380
ggtgttggct tgtttgcggc gatagtcttt gatgacggtg gcggagatgg ggtatccggc    19440
ttgggtgagc attcgggcta gctgtgtggc gggtatagac ttgtcggcga ggacgtctgc    19500
ggctttgttg ccgtagcgtt ggatgatggt ttcagttttg gttgccatga tgtcctaggg    19560
gttgtgtggt gggttgccat cctgtgcggc agtcgccgtc gtgtcctggt ttgcgtgtgc    19620
accacgatac ggttccgtct gtgtggttga gtgttttacc gcacatgacg ttttgtagat    19680
gctccggcgg ctcgctatcg ctatcgtctt gctcgtctag caaagttttt tgttgggtga    19740
aaaactcgga cacggtgccg ttgtggactg ggagtatcca tgttttccat tgttgttgca    19800
tccgggtgtt ccagtggaat tgtttggccg cgttttcggc ctgttttaag gttttgaaat    19860
agccgacgag gatgcgctgg tgttcacggt cgggaggggtt ttggcctcgc cagtattgtg    19920
ccgctacagc gtagcggttg ctggctgtga aggcgtccca gcagtattca ataatgtgtt    19980
gcaacatact gtctggcagg ctgtcagggt tgatggtggt gttttgggtg atcatgccac    20040
ggatggcttg ccggtttcgg gtggtgggtt tgaacgagat gctcacgata gtaccggctg    20100
gtcgtcttgc atgaactggt tgaaggtgtt gttcccggcg tgtttgggctt gtgtgatttg    20160 ttggtcggtc cagtctgggt gttgctgttt cagatagtgc cagcggcacg cattgtaggt    20220 ttcgtttttgt agccgggtga gattgttttc ggtgatgatt tgtttccaca ttgtccacga    20280
gacgtcgagt cgtttgagca tgtcgatggc tggcacgttg aaggagttga ggaacaggat    20340
ttcgtgggtg tagtagtttt tctcgtaggc gtcccatccg cttcggtgcc tgttgggctg    20400 gttttttgggg taggcttccc ggcatgcttt gtgtaaccgt ttggccatgt ctttgggtag    20460
tttaatgtcg gggttggcgc ggatcatgga tcgcatccca tcgtaggtgg tgccccaggt    20520
gtgcatgatg cggagtgggt cttcaccatc agcccatttt tcggcgatga tggcgaggcg    20580
gatacgcctc ctgccgcctt ggctggtgtt gcgccggtgg gggattgggc atgtgtcgag    20640
ggggtccatg atgctttta tacctttttct tgaggtgatg tttgtttgct ttgtgtggtt    20700
ttattgtagc actgtgttga gggcttgtgt caaccctgtt ttgccggcct gcaggtaggt    20760
gtctgtgaca tcccccaggg tgaggggcac gtgtatggct tggggggagtg ctgtctggag    20820 ggtttgggcc atctggtggc ctgcctggtc tgggtcggac cagatgtaga tgtggtcgta    20880
gccttcgaag aatttggtcc aaaagttttg ccacgaggtg gcgccgggta gggcgacggc    20940
cgaccatccg cattgttcga ggatcatgga gtcgaattcg ccttcgcaaa tgtgcatttc    21000
```

```
ggctgccggg ttggccatgg cgaccatgtt gtagatggag cctgtgtctc cggccggtgt   21060
caaatatttg gggtggttgt gggttttgca gtcgtgcggg agtgagcagc ggaaacgcat   21120
ttttcttatt tcggctggcc gcccccaaac ggggtacatg tagggggatgg tgatgcactg   21180
gttgtagttt tcgtggcctg ggatgggggtc attgtcgatg tatccaaggt ggtggtagcg   21240
ggctgtttct tcgctgatgc ctcttgctga gaggaggtcg agtatgtttt cgaggtgggt   21300
ttcgtagcgg gctgaggctt tctggattcg gcggcgttcc gcaatgttgt atgggcgtat   21360
gctgtcgtac attcgggttt tcttttctcta gtcgttgttg tagcttggtg agtccgcctc   21420
cgacaccgca tgtgtggcag taccagacgc ccttgtcgag gttgatgctc atggagggct   21480
ggtggtcgtc gtggaacggg cagaggatgt gttgctcgtt tttggacggg ttgtaccgta   21540
tctggtaggt gtcgaggagg cggcgggtgt cagaggtgtg ggaggagctc gttgagggtt   21600
gataccacat aggcttcgct ccagggtttg ttgcgttgtt tcatgacgac gagtccgatg   21660
gtggattggt tttcgcggtt tcggtgggtt tcgtagttgc gtgcctctcg gctggcttgt   21720
ttcacgaatt gggctaggtg tggttgcccg gctttggctt ctatcacata ggttttgttg   21780
ccggttgtga ggatgaggtc gccttcgtct tcgcggccgt tgaggtggag gcgttctata   21840
tcatggccgg tgtcgcgtag ctggtggagg agtcgtgttt cccattctgc tccggctcgg   21900
cggttgcgtg cctgttgtgt tgacatgata gtcctttgtg tgttggggtc atgttccatg   21960
gctgtttttc ggcgagggggc ccgaagaatg tgtattcggg gtaggctcgt agtcgttcgt   22020
atcgggtgcc gtcggggctg gatttgcctg tgcgttgttt gaggacggcg atgcgtgcct   22080
ctgccggtat cgtgagcccg ttgccgttgt cttcgccgcc atagagtgag actccgagga   22140
tgagttgtgg tttttcggag aggccgtttt tgatttctcg ccgggctggc gggtgttcga   22200
tgtcggagcc ggttttgtct gttgcgtggt gtgtgacgat gatggtggag ccagtatccc   22260
tacccaatgc tgtgatccat tgcatggctt cttgctgtgc ctggtagtcg gattcgcagt   22320
cttgaatgtc catcaggttg tcgatgacga tgatgggtgg gaaggtgttc cacatttcca   22380
tgtaggcttg tagctccatg gtgatgtcgg tccatgtgat gggtgactgg aatgagaatg   22440
tgatgtgttg gccgtggtgg atgctgtctc gatagtattc tggcccgtag tcgtcgatgt   22500
tttgttgtat ctgtgtggtg gtgtgttggg tgttgagtga gatgattcgt gtggaggcct   22560
cccagggtgt catgtcccct gatatgtaga gggctggctg gttgagcatc gctgtgatga   22620
acatggctag ccctgatttt tggctgccgg agcgccccgc gatcatgact aggtccccctt   22680
tgtggatgtg catgtccagg ttgtggtaga ggggttctag ttgtggtatg cggggcagct   22740
cggcggctgt ttgggaggct ctctcgaagg atctttggag agagagcatc ggagccttaa   22800
tctatctgtc tatcggttgg atgatgtttt ggtggtcaga tggagtcgat atcgatgtca   22860
gcatcagttg aggctgttgt gtcgtctagc tggccgttat cgcgcttgtc tacgtattcg   22920
gcaaccttat cgtagatggc gtcgtctagg ggtttgagca cgaccgcgtt gaagccgttt   22980
ttggtgcgta cggtggcgag tttgaaggcc tgctcctcgc caaggtaggt ttctaggtcg   23040
cggatcatgg agtgtgggcg atcattgttg cctcgcgctt tctcaataat ggcgttgggg   23100
atggtttctg gggtgccgtt gttgaggtcg tctagggtgt ggaagattgt gacatcagcg   23160
tagatgcggt ctgcgacctg tccgccgtag ccttcggtgt tgtgttctac gtcgtggact   23220
ttgaaggcga tggcggtggc gtcctggttt cgggaggggt tgaagaaggt gctgttgctg   23280
ttgttgttgc ggtagttggc gagtgccatg attgttgttt cctttactgt tttgttggtt   23340
tgtgtcggtt tttatcgggt gaggctgttt cgcttattcc ggaaagcttc ggaaacatca   23400
```

```
ctgttactgg tgatgatctt tttgtactgt ttgagtaggt cggctagctg tgctttactg    23460
gtggctttgt tgatctggtc gatgataatc tcattttcct gtgatgcgat gttgtttacg    23520
tagtctttgg ctgctttatc gtatttgtct tggaggatga tggctgcgct tgctaccaaa    23580
gtggctaaat cccaatcctc agagacggtg ttgtctttga gtccgcctag caggtcgatg    23640
atggcctgtt ttgtctgctc tgctgtgtct cctcggatga ccgcccatgg tgcagcatag    23700
tctccaccat atttgagtgt gatcgtgagt cgatcattgt cgatcttgtc tttatcggtc    23760
atttggtgtc cttttcttta ttgtctgttt ggggtggctg tacggtggat tctaccgggt    23820
atctgtaggc gtctttcccg tctacagccc agcaggcgtc cttgacgggg catcctttgc    23880
agagtgctgt gacgtggggt acgaagatgc cttgactgat tcctttcatt gcttgactgt    23940
acatggatga tacatgccgg taggtgttgt tgtcaagatc gtacagttcg gtggatgtgc    24000
cttgtgtcgg ggacttgtcg tcgttgcggc tggtggctgg cgtccaaaac atgcctttcg    24060
tgacgtttat gtcgtgttgg ttgagcatgt accggtatgt gtgcagctgc atgctgtcgg    24120
cgggtagacg gccggttttg aggtcgagga tgaaggtttc gccggtgtcg gtgtcggtga    24180
aaacgcggtc gatgtagccg actattttg tgtcatcgtc gaggatggtt tctaccgggt    24240
attcgatgcc tggctggccg tccaggattg cggtgatgta ttctgggtgg ttgcgcctcc    24300
aggttttcca gcggtcgacg aaggtggggc cgtaaaccat ccaccagccg tagtctttct    24360
tgtgtggccc gcccgactcg cacatgtttt tgcatattct gccggagggt ttgatttctg    24420
tgccttcgga ttcggcgagg gcgacttggg tgtcgaaaat gttttcgaag gatgagagtt    24480
tgtctggcag tgcagggtat tcggcgggat tgtacaggtg taggtcgtat tgttcggtga    24540
tgtggtgtat ggcgcttccg gcgatggtgg cgtaccaggt gtggtgttgg gcatggtagc    24600
cgtgtgagag gcgccatttt tcgccgcatt cggcccactg tgacagtgat gagtaggaga    24660
tgtggcctgg atggtggatg gttttcggat attgtgctag aggcattact tgtcgctttt    24720
gttccatggg ttgcgggtgt cttggccggc atcgtgttgc tggtatgcga ggagtgcgag    24780
gcagtgccag gctgcatggg ctagatgcgg cagcccggat tcacggtcga ggttgttgcc    24840
ttgctgccat gatagcaggt gccggtagag ggcgtcgaca ctgtggctcc acgggtatcc    24900
tccggtccag ttgttgtcgc cgtatttggt ggcaccgtat ccggctactt cgccgagagc    24960
gtgcaaggct gtagggtcga tgaggagag cctgcattgt ttgagttctt ttcgggctcc    25020
ggtgttgggg tcggtgtaca tgcgggtggg ctcatccatg ggtatgtgcg cctttctagg    25080
gggtgggtta ctggttgggg ttgtgggcga gtgctactgc gagaataatg atggcgaggg    25140
tttccgcgat gaggatgggt gttgtgatca tttgtggtct ttgggctggt aggtgagtgt    25200
ggaggcgcct aggagggtgg cgagggcgca tgcggcaata atggcgaggg ctgccttgtg    25260
tggggtgccg gttgcgtaca tccatgtgat gatggcgcct tggatccagg cgaggctggt    25320
gaagaacgtt tcatagctgt gtagctcaat gttgttgttg ggtgtgttca tgcttgctcc    25380
tgaagaatgg tgttgatggt tttataaatg ttgtacaggt cggcttcgat ggtttgtagc    25440
tgtttgattt ggtggtcgag atcaatgtct ggattgaggg tgttgatgcg ggaggcaata    25500
tcggttgctg tgcgtagtgt gccgccggtg tggtgaataa tgtgtgccgt gtcggctagt    25560
ccggtggtga cagcgtagtg ggagaggaga ggcatagctg gggggggtgct ccttggcggg    25620 ttactgttgc gggttgatgt tgaggtcggt gacgtgggg tggtcttctg ttccggtgac    25680
gaggcagtgg acggtgacgg gtagtttgga tgcgccgggc tgtttcgcgg tggcgccgta    25740
```

```
gacgatggag aaggtgtctt taccaataat tttgtggagt tggaggtcga tgtcggggtt    25800
gccgttccag ttgaggctgt gtgcggcggc ctgttgttcg gctttgcggt tgcaggtgtg    25860
tgcggccgtg atcatggtga gtccggtggc ggtttcttca ccccttgctt gggcttgctt    25920
gtgggctttc tgctgttcgg cttgtaggga gcggactgct gcggcctggc gggcttctt     25980 ctcggctttg cgctgttgga cggttttggg tgtccaatta gtgttggctg tggtggcctg    26040
tggggctggc tgtgaggcga gtggcgggtt gtcgtcgggt gctggtatga atgaggcggc    26100
ggcgatgatg gcggctgtga ttccggcgat ggtgtagccg tttttcttgt tcatggctgt    26160
tgtccccttt ccggggtgtt gttcgttgct gacatggtta atatttccag actggactac    26220
cactgtcaag gtgtcgctca gtttgtgtga gcgtttcctg tgtggctagg tgttttatcg    26280
ggcgaacagg gtgagtagat ggccaacatt gatgcggctc acgttccagt agagttgtgt    26340
ggcttcaccg ccggtgagcg gcttccactc gttgtggctg aacacggtgc catcggatgc    26400
gatgaatgtg tcggggcgta gcttgtgaag ctcggcttct acgctctgcc ggtaggcttc    26460
ggcgaggccc tcaaaatcca tgtggtcgca ggagaggttt cgaggcgtg tcaggtcgaa     26520 gggtgtaggg atgtcgtagc tggcggggct gtagagctgg gtgaagtggt tggcgatctt    26580
ctgcatgacg ggttccttc tggtgtgtgg atgttttta tcgtgtggct tctttgagga      26640
ttgtggtggt gtcgatggtg tcgatctgcc aggcgagttc ctcggcctca tccgccgtga    26700
gctgttgcca gtcttgtggg ccggtgactg atccgtcgag ggcgagggtc cagtcggggc    26760
ggaagaggtt taaggcttct tgcacagcat cccggtagac atgtttggcg gcgtcaaggt    26820
tgatgtgttt ggcgtgtcgg ccggctagct gagtgaggtc gagtgggtcg atttctgtct    26880
gcccatagag ggatgtgaag gatggggtga tgagtgtggt ggccattttt ggtgtgtcct    26940
ttcggtggtg taggggttgt tgtggttct agactgtgcg ggctgcgacc ccacagtcaa     27000
ggttgcgctc aaacccagtg agcgtttcat atgggtgtgg catgggatgt ggcgtatctc    27060
acttaagcct ttatggcctc tctcagcgcc tcaaatcctc tgggggtagg attatatagg    27120
gttgaccctg ctgatcgatt ctagagcact tctagggcgt ctcaggggta tgtctgggtt    27180
atggcagatg acccggcaga tccaccttgg ctttcatcgc ggggtcgag gtgccagatc     27240 tgggcatgga atctacaccc tcatactatg tgaaatgtat cacactcgcc tagtatggtg    27300
tgcactctcg aggccactct gtcgatctgg cgtggagggt gtagcccaga aatgccgttt    27360
aaagccttca cacggcgcct aggagcgcct tgcggggtgg gggctaggta tttatacccc    27420
cagcacattc tgatcgattc tagacgcctc ccagagcctg atacgcgatc cgctatacag    27480
acacagatca ccagcccta tcctggttag ctaagcctca actatgtgga cagtgtggga    27540
tgctcaaggg gaagaaggac acggtaaaag aaagaagggg gagcatcagc tttcacgcct    27600
taagtactta agttcacctg agggtcttag caccgagccc ctcaagggct cggcatcagt    27660
ccgagcaggc tcagcccatc cggcacggcc ctgaaagggg tacacgccat cagggaaggc    27720
ttgagagtac gaggagctct agcgacgagt actcgaaagc ctgagggaac accctcagca    27780
ctgatgggcc tagcgtgttc ggaaaggaca aagggtaca gtgtgagagc tgttcgggag     27840
tgaaacccgt tctgactagg agtttcagcc ttaacaaccc tcaaaggtta caagactcta    27900
agaaaattta aggaaaagtt taggtttaat ttttggacct ttactaccaa aaacgggtgt    27960
ctacacccct caaacccgcc tatagagcca aatccaccag tttgactcat cccaggtggg    28020
gtatgatagg ctggacaggt agccagctgg acgcaaggcc agaaagtgct gacgcacttc    28080
ccgacctcgc ttaccatcag tctaccaaac actttaaagc ttcaaggctt agcgttaagg    28140
```

-continued

```
tcttaagggc ttacacactt agcaccgagc cccctcaagg gctcggcatc agtataaaga    28200
ccttaacact taagttaata tttaaacctt aaaggcttag cacttaagga tacaaactta    28260
acatcagtgt ttaagatttt aaaacttaaa gttaaccatc agtcttaaac tttaatatta    28320
taacctataa gtcttaaagc ttataagtta taaaagtttt agaagagcta aggggttaac    28380
ttctttactt ctctactctc tttggtactt tctctcttct cttcttttct tcatcagggg    28440
agaagagaaa cctttttgccg tcaacgccga tggactttc accgtgtgac tcgtgtgctt    28500
ctggtcgcaa gctcccatcg cacactcacc gcacctcacc ttgcccgtgt actttaagct    28560
tagcgtgttt cacttcaggc gtacggcgtg tcacgctaac acccttaaca ccgggtgaga    28620
cttaaagtgt atattatatg tagaagactt taaaacctat aaggtgttcc cgcttagcct    28680
gtgtcctaca ccgctaggcg ccaagcgcta agctgtgaaa cgcgaacaca cacccacccc    28740 ccttttttctt tcgtgtcctt ctcttttgac acagctgggg ggcgatgtga tattttttcac    28800 atgccagggg gtagtggaga aaacaaacac cccagcacaa acagaacacc ccctcaaacg    28860
aacaaaacgc ccccccataat cgatgagcag ggcaagggca aggtattcat accccccaaca    28920 cctttcaggc cgttagagag gcaatgagag actcacaggc taccataggt gatcggagac    28980
gtgatggcac ataccaaccg caccgcatcc gcctcacacc ggcgctggcg gcaacgactc    29040
atcacccaag ccagacagca aggccaaact gaatgcccac tctgcggagc caccatcacc    29100
tggaacacac acgacctgcc aaccagcccc gaagccgacc acatcacacc cgtcagcagg    29160
ggaggactca acaccctcga caacgggcaa atcatctgca gaacatgcaa cagaagcaaa    29220
ggcaatcgca gcgaaccaaa catcaagttc caacaacaaa ccacaaaaac cttgatccca    29280
tggtgaaaaa cccgccaacc cccaccgggg acaccccctg cacaccccgtg caagacctcg    29340 tacggctt                                                              29348
```

<210> SEQ ID NO 8
<211> LENGTH: 441
<212> TYPE: PRT
<213> ORGANISM: Propionibacterium phage P1.1

<400> SEQUENCE: 8

```
Met Asn Ser Asp Glu Leu Ala Leu Ile Glu Gly Met Tyr Asp Arg Ile
1               5                   10                  15

Lys Arg Leu Ser Ser Trp His Cys Arg Ile Glu Gly Tyr Tyr Glu Gly
                20                  25                  30

Ser Asn Arg Val Arg Asp Leu Gly Val Ala Ile Pro Pro Glu Leu Gln
            35                  40                  45

Arg Val Gln Thr Val Val Ser Trp Pro Gly Ile Ala Val Asp Ala Leu
        50                  55                  60

Glu Glu Arg Leu Asp Trp Leu Gly Trp Thr Asn Gly Asp Gly Tyr Gly
65                  70                  75                  80

Leu Asp Gly Val Tyr Ala Ala Asn Arg Leu Ala Thr Ala Ser Cys Asp
                85                  90                  95

Val His Leu Asp Ala Leu Ile Phe Gly Leu Ser Phe Val Ala Val Ile
                100                 105                 110

Pro Gln Gly Asp Gly Ser Val Leu Val Arg Pro Gln Ser Pro Lys Asn
            115                 120                 125

Cys Thr Gly Arg Phe Ser Ala Asp Gly Ser Arg Leu Asp Ala Gly Leu
        130                 135                 140

Val Val Gln Gln Thr Cys Asp Pro Glu Val Val Glu Ala Glu Leu Leu
```

```
                145                 150                 155                 160
Leu Pro Asp Val Ile Val Gln Val Glu Arg Arg Gly Ser Arg Glu Trp
                165                 170                 175
Val Glu Thr Gly Arg Ile Val Asn Val Leu Gly Ala Val Pro Leu Val
                180                 185                 190
Pro Ile Val Asn Arg Arg Thr Ser Arg Ile Asp Gly Arg Ser Glu
            195                 200                 205
Ile Thr Arg Ser Ile Arg Ala Tyr Thr Asp Glu Ala Val Arg Thr Leu
            210                 215                 220
Leu Gly Gln Ser Val Asn Arg Asp Phe Tyr Ala Tyr Pro Gln Arg Trp
225                 230                 235                 240
Val Thr Gly Val Ser Ala Asp Glu Phe Ser Gln Pro Gly Trp Val Leu
                245                 250                 255
Ser Met Ala Ser Val Trp Ala Val Asp Lys Asp Asp Gly Asp Thr
            260                 265                 270
Pro Asn Val Gly Ser Phe Pro Val Asn Ser Pro Thr Pro Tyr Ser Asp
            275                 280                 285
Gln Met Arg Leu Leu Ala Gln Leu Thr Ala Gly Glu Ala Ala Val Pro
            290                 295                 300
Glu Arg Tyr Phe Gly Phe Ile Thr Ser Asn Pro Pro Ser Gly Glu Ala
305                 310                 315                 320
Leu Ala Glu Glu Ser Arg Leu Val Lys Arg Ala Glu Arg Gln
            325                 330                 335
Thr Ser Phe Gly Gln Gly Trp Leu Ser Val Gly Phe Leu Ala Ala Arg
            340                 345                 350
Ala Leu Asp Ser Ser Val Asp Glu Ala Asp Phe Phe Gly Asp Val Gly
            355                 360                 365
Leu Arg Trp Arg Asp Ala Ser Thr Pro Thr Arg Ala Ala Thr Ala Asp
            370                 375                 380
Ala Val Thr Lys Leu Val Gly Ala Gly Ile Leu Pro Ala Asp Ser Arg
385                 390                 395                 400
Thr Val Leu Glu Met Leu Gly Leu Asp Asp Val Gln Val Glu Ala Val
                405                 410                 415
Met Arg His Arg Ala Glu Ser Ser Asp Pro Leu Ala Ala Leu Ala Gly
            420                 425                 430
Ala Ile Ser Arg Gln Thr Asn Glu Val
            435                 440

<210> SEQ ID NO 9
<211> LENGTH: 159
<212> TYPE: PRT
<213> ORGANISM: Propionibacterium phage P1.1

<400> SEQUENCE: 9

Met Gln Gly Val Val Leu Met Gly Ile Ile Leu Lys Pro Glu Asp Ile
1               5                   10                  15
Glu Pro Phe Ala Asp Ile Pro Arg Glu Lys Leu Glu Ala Met Ile Ala
                20                  25                  30
Asp Val Glu Ala Val Ala Ile Ser Val Ala Pro Cys Ile Ala Lys Pro
            35                  40                  45
Asp Phe Lys Tyr Lys Asp Ala Ala Lys Ala Ile Leu Arg Arg Ala Leu
        50                  55                  60
Leu Arg Trp Asn Asp Thr Gly Val Ser Gly Gln Val Gln Tyr Glu Ser
65              70                  75                  80
```

Ala Gly Pro Phe Ala Gln Thr Thr Arg Ser Ser Thr Pro Thr Asn Leu
                85                  90                  95

Leu Trp Pro Ser Glu Ile Ala Ala Leu Lys Lys Leu Cys Glu Gly Asp
            100                 105                 110

Gly Gly Ala Gly Lys Ala Phe Thr Ile Thr Pro Thr Ile Asn Gly Arg
            115                 120                 125

Tyr Ala His Ser Glu Val Cys Ser Thr Val Trp Gly Glu Gly Cys Ser
            130                 135                 140

Cys Gly Ser Asn Ile Asn Gly Tyr Ala Gly Pro Leu Trp Glu Ile
145                 150                 155

<210> SEQ ID NO 10
<211> LENGTH: 96
<212> TYPE: PRT
<213> ORGANISM: Propionibacterium phage P1.1

<400> SEQUENCE: 10

Met Ala Gln Asp Val Asn Val Lys Leu Asn Leu Pro Gly Ile Arg Glu
1               5                   10                  15

Val Leu Lys Ser Ser Gly Val Gln Ser Met Leu Ala Glu Arg Gly Glu
            20                  25                  30

Arg Val Lys Arg Ala Ala Ser Ala Asn Val Gly Gly Asn Ala Phe Asp
            35                  40                  45

Lys Ala Gln Tyr Arg Ala Gly Leu Ser Ser Glu Val Gln Val His Arg
50                  55                  60

Val Glu Ala Val Ala Arg Ile Gly Thr Thr Tyr Lys Gly Gly Lys Arg
65                  70                  75                  80

Ile Glu Ala Lys His Gly Thr Leu Ala Arg Ser Ile Gly Ala Ala Ser
                85                  90                  95

<210> SEQ ID NO 11
<211> LENGTH: 386
<212> TYPE: PRT
<213> ORGANISM: Propionibacterium phage P1.1

<400> SEQUENCE: 11

Met Met Ala Gly Leu Val Pro His Val Thr Leu Phe Thr Pro Asp Tyr
1               5                   10                  15

Arg Arg Val Ala Pro Ile Asn Phe Phe Glu Ser Leu Lys Leu Ser Leu
            20                  25                  30

Lys Trp Asn Gly Leu Ser Thr Leu Glu Leu Val Val Ser Gly Asp His
            35                  40                  45

Ser Arg Leu Asp Gly Leu Thr Lys Pro Gly Ala Arg Leu Val Val Asp
50                  55                  60

Tyr Gly Gly Gln Ile Phe Ser Gly Pro Val Arg Arg Val His Gly
65                  70                  75                  80

Val Gly Pro Trp Arg Ser Ser Arg Val Thr Ile Thr Cys Glu Asp Asp
            85                  90                  95

Ile Arg Leu Leu Trp Arg Met Leu Met Trp Pro Val Asn Tyr Arg Pro
            100                 105                 110

Gly Met Val Gly Met Glu Trp Arg Ala Asp Arg Asp Tyr Ala His Tyr
            115                 120                 125

Ser Gly Ala Ala Glu Ser Val Ala Lys Gln Val Leu Gly Asp Asn Ala
            130                 135                 140

Trp Arg Phe Pro Pro Gly Leu Phe Met Thr Asp Asp Glu Arg Arg Gly
145                 150                 155                 160

```
Arg Tyr Ile Lys Asp Phe Gln Val Arg Phe His Leu Phe Ala Asp Lys
                165                 170                 175
Leu Leu Pro Val Leu Ser Trp Ala Arg Met Thr Val Thr Val Asn Gln
            180                 185                 190
Phe Glu Asp Ala Lys Phe Asp Gln Arg Gly Leu Val Phe Asp Cys Val
        195                 200                 205
Pro Ala Val Thr Arg Lys His Val Leu Thr Ala Glu Ser Gly Ser Ile
    210                 215                 220
Val Ser Trp Glu Tyr Val Arg Asp Ala Pro Lys Ala Thr Ser Val Val
225                 230                 235                 240
Val Gly Gly Arg Gly Glu Gly Lys Asp Arg Leu Phe Cys Glu Asp Val
                245                 250                 255
Asp Ser Met Ala Glu Gly Asp Trp Phe Asp Arg Val Glu Val Phe Lys
            260                 265                 270
Asp Ala Arg Asn Thr Asp Ser Glu Arg Val Ser Leu Val Glu Glu Ala
        275                 280                 285
Glu Gln Val Leu Ser Glu Ser Gly Ala Thr Ser Gly Phe Lys Ile Glu
    290                 295                 300
Leu Ala Glu Ser Asp Val Leu Arg Phe Gly Pro Gly Asn Leu Met Pro
305                 310                 315                 320
Gly Asp Leu Ile Tyr Val Asp Val Gly Ser Gly Pro Ile Ala Glu Ile
                325                 330                 335
Val Arg Gln Ile Asp Val Glu Cys Asp Ser Pro Gly Asp Gly Trp Thr
            340                 345                 350
Lys Val Thr Pro Val Ala Gly Asp Tyr Glu Asp Asn Pro Ser Ala Leu
        355                 360                 365
Leu Ala Arg Arg Val Ala Gly Leu Ala Ala Gly Val Arg Asp Leu Gln
    370                 375                 380
Lys Phe
385

<210> SEQ ID NO 12
<211> LENGTH: 29214
<212> TYPE: DNA
<213> ORGANISM: Propionibacterium phage P9.1

<400> SEQUENCE: 12
agtgaaatac ctcccttttg tggatttgtc tgtttgtcga cttttttgtgt tggtggtgag      60 tgttgtgcag cctgagcttc ctgatagtcg tgattggtgt ggggagacgc gtcgttggtg     120
gcgcgtgtgg ggtgaggatc cgcgtgccgg gtttgtgtct gatgaggagt ggttgtttct     180
catggatgct gcggtgattc atgattgtgt gtggcgtgag ggtcgtgcgg atctggtggc     240
ttcgcttcgt gctcatgtga aggcttttat gggtatgttg gatcggtatt cggttgatgt     300
ggtgtctggt ggccgtggtg ggggttctgc ggtggcgatg attgaccggt ataggaagcg     360 taaagggcc taatgtcgag cttttgttggt tctcaggtgc ctcgtcaccg ggtggctgcg     420
gcgtattcgg tgtctgctgg cggtgatgct ggggagttgg gtcgtgcgta tgggttgacg     480
cctgatccgt ggcagcagca ggtgttggat gattggctgg ctgtcggtag caatggcagg     540
cttgcttcgg gtgtgtgtgg ggtgtttgtg cctcgacaga atggcaagaa cgcgatcctt     600
gaggttgtgg agttgtttaa ggcgactatt cagggtcgcc gtattttgca tacggctcac     660
gagttgaagt cggctcgtaa ggcgtttatg cggttgaggt cgttttttga gaatgagcgg     720
cagtttcctg acttgtatcg tatggtgaag tcgattcgtg cgacgaatgg tcaggaggct     780
```

```
attgtgttgc atcatccgga ttgtgccacg tttgagaaga agtgtggttg tccgggttgg    840
ggttcggtgg agtttgtggc tcgttctcgg ggttcggctc gcgggtttac ggttgatgat    900
ttggtgtgtg atgaggctca ggagttgtcg gatgagcagt tggaggcttt gcttcctacg    960
gtgagcgcgt ctccttcggg tgatccgcag cagattttcc ttggcacgcc gcctgggccg   1020
ttggcggacg gtagcgtggt gttgcgtctt cgtgggcagg cgcttggtgg cggtaaaagg   1080
tttgcgtgga cggagttttc gattcctgac gagtctgatc cggatgatgt gtcgcggcag   1140
tggcggaagt tggctggtga tactaatcct gcgctgggtc gtcgcctgaa ttttgggacc   1200
gtaagcgatg agcatgagtc gatgtctgct gccgggtttg ctcgggagcg gcttggctgg   1260
tgggatcgtg gccagtctgc ttcgtcggtg ataccagccg ataagtgggt tcagtcggct   1320
gtgggtgagg cggctctggt tggcgggaag gttttttggtg tctcgttttc tcgttctggg   1380
gatcgggttg ctttggcggg tgctggccgg actgatgctg gggttcatgt tgaggtgatt   1440
gatgggctgt cggggacgat tgttgatggt gtgggccggt tggctgactg gttggcggtt   1500
cgttggggtg atactgaccg gatcatggtt gccgggtctg gtgcggtgtt gttgcagaag   1560
gcgttgacgg atcgtggtgt tccgggtcgt ggcgtgattg tggctgatac tggggtgtat   1620
gtggaggcgt gtcaggcgtt cctggagggt gtaaggtctg gtgtggtttc tcaccctagg   1680
gctgattcga ggcgtgacat gttggatatt gctgtgaggt cggctgtgca gaagaagaag   1740
ggttctgcgt ggggttgggg ttcctcgttt aagaatggtt ctgaggttcc tttgaggct   1800
gtgtctttgg cttatcttgg tgcgaagatg gcgaaggcta ggcggcgtga acggtctggt   1860
aggaagcggg tgtctgtggt atgaactcgg atgagttggc tctgattgag gcatgtttg    1920
atcgtatcca aaggttgtct tcgtggcatt gccgtattga gggctactat gagggctcta   1980
atcgggtgcg tgatttgggg gtggctattc cgccggagtt gcagcgtgtg cagacggtgg   2040
tgtcgtggcc tggtattgct gtggatgctt tggaggagcg tctggattgg cttggctgga   2100
ctaatggtga cggctacggt ctggatggtg tgtatgctgc gaatcggctt gctacgcgt    2160
cgtgtgacgt tcaccttgat gcactgattt ttgggttgtc gtttgtggcg atcattcccc   2220
aggggggatg gtcggtgttg gttcgtccgc agtcgccgaa gaattgtact ggccggtttt   2280
ctgctgatgg gtctcgtttg gatgctggtc ttgtggtgca gcagacgtgt gatcctgagg   2340
ttgttgaggc tgagttgttg ttgcctgatg tgattgttca ggtggagcgg cgtgggtctc   2400
gtgagtgggt tgagacgggc cgtataccga atgtgttggg tgctgttccg ttggtgcctg   2460
ttgtgaatcg tcgccgtacg tcgaggattg atggccgttc ggagatcact cggtcgatta   2520
gggcttacac ggatgaggct gtgcgcacac tgttggggca gtctgtgaat cgtgattttt   2580
atgcgtatcc tcagcgttgg gtgactggtg tgagcgcgga tgagttttcg cagcctggct   2640
gggtgttgtc gatggcttct gtgtgggctg tggataagga tgatgatggt gacactccga   2700
atgtggggtc gtttcctgtg aattctccta caccgtattc ggatcagatg cgtttgttgg   2760
cgcagttgac tgcgggtgag gcggctgttc cggaacgcta tttcgggttt atcacgtcta   2820
acccgccttc tggggaggct ttggctgcgg aggagtctcg gcttgtgaag cgtgctgaac   2880
gcaggcagac gtcgtttggt cagggttggt tgtcggttgg tttcctggct gcccgggcgt   2940
tggattcgag tgttgatgag gccgcgtttt ttggtgatgt tggtttgcgt tggcgtgatg   3000
cttcgacgcc gactcgggcg gctacggctg atgctgtgac gaagcttgtg ggtgccggta   3060
ttttgcctgc tgattctcgt acggtgttgg agatgttggg tttggatgat gtgcaggttg   3120
aggctgtgat gcggcatcgt gccgagtctt cggatccgtt ggcggcgctg gctggggcta   3180
```

```
tttctcgtca gactaacgag gtttgatagg cgatggcttc gggtgctatg tcgaggcttg    3240
ctgcgactga gtatcagcgt gaggcggtca ggtttgccgg gaagtatgcg ggctattatg    3300
ctgagcttgg tcgtttgtgg cattccggga agatgacaga tgcgcagtat gtgcgtttgt    3360
gtgtggagtt ggagcgtgcc ggccatgatg gttcggcgtc gttggctgcc aggtttgtgt    3420
cggattttcg ccggttgaat ggtgtggatc cgggtttgat cgtgtatgac gagtttgatg    3480
ctgcagccgc gttggctagg tcgttttcga ctatgaagat tcttaagagt gacccggata    3540
gggcgaatga cacgattggt tcgatggctg cgggtgttaa tcgggctgtc atgaatgctg    3600
gccgtgacac ggttgagtgg tctgcgggtg cgcagggtag tcgtggcgc agggtgactg    3660 atggtgatcc gtgcgcgttt tgtgccatgt tggctacgag gtcggattat acgaccaaag    3720
agcgggcgct tactactggt catacgcggc gtcataagcg tgccggtagg cgtccgtttg    3780
gttcgaagta tcatgatcat tgcgggtgta cggtggttga ggttgttggc ccttgggaac    3840
caaatagggc tgatgccgag tatcagagga cgtatgagaa ggctcgtgaa tgggttgatg    3900
atcacgggtt gcagcagtcg cctggcaata ttttgaaggc tatgcgtact gttggcgaca    3960
tgagatgatg gtttccggtt gtgtgccgcc ggttatcggt gcacagggtt gtctcccgca    4020
cgggggtcaa caatgttgtg ttgttttccg caaggagtat agggttaggc tatggccgat    4080
caaaaagttg aagaacagaa tgttgacaat gatgctgttg agcccggaaa gggtggagac    4140
gttgttgatg ttgtgaagga tgggcaggct gccggcgatg atcatgccgg tgatgtttcc    4200
gtgaaggagg agtcttcttc tggcacggat tggaaggctg aggcccgtaa gtgggagtct    4260
cgtgctaaaa gtaatttcgc cgagttggag aagcttcgcg cctcggatgg tgatgcgggg    4320
tctgtgattg atgatcttcg ccgcaagaat gaggaactcg aagaccggat taatgggttt    4380
gttcttgggg gtgtgaagcg tgaggtgct gccgagtgtg gcctgtcggg tgatgcggtc    4440
gctttcttgc acggtggcga ccgtgaagcg ttggtggagt ctgctaaggc tttgaagggt    4500
ttgattgacc atagtggtgg tggcgcgggt gtgcgccgtc ttgcggggag tgccccgtt    4560 gatgatgtta aacgacgtga gggtgtcgcg tttgtggatg ctcttgtcaa taattctagg    4620
agatgatttg tgatggctga cgattttctt tctgcaggga agcttgagct tcctggttct    4680
atgattggtg cggttcgtga ccgtgctatc gattctggtg ttttggcgaa gctttcgccg    4740
gagcagccga ctatttttgg ccctgttaag ggtgccgtgt ttagtggtgt tcctcgcgcc    4800
aagattgttg atgagggcga ggttaagcct tccgcatctg ttgatgtttc ggcgtttact    4860
gcgcagccta tcaaggttgt gactcagcag cgtgtctcgg acgagtttat gtgggctgat    4920
gcggattacc gtctgggtgt tttgcaggat ctgatttcgc ctgctcttgg tgcttcgatt    4980
ggtcgcgccg tggatctgat tgcttttccat ggtgttgatc ctgctacggg taagcctgct    5040
gcggctgtga agacttcgct ggataagacg aagcatattg ttgatgccac ggattctgct    5100
acgaccgatc ttgtcaaggc tgtcggtctt atcgctggtg ctggtttgca ggttcctaac    5160
ggtgttgctt tggatccggc gttctcgttt gccctgtcta ctgaggtgta tcctaagggt    5220
tcgcctcttg ctggccagcc tatgtatcct gccgccggtt tcgctggttt ggataactgg    5280
cgtggcttga atgttggtgc ttcttcgact gtttcgggtg ccccgagat gtcgcctgcc    5340 tctggtgtta aggctattgt tggtgatttc tcgcgtgttc attggggttt ccagcgtaac    5400
ttcccgatcg agcttatcga gtatggtgac ccggatcaga ctgggcgtga cctgaagggt    5460
cataatgagg ttatggttcg tgccgaggct gtgctgtatg tggctatcga gtcgcttgat    5520
```

```
tcgtttgctg ttgtgaagga gaaggctgcc ccgaagccta atccgccggc cgagaactga    5580
tctatttgtt gcgataatgt tcatgctgtg tgcagggggt ggtgttgatg ggtatcattt    5640
tgaagcctga ggatattgag cctttcgccg atattcctag agagaagctt gaggcgatga    5700
ttgccgatgt ggaggctgtg gctgtcagtg tcgcccctg tatcgctaaa ccggatttca    5760
aatacaagga tgccgctaag gctattctgc gcagggcttt gttgcgctgg aatgatactg    5820
gcgtttctgg tcaggtgcag tatgagtctg cgggtccttt cgctcagact acacggtcta    5880
gtactcccac gaatttgttg tggccttctg agattgctgc gttgaagaag ttgtgtgagg    5940
gtgatggtgg ggctggtaaa gcgttcacta ttacaccgac catgaggagt agtgtgaatc    6000
attctgaggt gtgttccacg gtgtggggcg agggttgctc gtgcgggtcg aatattaacg    6060
gctacgctgg ccctttgtgg gagatatgat atgaccagtt ttccttacgg tgaaacggtt    6120
gtgatgcttc aaccgactgt tcgtgtcgat gatcttggcg acaaggtgga agactggtct    6180
aagcctgtcg agactgtgtt tcataacgtg gccatctatg cttccgtttc gcaggaggat    6240
gaggccgcgg ggcgcgactc tgactatgag cattggtcga tgcttttcaa gcagtctgtt    6300
gtgggtgccg gttatcgttg ccggtggcgt atccggggtg ttgtgtggga ggctgacggg    6360
tctcctatgg tgtggcatca tcccatgtcc ggttgggatg cgggcacgca gatcaatgtg    6420
aagcgtaaga agggctgata ggtagtggct caggatgtga atgtgaagct gaacttgccg    6480
ggtattcgta aggtgttgaa gtcttctggg gtgcagggca tgttggctga gcgtggtgag    6540
cgtgtcaagc gtgcggcctc ggcgaatgtg ggcggtaacg ctttcgataa ggctcaatac    6600
cgtaatggtt tgtcgtcgga ggtgcaggtt caccgtgttg aggctgtcgc caggattggc    6660
accacatata agggtgggaa gcgtattgag gcgaagcatg gcacgctggc taggtcgatt    6720
ggggctgcgt cgtgatcatt tacggtgacc caagagtctg ggctaaacgc gtgctcaagg    6780
atgatggctg gctgtctgat ataccatgca ccgggacagt gcctgaccgg tttgagggtg    6840
accttatttg gttggctctt gatggtgcc cgcagttgca tgttcgtgag caggtttttt    6900
tgcgcgtgaa tgtgtttttct gatacgccgg atcgtgctat gtcgttggcg cgtcgtgttg    6960
aggctgtcct ggctgacggg gtggacggtg acccggtgg gtactgtaag cggtctactg    7020
gtcctgattt gctggttgat ggtgcacgtt ttgatgtgta ttcgctgttc gagctgatat    7080
gtaggcctgt cgaatctgag taaacgtatt tgttttgtt ttaatgtaat tgtttgatat    7140
ttaatgggg ttgtgatggc tgcaacacgt aaagcgtcta atgttcgttc agcggttact    7200
ggcgacgttt atattggtga cgcgcacgcg ggtgatacta ttaagggtgt ggaggcggtt    7260
ccttccgggc ttaccgcttt agggtatctg tcggatgacg ggtttaagat taagcctgag    7320
cgtaaaacgg atgatttgaa ggcttggcag aatgcggatg ttgttcgcac tgtggctacc    7380
gagtcttcta tcgagatttc tttccagctg atcgaatcca agaaagaggt catcgagctg    7440
ttttggcagt cgaaggttac tgccggagcc gattcgggtt cgttcgatat ttctccgggt    7500
gccaccactg gcgtgcacgc tttactgatg gatattgttg atgggatca ggttattcgc    7560
tactatttcc ccgaggttga gcttatcgat cgtgacgaga ttaagggtaa gaatggcgaa    7620
gtgtacgggt atggtgtgac gttgaaggct taccctgccc agattaataa gactggtaat    7680
gcggtgtcgg gtcgggggtg gatgacggct ttaaaagctg atactcctcc ggtgcctcct    7740
aagccgccta agcctgagcc ggatccgaat ccgccgtctg agaactgata cacgatttta    7800
gggattgttg atagatgagt gacactggtt tcacgttgaa gattggtgac cgtagctggg    7860
tgttggcgga tgcggaggag acgactcagg ctgttcctgc ccgcgttttc cgtcgtgccg    7920
```

```
ccaggattgc ccagtctggg gagtctgcgg atttcgccca ggttgaggtg atgttttcta   7980
tgttggaggc tgccgccccg gctgacgcgg tggaggccct ggaggggctt cctatggttc   8040
gtgtggccga gattttccgc cagtggatgg aatacaagcc tgacggtaag ggtgcctccc   8100
tgggggaata gtttggctcc acggcctgat tgatgattat cgtggggcca tcgaatacga   8160
ttttcgcact aaatttggtg tttctgttta tagtgttggt ggcccgcaga tgtgttgggg   8220
tgaggctgtc cggctggctg gcgtgttgtg taccgatacg tctagccagt tggcggccca   8280
cctgaatggt tggcagcgcc cgtttgagtg gtgcgagtgg gctgtactgg acatgctgga   8340
tcattacagg tctgctaata gtgaggggca gccgagcct gtggcgaggc ctacggatga   8400
gcgtagggcc cggtttacgt ccgggcaggt ggacgatatt ttggcgcgtg ttcgtgccgg   8460
tggcggggtg tctcgcgaga ttaatattat ggggtgaata gtgtatgtct ggtgagattg   8520
cttccgcata tgtgtctttg tatacgaaga tgcctggttt gaaggcggat gttggtaaac   8580
agctttctgg ggtgatgcct gcggagggtc agcgttcggg tagcttgttt gctaagggta   8640
tgaagttggc gcttggtggt gccgcaatgg tgggtgccat caatgttgcc aagaagggcc   8700
tcaagtctat ctatgatgtg actattggtg gcggtattgc tagggcgatg gctatcgatg   8760
aggctcaggc taaactgact ggtttgggtc acacgtcttc tgacacgtct tcgattatga   8820
attcggctat tgaggctgtg actggtacgt cgtatgcgtt gggtgatgcg gcttctactg   8880
cggcggcgtt gtctgcttcg ggtgtgaagt ctggcgggca gatgactgac gtgttgaaga   8940
ctgtcgccga tgtgtcttat atttcgggta agtcgtttca ggatacgggc gctattttta   9000
cgtctgtgat ggcgcgcggt aagttgcagg gcgatgacat gttgcagctt acgatggcgg   9060
gtgttcctgt actgtctttg cttgccaggc agacaggtaa aacctcggct gaggtgtcgc   9120
agatggtgtc gaaggggcag attgattttg ccacgtttgc ggctgcgatg aagcttggca   9180
tgggtggtgc tgcgcaggcg tctggtaaga cgtttgaggg cgctatgaag aatgttaagg   9240
gcgccctggg ttatcttggt gctacggcta tggcgccgtt tcttaacggg ttgcggcaga   9300
tttttgttgc cttgaatccg gttatcaagt cggtgacgga ttccgtgaag ccctgtttg   9360
cgtcggtgga tcagggatt cagcgggtaa tgccgtctat tttggcgtgg attaaccgta   9420
tgccgggcat gatcacgaga atgaatgcac agatgcgcgc caaggtggag cagttgaagg   9480
gcattttgc gagaatgcat ttgcctgtcc ctaaagtgaa tttgggtgcc atgtttgcgg   9540
gtggcaccgc agtgtttggt attgttgctg ccggtgtggg gaagcttgtt gcagggtttg   9600
ccccgttggc ggtgtcgttg aagaatctgt tgccgtcgtt tggtgctttg aagggtgccg   9660
ccggggggct tggcggcgtg tttcgcgccc tgggtggccc tgtcgggatt gtgattggct   9720
tgtttgcggc aatgtttgct acgaacgccc agttccgtgc cgctgttatg cagcttgtgg   9780
ggtttgttgg tcaggctttg gggcagatta tggccgctgt gcagccgctg tttggtttgg   9840
ttgctgggct ggtggcacag ttggcgccag tgttcggcca gattatcggt atggtggccg   9900
ggttggctgc ccagattgtg cctttgatta gtatgcttgt cgcccggctg gttcctgtga   9960
tcacccagat tattggcatg gtgacacagg ttgcggccat gttgctgcct acgttgatgc  10020
cggtgttgca ggctgttgtt gctgtgatac ggcaggttgt tggcgtgatc atgcagttgg  10080
tgccggtttt gatgccggtg attcagcaga ttttgggtgc tgtcatgtct gttctgccac  10140
ctatcgtcgg tctgatccgg tcgctgatac ccgtcatcat gtcgattatg cgtgtggtgg  10200
tgcaggttgt ttcggttgtg ttgcaggtgg tggcccgcat tattccggtt gtgatgccaa  10260
```

```
ttgtgacagc tgtgatcggg tttgttgcac gtattcttgg cgctattgtg tctgctgaag    10320
cccgcattat tgggactgtc actcgtgtca tctcatgggt tgtgaatcat ttagtgtctg    10380
gcgtgaggtc tatgggcacg gccatcttga atggctggaa tcatattaga gcgtttacgt    10440
cagcgtttat taacggtttc aagtcgattg tttctggcgg tgtgaacgcg gttgtggggt    10500
tttttgcccg gcttggttct tcggttgcct cccatgtgag gtctggtttt aacgcggctc    10560
gtggcgctgt ttcttctgcg atgaatgcta tccggagtgt tgtgtcttcg gtggcgtctg    10620
ctgttggcgg gttttttcagt tcgatggcgt ctagggttcg tagtggtgct gggcgcgggt    10680
ttaatggtgc ccggagtgcg gcttcttctg ctatgcatgc tatggggtcc gctgtatcta    10740
gcggggtgca tggtgtgctg ggttttttcc ggaatttgcc tggcaatatt cggcatgctc    10800
tcggtaatat ggggtccttg ttggtgtctg ctggccgtga tgtggtgtct ggtttgggta    10860
atggtatccg gaatgctatg agtggcttgt tggatacggt gcgtaatatg ggttcccagg    10920
ttgctaatgc ggcgaagtcg gtgttgggta ttcattcccc atctagggtg tttcgtgacc    10980
aggttggccg tcaggttgtt gccggtttgg ctgaggggat caccgggaat gccggtttgg    11040
cgttggatgc gatgtcgggt gtagctggac ggctgcctga tgctgtagat gcccggtttg    11100
gtgtgcgatc gtcgtgtgggc tcgtttacac cgtacgaccg gtatcggcgt gcgagcgaga    11160
agagtgttgt ggttaatgtg aatggaccca cgtatgggga tccgaacgag tttgcgaagc    11220
ggattgagcg gcagcagcgt gacgcgttga acgcgttggc ttacgtgtga ttgggggtgt    11280
tgtgcatgtt tattcctgac ccgtctgatc gttctggttt gactgtgacc tggtctatgt    11340
tgccgttgat tggtaatgat ccggagcgtg tgcttcattt aacggattat acgggcgcgt    11400
ctcctgtcat gttgttgaat gattcgttgc gcggtttggg tgttcccgag gttgagcatt    11460
tttctcaaac tcatgttggg gtgcacggct cggagtggcg cgggtttaat gtgaagcctc    11520
gcgaggtgac tttgccggtg ttggtgtcgg gtgttgaccc ggatccggat ggcgggtttc    11580
gtgacggttt tttgaaagcc tatgacgagt tgtggtcggc gtttccccccg ggcgaggtgg    11640 gggagttgtc ggttaaaacc ccgtctggtc gtgagcgtgt gttgaagtgc cggtttgatt    11700
cggtggatga cacgtttacg gttgatccgg tgaacagggg ctatgcccgc tatctgttgc    11760
atttgacagc ctatgacccg ttttggtatg gggatgagca gaagtttcgt ttcagtaacg    11820
cgaagttgca ggattggttg ggtggcggcc tgtcggcaa gaagggtaca gcgtttcctg    11880
tggtgttgac gcctggtgtt ggttcgggct gggataatct gtctaataag ggtgatgtgc    11940
cggcgtggcc tgtgattcgt gtggagggcc ccctggagtc gtggtctgtg cagattgatg    12000
gtttgcgtgt gtcttcggat tatcctgtcg aggagtatga ttggatcact attgatacgg    12060
atcctcgtaa gcagtctgcg ttgttggatg ggtttgagga tgtgatggat cgtttgacgg    12120
agtgggagtt tgcgcctatt cctccgggtg gttcgaagag tgtgaatatt gagatggttg    12180
gtttgggtgc cattgttgtg tcggtgcagt acaggttttt gagggcttgg tgaatggttg    12240
atggctggtc ttgttccgca tgtaacattg tttacaccgg attatcgccg tgtggcgcct    12300
atcaattttt ttgagtcgtt gaaactgtcg ttgaagtgga atggtttgtc cactttggag    12360
ttggtggtgt ctggtgatca ttccaggctt gacgggttga ctaagccggg tgcacggctg    12420
gttgttgatt atggtggtgg ccagattttt tctgggcctg tgcgtaaggt tcatggtgtg    12480
ggtccgtggc gttcttcgcg ggtgactatc acgtgtgagg atgatatccg cctgttgtgg    12540
cgtatgctga tgtggcctgt gaattatcgt cctggtatgg ttggtatgga gtggcgtgcg    12600
gacagggatt atgcccacta ttctggtgcg gcggagtcgg ttgctaagca ggtgttggtg    12660
```

-continued

```
gataatgctt ggcgttttcc gcctggtttg tttatgaacg atgatgagag tcgtggccgc    12720
tatattaagg attttcaggt gcggtttcac gtgtttgccg ataagttgtt gccggtgttg    12780
tcgtgggctc ggatgactgt cacggtgaac cagtttgaga atgcgaagtt tgatcagcgg    12840
ggtttgctgt ttgattgtgt gcctgctgtg acccggaaac atgtgttgac tgccgagtct    12900
ggttcgattg tgtcgtggga gtatgtgcgt gacgcccta aggctacgtc tgtggtggtt    12960
ggtggccgcg gcgagggcaa ggatcggctg ttttgcgagg atgttgattc ggcggccgag    13020
gatgactggt ttgatcgtgt cgaggtgttt aaggatgccc gtaacacgga ttctgaacat    13080
gtgcatctca ttgatgaggc tgagcgggtg ttgtccgagt cggggggctac gtcgggggttt   13140 aagatcgagt tggctgagtc ggatgtgttg cggtttgggc ccggcaatct gatgccaggt    13200
gatcttatct atgttgatgt gggttctggc cctattgcgg agattgttcg gcagattgat    13260
gtggagtgtg attcgcctgg tgatggttgg acgaaggtga cacctgttgc ggggggattat   13320 gaggataatc cgtcggcttt gctggcgcgg cgtgtggctg gtttggctgc cggtgtgcgg    13380
gatttgcaaa aattctagaa tgatgggggt ttgttgtggg tattgtgtgc aagggttttg    13440
atggtgtgtt gaccgagtat gattgggctc aaatgtctgg tctgatgggt aatatgccgt    13500
ccgtgaaggg cccggacgat tttcatgtcg gcactactgt tcagggtgcc accgtgttgt    13560
gtgaggtttt gccggggcag gcttgggctc acggggtgat gtgcacgtcg aatagtgttg    13620
agacggtgac agggcagctg cctggccctg gcgagacccg atacgactat gtggtgttat    13680
ctcgggattg ggagcagaac acggccaggt tggagattgt tcagggtggc cgtgcggagc    13740
gtgcccgtga cgtgttgcgt gcggagcctg gcgtgttcca tcagcagttg ttggcgactt    13800
tggtgttgtc gtctaacggg ttgcagcagc agctggatcg gcgtgctgtt gcggctaggg    13860
tggcgtttgg ggagtctgct gcgtgtgatc ctaccccgt ggagggtgat cgtgtgatgg    13920
tgccttcggg ggctgtgtgg gctaaccatg ccaatgagtg gatgttgttg tctccgcgta    13980
tcgaaacggg ttctaagtcg atcatgtttg gtggttctgc tgtgtatgct tacacgatcc    14040
cgtttgcccg cccctttggt agtgcgcctg ttgtggtggc gtctatggct acggcggctg    14100
ggggcacggc acagattgat gtgaaagcct acaatattac taataaggat tttagtttag    14160
cgtttattac gaatgacggg tctaagcctt ctggtgtgcc cgcgatagct aactggattg    14220
ctgtcggcgt gtgaccggc tgttgttgtg gcggatggtg tgatgttggg gggctgtggt    14280
gtcgtggatt actcctgcac tggtggcctc tatttgtacc gcgttggcca cggttttggg    14340
ttctgttcag gcggtcacgt ctaaatctcg gaggcgtttg cggcggctgt cggctcaggt    14400
ggatgctttg gaggagtata cgtggggtgt gcggtgtgag gttcgccggt ttaacgccgg    14460
gcttcctgat gatgtggagc cgatgcatct ccctgatgtg cccgagtttt tgaaggatac    14520
tgttgatggt ggaggtgagt agggttgagg gagttggagg aagagaagcg gcagcgccgc    14580
aattttgaga aggattccct gatactgttg ttttttgtcgc ttgtgctgtt ggtggcgatg    14640
gctgggggtg ctttgcggta tggttctgtg gcttcgcaaa gggattcgga gcaggctaaa    14700
gcccagtcga atggtacagc cgctaaaggt ttggctgccc gtgtgaagca ggcgtgtgct    14760
tcgagtgggg tggagtctgc gcggcttcac cagtctggct tgtgtgtgga tgctcagcgt    14820
gttgagcgga gtgtgcaggg tgtgccgggc ccggctggtg tgcgtggccc gcaaggccct    14880
gcaggtgtgg atgccgggga tggtgttaat ggttcggctg gcttgttgg ccctgttggt     14940 ccgcagggtt ctcctggttt gaatggtgtg aagggtcctg acgggttgcc tggtgtgaat    15000
```

```
ggatcggatg gccgtgatgg tgttccgggt cgtacaggtg ctgatggtgt gaatggagtt    15060
gccggggctg atggtaaaga tggcgcgaat ggcgccgatg gtgagcgtgg tgctgtgggc    15120
ccttcaggtc ctgccggccc ccaaggcgaa cggggtgagc gcggtgccgc tggtgtgaac    15180
ggatccgatg gtaaagatgg taaggatggg cgctcggtgg tgtccgtgta ctgttctgag    15240
ggccgcctat ttgtgaaata tagtgatggt gtggcttcta ctatatcggg ttcggttgcc    15300
tgccagaagg tgaaaccgtc tcctgtggtt accgtgtcat cccacaaata aaagatagaa    15360
aaggagtgac ttatgtcgat ggtgtttggg ggtggtgtgt ggtgagatac attcctgcgg    15420
cgcatcattc tgccggatca aataagccgg tgaaccgggt tgtgattcat gcaacatgcc    15480
cggatgtggg gtttccgtct gcttcgcgta agggtcgggc ggtgtctaca gcaaactatt    15540
ttgcttcccc atcgtctggt ggttcggcgc attatgtgtg tgatattggg gagacggtgc    15600
agtgcttgtc ggagtctacg attggttggc atgccccgcc gaatccgcat agtttgggta    15660
tagagatttg cgcggatggg ggttcgcacg cctcattccg tgttccaggg catgcctata    15720
cgcgggagca gtggcttgac cctcgggtgt ggcccgcggt ggagagggcc gccatcctgt    15780
gtcggcagtt gtgtgataag catggtgttc cgaagaggaa actgtctgtg gctgatttga    15840
aggccggtaa acggggtgtt tgcgggcatg tggatgttac ggatgcgtgg catcagtcgg    15900
atcatgacga tccggggccg tggttttccgt gggacaaatt tatggctgtg gtgaatggcc    15960
acggcggcgg ttcaagtagt gaggagttga gtatggctga gtacaagcg ttacataatc    16020 agattaaaca gttgtcggca caggtggccc agtcggtgaa taagctgcat cacgatgttg    16080
gtgtggttca ggttcagaat ggtgatttgg gtaaacgtgt tgatgccttg tcgtgggtga    16140
agaatccggt gacggggaag ctgtggcgca gcaaggatgc tttgtggagt gtctggtatt    16200
acgtgttgga gtgtcgtagc cgtcttgaca ggctcgagtc tgctgtcaac gatttgaaaa    16260
agtgatggtg gtttgttgtg ggtaaacagt tttggttagg tttgctagag cgggcgttaa    16320 agactttttgt tcaaacgttt gtggctgtgt tgggggttac cgcgggtgtc acgtatactg    16380
cggagtcgtt tcgcggtttg ccgtgggagt ctgccctgat tacggccacg gttgctgcgg    16440
tcctgtcggt ggctacctcg tttggtagcc cgtcgtttgt ggccggtaag ccgaaaacca    16500
cgcctgtgga tgcgggtttg gttccgccgg atgatcccgg aatagtggag cctcacatgg    16560
tggatgtgtc ggatcctggc atgatcgagc ctgcagatga tgtggatctt ggtgtaggct    16620
atgtgccgaa acatgctgcc gagtcggagg ttggcacagt agagtctact gttgcataag    16680
tgaatataga tgtgtgcccc agcggtgctg ccacgattgt gtggtggttg ccgctggggc    16740
actatttttg tatattgcgg tgtggctatg attcgttgct gtcgatggtg tcttcgagca    16800
tctgatacag gtggaggcag gtagagatcg tttcgttggc ctggtcgaga acgttccggc    16860
cgataacgtt tttgtggttg tcgcggtggc ggatgatagc ccacatgatc tcgccggctg    16920
ccgcctgtaa tagtttggcc tggtatgcga ttccggcgag ccagtctagt gcttcctggc    16980
ttgcataggg gctctggttc tcgctgttgc cgcgggtgtt gctgttgttt gtggggtgtc    17040
ctgcactgtc gcagaaccat aggatttcgc tgcactcgtc tagcgtgtct tggtcgatag    17100
cgagatcgtc gaggctgaca ttgttgacgg taaggttcac gttgtcgagg gagatgggta    17160
caccgtactg gttttcgaca ctgtcaacaa tgttttgtag ttgttgcatg ttggtgggct    17220
gttgttggac gatgcggtgt atcgctgtgt tgagggtggt gtaggtgatg ttgtgtgtgt    17280
tgttcatcgt gttatgccat tccttcgtta tcgtctggca tgtagtatgt gctgtttgcg    17340
tactcggtta acgtcatcag tgtttggtct gcccactgtt tcacggtttg ccgggtgata    17400
```

```
cctaatcgtt gggcggctgt ggcgtaggtt tggtcgtatc cgtagacttc ccggaatgct    17460
gccagcctag ctaaatgttt tcgctgtttg gatggttcac aggtgagtgt gtagtcgtcg    17520
atggctagct gtagatcgat catggtgacg atgttgttgc cgtgatgctg ggggcggtt    17580 ggtggggtg gcattcctgg ttcgacggat ggtttccatg gtccgccgtt ccagatccat    17640
tgggcggctt ggatgatgtc ggcggtggtg taggttcggc tcacttggtc accccctgaa    17700
catgttgtcg aggttgttgg tgttgctggt gtcgaatcgt ccgacgcagt ggcagtagtc    17760
gtacatgagt ttgataatgt gttggtgatc tcccaaatag gtgtttccgc tgatgctgta    17820
ggtggctgtg ccgtctttgc tgatggtgta tttggcggtg atggtttcgg ggttttcggt    17880
gtcggtgatg atggctgtgg tggtggcgcc tactgtttgt agcacggtgg tttgagttcc    17940
gtcgtcgatg gtggttttaa ccatggtgtg tgttctcccc tttcagttgc tggtttggtt    18000
gtcggctaga tgaatgatat cggataaagg tttcggctgg tcgaggtgtt gtatggtttt    18060
gttggctaaa cgtttggcta ccctgtaaca cattttggtg tagtgtttgt tgtctaggtt    18120
gtggtattgt tcccgcaccg caatatatag tagagagtct tggtacaggt cgtctgcact    18180
gattgcgggg tagtgtgcgg ctgttttggt gcatgcccgg ttgagtgtgc gtagatgatg    18240
gtctgtggcc caaacccacg atgcggtggt ggcgaggtct gctttggttg gtcgtcggct    18300
catggcatct ctttcatcgg gctatctggt agttgtttgg tgttttgttg ttgatagtgt    18360
agcacacgag tccggggttt ccggtggtgc ctgtcttgtg ccggtaccat gtggattcgc    18420
cttccatgga ggggcattgg atgaaggtgc gttgtccttg ttcggagatt tctaggtgat    18480
gccggtgccc ggccatgaga atattagatg tggtgccgtt gtggaattct tggccgcgcc    18540
accaatcata gtgttggttg ttgcgccatt ggtgcccgtg ggcgtgcagt atccgtgtgc    18600
ctgccacgtc gacggtggtg gtcatttcgt ctcggctggg gaagtggaag tgaaggttgg    18660
ggtattggtt ggtgagctgg taggcttctg cgatggcgcg gcagcagtcc acgtcgaagg    18720
agtcgtcgta ggtggtgact cctttgccga atcgtacggc ttcgccgtgg ttgccgggga    18780
tggatgtgat ggtcacgttt ttgcactggt cgaattggtg gatgagttgc atcatggcca    18840
tgcgggtgag cctgatttgt tcggtcaggg gggtttgtgt gcgccaggcg ttgttgcctc    18900
cttgtgacac gtatccttcg atcatgtcgc cgaggaatgc gatgtggact cgctcgggtt    18960
tgcctgcttg ttgccagtag tgttttgcga ctatgagtga gtgtaggtag tcgtcggcga    19020
agtgtgatgt ttctcctccg gggatgcctt tgccgatttg gaagtctcct gccccgatga    19080
cgaaggctgc ggttctgtag tcggtgtggg tgtcttgttc gggttttggt ggctgccatt    19140
cggctagctt gtcgacgagt tcgtctacag ggtagggggtt ggttgcgggt tggtggtcga    19200 tgatttttg tatggatcgg ccggtttctc cgttgggtaa ggtccattca gagatgcgtg    19260
tgcggcgtac ggtgccgttg gctagattgt cgtcgatggt gtcgatggcg ttgtcgtggt    19320
tggctagttg tgtgagtagc cggtctatgt tgtctatcac tgggtatcct cctcgtgtgg    19380
ggtggtgttg gcttgtttgc ggcggtagtc tttgatgacg gtggcggaga tggggtatcc    19440
ggcttgggtg agttgttgtg ctagccagga ggcgggtatg gacctgtctg cgagcacgtc    19500
tgcagcctta tcaccgtagc gttggatgag ggtttcagtt ttggttgcca tggtgtccta    19560
tcggttgtgt ggtgggctgc catcctgtgc ggcagtcgcc gtcgtgtcct ggtttgcgtg    19620
tgcaccacga tgttgttccg tctgtgtggt tgagtgtttt accgcacatg acgttttgga    19680
gatgttccgg cagctggtca tcctggttgc tggtttgtgt gtcgaagagt gttttttggt    19740
```

```
tggtgaaatg ctcggacacg gtgccgttgt ggacgggtag tatccatgtt ttccattgtt   19800
gttgtatccg ggtgttccag tggaattgtt tggccgcgtt ttcggcttgt ttggcggttt   19860
tgtagtagcc gactagtatg cgctggtgtt cactgtcggg tgggttttgg cctcgccagt   19920
attgtgccgc cacggcgtaa cggttgtttt ctgtgaaggt gttccagcag tattcgatga   19980
tgtgttgcag tacactatcg ggaatgtctt gtgcctggtt ttcgttgagc cattcggctt   20040
cgatgatgcc gtgtatggcg tgtttgtctg tggtggtggg tttgaacgag atgctcacaa   20100
tgcgggcctg tcgtcttgca tgaaatcgtt gaaggatgat tcgcttgcgc ggcgtgcctg   20160
ggtgatttgc tggtcggtcc agtctgggtg ttgctgtttc agatagtgcc agcggcacgc   20220
attgtaggtt tcgttctgta agcgggtgag attgttttct tcgatgattt ggttccacat   20280
ggcccaggat acgtctagcc tgtccaggat ttcgagggct ggggtgttgt attggttgag   20340
gaagagggtt tcgtgggtgt agtattcttt ttcatactgt tcccagtttg atttgttttg   20400
cgattttttg cctttagggt acacggttcg tgcaactttg tgcatctgtt tgcgcatgat   20460
gtcggggatg tgcacgtcgg ggtttgagcg gatcatggat ttcatgccat catatgtggc   20520
accgtattcc cgtatgatct cgtatgggtc gtctccgtct tcccattttt cggcgataat   20580
ctggaggcgt gcgtgttgcc ttgatgcggc ggtgcggtcg cggcggtcgg ggatggggca   20640
ggtttccatg gttggcatcg gatcggttct ttctggtttc gtgttgttga caggttttac   20700
tgtagcacag tgtctagtgc ttgtgtcaac cctgtttttc cggcctgcag gtaggtgtct   20760
gtgacatccc cgacagtgag gggcacatgg gtggcttggg ggagcgcggt ttggatggtt   20820
tgtgccatct ggtcgcctgc cgagtctggg tctgaccaga tgtagatgtg gtcgtagcct   20880
tcgaagaatt tggtccaaaa ggtttgccac gaggttgcgc cgggtagggc tactgccggc   20940
catccgcatt gttcgaggat catggagtcg aattcgcctt cgcaaatgtg tatttcggct   21000
gccgggttgg ccatggcggc catgttgtag atggagcctg tgtccccggc tggggttaag   21060
tatttggggt ggttgtgggt tttgcagtcg tgtgggagtg agcagcggaa acgcattttt   21120
cgtatttcgg ctggcccttc ccagacgggg tacatgtagg ggatggtgat gcactggttg   21180
tagttttcgt ggcctgggat ggggtcattg tcgatgtatc caaggtggtg gtagcgggct   21240
gtttcttcgc tgatgcctct tgccgagagc aggtcgagta tgttttcgag gtgggtttcg   21300
tagcgggctg aggcttttctg gattcgacga cgttccgcaa tgttgtaggg gcgtatgctg   21360
tcgtacattc gggttttctt tctctaatcg ttgtttcagt ttgtggagtc ctcctccgat   21420
accgcatgtg tggcagtacc agacgcccctt gtcgaggttg atgctcatgg agggctggtg   21480
gtcgtcgtgg aacgggcaga ggatgtgttg ctcgtttctg gacggattgt agcgtatctg   21540
gtgggcgtct aggaggcggc aggtgtcaga ggtgtgggag gagctcgttg agggttgata   21600
ccacataggc ttcgctccag ggtttgttgc gctgtttcat gatgacgagt ccgatggtgg   21660
actggttttc gcggtttcgg tgggtttcgt agttgcgtgc ctcccggctg gcttgtttca   21720
cgaattcggc taggtgtggc tgtcctgctt tggcttcgat cacataggtt ttgttgccgg   21780
ttgtgaggat gaggtcgcct tcgtcctcgc ggccgttgag gtggaggcgt tcgatattgt   21840
ggccggtgtc gcgtagctgg tgcaataatc gtgtttccca ttccgcgccg gcccggcggt   21900
tgcgtgcctg ctgtgtggcc atcatagtcc tttgtgtgtt gtggtcatgt tccagggctg   21960
tttttcaacc aggggtccga agaatgtgta ttcggggtag gctctgagcc gctcatattt   22020
tgttccgtct gggctggatt tgccggttct ctgtttcaac actgcgatgc gtgcctctgc   22080
cgggatggtg agcccgttgc cgttgtcttc gccaccatac agggagactc ccaatatgag   22140
```

```
ttgtggtttt tcggagaggc cgttttttgat ttcccgccta gccgggggt gttcaatatc    22200 ggagccggtt ttgtcggtgg cgtggtgggt gacaataatg gtggatccgg tatccctacc    22260
taatgctgtg atccattgca tggcttcttg ctgtgcctga tagtcggatt cgcagtcttg    22320
gatgtccatc aggttgtcga taacaataat gggtgggaag gtgttccaca tttccatgta    22380
ggcttggagt tccatggtga tgtcggtcca ggtgatgggt gactggaatg agaatgtgat    22440
gtgttggccg tggtggatgc tgtctcgata gtattctggc ccgtagtcgt cgatgttgtg    22500
ttgtatctgg gcggtggtgt gttgggtgtt gagtgagatt attcgtgtgg aggcctccca    22560
gggtgtcatg tcccctgata tgtagagggc tggctggttg agcatggcgg tgatgaacat    22620
ggctagccct gattttggc tgccggaccg ccccgcgatc atgacgagat cccctttgtg    22680
tatgtgcatg tccaggttgc ggtagagggg ttctagttgt ggtatgcggg gcagttcggc    22740
tgctgtttgg gaggctctct cgaaggatct ttggagagag agcatcggag cctttatcta    22800
tctgtctatc ggttggatga tgttttggtg gtcagatgga gtcgatatcg atgtcagtag    22860
aggctgtggt gtcgtctagc tggccgttat cgcgtttgtc tacgtattcg gcaaccttat    22920
cgtagatggc gtcgtctaat ggtttgagca cgaccgcgtt gaacccgttt ttggtgcgca    22980
cggtggcgag tttaaaggcc tgctcctcgc caaggtacgc ttctaggtcg cggatcatgg    23040
agtgtgggcg gtcgttgttg ccgcgggctt tctcaataat agcgttgggg atggtttctg    23100
gggtgccgtt gttgagatcg tctagggtgt ggaagatggt gacatcagcg tagatgcggt    23160
ctgcgacctg tccaccgtag ccttcggtgt tgtgttctac gtcgcggact ttgaaggcga    23220
tggcggtggc gtcctggttt cgggaggggt tgaagaaggt gctgttgctg ttgttgcggt    23280
agttggcgag tcccataatg gtgttatcct ttactgttgt gtctgttatt gttggcttat    23340
attggtttat cgggtgaggc tgtttcgttt agtgcggaac gcctcagaca cgtcactgtt    23400
actagtgatg gtctttttgt actgtttgag taggtctgct agctgtgtct tgctggtggc    23460
tttgttgatc cggtcaatga tgatgtcgtt ttcctgattg gcgattttgt ttacgtagtc    23520
tttggtggcc tgattgtatc ggtcttggag gatgatggat gcgctggcga tgagggttgc    23580
gaggtcccat tctttggata cggtttcgtc tttcaatcct cccaataaat cgataatgga    23640
ttgtttgatg tcttctgcgg tgtctccgcg gatgactgtc catgggcag catagtctcc    23700 accgtatttg agtgtgatag ttagcttttc gttgtctgtg gtgtgctcgt cggtcacgtg    23760 ttttccttt ctttactgtc ggtttgggtt ggctgtacgg tggtttctat cgggtatctg    23820
tacgagtttt tcccgttgac ggcccagcag gcgtccctga cggggcatcc tttacagagt    23880
gtggtgacgt gtgggacgaa gatgccttgg ctgattcctt tcattgcttg actgtacatg    23940
gatgatacat gccggtaggt gttgttgtca aggtcgtata gttcggttgc tgtgccctgc    24000
tcggccgatt gctcgtctcc cttggttgtg gcgggtgtcc aaaacatgcc tttcgtgaca    24060
tggatgccat gttggttgag catgtaccgg tatgtgtgca gctgcatact gtcggcgggt    24120
aggcgtcctg ttttgaggtc caaaatgaag gtttcacccg tattcgtatc tgtgaatacc    24180
cggtcgatgt agccaacaat ctgggtgccg tcttggaggg tggtttctac cgggtattcg    24240
atgcctggct ggccgtcaat aacagcggta gcgtattctg ggtggttgcg cctccatgtt    24300
ttccaccggt ccacaaagat ggggccgtac atcatccacc aattgtagtc tttcttgttg    24360 gggccccgc tttcgcacat gttttttgcac actcggccgg aggtttgat gtttgtgcct    24420 tcggattcgg cgagggcgac ttgggtgtcg aaaatgtttg tgaaggatga gagtttgtct    24480
```

```
ggcagttcag ggtattcgtc gggattgtac aggtgtaggt cgtattgttc ggtgatgtgg   24540
tgtatggcgc ttccggcgat ggtggcgtac caggtgtggt gttgggtgtg gtagccgtgt   24600
tggaggcgcc attttttcacc acattcggcc cactgtgaca gtgatgagta ggagatgtgg   24660
cctggatggt ggatggtttt cgggtattgt gctaggggca ttacttgccg cctttgtggg   24720
tgttccatgg gttgcgggtg tctacccctg catcgtgttg ctggtaggcg aggagtgcga   24780
ggcagtgcca tgcagcatgg gccagatgcg gtagcccgga ttcataatcg aggttgtttc   24840
cttgctgcca tgataacagg tgcctgtaga gggcgtcaac gctgtggctc cacgggtatc   24900
cgccggtcca gttgttgtcg ccgtatttgg tggcaccgta tccggccacg gagccgaggg   24960
cgtggagggc tgtagggtcg atgagggata gcctgcaaag tttgagttct ttcttggcgc   25020
cagtatcagg gttggtgtac atgctggtgg gctcatccat ggtgtgtgtg ctccttacgt   25080
gtggggttac tggttggggt tgtgggcgag tgctacggcg aggatgatga tggcgagggt   25140
ttccgcgatc aggatgggtg ttgtgatcat ttgtggtttt ttggctggta ggtgagggtt   25200
gaggcaccca ggaggatagt gagggcgcat gcggcaataa tggcgagagc tgccttgtgt   25260
ggggtaccgg tggcgtacat ccatgtgatg atggcgccct ggatccaggc cagtgtggtg   25320
aagaacgttt cgtagctgtg cagctcgata ctgttgggtg tgttcatgct tgttcctgaa   25380
gaatggtgtt gatggttttg taaatgttgt acaggtcggc ttcgatggtt tgtagctgtt   25440
tgatttggtg gtcgagattg atgtgtgggt tgagggtgtt gatgcgggag gcgatgtcgg   25500
tggctgtgcg tagtgtgccg ccggtgtggt gaatgatgtg tgccgtgtcg gcgagtccgg   25560
tggtgacagc gtagtgggag aggagaggca tagcggtcct tgacgggggtt actgttgcgg   25620 gttgatgttg aggtcggtga cgttggggtg ttcttctgtt ccggtgacga ggcagtggac   25680
ggtgactggg agtttggatg ctcccggctg gcggacggtg gcgccgtaga cgatgctgaa   25740
tgtgtctttg tgtgctccga tgactttgtg gagttggagg tcgatgtcgg ggttgccgtt   25800
ccatttgaca ccgttttctg cgactgcctg ggtggctttc tggtcgcaag catgggctgc   25860
cgtaatcatg gtcaggccgg tggaggtttc ttcacccctt gcttgggctt gcttgtgggc   25920
tttggcctgc tctgcttgta gggagtggac tgctgcggcc tggcgggctt tcttctcggc   25980
tttgcgctgt tggacggttt tgggtgtcca ttcagtgtta gctgtggtgg cctgtgggc   26040 tggctgtgat gcgagtggcg ggttgtcgtc tgggctggc atgaatgagg cggcggcgat   26100
gatggcggct gtgattccgg cgatggtgta gccttttttc ttgttcatga ctgttgtccc   26160 cttttccgggg tgttgttcgt tgctgacatg attaatcatg gtgtgggcgg tggcccatgt   26220
caaggctgcg ctcaacgatt gtgagcgttt ggtgtgtggc taggggtttt atcgagcaca   26280
cagagtgagt aggtggccaa cattgatgcg gctcacattc cagtagagtt gtgtggcttc   26340
cccactggtg agtggcttcc actcgttgtg gctgaacacg gtgccatcgg atgcgatgaa   26400
cgtgttgggg cgtagcttgt ggagttcggc ttccacgctc tgccggtagg cttcggcgag   26460
gccctcaaaa tcgaggtggt cgcaggagag gttttcgagg cgtgtcaggt cgaagggtgt   26520
ggggcagtcg tagctggcgg gggtgtagag ctgggtgaag tggttggcga tcttctgcat   26580
gatgatgtcc ttttcgttgc tgataacgtt gttgagggtt tatcgggtgg atgcgaccag   26640
gatggcgtct acgtcgatca tgtcgatcat gtcgtggagt tcctcggctt cgttctcgga   26700
gaggtggcgc cagtcgtagt ctccgtatac ggcgccgtcg agggtgacag tccacagtgg   26760
ccggatgagt cgtacggctt cttgtacttt agcgtggtac atgcggcgca ccatatcgag   26820
atcgatgtcg tctgaatggt ttccggtgag gctgtggagg ctgagcgggt cgatttctgt   26880
```

```
ctgcctgtag agggatgtga aggatggggt gatgagtgtg ccatccatga gtgtgctcct   26940
ttcggtggtg taggggttgt tgtggtttct agagtgtgtg ggctgtgacc cacagtcaag   27000
gtggcgctca aacccagtga gcgtttcatg ctggagtgtt gggtgtggca gatgatctag   27060
cgagtcaagg tgccgagctg agacataaga tctatcatct aggtgtgtga gatgtatcac   27120
atcctcctgg cttgatgtgc accctcgagg ctactctgcc gatctgacgt ggagggtgta   27180
gcccagaaag gccgtttaaa gccttcgcac ggcgcctagg agcgccttac agggtggggg   27240
ctaggtattc ataccccccaa gcaattctga tcgattctag acgcctccca tgagcccgat   27300
acacgatcag ccatctctgc atagatcatc agcccctatc ctggttagct aagcctcaac   27360
tatgtggaca gtgtgggatg ctaaggggga agaaggacac ggtaaaagaa agaggggag    27420
tatcagcctt caagccttaa ggtcttagca gttagcaccg agcccctca agggctcggc    27480
atcagcccga acaggcacag ccctgaaaag ggtacacacc atcagggaag gctttcgagt   27540
acgaggagcc tcagcgacga gtactcgaaa gcctgaggga acaccctcag cactgatggg   27600
cctagcgtat tcggaaagga cacaagagtc aagtgtgaca gctgtccggg agtgaaacct   27660
gttctgacta ggggtttcag cctgaaccac cctcaaaggt tacaagactc taagaaaatt   27720
taagaaaact cttaggaaga aagttgtgtt catatccccc taaaaacacc caaaatagcc   27780
ctcaaacccg cctatagagc caaacagtca agtttgactc gtctaaacgg cgtatgatag   27840
gctggacagg tagccagctg gacgcgaggc cagaaagtgc tgacgcactt cccgacctcg   27900
cttaccatca gtctaccaaa gacttaaaag cttcaaggct tagcccttaa ggatctaagt   27960
tactataaaa gctttaaaag ctttaagagc ttaacactta agttaagtat aaaaccttaa   28020
aggctaagca cttaaggata taaacttaac atcagtgttt aagactttaa gagttaaagt   28080
aactattaag acttaaaggc ttataagctt taatacttta agtaactata agactttaaa   28140
aaccttcagt acttaaagtt aaccatcagt cttaaacttt aatattataa cctataagtc   28200
ttaaagctta taggtataat aatataatat aagtattaaa gcttataagt tataaaagtt   28260
ttagaagagt taaagggtta acttctttac ttctcttctc tctttggttc tttctctctt   28320
ctcttctttt cttcatcagg ggagaagagg aaccttacc gtcaacgctg atggacttt    28380
cgccgtgtgt ctcgtgtgct tctggtcgca agctcccatc gcacactccc cacactctga   28440
cactcgtgtc cctttacggc ttagcgtgtt cggctgaagg cgtacggcgt gtcacgctta   28500
aacccttaac accaggtaag acttaaagta catattataa gtagaagact ttaaaacctt   28560
taaggtgttc ccgctgagcc tgtgtccttc aacgctaggc gctaagcctt gaaacgtgaa   28620
caccccacccc accttttttc tttcgtgtcc ttcttctttt gacaccgctg gggggtagt   28680
ggagacaaca aacaccccgg cacaaaaaag aacaccccc taaacgaaca aaacaggtcc    28740
taggatcgac tagcagggca ccggtaggat attcctacca ccaatggttc ccaggccgct   28800
agaggagcaa tgagggctc acagggacca taggtgattg ggggatgtga tggcacacac    28860
caaccgcaca gcatcctccg cccatcggcg ctggcgggca aggctcatca cccaagccca   28920
acaacaaggc caaaccgaat gcccactctg cggagcccag atagcctggg gcacacacga   28980
tctgccaacc agccccgaag ccgaccacat cacacccgtc agccgcggag gactcaacac   29040
cctcgacaac gggcaaatca tctgcagaac atgcaacaga agcaaaggca atcgcagcga   29100
accaaacatt agtttccaac aacaaaccac aaaaacattg atcccatggt gaaaaaaacc   29160
acaaaccccca cgggaaccac ccctggcaca cccgtgcaag acctcgtacg gctt         29214
```

```
<210> SEQ ID NO 13
<211> LENGTH: 441
<212> TYPE: PRT
<213> ORGANISM: Propionibacterium phage P9.1

<400> SEQUENCE: 13

Met Asn Ser Asp Glu Leu Ala Leu Ile Glu Gly Met Phe Asp Arg Ile
1               5                   10                  15

Gln Arg Leu Ser Ser Trp His Cys Arg Ile Glu Gly Tyr Tyr Glu Gly
            20                  25                  30

Ser Asn Arg Val Arg Asp Leu Gly Val Ala Ile Pro Pro Glu Leu Gln
        35                  40                  45

Arg Val Gln Thr Val Val Ser Trp Pro Gly Ile Ala Val Asp Ala Leu
50                  55                  60

Glu Glu Arg Leu Asp Trp Leu Gly Trp Thr Asn Gly Asp Gly Tyr Gly
65                  70                  75                  80

Leu Asp Gly Val Tyr Ala Ala Asn Arg Leu Ala Thr Ala Ser Cys Asp
                85                  90                  95

Val His Leu Asp Ala Leu Ile Phe Gly Leu Ser Phe Val Ala Ile Ile
            100                 105                 110

Pro Gln Gly Asp Gly Ser Val Leu Val Arg Pro Gln Ser Pro Lys Asn
        115                 120                 125

Cys Thr Gly Arg Phe Ser Ala Asp Gly Ser Arg Leu Asp Ala Gly Leu
130                 135                 140

Val Val Gln Gln Thr Cys Asp Pro Glu Val Val Glu Ala Glu Leu Leu
145                 150                 155                 160

Leu Pro Asp Val Ile Val Gln Val Glu Arg Arg Gly Ser Arg Glu Trp
                165                 170                 175

Val Glu Thr Gly Arg Ile Pro Asn Val Leu Gly Ala Val Pro Leu Val
            180                 185                 190

Pro Val Val Asn Arg Arg Arg Thr Ser Arg Ile Asp Gly Arg Ser Glu
        195                 200                 205

Ile Thr Arg Ser Ile Arg Ala Tyr Thr Asp Glu Ala Val Arg Thr Leu
210                 215                 220

Leu Gly Gln Ser Val Asn Arg Asp Phe Tyr Ala Tyr Pro Gln Arg Trp
225                 230                 235                 240

Val Thr Gly Val Ser Ala Asp Glu Phe Ser Gln Pro Gly Trp Val Leu
                245                 250                 255

Ser Met Ala Ser Val Trp Ala Val Asp Lys Asp Asp Asp Gly Asp Thr
            260                 265                 270

Pro Asn Val Gly Ser Phe Pro Val Asn Ser Pro Thr Pro Tyr Ser Asp
        275                 280                 285

Gln Met Arg Leu Leu Ala Gln Leu Thr Ala Gly Glu Ala Ala Val Pro
290                 295                 300

Glu Arg Tyr Phe Gly Phe Ile Thr Ser Asn Pro Pro Ser Gly Glu Ala
305                 310                 315                 320

Leu Ala Ala Glu Glu Ser Arg Leu Val Lys Arg Ala Glu Arg Arg Gln
                325                 330                 335

Thr Ser Phe Gly Gln Gly Trp Leu Ser Val Gly Phe Leu Ala Ala Arg
            340                 345                 350

Ala Leu Asp Ser Ser Val Asp Glu Ala Ala Phe Phe Gly Asp Val Gly
        355                 360                 365

Leu Arg Trp Arg Asp Ala Ser Thr Pro Thr Arg Ala Ala Thr Ala Asp
370                 375                 380
```

```
Ala Val Thr Lys Leu Val Gly Ala Gly Ile Leu Pro Ala Asp Ser Arg
385                 390                 395                 400

Thr Val Leu Glu Met Leu Gly Leu Asp Asp Val Gln Val Glu Ala Val
                405                 410                 415

Met Arg His Arg Ala Glu Ser Ser Asp Pro Leu Ala Ala Leu Ala Gly
            420                 425                 430

Ala Ile Ser Arg Gln Thr Asn Glu Val
        435                 440

<210> SEQ ID NO 14
<211> LENGTH: 159
<212> TYPE: PRT
<213> ORGANISM: Propionibacterium phage P9.1

<400> SEQUENCE: 14

Met Gln Gly Val Val Leu Met Gly Ile Ile Leu Lys Pro Glu Asp Ile
1               5                   10                  15

Glu Pro Phe Ala Asp Ile Pro Arg Glu Lys Leu Glu Ala Met Ile Ala
            20                  25                  30

Asp Val Glu Ala Val Ala Val Ser Val Ala Pro Cys Ile Ala Lys Pro
        35                  40                  45

Asp Phe Lys Tyr Lys Asp Ala Ala Lys Ala Ile Leu Arg Arg Ala Leu
    50                  55                  60

Leu Arg Trp Asn Asp Thr Gly Val Ser Gly Gln Val Gln Tyr Glu Ser
65                  70                  75                  80

Ala Gly Pro Phe Ala Gln Thr Thr Arg Ser Ser Thr Pro Thr Asn Leu
                85                  90                  95

Leu Trp Pro Ser Glu Ile Ala Ala Leu Lys Lys Leu Cys Glu Gly Asp
            100                 105                 110

Gly Gly Ala Gly Lys Ala Phe Thr Ile Thr Pro Thr Met Arg Ser Ser
        115                 120                 125

Val Asn His Ser Glu Val Cys Ser Thr Val Trp Gly Glu Gly Cys Ser
    130                 135                 140

Cys Gly Ser Asn Ile Asn Gly Tyr Ala Gly Pro Leu Trp Glu Ile
145                 150                 155

<210> SEQ ID NO 15
<211> LENGTH: 96
<212> TYPE: PRT
<213> ORGANISM: Propionibacterium phage P9.1

<400> SEQUENCE: 15

Met Ala Gln Asp Val Asn Val Lys Leu Asn Leu Pro Gly Ile Arg Glu
1               5                   10                  15

Val Leu Lys Ser Ser Gly Val Gln Gly Met Leu Ala Glu Arg Gly Glu
            20                  25                  30

Arg Val Lys Arg Ala Ala Ser Ala Asn Val Gly Gly Asn Ala Phe Asp
        35                  40                  45

Lys Ala Gln Tyr Arg Asn Gly Leu Ser Ser Glu Val Gln Val His Arg
    50                  55                  60

Val Glu Ala Val Ala Arg Ile Gly Thr Thr Tyr Lys Gly Gly Lys Arg
65                  70                  75                  80

Ile Glu Ala Lys His Gly Thr Leu Ala Arg Ser Ile Gly Ala Ala Ser
                85                  90                  95

<210> SEQ ID NO 16
```

```
<211> LENGTH: 386
<212> TYPE: PRT
<213> ORGANISM: Propionibacterium phage P9.1

<400> SEQUENCE: 16
```

| Met | Met | Ala | Gly | Leu | Val | Pro | His | Val | Thr | Leu | Phe | Thr | Pro | Asp | Tyr |
|---|---|---|---|---|---|---|---|---|---|---|---|---|---|---|---|
| 1 | | | | 5 | | | | | 10 | | | | | 15 | |

| Arg | Arg | Val | Ala | Pro | Ile | Asn | Phe | Phe | Glu | Ser | Leu | Lys | Leu | Ser | Leu |
|---|---|---|---|---|---|---|---|---|---|---|---|---|---|---|---|
| | | | 20 | | | | | 25 | | | | | 30 | | |

| Lys | Trp | Asn | Gly | Leu | Ser | Thr | Leu | Glu | Leu | Val | Val | Ser | Gly | Asp | His |
|---|---|---|---|---|---|---|---|---|---|---|---|---|---|---|---|
| | | 35 | | | | | 40 | | | | | 45 | | | |

| Ser | Arg | Leu | Asp | Gly | Leu | Thr | Lys | Pro | Gly | Ala | Arg | Leu | Val | Val | Asp |
|---|---|---|---|---|---|---|---|---|---|---|---|---|---|---|---|
| | 50 | | | | | 55 | | | | | 60 | | | | |

| Tyr | Gly | Gly | Gly | Gln | Ile | Phe | Ser | Gly | Pro | Val | Arg | Lys | Val | His | Gly |
|---|---|---|---|---|---|---|---|---|---|---|---|---|---|---|---|
| 65 | | | | | 70 | | | | | 75 | | | | | 80 |

| Val | Gly | Pro | Trp | Arg | Ser | Ser | Arg | Val | Thr | Ile | Thr | Cys | Glu | Asp | Asp |
|---|---|---|---|---|---|---|---|---|---|---|---|---|---|---|---|
| | | | | 85 | | | | | 90 | | | | | 95 | |

| Ile | Arg | Leu | Leu | Trp | Arg | Met | Leu | Met | Trp | Pro | Val | Asn | Tyr | Arg | Pro |
|---|---|---|---|---|---|---|---|---|---|---|---|---|---|---|---|
| | | | 100 | | | | | 105 | | | | | 110 | | |

| Gly | Met | Val | Gly | Met | Glu | Trp | Arg | Ala | Asp | Arg | Asp | Tyr | Ala | His | Tyr |
|---|---|---|---|---|---|---|---|---|---|---|---|---|---|---|---|
| | | 115 | | | | | 120 | | | | | 125 | | | |

| Ser | Gly | Ala | Ala | Glu | Ser | Val | Ala | Lys | Gln | Val | Leu | Val | Asp | Asn | Ala |
|---|---|---|---|---|---|---|---|---|---|---|---|---|---|---|---|
| | 130 | | | | | 135 | | | | | 140 | | | | |

| Trp | Arg | Phe | Pro | Pro | Gly | Leu | Phe | Met | Asn | Asp | Asp | Glu | Ser | Arg | Gly |
|---|---|---|---|---|---|---|---|---|---|---|---|---|---|---|---|
| 145 | | | | | 150 | | | | | 155 | | | | | 160 |

| Arg | Tyr | Ile | Lys | Asp | Phe | Gln | Val | Arg | Phe | His | Val | Phe | Ala | Asp | Lys |
|---|---|---|---|---|---|---|---|---|---|---|---|---|---|---|---|
| | | | | 165 | | | | | 170 | | | | | 175 | |

| Leu | Leu | Pro | Val | Leu | Ser | Trp | Ala | Arg | Met | Thr | Val | Thr | Val | Asn | Gln |
|---|---|---|---|---|---|---|---|---|---|---|---|---|---|---|---|
| | | | 180 | | | | | 185 | | | | | 190 | | |

| Phe | Glu | Asn | Ala | Lys | Phe | Asp | Gln | Arg | Gly | Leu | Leu | Phe | Asp | Cys | Val |
|---|---|---|---|---|---|---|---|---|---|---|---|---|---|---|---|
| | | 195 | | | | | 200 | | | | | 205 | | | |

| Pro | Ala | Val | Thr | Arg | Lys | His | Val | Leu | Thr | Ala | Glu | Ser | Gly | Ser | Ile |
|---|---|---|---|---|---|---|---|---|---|---|---|---|---|---|---|
| | 210 | | | | | 215 | | | | | 220 | | | | |

| Val | Ser | Trp | Glu | Tyr | Val | Arg | Asp | Ala | Pro | Lys | Ala | Thr | Ser | Val | Val |
|---|---|---|---|---|---|---|---|---|---|---|---|---|---|---|---|
| 225 | | | | | 230 | | | | | 235 | | | | | 240 |

| Val | Gly | Gly | Arg | Gly | Glu | Gly | Lys | Asp | Arg | Leu | Phe | Cys | Glu | Asp | Val |
|---|---|---|---|---|---|---|---|---|---|---|---|---|---|---|---|
| | | | | 245 | | | | | 250 | | | | | 255 | |

| Asp | Ser | Ala | Ala | Glu | Asp | Asp | Trp | Phe | Asp | Arg | Val | Glu | Val | Phe | Lys |
|---|---|---|---|---|---|---|---|---|---|---|---|---|---|---|---|
| | | | 260 | | | | | 265 | | | | | 270 | | |

| Asp | Ala | Arg | Asn | Thr | Asp | Ser | Glu | His | Val | His | Leu | Ile | Asp | Glu | Ala |
|---|---|---|---|---|---|---|---|---|---|---|---|---|---|---|---|
| | | 275 | | | | | 280 | | | | | 285 | | | |

| Glu | Arg | Val | Leu | Ser | Glu | Ser | Gly | Ala | Thr | Ser | Gly | Phe | Lys | Ile | Glu |
|---|---|---|---|---|---|---|---|---|---|---|---|---|---|---|---|
| | 290 | | | | | 295 | | | | | 300 | | | | |

| Leu | Ala | Glu | Ser | Asp | Val | Leu | Arg | Phe | Gly | Pro | Gly | Asn | Leu | Met | Pro |
|---|---|---|---|---|---|---|---|---|---|---|---|---|---|---|---|
| 305 | | | | | 310 | | | | | 315 | | | | | 320 |

| Gly | Asp | Leu | Ile | Tyr | Val | Asp | Val | Gly | Ser | Gly | Pro | Ile | Ala | Glu | Ile |
|---|---|---|---|---|---|---|---|---|---|---|---|---|---|---|---|
| | | | | 325 | | | | | 330 | | | | | 335 | |

| Val | Arg | Gln | Ile | Asp | Val | Glu | Cys | Asp | Ser | Pro | Gly | Asp | Gly | Trp | Thr |
|---|---|---|---|---|---|---|---|---|---|---|---|---|---|---|---|
| | | | 340 | | | | | 345 | | | | | 350 | | |

| Lys | Val | Thr | Pro | Val | Ala | Gly | Asp | Tyr | Glu | Asp | Asn | Pro | Ser | Ala | Leu |
|---|---|---|---|---|---|---|---|---|---|---|---|---|---|---|---|
| | | 355 | | | | | 360 | | | | | 365 | | | |

| Leu | Ala | Arg | Arg | Val | Ala | Gly | Leu | Ala | Ala | Gly | Val | Arg | Asp | Leu | Gln |
|---|---|---|---|---|---|---|---|---|---|---|---|---|---|---|---|
| | 370 | | | | | 375 | | | | | 380 | | | | |

| Lys | Phe |
|---|---|

```
<210> SEQ ID NO 17
<211> LENGTH: 33
<212> TYPE: DNA
<213> ORGANISM: Propionibacterium acnes

<400> SEQUENCE: 17
gtcttctggg gtgcagggca tgttggctga gcg                                33

<210> SEQ ID NO 18
<211> LENGTH: 33
<212> TYPE: DNA
<213> ORGANISM: Propionibacterium phage P9.1-2A

<400> SEQUENCE: 18
ggcttctggg gtgcagggca tgttggctga gcg                                33

<210> SEQ ID NO 19
<211> LENGTH: 33
<212> TYPE: DNA
<213> ORGANISM: Propionibacterium phage P9.1-2B

<400> SEQUENCE: 19
ggcttctggg gtgcagggca tgttggctga gcg                                33

<210> SEQ ID NO 20
<211> LENGTH: 33
<212> TYPE: DNA
<213> ORGANISM: Propionibacterium phage P.1-3

<400> SEQUENCE: 20
gtcttctggg gtgaagggca tgttggctga gcg                                33

<210> SEQ ID NO 21
<211> LENGTH: 33
<212> TYPE: DNA
<213> ORGANISM: Propionibacterium phage P9.1-4

<400> SEQUENCE: 21
ggcttctggg gtgcagggca tgttggctga gcg                                33

<210> SEQ ID NO 22
<211> LENGTH: 33
<212> TYPE: DNA
<213> ORGANISM: Propionibacterium acnes

<400> SEQUENCE: 22
ctgcgccaac aaacgcatct gatccgaata cgg                                33

<210> SEQ ID NO 23
<211> LENGTH: 33
<212> TYPE: DNA
<213> ORGANISM: Propionibacterium phage P9.1-2A

<400> SEQUENCE: 23
ctgcgccaac aaacgcatct gatccgaata cgg                                33

<210> SEQ ID NO 24
<211> LENGTH: 33
<212> TYPE: DNA
<213> ORGANISM: Propionibacterium phage P9.1-2B

<400> SEQUENCE: 24
```

-continued ctgagccaac aaacgcatct gatccgaata cgg          33

<210> SEQ ID NO 25
<211> LENGTH: 33
<212> TYPE: DNA
<213> ORGANISM: Propionibacterium phage P.1-3

<400> SEQUENCE: 25
ctgagccaac aaacgcatct gatccgaata cgg          33

<210> SEQ ID NO 26
<211> LENGTH: 33
<212> TYPE: DNA
<213> ORGANISM: Propionibacterium phage P9.1-4

<400> SEQUENCE: 26
ctgcgccagc aaacgcatct gatccgaata cgg          33

<210> SEQ ID NO 27
<211> LENGTH: 33
<212> TYPE: DNA
<213> ORGANISM: Propionibacterium acnes

<400> SEQUENCE: 27
cgcagcaatc tcagaaggcc acaacaaatt cgt          33

<210> SEQ ID NO 28
<211> LENGTH: 33
<212> TYPE: DNA
<213> ORGANISM: Propionibacterium phage P9.1-2A

<400> SEQUENCE: 28
cgaagcaatc tcagaaggcc acaacaaatt cgt          33

<210> SEQ ID NO 29
<211> LENGTH: 33
<212> TYPE: DNA
<213> ORGANISM: Propionibacterium phage P9.1-2B

<400> SEQUENCE: 29
cgaagcaatc tcagaaggcc acaacaaatt cgt          33

<210> SEQ ID NO 30
<211> LENGTH: 33
<212> TYPE: DNA
<213> ORGANISM: Propionibacterium phage P.1-3

<400> SEQUENCE: 30
cgcatcaatc tcagaaggcc acaacaaatt cgt          33

<210> SEQ ID NO 31
<211> LENGTH: 33
<212> TYPE: DNA
<213> ORGANISM: Propionibacterium phage P9.1-4

<400> SEQUENCE: 31
cgcagcaatc tcagaaggcc acaacaaatg cgt          33

<210> SEQ ID NO 32
<211> LENGTH: 33
<212> TYPE: DNA
<213> ORGANISM: Propionibacterium phage P9.1

```
<400> SEQUENCE: 32
gtcttctggg gtgcagggca tgttggctga gcg                                  33

<210> SEQ ID NO 33
<211> LENGTH: 33
<212> TYPE: DNA
<213> ORGANISM: Propionibacterium phage P9.1

<400> SEQUENCE: 33
ctgcgccaac aaacgcatct gatccgaata cgg                                  33

<210> SEQ ID NO 34
<211> LENGTH: 33
<212> TYPE: DNA
<213> ORGANISM: Propionibacterium phage P9.1

<400> SEQUENCE: 34
cgcagcaatc tcagaaggcc acaacaaatt cgt                                  33

<210> SEQ ID NO 35
<211> LENGTH: 33
<212> TYPE: DNA
<213> ORGANISM: Propionibacterium acnes

<400> SEQUENCE: 35
gtcttctggg gtgcagtcga tgttggctga gcg                                  33

<210> SEQ ID NO 36
<211> LENGTH: 36
<212> TYPE: DNA
<213> ORGANISM: Propionibacterium phage P14.4

<400> SEQUENCE: 36
gaagtcttct ggggtgcagg ctatgttggc tgagcg                               36

<210> SEQ ID NO 37
<211> LENGTH: 36
<212> TYPE: DNA
<213> ORGANISM: Propionibacterium phage P100.1

<400> SEQUENCE: 37
gaagtcttct ggggtgcagt cgatgttggc tgagcg                               36

<210> SEQ ID NO 38
<211> LENGTH: 36
<212> TYPE: DNA
<213> ORGANISM: Propionibacterium phage P100A

<400> SEQUENCE: 38
gaagtctcct ggggtgcagg ccatgttggc tgagcg                               36

<210> SEQ ID NO 39
<211> LENGTH: 36
<212> TYPE: DNA
<213> ORGANISM: Propionibacterium phage P100D

<400> SEQUENCE: 39
gaagtcttct ggggtgcagg gcatgttggc tgagcg                               36

<210> SEQ ID NO 40
<211> LENGTH: 36
<212> TYPE: DNA
<213> ORGANISM: Propionibacterium phage P101A
```

```
<400> SEQUENCE: 40
gaagtctcct ggggtgcagg gtatgttggc tgagcg                                 36

<210> SEQ ID NO 41
<211> LENGTH: 36
<212> TYPE: DNA
<213> ORGANISM: Propionibacterium phage P104A

<400> SEQUENCE: 41
gaagtcttct ggggtgcagg gcatgttggc tgagcg                                 36

<210> SEQ ID NO 42
<211> LENGTH: 36
<212> TYPE: DNA
<213> ORGANISM: Propionibacterium phage P105

<400> SEQUENCE: 42
gaagtcttct ggggtgcagg gcatgttgtc tgagcg                                 36

<210> SEQ ID NO 43
<211> LENGTH: 36
<212> TYPE: DNA
<213> ORGANISM: Propionibacterium phage ATCC_29399B

<400> SEQUENCE: 43
gaagtcttct ggggtgcagg ctatgttggc tgagcg                                 36

<210> SEQ ID NO 44
<211> LENGTH: 36
<212> TYPE: DNA
<213> ORGANISM: Propionibacterium phage ATCC_29399B

<400> SEQUENCE: 44
aaaagcgccg ggtgtgcagg gcatgttggc tgagcg                                 36

<210> SEQ ID NO 45
<211> LENGTH: 33
<212> TYPE: DNA
<213> ORGANISM: Propionibacterium acnes

<400> SEQUENCE: 45
ctgcgccaac agccgcatct gatccgaata cgg                                    33

<210> SEQ ID NO 46
<211> LENGTH: 36
<212> TYPE: DNA
<213> ORGANISM: Propionibacterium phage P14.4

<400> SEQUENCE: 46
caactgcgcc aacagccgca tctgatccga atacgg                                 36

<210> SEQ ID NO 47
<211> LENGTH: 36
<212> TYPE: DNA
<213> ORGANISM: Propionibacterium phage P100.1

<400> SEQUENCE: 47
caattgcgcc aataatctca tctgatccga atacgg                                 36

<210> SEQ ID NO 48
<211> LENGTH: 36
<212> TYPE: DNA
```

<213> ORGANISM: Propionibacterium phage P100A

<400> SEQUENCE: 48
caactgggct aatagccgca tctgatccga atacgg                36

<210> SEQ ID NO 49
<211> LENGTH: 36
<212> TYPE: DNA
<213> ORGANISM: Propionibacterium phage P100D

<400> SEQUENCE: 49
caactgcgcc aacagtctca tctgatccga atacgg                36

<210> SEQ ID NO 50
<211> LENGTH: 36
<212> TYPE: DNA
<213> ORGANISM: Propionibacterium phage P101A

<400> SEQUENCE: 50
caactgcgcc aacaaacgca tctgatccga atacgg                36

<210> SEQ ID NO 51
<211> LENGTH: 36
<212> TYPE: DNA
<213> ORGANISM: Propionibacterium phage P104A

<400> SEQUENCE: 51
caactgcgcc aacagtctca tctgatccga atacgg                36

<210> SEQ ID NO 52
<211> LENGTH: 36
<212> TYPE: DNA
<213> ORGANISM: Propionibacterium phage P105

<400> SEQUENCE: 52
caactgcgcc aacaaacgca tctgatccga atacgg                36

<210> SEQ ID NO 53
<211> LENGTH: 36
<212> TYPE: DNA
<213> ORGANISM: Propionibacterium phage ATCC_29399B

<400> SEQUENCE: 53
caactgcgcc aacaatctca tctgatccga atacgg                36

<210> SEQ ID NO 54
<211> LENGTH: 36
<212> TYPE: DNA
<213> ORGANISM: Propionibacterium phage ATCC_29399B

<400> SEQUENCE: 54
caactgagcc aataagcgca tctgatccga atacgg                36

<210> SEQ ID NO 55
<211> LENGTH: 33
<212> TYPE: DNA
<213> ORGANISM: Propionibacterium acnes

<400> SEQUENCE: 55
cgcagcaatc tcagaaggcc acaacaagtt cgt                33

<210> SEQ ID NO 56
<211> LENGTH: 36

```
<212> TYPE: DNA
<213> ORGANISM: Propionibacterium phage P1.1

<400> SEQUENCE: 56
caacgcggca atctcagaag gccacaacaa attcgt                                    36

<210> SEQ ID NO 57
<211> LENGTH: 36
<212> TYPE: DNA
<213> ORGANISM: Propionibacterium phage P14.4

<400> SEQUENCE: 57
caacgcggca atctcagaag gccacaacaa attcgt                                    36

<210> SEQ ID NO 58
<211> LENGTH: 36
<212> TYPE: DNA
<213> ORGANISM: Propionibacterium phage P100.1

<400> SEQUENCE: 58
caacgcagca atctcagaag gccacaacaa attcgt                                    36

<210> SEQ ID NO 59
<211> LENGTH: 36
<212> TYPE: DNA
<213> ORGANISM: Propionibacterium phage P100A

<400> SEQUENCE: 59
caacgcagca atctcggaag gccacaacaa attcgt                                    36

<210> SEQ ID NO 60
<211> LENGTH: 36
<212> TYPE: DNA
<213> ORGANISM: Propionibacterium phage P100D

<400> SEQUENCE: 60
caacgcggca atctcggaag gccacaacaa attcgt                                    36

<210> SEQ ID NO 61
<211> LENGTH: 36
<212> TYPE: DNA
<213> ORGANISM: Propionibacterium phage P101A

<400> SEQUENCE: 61
caacgcggca atctcagaag gccacaacaa attcgt                                    36

<210> SEQ ID NO 62
<211> LENGTH: 36
<212> TYPE: DNA
<213> ORGANISM: Propionibacterium phage P104A

<400> SEQUENCE: 62
caacgcggca atctcagaag gccacaacaa attcgt                                    36

<210> SEQ ID NO 63
<211> LENGTH: 36
<212> TYPE: DNA
<213> ORGANISM: Propionibacterium phage P105

<400> SEQUENCE: 63
caacgcggca atctcagaag gccacaacaa attcgt                                    36

<210> SEQ ID NO 64
```

```
<211> LENGTH: 36
<212> TYPE: DNA
<213> ORGANISM: Propionibacterium phage ATCC_29399B

<400> SEQUENCE: 64
caacgcagca atctcagaag gccacaacaa gttcgt                              36

<210> SEQ ID NO 65
<211> LENGTH: 36
<212> TYPE: DNA
<213> ORGANISM: Propionibacterium phage ATCC_29399B

<400> SEQUENCE: 65
caacgtagca acctcggaag gccacaacag attaga                              36

<210> SEQ ID NO 66
<211> LENGTH: 33
<212> TYPE: DNA
<213> ORGANISM: Propionibacterium acnes

<400> SEQUENCE: 66
gatcgagttg gctgagtcga aggtgttgcg gtt                                 33

<210> SEQ ID NO 67
<211> LENGTH: 36
<212> TYPE: DNA
<213> ORGANISM: Propionibacterium phage P9.1

<400> SEQUENCE: 67
taagatcgag ttggctgagt cggatgtgtt gcggtt                              36

<210> SEQ ID NO 68
<211> LENGTH: 36
<212> TYPE: DNA
<213> ORGANISM: Propionibacterium phage P14.4

<400> SEQUENCE: 68
taagattgag ttggctgagt cggatgtgtt gcggtt                              36

<210> SEQ ID NO 69
<211> LENGTH: 36
<212> TYPE: DNA
<213> ORGANISM: Propionibacterium phage P100.1

<400> SEQUENCE: 69
taagatcgag ttggctgagt cggatgtgtt gcggtt                              36

<210> SEQ ID NO 70
<211> LENGTH: 36
<212> TYPE: DNA
<213> ORGANISM: Propionibacterium phage P100A

<400> SEQUENCE: 70
taagatcgag ttggcggagt cggatgtgtt gcgttt                              36

<210> SEQ ID NO 71
<211> LENGTH: 36
<212> TYPE: DNA
<213> ORGANISM: Propionibacterium phage P100D

<400> SEQUENCE: 71
taagatcgag ttggctgagt cggatgtgtt gcggtt                              36
```

-continued

```
<210> SEQ ID NO 72
<211> LENGTH: 36
<212> TYPE: DNA
<213> ORGANISM: Propionibacterium phage P101A

<400> SEQUENCE: 72
taagatcgag ttggctgagt cggatgtgtt gcggtt                         36

<210> SEQ ID NO 73
<211> LENGTH: 36
<212> TYPE: DNA
<213> ORGANISM: Propionibacterium phage P104A

<400> SEQUENCE: 73
taagatcgag ttggcagagt cggatgtgtt gcggtt                         36

<210> SEQ ID NO 74
<211> LENGTH: 36
<212> TYPE: DNA
<213> ORGANISM: Propionibacterium phage P105

<400> SEQUENCE: 74
taagatcgag ttggctgaat cggatgtgtt gcggtt                         36

<210> SEQ ID NO 75
<211> LENGTH: 36
<212> TYPE: DNA
<213> ORGANISM: Propionibacterium phage ATCC_29399B

<400> SEQUENCE: 75
taagatcgag ttggctgagt cggatgtgtt gcggtt                         36

<210> SEQ ID NO 76
<211> LENGTH: 36
<212> TYPE: DNA
<213> ORGANISM: Propionibacterium phage ATCC_29399B

<400> SEQUENCE: 76
taagatcgag ttggctgagt cggatgtgtt gcgttt                         36

<210> SEQ ID NO 77
<211> LENGTH: 36
<212> TYPE: DNA
<213> ORGANISM: Propionibacterium phage P9.1-2A

<400> SEQUENCE: 77
gaaggcttct ggggtgcagg gcatgttggc tgagcg                         36

<210> SEQ ID NO 78
<211> LENGTH: 36
<212> TYPE: DNA
<213> ORGANISM: Propionibacterium phage P9.1-2B

<400> SEQUENCE: 78
gaaggcttct ggggtgcagg gcatgttggc tgagcg                         36

<210> SEQ ID NO 79
<211> LENGTH: 36
<212> TYPE: DNA
<213> ORGANISM: Propionibacterium phage P9.1-3

<400> SEQUENCE: 79
gaagtcttct ggggtgaagg gcatgttggc tgagcg                         36
```

<210> SEQ ID NO 80
<211> LENGTH: 36
<212> TYPE: DNA
<213> ORGANISM: Propionibacterium phage P9.1-4

<400> SEQUENCE: 80
gaaggcttct ggggtgcagg gcatgttggc tgagcg      36

<210> SEQ ID NO 81
<211> LENGTH: 36
<212> TYPE: DNA
<213> ORGANISM: Propionibacterium phage P9.1-5

<400> SEQUENCE: 81
gaagtcttct tgggtgcagg gcatgttggc tgagcg      36

<210> SEQ ID NO 82
<211> LENGTH: 36
<212> TYPE: DNA
<213> ORGANISM: Propionibacterium phage P9.1-6

<400> SEQUENCE: 82
gaaggcttct ggggtgcagg gcatgttggc tgagcg      36

<210> SEQ ID NO 83
<211> LENGTH: 36
<212> TYPE: DNA
<213> ORGANISM: Propionibacterium phage P9.1-7/8

<400> SEQUENCE: 83
gaagtcttct gggttgcagg gcatgttggc tgagcg      36

<210> SEQ ID NO 84
<211> LENGTH: 36
<212> TYPE: DNA
<213> ORGANISM: Propionibacterium phage P9.1-10

<400> SEQUENCE: 84
gtagtcttct ggggtgcagg gcatgttggc tgagcg      36

<210> SEQ ID NO 85
<211> LENGTH: 36
<212> TYPE: DNA
<213> ORGANISM: Propionibacterium phage P1.1-1

<400> SEQUENCE: 85
gacgtcttct ggggtgcagt ctatgttggc tgagcg      36

<210> SEQ ID NO 86
<211> LENGTH: 36
<212> TYPE: DNA
<213> ORGANISM: Propionibacterium phage P1.1-2

<400> SEQUENCE: 86
gcagtcttct ggggtgcagt ctatgttggc tgagcg      36

<210> SEQ ID NO 87
<211> LENGTH: 36
<212> TYPE: DNA
<213> ORGANISM: Propionibacterium phage P1.1-3

<400> SEQUENCE: 87
gcagtcttct ggggtgcagt ctatgttggc tgagcg      36

```
<210> SEQ ID NO 88
<211> LENGTH: 36
<212> TYPE: DNA
<213> ORGANISM: Propionibacterium phage P1.1-4

<400> SEQUENCE: 88
gcagtcttct ggggtgcagt ctatgttggc tgagcg                              36

<210> SEQ ID NO 89
<211> LENGTH: 36
<212> TYPE: DNA
<213> ORGANISM: Propionibacterium phage P1.1-5

<400> SEQUENCE: 89
gaagtcttct ggggtgcagt ctatgttggc tgagcg                              36

<210> SEQ ID NO 90
<211> LENGTH: 36
<212> TYPE: DNA
<213> ORGANISM: Propionibacterium phage P1.1-6

<400> SEQUENCE: 90
gaagtcttct ggggtgcagt ctatgttggc tgagcg                              36

<210> SEQ ID NO 91
<211> LENGTH: 36
<212> TYPE: DNA
<213> ORGANISM: Propionibacterium phage P1.1-7

<400> SEQUENCE: 91
gaagtcttct ggggtgcagt ctatgttggc tgagcg                              36

<210> SEQ ID NO 92
<211> LENGTH: 36
<212> TYPE: DNA
<213> ORGANISM: Propionibacterium phage P1.1-8

<400> SEQUENCE: 92
gaagtcttct ggggtgcagt ctatgttggc tgagcg                              36

<210> SEQ ID NO 93
<211> LENGTH: 36
<212> TYPE: DNA
<213> ORGANISM: Propionibacterium phage P9.1-2A

<400> SEQUENCE: 93
taagatcgag ttggctgagt cggatgtgtt gcggtt                              36

<210> SEQ ID NO 94
<211> LENGTH: 36
<212> TYPE: DNA
<213> ORGANISM: Propionibacterium phage P9.1-2B

<400> SEQUENCE: 94
taagatcgag ttggctgagt cggatgtgtt gcggtt                              36

<210> SEQ ID NO 95
<211> LENGTH: 36
<212> TYPE: DNA
<213> ORGANISM: Propionibacterium phage P9.1-3

<400> SEQUENCE: 95
```

```
taagatcgag ttggctgagt cggatgtgtt gcggtt                                    36

<210> SEQ ID NO 96
<211> LENGTH: 36
<212> TYPE: DNA
<213> ORGANISM: Propionibacterium phage P9.1-4

<400> SEQUENCE: 96
taagatcgag ttggctgagt cggatgtgtt gcggtt                                    36

<210> SEQ ID NO 97
<211> LENGTH: 36
<212> TYPE: DNA
<213> ORGANISM: Propionibacterium phage P9.1-5

<400> SEQUENCE: 97
taagatcgag ttggctgagt cggatgtgtt gcggtt                                    36

<210> SEQ ID NO 98
<211> LENGTH: 36
<212> TYPE: DNA
<213> ORGANISM: Propionibacterium phage P9.1-6

<400> SEQUENCE: 98
taagatcgag ttggctgagt cggatgtgtt gcggtt                                    36

<210> SEQ ID NO 99
<211> LENGTH: 36
<212> TYPE: DNA
<213> ORGANISM: Propionibacterium phage P9.1-7/8

<400> SEQUENCE: 99
taagatcgag ttggctgagt cggatgtgtt gcggtt                                    36

<210> SEQ ID NO 100
<211> LENGTH: 36
<212> TYPE: DNA
<213> ORGANISM: Propionibacterium phage P9.1-10

<400> SEQUENCE: 100
taagatcgag ttggctgagt cggatgtgtt gcggtt                                    36

<210> SEQ ID NO 101
<211> LENGTH: 36
<212> TYPE: DNA
<213> ORGANISM: Propionibacterium phage P1.1-1

<400> SEQUENCE: 101
taagattgag ttggctgagt cggatgtgtt gcggtt                                    36

<210> SEQ ID NO 102
<211> LENGTH: 36
<212> TYPE: DNA
<213> ORGANISM: Propionibacterium phage P1.1-2

<400> SEQUENCE: 102
taagattgag ttggctgagt cggatgtgtt gcggtt                                    36

<210> SEQ ID NO 103
<211> LENGTH: 36
<212> TYPE: DNA
<213> ORGANISM: Propionibacterium phage P1.1-3

<400> SEQUENCE: 103
```

```
taagattgag ttggctgagt cggatgtgtt gcggtt                                36

<210> SEQ ID NO 104
<211> LENGTH: 36
<212> TYPE: DNA
<213> ORGANISM: Propionibacterium phage P1.1-4

<400> SEQUENCE: 104
taagattgag ttggctgagt cggatgtgtt gcggtt                                36

<210> SEQ ID NO 105
<211> LENGTH: 36
<212> TYPE: DNA
<213> ORGANISM: Propionibacterium phage P1.1-5

<400> SEQUENCE: 105
taagattgag ttggctgagt cggatgtgtg gcggtt                                36

<210> SEQ ID NO 106
<211> LENGTH: 36
<212> TYPE: DNA
<213> ORGANISM: Propionibacterium phage P1.1-6

<400> SEQUENCE: 106
taagattgag ttggctgagg cggatgtgtt gcggtt                                36

<210> SEQ ID NO 107
<211> LENGTH: 36
<212> TYPE: DNA
<213> ORGANISM: Propionibacterium phage P1.1-7

<400> SEQUENCE: 107
taagattgag ttggctgagt cggatgtgtg gcggtt                                36

<210> SEQ ID NO 108
<211> LENGTH: 36
<212> TYPE: DNA
<213> ORGANISM: Propionibacterium phage P1.1-8

<400> SEQUENCE: 108
taagattgag ttggctgagt cggatgtgtt tcggtt                                36

<210> SEQ ID NO 109
<211> LENGTH: 36
<212> TYPE: DNA
<213> ORGANISM: Propionibacterium phage P9.1-2A

<400> SEQUENCE: 109
caactgagcc aacaaacgca tctgatccga atacgg                                36

<210> SEQ ID NO 110
<211> LENGTH: 36
<212> TYPE: DNA
<213> ORGANISM: Propionibacterium phage P9.1-2B

<400> SEQUENCE: 110
caactgagcc aacaaacgca tctgatccga atacgg                                36

<210> SEQ ID NO 111
<211> LENGTH: 36
<212> TYPE: DNA
<213> ORGANISM: Propionibacterium phage P9.1-3
```

```
<400> SEQUENCE: 111
caactgagcc aacaaacgca tctgatccga atacgg                                 36

<210> SEQ ID NO 112
<211> LENGTH: 36
<212> TYPE: DNA
<213> ORGANISM: Propionibacterium phage P9.1-4

<400> SEQUENCE: 112
caactgcgcc agcaaacgca tctgatccga atacgg                                 36

<210> SEQ ID NO 113
<211> LENGTH: 36
<212> TYPE: DNA
<213> ORGANISM: Propionibacterium phage P9.1-5

<400> SEQUENCE: 113
caactgcgac aacaaacgca tctgatccga atacgg                                 36

<210> SEQ ID NO 114
<211> LENGTH: 36
<212> TYPE: DNA
<213> ORGANISM: Propionibacterium phage P9.1-6

<400> SEQUENCE: 114
caactgcgac aacaaacgca tctgatccga atacgg                                 36

<210> SEQ ID NO 115
<211> LENGTH: 36
<212> TYPE: DNA
<213> ORGANISM: Propionibacterium phage P9.1-7/8

<400> SEQUENCE: 115
catctgcgcc aacaaacgca tctgatccga atacgg                                 36

<210> SEQ ID NO 116
<211> LENGTH: 36
<212> TYPE: DNA
<213> ORGANISM: Propionibacterium phage P9.1-10

<400> SEQUENCE: 116
caactgcgcc agcaaacgca tctgatccga atacgg                                 36

<210> SEQ ID NO 117
<211> LENGTH: 36
<212> TYPE: DNA
<213> ORGANISM: Propionibacterium phage P1.1-1

<400> SEQUENCE: 117
caactgcgcc aaaagtctca tctgatccga atacgg                                 36

<210> SEQ ID NO 118
<211> LENGTH: 36
<212> TYPE: DNA
<213> ORGANISM: Propionibacterium phage P1.1-2

<400> SEQUENCE: 118
caactgagcc aacagtctca tctgatccga atacgg                                 36

<210> SEQ ID NO 119
<211> LENGTH: 36
<212> TYPE: DNA
<213> ORGANISM: Propionibacterium phage P1.1-3
```

```
<400> SEQUENCE: 119
caactgagcc aaaagtctca tctgatccga atacgg                                36

<210> SEQ ID NO 120
<211> LENGTH: 36
<212> TYPE: DNA
<213> ORGANISM: Propionibacterium phage P1.1-4

<400> SEQUENCE: 120
caactgcgcc agcagtctca tctgatccga atacgg                                36

<210> SEQ ID NO 121
<211> LENGTH: 36
<212> TYPE: DNA
<213> ORGANISM: Propionibacterium phage P1.1-5

<400> SEQUENCE: 121
cacctgcgcc aacagtctca tctgatccga atacgg                                36

<210> SEQ ID NO 122
<211> LENGTH: 36
<212> TYPE: DNA
<213> ORGANISM: Propionibacterium phage P1.1-6

<400> SEQUENCE: 122
cagctgcgcc aacagtctca tctgatccga atacgg                                36

<210> SEQ ID NO 123
<211> LENGTH: 36
<212> TYPE: DNA
<213> ORGANISM: Propionibacterium phage P1.1-7

<400> SEQUENCE: 123
cacctgcgcc aacagtctca tctgatccga atacgg                                36

<210> SEQ ID NO 124
<211> LENGTH: 36
<212> TYPE: DNA
<213> ORGANISM: Propionibacterium phage P1.1-8

<400> SEQUENCE: 124
cacctgcgcc aacagtctca tctgatccga atacgg                                36

<210> SEQ ID NO 125
<211> LENGTH: 36
<212> TYPE: DNA
<213> ORGANISM: Propionibacterium phage P9.1-2A

<400> SEQUENCE: 125
caacgaagca atctcagaag gccacaacaa attcgt                                36

<210> SEQ ID NO 126
<211> LENGTH: 36
<212> TYPE: DNA
<213> ORGANISM: Propionibacterium phage P9.1-2B

<400> SEQUENCE: 126
caacgaagca atctcagaag gccacaacaa attcgt                                36

<210> SEQ ID NO 127
<211> LENGTH: 36
<212> TYPE: DNA
```

```
<213> ORGANISM: Propionibacterium phage P9.1-3

<400> SEQUENCE: 127
caacgcatca atctcagaag gccacaacaa attcgt                              36

<210> SEQ ID NO 128
<211> LENGTH: 36
<212> TYPE: DNA
<213> ORGANISM: Propionibacterium phage P9.1-4

<400> SEQUENCE: 128
caacgcagca atctcagaag gccacaacaa atgcgt                              36

<210> SEQ ID NO 129
<211> LENGTH: 36
<212> TYPE: DNA
<213> ORGANISM: Propionibacterium phage P9.1-5

<400> SEQUENCE: 129
caacgcagca atctcagaag gccacaacaa attcat                              36

<210> SEQ ID NO 130
<211> LENGTH: 36
<212> TYPE: DNA
<213> ORGANISM: Propionibacterium phage P9.1-6

<400> SEQUENCE: 130
caacgcatca atctcagaag gccacaacaa attcgt                              36

<210> SEQ ID NO 131
<211> LENGTH: 36
<212> TYPE: DNA
<213> ORGANISM: Propionibacterium phage P9.1-7/8

<400> SEQUENCE: 131
caacgcatca atctcagaag gccacaacaa attcgt                              36

<210> SEQ ID NO 132
<211> LENGTH: 36
<212> TYPE: DNA
<213> ORGANISM: Propionibacterium phage P9.1-10

<400> SEQUENCE: 132
caacgcagca atctcagaag gccacaacaa attctt                              36

<210> SEQ ID NO 133
<211> LENGTH: 36
<212> TYPE: DNA
<213> ORGANISM: Propionibacterium phage P1.1-1

<400> SEQUENCE: 133
caacgcggca atctcagaag gccacaacaa attcgt                              36

<210> SEQ ID NO 134
<211> LENGTH: 36
<212> TYPE: DNA
<213> ORGANISM: Propionibacterium phage P1.1-2

<400> SEQUENCE: 134
caacgcggca atctcagaag gccacaacaa attcgt                              36

<210> SEQ ID NO 135
<211> LENGTH: 36
```

```
<212> TYPE: DNA
<213> ORGANISM: Propionibacterium phage P1.1-3

<400> SEQUENCE: 135
caacgcggca atctcagaag gccacaacaa attcgt                              36

<210> SEQ ID NO 136
<211> LENGTH: 36
<212> TYPE: DNA
<213> ORGANISM: Propionibacterium phage P1.1-4

<400> SEQUENCE: 136
caacgcggca atctcagaag gccacaacaa attcgt                              36

<210> SEQ ID NO 137
<211> LENGTH: 36
<212> TYPE: DNA
<213> ORGANISM: Propionibacterium phage P1.1-5

<400> SEQUENCE: 137
caacgcggca atctcagaag gccacaacaa attcgt                              36

<210> SEQ ID NO 138
<211> LENGTH: 36
<212> TYPE: DNA
<213> ORGANISM: Propionibacterium phage P1.1-6

<400> SEQUENCE: 138
caacgcggca atctcagaag gccacaacaa attcgt                              36

<210> SEQ ID NO 139
<211> LENGTH: 36
<212> TYPE: DNA
<213> ORGANISM: Propionibacterium phage P1.1-7

<400> SEQUENCE: 139
caacgcggca atctcagaag gccacaacaa attcgt                              36

<210> SEQ ID NO 140
<211> LENGTH: 36
<212> TYPE: DNA
<213> ORGANISM: Propionibacterium phage P1.1-8

<400> SEQUENCE: 140
caacgcggca atctcagaag gccacaacaa attcgt                              36

<210> SEQ ID NO 141
<211> LENGTH: 36
<212> TYPE: DNA
<213> ORGANISM: Propionibacterium acnes

<400> SEQUENCE: 141
gaagtcttct ggggtgcagt ctatgttggc tgagcg                              36

<210> SEQ ID NO 142
<211> LENGTH: 36
<212> TYPE: DNA
<213> ORGANISM: Propionibacterium phage P1.1-6

<400> SEQUENCE: 142
gcagtcttct ggggtgcagt ctatgttggc tgagcg                              36

<210> SEQ ID NO 143
```

```
<211> LENGTH: 36
<212> TYPE: DNA
<213> ORGANISM: Propionibacterium phage P1.1-7

<400> SEQUENCE: 143
gcagtcttct ggggtgcagt ctatgttggc tgagcg                          36

<210> SEQ ID NO 144
<211> LENGTH: 36
<212> TYPE: DNA
<213> ORGANISM: Propionibacterium phage P1.1-8

<400> SEQUENCE: 144
gacgtcttct ggggtgcagt ctatgttggc tgagcg                          36

<210> SEQ ID NO 145
<211> LENGTH: 33
<212> TYPE: DNA
<213> ORGANISM: Propionibacterium acnes

<400> SEQUENCE: 145
ggcgtatgac gagttgtggt cggcgttttcc tcc                            33

<210> SEQ ID NO 146
<211> LENGTH: 33
<212> TYPE: DNA
<213> ORGANISM: Propionibacterium phage P1.1

<400> SEQUENCE: 146
agcctatgac gcgttgtggt ctgcttttcc tcc                             33

<210> SEQ ID NO 147
<211> LENGTH: 33
<212> TYPE: DNA
<213> ORGANISM: Propionibacterium phage P9.1

<400> SEQUENCE: 147
agcctatgac gagttgtggt cggcgttttcc ccc                            33

<210> SEQ ID NO 148
<211> LENGTH: 33
<212> TYPE: DNA
<213> ORGANISM: Propionibacterium phage P14.4

<400> SEQUENCE: 148
ggcgtatgac gcgttgtggt ctgcgtttcc ccc                             33

<210> SEQ ID NO 149
<211> LENGTH: 33
<212> TYPE: DNA
<213> ORGANISM: Propionibacterium phage P100.1

<400> SEQUENCE: 149
agcctatgac gcgttgtggt ctgcttttcc tcc                             33

<210> SEQ ID NO 150
<211> LENGTH: 33
<212> TYPE: DNA
<213> ORGANISM: Propionibacterium phage P100A

<400> SEQUENCE: 150
ggcgtatgac gagttgtggt ctgcgtttcc tcc                             33
```

```
<210> SEQ ID NO 151
<211> LENGTH: 33
<212> TYPE: DNA
<213> ORGANISM: Propionibacterium phage P100D

<400> SEQUENCE: 151
ggcgtatgac gagttgtggt ctgcttttcc ccc                                 33

<210> SEQ ID NO 152
<211> LENGTH: 33
<212> TYPE: DNA
<213> ORGANISM: Propionibacterium phage P101A

<400> SEQUENCE: 152
agcctatgac gcgttgtggt ctgcttttcc tcc                                 33

<210> SEQ ID NO 153
<211> LENGTH: 33
<212> TYPE: DNA
<213> ORGANISM: Propionibacterium phage P104A

<400> SEQUENCE: 153
ggcgtatgac gagttgtggt ctgcttttcc tcc                                 33

<210> SEQ ID NO 154
<211> LENGTH: 33
<212> TYPE: DNA
<213> ORGANISM: Propionibacterium phage P105

<400> SEQUENCE: 154
ggcctatgac gagttgtggt cggcgtttcc tcc                                 33

<210> SEQ ID NO 155
<211> LENGTH: 33
<212> TYPE: DNA
<213> ORGANISM: Propionibacterium phage ATCC_29399B

<400> SEQUENCE: 155
agcgtatgac gagttgtggt ctgcttttcc tcc                                 33

<210> SEQ ID NO 156
<211> LENGTH: 33
<212> TYPE: DNA
<213> ORGANISM: Propionibacterium phage ATCC_29399B

<400> SEQUENCE: 156
agcatacgat cagttgtggt ctgcgtttcc tcc                                 33
```